US012630560B2

(12) United States Patent
Chen et al.

(10) Patent No.: US 12,630,560 B2
(45) Date of Patent: May 19, 2026

(54) SOLID FORMS, PHARMACEUTICAL COMPOSITIONS AND PREPARATION OF HETEROAROMATIC MACROCYCLIC ETHER COMPOUNDS

(71) Applicant: Nuvalent, Inc., Cambridge, MA (US)

(72) Inventors: Sibao Chen, East Greenwich, RI (US); Christopher G. F. Cooper, Rehoboth, MA (US); Baudouin Gerard, Arlington, MA (US); Joshua Courtney Horan, Somerville, MA (US); Jason T. Kropp, Westford, MA (US); Benjamin Stephen Lane, Lynnfield, MA (US); David James Pearson, Derby (GB)

(73) Assignee: Nuvalent, Inc., Cambridge, MA (US)

( * ) Notice: Subject to any disclaimer, the term of this patent is extended or adjusted under 35 U.S.C. 154(b) by 0 days.

(21) Appl. No.: 18/735,898

(22) Filed: Jun. 6, 2024

(65) Prior Publication Data

US 2024/0317771 A1 Sep. 26, 2024

Related U.S. Application Data

(62) Division of application No. 17/957,725, filed on Sep. 30, 2022, now Pat. No. 12,043,626.

(60) Provisional application No. 63/251,514, filed on Oct. 1, 2021.

(51) Int. Cl.

| | |
|---|---|
| ***C07D 491/22*** | (2006.01) |
| ***A61K 9/20*** | (2006.01) |
| ***A61K 9/28*** | (2006.01) |

(52) U.S. Cl.

CPC .......... *C07D 491/22* (2013.01); *A61K 9/2013* (2013.01); *A61K 9/2018* (2013.01); *A61K 9/2054* (2013.01); *A61K 9/2059* (2013.01); *A61K 9/2833* (2013.01); *C07B 2200/13* (2013.01)

(58) Field of Classification Search

CPC .. C07D 491/22; A61K 9/2013; A61K 9/2018; A61K 9/2054; A61K 9/2059; A61K 9/2833; C07B 2200/13

USPC .......................................................... 514/286

See application file for complete search history.

(56) References Cited

U.S. PATENT DOCUMENTS

| | | | |
|---|---|---|---|
| 4,172,896 | A | 10/1979 | Uno et al. |
| 5,358,970 | A | 10/1994 | Ruff et al. |
| 5,427,798 | A | 6/1995 | Ludwig et al. |
| 5,541,231 | A | 7/1996 | Ruff et al. |
| 5,569,655 | A | 10/1996 | Dority, Jr. et al. |
| 5,731,000 | A | 3/1998 | Ruff et al. |
| 5,763,493 | A | 6/1998 | Ruff et al. |
| 5,849,735 | A | 12/1998 | Albright et al. |
| 6,110,973 | A | 8/2000 | Young |
| 6,583,124 | B2 | 6/2003 | Asgharian |
| 6,660,867 | B2 | 12/2003 | Shimizu et al. |
| 7,312,225 | B2 | 12/2007 | Luecking et al. |
| 7,338,973 | B2 | 3/2008 | Sui et al. |
| 7,445,211 | B1 | 11/2008 | Walton |
| 7,514,466 | B2 | 4/2009 | Wilk et al. |
| 7,641,703 | B2 | 1/2010 | Guerin et al. |
| 7,696,239 | B2 | 4/2010 | Sui et al. |
| 7,915,414 | B2 | 3/2011 | Chi et al. |
| 8,012,603 | B2 | 9/2011 | Doi et al. |
| 8,039,450 | B2 | 10/2011 | Akama et al. |
| 8,129,523 | B2 | 3/2012 | Wilk et al. |
| 8,168,614 | B2 | 5/2012 | Baker et al. |
| 8,178,520 | B2 | 5/2012 | Di Francesco et al. |
| 8,308,996 | B2 | 11/2012 | Takahashi et al. |
| 8,309,594 | B2 | 11/2012 | Wilk et al. |
| 8,410,091 | B1 | 4/2013 | Eriksson et al. |
| 8,461,135 | B2 | 6/2013 | Akama et al. |
| 8,580,840 | B2 | 11/2013 | Sui et al. |
| 8,609,712 | B2 | 12/2013 | Wilk et al. |
| 8,680,111 | B2 | 3/2014 | Bailey et al. |
| 9,012,431 | B2 | 4/2015 | Akama |
| 9,133,168 | B2 | 9/2015 | Brollo et al. |
| 9,133,215 | B2 | 9/2015 | Bailey et al. |
| 9,181,265 | B2 | 11/2015 | Feron et al. |
| 9,221,818 | B2 | 12/2015 | Pinto et al. |
| 9,318,714 | B2 | 4/2016 | Ise |
| 9,388,161 | B2 | 7/2016 | Bair et al. |
| 9,422,292 | B2 | 8/2016 | Albrecht et al. |
| 9,446,995 | B2 | 9/2016 | Chong |
| 9,502,667 | B2 | 11/2016 | Saito et al. |

(Continued)

FOREIGN PATENT DOCUMENTS

| | | |
|---|---|---|
| CA | 2160092 | 4/1996 |
| CN | 105669733 | 6/2016 |

(Continued)

OTHER PUBLICATIONS

Cancer [online], [retrieved on Jul. 6, 2007] Retrieved from the Internet, URL: http://www.nim.nih.gov/medlineplus/cancer.html (Year: 2007).*

Lala et al., Role of nitric oxide in tumor progression: Lessons from experimental tumors, Cancer and Metastasis Reviews (1998), 17 , 91-106 (Year: 1998).*

Golub et al., Molecular Classification of Cancer: Class Discovery and Class Prediction by Gene Expression Monitoring, Science (1999), vol. 286, 531-537 (Year: 1999).*

Ahn et al., "Entrectinib in patients with locally advanced or metastatic ROS1 fusion-positive non-small cell lung cancer (NSCLC)," IASLC 18th World Conference on Lung Cancer: 16 pages Abstract 8564 (Oct. 15-18, 2017).

(Continued)

*Primary Examiner* — Kristin A Vajda

(74) *Attorney, Agent, or Firm* — Jones Day

(57) ABSTRACT

Provided herein are solid forms comprising a compound of formula (I), or a stereoisomer, or a mixture of stereoisomers thereof, or a pharmaceutically acceptable salt thereof. Also provided herein are methods of synthesizing a compound of formula (I), pharmaceutical compositions comprising the same, and methods of treating, preventing, and managing various disorders using the compositions provided herein.

30 Claims, 19 Drawing Sheets

(56) References Cited

U.S. PATENT DOCUMENTS

| | | | |
|---|---|---|---|
| 9,518,217 | B2 | 12/2016 | Cheng et al. |
| 9,611,274 | B2 | 4/2017 | Pinto et al. |
| 9,666,809 | B2 | 5/2017 | Lee |
| 9,768,393 | B2 | 9/2017 | Shin et al. |
| 9,887,372 | B2 | 2/2018 | Jun et al. |
| 9,902,742 | B2 | 2/2018 | Pinto et al. |
| 9,929,358 | B2 | 3/2018 | Hwang et al. |
| 10,147,887 | B2 | 12/2018 | Lee |
| 10,189,803 | B2 | 1/2019 | Chong |
| 10,208,068 | B2 | 2/2019 | Pinto et al. |
| 10,243,153 | B2 | 3/2019 | Ise |
| 10,335,392 | B2 | 7/2019 | Xiao et al. |
| 10,336,722 | B2 | 7/2019 | Bair et al. |
| 10,487,063 | B2 | 11/2019 | Jiang et al. |
| 10,593,889 | B1 | 3/2020 | Takahashi et al. |
| 10,611,750 | B2 | 4/2020 | Bair et al. |
| 10,774,053 | B2 | 9/2020 | Cai et al. |
| 10,800,791 | B2 | 10/2020 | Ghosh et al. |
| 10,954,215 | B2 | 3/2021 | Hughes et al. |
| 11,008,323 | B2 | 5/2021 | Schann et al. |
| 11,111,229 | B2 | 9/2021 | Bair et al. |
| 11,352,329 | B2 | 6/2022 | Cai et al. |
| 11,542,278 | B1 | 1/2023 | Horan et al. |
| 11,548,871 | B2 | 1/2023 | Bestvater |
| 11,584,738 | B2 | 2/2023 | Bestvater |
| 11,661,437 | B2 | 5/2023 | Su et al. |
| 11,667,649 | B2 | 6/2023 | Horan et al. |
| 11,702,407 | B2 | 7/2023 | Phillips et al. |
| 11,814,367 | B2 | 11/2023 | La. |
| 11,866,414 | B2 | 1/2024 | Spergel et al. |
| 2003/0187272 | A1 | 10/2003 | Shimizu et al. |
| 2005/0004074 | A1 | 1/2005 | Lyons et al. |
| 2005/0031697 | A1 | 2/2005 | Vehige et al. |
| 2005/0059744 | A1 | 3/2005 | Donello et al. |
| 2005/0080056 | A1 | 4/2005 | Horn |
| 2005/0250766 | A1 | 11/2005 | Wilk et al. |
| 2005/0272702 | A1 | 12/2005 | Wilk et al. |
| 2006/0116415 | A1 | 6/2006 | Sui et al. |
| 2007/0116984 | A1 | 5/2007 | Park et al. |
| 2007/0213526 | A1 | 9/2007 | Levent et al. |
| 2007/0293457 | A1 | 12/2007 | Baker et al. |
| 2008/0125591 | A1 | 5/2008 | Chi et al. |
| 2008/0138651 | A1 | 6/2008 | Doi et al. |
| 2008/0244838 | A1 | 10/2008 | Guerin et al. |
| 2009/0022694 | A1 | 1/2009 | Distefano |
| 2009/0042726 | A1 | 2/2009 | Black et al. |
| 2009/0054663 | A1 | 2/2009 | Wilk et al. |
| 2009/0143577 | A1 | 6/2009 | Wilk et al. |
| 2009/0291917 | A1 | 11/2009 | Akama et al. |
| 2010/0210658 | A1 | 8/2010 | Sui et al. |
| 2010/0216988 | A1 | 8/2010 | Alonso et al. |
| 2010/0261719 | A1 | 10/2010 | Basarab et al. |
| 2011/0049497 | A1 | 3/2011 | Ise |
| 2011/0071136 | A1 | 3/2011 | Haddach et al. |
| 2011/0178311 | A1 | 7/2011 | Levent et al. |
| 2012/0008068 | A1 | 1/2012 | Doi et al. |
| 2012/0121934 | A1 | 5/2012 | Takahashi et al. |
| 2012/0157448 | A1 | 6/2012 | Cook et al. |
| 2012/0214765 | A1 | 8/2012 | Akama et al. |
| 2013/0012702 | A1 | 1/2013 | Wilk et al. |
| 2013/0056716 | A1 | 3/2013 | Cheng et al. |
| 2013/0196952 | A1 | 8/2013 | Bunnage et al. |
| 2013/0252961 | A1 | 9/2013 | Bailey et al. |
| 2013/0274253 | A1 | 10/2013 | Brollo et al. |
| 2013/0289030 | A1 | 10/2013 | Feron et al. |
| 2013/0310555 | A1 | 11/2013 | Chong |
| 2014/0011768 | A1 | 1/2014 | Akama |
| 2014/0066479 | A1 | 3/2014 | Sui et al. |
| 2014/0135316 | A1 | 5/2014 | Albrecht et al. |
| 2014/0135339 | A1 | 5/2014 | Bailey et al. |
| 2014/0221338 | A1 | 8/2014 | Pinto et al. |
| 2015/0045349 | A1 | 2/2015 | Nagamiya et al. |
| 2015/0060791 | A1 | 3/2015 | Shin et al. |
| 2015/0155497 | A1 | 6/2015 | Lee |
| 2015/0207084 | A1 | 7/2015 | Hwang et al. |
| 2015/0218441 | A1 | 8/2015 | Cho et al. |
| 2015/0232445 | A1 | 8/2015 | Bair et al. |
| 2015/0255731 | A1 | 9/2015 | Lee |
| 2016/0068544 | A1 | 3/2016 | Pinto et al. |
| 2016/0163998 | A1 | 6/2016 | Saito et al. |
| 2016/0214996 | A1 | 7/2016 | Song et al. |
| 2016/0254462 | A1 | 9/2016 | Ise |
| 2016/0256448 | A1 | 9/2016 | Bair et al. |
| 2016/0257692 | A1 | 9/2016 | Bair et al. |
| 2016/0365521 | A1 | 12/2016 | Jun et al. |
| 2017/0008863 | A1 | 1/2017 | Chong |
| 2017/0054094 | A1 | 2/2017 | Cheng et al. |
| 2017/0158712 | A1 | 6/2017 | Pinto et al. |
| 2018/0029985 | A1 | 2/2018 | Shiers et al. |
| 2018/0029999 | A1 | 2/2018 | Jiang et al. |
| 2018/0148461 | A1 | 5/2018 | Pinto et al. |
| 2018/0215766 | A1 | 8/2018 | Bair et al. |
| 2018/0221344 | A1 | 8/2018 | Xiao et al. |
| 2018/0346468 | A1 | 12/2018 | Schann et al. |
| 2019/0060292 | A1 | 2/2019 | Wang et al. |
| 2019/0127347 | A1 | 5/2019 | Bair et al. |
| 2019/0210978 | A1 | 7/2019 | Cai et al. |
| 2019/0241582 | A1 | 8/2019 | Gjosh et al. |
| 2020/0017519 | A1 | 1/2020 | Ghosh et al. |
| 2020/0071298 | A1 | 3/2020 | Hughes et al. |
| 2020/0098994 | A1 | 3/2020 | Takahashi et al. |
| 2020/0303663 | A1 | 9/2020 | Jeon et al. |
| 2020/0317646 | A1 | 10/2020 | He et al. |
| 2020/0369642 | A1 | 11/2020 | Bair et al. |
| 2020/0385396 | A1 | 12/2020 | Zhou et al. |
| 2021/0012274 | A1 | 1/2021 | Forgatch et al. |
| 2021/0078959 | A1 | 3/2021 | Cai et al. |
| 2021/0171500 | A1 | 6/2021 | Bestvater |
| 2021/0309682 | A1 | 10/2021 | Arefyev et al. |
| 2021/0380561 | A1 | 12/2021 | Phillips et al. |
| 2021/0395233 | A1 | 12/2021 | Takahashi et al. |
| 2022/0017565 | A1 | 1/2022 | Su et al. |
| 2022/0098212 | A1 | 3/2022 | Horan et al. |
| 2022/0340586 | A9 | 10/2022 | Horan et al. |
| 2022/0402948 | A1 | 12/2022 | Liu et al. |
| 2022/0411384 | A1 | 12/2022 | Spergel et al. |
| 2022/0411406 | A1 | 12/2022 | Bestvater et al. |
| 2023/0012262 | A1 | 1/2023 | Bestvater et al. |
| 2023/0020273 | A1 | 1/2023 | Spergel et al. |
| 2023/0061891 | A1 | 3/2023 | Bair et al. |
| 2023/0076627 | A1 | 3/2023 | Horan et al. |
| 2023/0104740 | A1 | 4/2023 | Morgans et al. |
| 2023/0107663 | A1 | 4/2023 | Xinxing et al. |
| 2023/0124705 | A1 | 4/2023 | Chen et al. |
| 2023/0174513 | A1 | 6/2023 | Su et al. |
| 2023/0174553 | A1 | 6/2023 | Pandey et al. |
| 2023/0174554 | A1 | 6/2023 | Wang et al. |
| 2023/0183264 | A1 | 6/2023 | Pandey et al. |
| 2023/0212151 | A1 | 7/2023 | Bestvater et al. |
| 2024/0002367 | A1 | 1/2024 | Phillips et al. |

FOREIGN PATENT DOCUMENTS

| | | |
|---|---|---|
| CN | 106243096 | 12/2016 |
| CN | 108912175 | 11/2018 |
| CN | 105130966 | 5/2019 |
| CN | 109912433 | 6/2019 |
| CN | 110357905 | 10/2019 |
| CN | 110734456 | 1/2020 |
| CN | 111362967 | 7/2020 |
| CN | 111808147 | 10/2020 |
| CN | 112321604 | 2/2021 |
| CN | 112812128 | 5/2021 |
| CN | 113105440 | 7/2021 |
| CN | 113121607 | 7/2021 |
| CN | 111440154 | 4/2022 |
| FR | 2969611 | 6/2012 |
| JP | 60243083 | 12/1985 |
| JP | 2009-234928 | 10/2009 |
| JP | 2009-266927 | 11/2009 |
| JP | 2010-278114 | 12/2010 |
| JP | 2018-062496 | 4/2018 |
| KR | 2016-0038813 | 4/2016 |
| KR | 2019-0103769 | 9/2019 |

(56) References Cited

FOREIGN PATENT DOCUMENTS

| | | |
|---|---|---|
| WO | WO 1996/022282 | 7/1996 |
| WO | WO 2002/050190 | 6/2002 |
| WO | WO 2004/039859 | 5/2004 |
| WO | WO 2005/105817 | 11/2005 |
| WO | WO 2006/014413 | 2/2006 |
| WO | WO 2006/034090 | 3/2006 |
| WO | WO 2007/047604 | 4/2007 |
| WO | WO 2007/096576 | 8/2007 |
| WO | WO 2009/000412 | 12/2008 |
| WO | WO 2009/004382 | 1/2009 |
| WO | WO 2011/016582 | 2/2011 |
| WO | WO 2011/035019 | 3/2011 |
| WO | WO 2012/016147 | 2/2012 |
| WO | WO 2012/071458 | 5/2012 |
| WO | WO 2012/073143 | 6/2012 |
| WO | WO 2012/085222 | 6/2012 |
| WO | WO 2012/089633 | 8/2012 |
| WO | WO 2012/102409 | 8/2012 |
| WO | WO 2012/138648 | 10/2012 |
| WO | WO 2012/174685 | 12/2012 |
| WO | WO 2013/022818 | 2/2013 |
| WO | WO 2013/127028 | 9/2013 |
| WO | WO 2013/132376 | 9/2013 |
| WO | WO 2014/038867 | 3/2014 |
| WO | WO 2014/138912 | 9/2014 |
| WO | WO 2014/207606 | 12/2014 |
| WO | WO 2015/025197 | 2/2015 |
| WO | WO 2015/050989 | 4/2015 |
| WO | WO 2015/074064 | 5/2015 |
| WO | WO 2015/104711 | 7/2015 |
| WO | WO 2015/175579 | 11/2015 |
| WO | WO 2016/026423 | 2/2016 |
| WO | WO 2016118774 | 7/2016 |
| WO | WO 2017/023902 | 2/2017 |
| WO | WO 2017/080980 | 5/2017 |
| WO | WO 2017/081483 | 5/2017 |
| WO | WO 2017/148325 | 9/2017 |
| WO | WO 2019/057175 | 3/2019 |
| WO | WO 2019/113071 | 6/2019 |
| WO | WO 2019/120263 | 6/2019 |
| WO | WO 2019/149131 | 8/2019 |
| WO | WO 2019/164301 | 8/2019 |
| WO | WO 2020/021113 | 1/2020 |
| WO | WO 2020/067290 | 4/2020 |
| WO | WO 2020/069106 | 4/2020 |
| WO | WO 2020/085742 | 4/2020 |
| WO | WO 2020/228747 | 11/2020 |
| WO | WO 2021/025371 | 2/2021 |
| WO | WO 2021/058969 | 4/2021 |
| WO | WO 2021/062327 | 4/2021 |
| WO | WO 2021/122868 | 6/2021 |
| WO | WO 2021/125791 | 6/2021 |
| WO | WO 2021/224040 | 11/2021 |
| WO | WO 2021/224320 | 11/2021 |
| WO | WO 2021/225833 | 11/2021 |
| WO | WO 2021/226003 | 11/2021 |
| WO | WO 2021/226168 | 11/2021 |
| WO | WO 2021/226208 | 11/2021 |
| WO | WO 2021/226269 | 11/2021 |
| WO | WO 2022/017408 | 1/2022 |
| WO | WO 2022/194399 | 9/2022 |
| WO | WO 2022/212538 | 10/2022 |
| WO | WO 2023/056405 | 4/2023 |
| WO | WO 2023/056431 | 4/2023 |
| WO | WO 2023/059801 | 4/2023 |
| WO | WO 2023/179600 | 9/2023 |
| WO | WO 2023/196900 | 10/2023 |
| WO | WO 2023/196910 | 10/2023 |
| WO | WO 2024/036097 | 2/2024 |
| WO | WO 2024/036098 | 2/2024 |
| WO | WO 2024/046512 | 3/2024 |
| WO | WO 2024/086634 | 4/2024 |
| WO | WO 2025/072117 | 4/2025 |
| WO | WO 2025/072120 | 4/2025 |
| WO | WO 2025/131085 | 6/2025 |
| WO | WO 2025/212478 | 10/2025 |

OTHER PUBLICATIONS

Alecensa FDA Approval Media Release., "FDA approves Roche's Alecensa (alectinib) as first-line treatment for people with specific type of lung cancer," Hoffmann-La Roche Ltd.: 6 pages (Nov. 7, 2017).

Alectinib Prescribing Information., "Alecensa® (alectinib) capsules, for oral use Initial U.S. Approval: 2015," U.S. Food and Drug Administration: 21 pages (Nov. 2017).

Antonescu et al., "Molecular Characterization of Inflammatory Myofibroblastic Tumors with Frequent ALK and ROS1 Fusions and Rare Novel RET Gene Rearrangement," Am. J. Surg. Pathol., 39(7): Author Manuscript pp. 1-19 (2015).

Arai et al., "Mouse Model for ROS1-Rearranged Lung Cancer," Plos One, 8(2): e56010 pp. 1-7 (2013).

Bauer et al., "Clinical Management of Adverse Events Associated with Lorlatinib," The Oncologist, 24: 1103-1110 (Aug. 24, 2019).

Bayliss et al., "Molecular mechanisms that underpin EML4-ALK driven cancers and their response to targeted drugs," Cellular and Molecular Life Sciences, 73: 1209-1224 (2016).

Besse et al., "Clinical Evaluation of NVL-520, a Highly Selective ROS1 Inhibitor, in Patients with Advanced ROS1-Positive Solid Tumors: The Phase 1/2 ARROS-1 Study," European Lung Cancer Congress: Nuvalent Poster Abstract #78TiP (Mar. 30, 2022).

Bestvina et al., "ALK and ROS1 rearrangement in NSCLC: rapidly evolving standards," Oncology, 18: 1555-1556 (Nov. 29, 2017).

Birch et al., "Chromosome 3 Anomalies Investigated by Genome Wide SNP Analysis of Benign, Low Malignant Potential and Low Grade Ovarian Serous Tumours, " Plos One, 6(12): e28250 pp. 1-20 (2011).

Bresler et al., "ALK mutations confer differential oncogenic activation and sensitivity to ALK inhibition therapy in neuroblastoma," Cancer Cell., 26(5): Author Manuscript pp. 1-29 (2014).

Camidge et al., "Clinical trial design for systemic agents in patients with brain metastases from solid tumours: a guideline by the Response Assessment in Neuro-Oncology Brain Metastases working group," The Lancet Oncology, 19(1): e20-e32 (Jan. 2018).

Camidge et al., "Exploratory Analysis of Brigatinib Activity in Patients With Anaplastic Lymphoma Kinase-Positive Non-Small-Cell Lung Cancer and Brain Metastases in Two Clinical Trials," Journal of Clinical Oncology, 36(26): 2693-2701 (May 16, 2018).

Charest et al., "Fusion of FIG to the Receptor Tyrosine Kinase ROS in a Glioblastoma with an Interstitial del(6)(q21q21)," Genes, Chromosomes & Cancer, 37: 58-71 (2003).

Chia et al., "Prevalence and natural history of ALK positive non-small-cell lung cancer and the clinical impact of targeted therapy with ALK inhibitors," Clinical Epidemiology, 6: 423-432 (2014).

Cho et al., "Phase 1/2 Trident-1 Study of Repotrectinib in Patients with ROS1+ or NTRK+ Advanced Solid Tumors," 2020 World Conference on Lung Cancer Singapore: 7 pages Abstract #3255 (Jan. 28-31, 2021).

Cho et al., "Safety and Preliminary Clinical Activity of Repotrectinib in Patients with Advanced ROS1 Fusion-Position Non-Small Cell Lung Cancer (TRIDENT-1 Study)," 2019 ASCO Annual Meeting: 13 pages (May 2019).

Chong et al., "Identification of Existing Drugs That Effectively Target NTRK1 and ROS1 Rearrangements in Lung Cancer," Clinical Cancer Research, 23(1): 204-213 (Jan. 1, 2017).

Cocco et al., "NTRK fusion-positive cancers and TRK inhibitor therapy," Nat. Rev. Clin. Oncol., 15(12): Author Manuscript pp. 1-34 (2018).

Cocco et al., "NTRK fusion-positive cancers and TRK inhibitor therapy," Nature Reviews Clinical Oncology, 15: 731-747 (Oct. 17, 2018).

Coleman et al., "Lorlatinib Salvages Central Nervous System Only Relapse on Entrectinib in ROS1-Positive NSCLC," Journal of Thoracic Oncology, 15(8): e142-e144 (Aug. 1, 2020).

(56) References Cited

OTHER PUBLICATIONS

Conde et al., "Assessment of a New ROS1 Immunohistrochemistry Clone (SP384) for the Identification of ROS1," Journal of Thoracic Oncology, 14(12): 2120-2132 (Dec. 1, 2019).
Cortinovis et al., "Challenges in ALK inhibition of ALK-positive non-small-cell lung cancer: from ALK positivity detection to treatment strategies after relapse," Future Oncology, 14(22): 2303-2317 (Aug. 8, 2018).
Cui et al., "Abstract 5226: TPX-0131: A next generation macrocyclic ALK inhibitor that overcomes ALK resistant mutations refractory to current approved ALK inhibitors," American Association for Cancer Research: Poster Abstract#5226 (Aug. 2020).
Dagogo-Jack et al., "MET Alterations Are a Recurring and Actionable Resistance Mechanism in ALK- Positive Lung Cancer," Clinical Cancer Research, 26(11): 2535-2545 (Jun. 1, 2020).
Dagogo-Jack et al., "Tracking the Evolution of Resistance to ALK Tyrosine Kinase Inhibitors Through Longitudinal Analysis of Circulating Tumor DNA," JCO Precision Oncology, 2: pp. 1-14 (Jan. 23, 2018).
Dagogo-Jack et al., "Tracking the Evolution of Resistance to ALK Tyrosine Kinase Inhibitors Through Longitudinal Analysis of Circulating Tumor DNA," Jco Precision Oncology, 2: Supplementary Information pp. 1-9 (Jan. 23, 2018).
Dagogo-Jack et al., "Treatment with Next-Generation ALK Inhibitors Fuels Plasma ALK Mutation Diversity," Clinical Cancer Research, 25(22): 6662-6670 (Nov. 15, 2019).
Davare et al., "Rare but recurrent ROS1 fusions resulting from chromosome 6q22 microdeletions are targetable oncogenes in glioma," Clin. Canc. Res., 24(24): Author Manuscript pp. 1-27 (2018).
Davies et al., "Molecular Pathways: ROS1 Fusion Proteins in Cancer," Clinical Cancer Research, 19(15): 4040-4045 (Aug. 1, 2013).
Dearden et al., "Mutation incidence and coincidence in non small-cell lung cancer: meta-analyses by ethnicity and histology (mutMap)," Annals of Oncology, 24: 2371-2376 (Sep. 1, 2013).
Demicco et al., "New Therapeutic Targets in Soft Tissue Sarcoma," Adv. Anat. Pathol., 19(3): Author Manuscript pp. 1-21 (2012).
Deshpande et al., "Abstract P249: Preclinical antitumor activity of NVL-520 in patient-derived models harboring ROS1 fusions, including G2032R solvent front mutation," Mol. Canc. Ther., 20(Supplement 12): P249 (2021).
Doebele et al., "Genomic landscape of entrectinib resistance from ctDNA analysis in STARTRK-2," Annals of Oncology, 30(Supplement 5): v865 (2019).
Doebele et al., "TRIDENT-1: A Global, Multicenter, Open-label Phase 2 Study Investigating the Activity of Repotrectinib in Advanced Solid Tumors Harboring ROS1 or NTRK1-3 Rearrangements," Turning Point Therapeutics: Poster Abstract #TPS9637 (May 29-Jun. 2, 2020).
Drilon et al., "A Phase 1 Study of the Next-Generation ALK/ROS1/TRK Inhibitor Ropotrectinib (TPX-0005) in Patients with Advanced ALK/ROS1/NTRK+ Cancers (TRIDENT-1)," American Society of Clinical Oncology (ASCO) Annual Meeting: Poster Abstract #2513 (Jun. 1-5, 2018).
Drilon et al., "Entrectinib in ROS1 fusion-positive non-small-cell lung cancer: integrated analysis of three phase 1-2 trials," Lancet Oncol., 21(2): Author Manuscript pp. 1-23 (2020).
Drilon et al., "Entrectinib in ROS1 fusion-positive non-small-cell lung cancer: integrated analysis of three phase 1-2 trials," Lancet Oncology, 21: 261-270 (Dec. 11, 2019).
Drilon et al., "Repotrectinib (TPX-0005) Is a Next-Generation ROS1/TRK/ALK Inhibitor That Potently Inhibits ROS1/TRK/ALK Solvent-Front Mutations," Cancer Discovery, 8: 1227-1236 (Aug. 9, 2018).
Drilon et al., "ROS1—dependent cancers—biology, diagnostics and therapeutics," Nature Reviews Clinical Oncology, 18: 35-55 (Jan. 1, 2021).
Drilon et al., "ROS1—dependent cancers—biology, diagnostics and therapeutics," Nature Reviews Clinical Oncology, 18: Supplementary Information, pp. 1-7 (Jan. 1, 2021).
Drilon et al., "ROS1-dependent cancers—biology, diagnostics and therapeutics," Nat. Rev. Clin. Oncol., 18(1): Author Manuscript pp. 1-45 (2021).
Drilon et al., "Safety and Antitumor Activity of the Multitargeted Pan-TRK, ROS1, and ALK Inhibitor Entrectinib: Combined Results from Two-Phase I Trials (ALKA-372-001 and STARTRK-1)," Cancer Discovery, 7(4): 400-409 (Feb. 9, 2017).
Drilon et al., "Safety and Antitumor Activity of the Multitargeted Pan-TRK, ROS1, and ALK Inhibitor Entrectinib: Combined Results from Two-Phase I Trials (ALKA-372-001 and STARTRK-1)," Cancer Discovery, 7(4): Supplementary Information 1 of 2, pp. 1-2 (Feb. 9, 2017).
Drilon et al., "Safety and Antitumor Activity of the Multitargeted Pan-TRK, ROS1, and ALK Inhibitor Entrectinib: Combined Results from Two-Phase I Trials (ALKA-372-001 and STARTRK-1)," Cancer Discovery, 7(4): Supplementary Information 2 of 2, pp. 1-6 (Feb. 9, 2017).
Drilon et al., "Safety and Preliminary Clinical Activity of Repotrectinib in Patients with Advanced ROS1/TRK Fusion-Positive Solid Tumors (TRIDENT-1 Study)," European Society for Medical Oncology (ESMO): Poster Abstract #4536 (Sep. 27-Oct. 1, 2019).
Eid et al., "KinMap: a web-based tool for interactive navigation through human kinome data," BMC Bioinformatics, 18(16): pp. 1-6 (2017).
Elleraas et al., "Conformational Studies and Atropisomerism Kinetics of the ALK Clinical Candidate Lorlatinib (PF-06463922) and Desmethyl Congeners," Angewandte Chemie, 128(11): 3654-3659 (Feb. 15, 2016).
Entrectinib Multi-Discipline Review., "NDA/BLA Multi-disciplinary Review and Evaluation NDA 212725," Center for Drug Evaluation and Research: 632 pages (Feb. 1, 2016).
Entrectinib Prescribing Information Label., "Rozlytrek (entrectinib) capsules, for oral use Initial U.S. Approval: 2019," U.S. Food and Drug Administration: 25 pages (Aug. 2019).
Felip Font et al., "Efficacy and safety of lorlatinib in patients (pts) with ALK+ non-small cell lung cancer (NSCLC) previously treated with 2nd-generation ALK TKIs," Annals of Oncology, 28(5): 478-479 (Sep. 1, 2017).
Fleuren et al., "Phosphoproteomic Profiling Reveals ALK and MET as Novel Actionable Targets across Synovial Sarcoma Subtypes," Cancer Research, 77(16): 4279-4292 (2017).
Fujiwara et al., "Safety and pharmacokinetics of DS-6051b in Japanese patients with non-small cell lung cancer harboring ROS1 fusions: a phase I study," Oncotarget, 9(34): 23729-23737 (May 4, 2018).
Gadgeel et al., "Cumulative incidence rates for CNS and non-CNS progression in two phase II studies of alectinib in ALK-positive NSCLC," BJC, 118: 38-42 (2018).
Gadgeel et al., "Safety and activity of alectinib against systemic disease and brain metastases in patients with crizotinib-resistant ALK-rearranged non-small-cell lung cancer (AF 002JG): results from the dose-finding portion of a phase 1/2 study," The Lancet Oncology, 15(1): 1119-1128 (Sep. 2014).
Gainor et al., "Molecular Mechanisms of Resistance to First- and Second-Generation ALK Inhibitors in ALK-Rearranged Lung Cancer," Cancer Discovery, 6(10): 1119-1133 (Oct. 2016).
Gainor et al., "Patterns of Metastatic Spread and Mechanisms of Resistance to Crizotinib in ROS1-Positive Non-Small-Cell Lung Cancer," JCO Precision Oncology, 1: pp. 1-13 (2017).
George et al., "Activating mutations in ALK provide a therapeutic target in neuroblastoma," Nature, 455(7215): Author Manuscript pp. 1-11 (2008).
Giacomini et al., "Breakpoint Analysis of Transcriptional and Genomic Profiles Uncovers Novel Gene Fusions Spanning Multiple Human Cancer Types," Plos Genetics, 9(4): e1003464 pp. 1-19 (2013).
Gobbini et al., "Real-world outcomes according to treatment strategies in ALK-rearranged non-small-cell lung cancer (NSCLC) patients: an Italian retrospective study," Clinical and Translational Oncology, 22: 294-301 (Mar. 3, 2020).
Golding et al., "The function and therapeutic targeting of anaplastic lymphoma kinase (ALK) in non-small cell lung cancer (NSCLC)," Molecular Cancer, 17(52): pp. 1-15 (2018).

(56) References Cited

OTHER PUBLICATIONS

Gu et al., "Survey of Tyrosine Kinase Signaling Reveals ROS Kinase Fusions in Human Cholangiocarcinoma," Plos One, 6(1): e15640 pp. 1-9 (2011).
Guo et al., "Dual potent ALK and ROS1 inhibitors combating drug-resistant mutants: Synthesis and biological evaluation of aminopyridine containing diarylaminopyrimidine derivatives," European Journal of Medicinal Chemistry, 158: 322-333 (Sep. 6, 2018).
Hallberg et al., "The role of the ALK receptor in cancer biology," Annals of Oncology, 27(Supplement 3): ii4-ii15 (2016).
Holla et al., "ALK: a tyrosine kinase target for cancer therapy," Cold Spring Harbor Molecular Case Studies, 3: a001115 pp. 1-20 (2017).
Hong et al., "Will the clinical development of 4th-generation "double mutant active" ALK TKIs (TPX-0131 and NVL-655) change the future treatment paradigm of ALK+ NSCLC?," Translational Oncology, 14(11): Article 101191 pp. 1-9 (Aug. 5, 2021).
Horn et al., "Monitoring Therapeutic Response and Resistance: Analysis of Circulating Tumor DNA in Patients With ALK+ Lung Cancer," Journal of Thoracic Oncology, 14(11): 1901-1911 (Nov. 2019).
Hua et al., "Real-world circulating tumor DNA analysis depicts resistance mechanism and clonal evolution in ALK inhibitor-treated lung adenocarcinoma patients," ESMO Open Cancer Horizons, 7(1): 8 pages (2022).
Huang et al., "Discovery of Brigatinib (AP26113), a Phosphine Oxide-Containing, Potent, Orally Active Inhibitor of Anaplastic Lymphoma Kinase," Journal of Medicinal Chemistry, 59: 4948-4964 (May 4, 2016).
International Search Report and Written Opinion for International Application No. PCT/CN2020/088589 dated Feb. 10, 2021.
International Search Report and Written Opinion for International Application No. PCT/CN2020/088590 dated Feb. 3, 2021.
International Search Report and Written Opinion for International Application No. PCT/US2021/030842 dated Nov. 5, 2021.
International Search Report and Written Opinion for International Application No. PCT/US2021/030940 mailed Sep. 17, 2021.
Johnson et al., "Discovery of (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (PF-06463922), a Macrocyclic Inhibitor of Anaplastic Lymphoma Kinase (ALK) and c-ros Oncogene 1 (ROS1) with Preclinical Brain Exposure and Broad-Spectrum Potency against ALK-Resistant Mutations," Journal of Medicinal Chemistry, 57(11): 4720-4744 (May 13, 2014).
Johnson et al., "Discovery of PF-06463922, a macrocyclic inhibitor of ALK/ROSI with pre-clinical brain exposure and broad spectrum potency against ALK-resistant mutations," Journal of Medicinal Chemistry, 57(11): Supporting Information S1-S57 (May 13, 2014).
Jordan et al., "Prospective comprehensive molecular characterization of lung adenocarcinomas for efficient patient matching to approved and emerging therapies," Cancer Discov., 7(6): Author Manuscript pp. 1-21 (2017).
Katayama et al., "The new-generation selective ROS1/NTRK inhibitor DS-6051b overcomes crizotinib resistant ROS1-G2032R mutation in preclinical models," Nature Communications, 10: Article No. 3604 pp. 1-12 (Aug. 9, 2019).
Katayama et al., "Two Novel ALK Mutations Mediate Acquired Resistance to the Next-Generation ALK Inhibitor Alectinib," Clinical Cancer Research, 20(22): 5686-5696 (Nov. 15, 2014).
Keddy et al., "Resistance Profile and Structural Modeling of Next-Generation ROS1 Tyrosine Kinase Inhibitors," Molecular Cancer Therapeutics, 21(2): 336-346 (2022).
Kong et al., "Drug Discovery Targeting Anaplastic Lymphoma Kinase (ALK)," Journal of Medicinal Chemistry: 28 pages (2019).
Ku et al., "Entrectinib resistance mechanisms in ROS1-rearranged non-small cell lung cancer," Investigational New Drugs, 38: 360-368 (Apr. 2020).
Leonetti et al., "COVID-19 in lung cancer patients receiving ALK/ROS1 inhibitor," European Journal of Cancer, 132: 122-124 (Jun. 2020).
Li et al., "Efficacy of Crizotinib among Different Types of ROS1 Fusion Partners in Patients with ROS1-Rearranged Non-Small Cell Lung Cancer," Journal of Thoracic Oncology, 13(7): 987-995 (2018).
Lin et al., "ALK and ROS1 Inhibitors: New Agents Not Yet Approved," 2021 Targeted Therapies of Lung Cancer Meeting: 17 pages (Feb. 17-21, 2021).
Lin et al., "Efficacy of Platinum/Pemetrexed Combination Chemotherapy in ALK-Positive NSCLC Refractory to Second-Generation ALK Inhibitors," Journal of Thoracic Oncology, 15(2): 258-265 (Feb. 2020).
Lin et al., "Impact of EML4-ALK Variant on Resistance Mechanisms and Clinical Outcomes in ALK-Positive Lung Cancer," Journal of Clinical Oncology, 36(12): 1199-1206 (Apr. 20, 2018).
Lin et al., "Recent Advances in Targeting ROS1 in Lung Cancer," Journal of Thoracic Oncology, 12(11): 1611-1625 (Nov. 2017).
Lin et al., "Small cell transformation of ROS1 fusion-positive lung cancer resistant to ROS1 inhibition," NPJ Precision Oncology, 4: Article No. 21 pp. 1-8 (2020).
Lin et al., "Spectrum of Mechanisms of Resistance to Crizotinib and Lorlatinib in ROS1 Fusion-Positive Lung Cancer," Clin. Canc. Res., 27(10): Author Manuscript pp. 1-24 (2021).
Lin et al., "Spectrum of Mechanisms of Resistance to Crizotinib and Lorlatinib in ROS1 Fusion-Positive Lung Cancer," Clinical Cancer Research, 27(10): OF1-OF11 (Mar. 8, 2021).
Liu et al., "Characterization of On-Target Adverse Events Caused by TRK Inhibitor Therapy," Ann. Oncol., 31(9): Author Manuscript pp. 1-17 (2020).
Liu et al., "Characterization of on-target adverse events caused by TRK inhibitor therapy," Annals of Oncology, 31(9): 1207-1215 (Sep. 2020).
Liu et al., "Design, synthesis and biological evaluations of 2-amino-4-(1-piperidine) pyridine derivatives as novel anti crizotinib-resistant ALK/ROS1 dual inhibitors," European Journal of Medicinal Chemistry, 179: 358-375 (Oct. 1, 2019).
Lorbrena (Lorlatinib) Full Prescribing Information and Label Initial U.S. Approval: Nov. 2018.
Lorbrena (lorlatinib) Prescribing Information Label; Food and Drug Administration: 31 pages (2021).
Lorlatinib Multi-Discipline Review., "NDA/BLA Multi-disciplinary Review and Evaluation NDA 210868," Center for Drug Evaluation and Research: 302 pages (Feb. 1, 2016).
Lorviqua Public Assessment Report., Published by the European Medicines Agency on Feb. 28, 2019 (148 pages).
Mallinson et al., "Macrocycles in drug discovery," Future Med Chem, 4(11): 1409-1438 (2012).
Marks et al., "ROS1-GOPC/FIG: a novel gene fusion in hepatic angiosarcoma," Oncotarget, 10(2): 245-251 (2019).
Moog-Lutz et al., "Activation and Inhibition of Anaplastic Lymphoma Kinase Receptor Tyrosine Kinase by Monoclonal Antibodies and Absence of Agonist Activity of Pleiotrophin," The Journal of Biological Chemistry, 280(28): 26039-26048 (2005).
Murray et al., "TPX-0131, a Potent CNS-penetrant, Next-generation Inhibitor of Wild-type ALK and ALK-resistant Mutations," Molecular Cancer Therapeutics, 20(9): 1499-1507 (2021).
Murugan et al., "Anaplastic Thyroid Cancers Harbor Novel Oncogenic Mutations of the ALK Gene," Cancer Research, 71(13): Author Manuscript pp. 1-14 (2011).
Neel et al., "Differential subcellular localization regulates oncogenic signaling by ROSI kinase fusion proteins," Cancer Research, 79(3): Author Manuscript pp. 1-19 (2019).
Noe et al., "ALK Mutation Status Before and After Alectinib Treatment in Locally Advanced or Metastatic ALK-Positive NSCLC: Pooled Analysis of Two Prospective Trials," Journal of Thoracic Oncology, 15(4): 601-608 (Apr. 2020).
Nosaki et al., "P2.06-002 Phase I Study of DS-6051b, a ROS1/NTRK Inhibitor, in Japanese Subjects with Advanced Solid Tumors Harboring Either a ROSI or NTRK Fusion Gene," Journal of Thoracic Oncology, 12(1): Supplement S1069 (Jan. 1, 2017).
Okubo et al., "Aberrant activation of ALK kinase by a novel truncated form ALK protein in neuroblastoma," Oncogene, 31: 4667-4676 (2012).

(56) References Cited

OTHER PUBLICATIONS

Ou et al., "A Catalog of 5' Fusion Partners in ROS1-Positive NSCLC Circa 2020," JTO Clinical and Research Reports, 1(3): pp. 1-5 (2020).
Ou et al., "CNS metastasis in ROS1+ NSCLC: An urgent call to action, to understand, and to overcome," Lung Cancer, 130: 201-207 (Apr. 2019).
Ou et al., "OA02.03 Clinical Activity of Lorlatinib in Patients with ROS1+ Advanced Non-Small Cell Lung Cancer: Phase 2 Study Cohort EXP-6," Journal of Thoracic Oncology, 13(10): Supplement S322-S323 (Oct. 1, 2018).
Papadopoulos et al., "U.S. Phase I First-in-human Study of Taletrectinib (DS-6051b/AB-106), a ROS1/TRK Inhibitor, in Patients with Advanced Solid Tumors," Clinical Cancer Research, 26(18):4785-4974 (Sep. 15, 2020).
Patil et al., "The incidence of brain metastases in stage IV ROS1-rearranged non-small cell lung cancer and rate of central nervous system progression on crizotinib," J. Thorac. Oncol., 13(11): Author Manuscript pp. 1-17 (2018).
Pelish et al., "Abstract 1465: NUV-520 (NVL-520) is a brain-penetrant and highly selective ROS1 inhibitor with antitumor activity against the G2032R solvent front mutation," Cancer Res., 81(Supplement 13): Abstract 1465 (2021).
Pelish et al., "NUV-520 is a brain-penetrant and highly selective ROS1 inhibitor with antitumor activity against the G2032R solvent front mutation," American Association for Cancer Research (AACR): Nuvalent Poster Abstract #1465 (Apr. 2021).
Pelish et al., "NUV-655 is a selective, brain-penetrant ALK inhibitor with antitumor activity against the lorlatinib-resistant G1202R/L1196M compound mutation," American Association for Cancer Research (AACR): Nuvalent Poster Abstract #1468 (Apr. 2021).
Perkins et al., "Childhood anaplastic large cell lymphoma has a high incidence of ALK gene rearrangement as determined by immunohistochemical staining and fluorescent in situ hybridisation: a genetic and pathological correlation," British Journal of Haematology, 131(5): 624-627 (2005).
Peters et al., "Alectinib versus Crizotinib in Untreated ALK-Positive Non-Small-Cell Lung Cancer," The New England Journal of Medicine, 377: 829-838 (Aug. 31, 2017).
Pubchem SID 327469789: 7 pages (2017).
Rajan et al., "The mechanism of cancer drug addiction in ALK-positive T-Cell lymphoma," Oncogene, 39: 2103-2117 (Mar. 2020).
Recondo et al., "Diverse Resistance Mechanisms to the Third-Generation ALK Inhibitor Lorlatinib in ALK-Rearranged Lung Cancer," Clinical Cancer Research, 26(1): 242-255 (Oct. 4, 2019).
Rikova et al., "Global Survey of Phosphotyrosine Signaling Identifies Oncogenic Kinases in Lung Cancer," Cell, 131(6): 1190-1203 (2007).
Rimkunas et al., "Analysis of Receptor Tyrosine Kinase ROS1-Positive Tumors in Non-Small Cell Lung Cancer: Identification of a FIG-ROS1 Fusion," Clinical Cancer Research, 18(16): 4449-4457 (2012).
Rizvi et al., "Cholangiocarcinoma—evolving concepts and therapeutic strategies," Nat. Rev. Clin. Oncol., 15(2): Author Manuscript pp. 1-37 (2018).
Rozlytrek (entrectinib) Prescribing Information Label; Food and Drug Administation: 25 pages (2019).
Sabari et al., "The activity, safety, and evolving role of brigatinib in patients with ALK-rearranged non-small cell lung cancers," OncoTargets and Therapy, 10: 1983-1992 (Apr. 6, 2017).
Sakamoto et al., "CH5424802, a Selective ALK Inhibitor Capable of Blocking the Resistant Gatekeeper Mutant," Cancer Cell, 19(5): 679-690 (May 17, 2011).
Sehgal et al., "Cases of ROS1-rearranged lung cancer: when to use crizotinib, entrectinib, lorlatinib, and beyond?" Precis Cancer Med, 3(17): pp. 1-11 (Jun. 15, 2020).
Shaw et al., "ALK in Lung Cancer: Past, Present, and Future," Journal of Clinical Oncology, 31(8):1105-1111 (2013).
Shaw et al., "ALK Resistance Mutations and Efficacy of Lorlatinib in Advanced Anaplastic Lymphoma Kinase-Positive Non-Small-Cell Lung Cancer," Journal of Clinical Oncology, 37(16): 1370-1379 (Mar. 20, 2019).
Shaw et al., "Crizotinib in ROS1-rearranged advanced non-small-cell lung cancer (NSCLC): updated results, including overall survival, from Profile 1001," Annals of Oncology, 30(7): 1121-1126 (Jul. 2019).
Shaw et al., "First-Line Lorlatinib or Crizotinib in Advanced ALK-Positive Lung Cancer," The New England Journal of Medicine, 383: 2018-2029 (Nov. 19, 2020).
Shaw et al., "First-Line Lorlatinib or Crizotinib in Advanced ALK-Positive Lung Cancer," The New England Journal of Medicine, 383: Supplementary Appendix pp. 1-29 (Nov. 19, 2020).
Shaw et al., "Lorlatinib in ALK- or ROS1-rearranged non-small cell lung cancer: an international, multicenter, open-label phase 1 trial," Lancet Oncology, 18(12): Author Manuscript pp. 1-20 (2017).
Shaw et al., "Lorlatinib in non-small-cell lung cancer with ALK or ROS1 rearrangement: an international, multicentre, open-label, single-arm first-in-man phase 1 trial," Lancet Oncology, 18: 1590-1599 (Dec. 2017).
Shaw et al., "Lorlatinib in non-small-cell lung cancer with ALK or ROS1 rearrangement: an international, multicentre, open-label, single-arm first-in-man phase 1 trial, " Supplementary Appendix: 1-305 (Dec. 2017).
Shults et al., "Versatile Fluorescence Probes of Protein Kinase Activity," Journal of the American Chemical Society, 125(47): 14248-14249 (2003).
Soda et al., "Identification of the transforming EML4-ALK fusion gene in non-small-cell lung cancer," Nature, 448: 561-566 (Jul. 11, 2007).
Solomon et al., "Lorlatinib in patients with ALK-positive non-small-cell lung cancer: results from a global phase 2 study," The Lancet Oncology, 19(12): 1654-1667 (Dec. 2018).
Stypinski et al., "Metabolism, Excretion, and Pharmacokinetics of Lorlatinib (PF-06463922) and Evaluation of the Impact of Radiolabel Position and Other Factors on Comparability of Data Across 2 ADME Studies," The Journal of Clinical Pharmacology, 60(9): 1254-1267 (May 22, 2020).
Syed., "Lorlatinib: First Global Approval," Drugs, 79: 93-98 (Jan. 2, 2019).
Syeda-Mahmood et al., "Shape-based Similarity Retrieval of Doppler Images for Clinical Decision Support," IEEE Computer Society Conference on Computer Vision and Pattern Recognition: 8 pages (Aug. 5, 2010).
Takeuchi et al., "RET, ROS1 and ALK fusions in lung cancer," Nature Medicine, 18(3): 378-381 (2012).
Tangpeerachaikul et al., "Abstract P247: Evaluating TRKB activity of novel preclinical brain-penetrant ROS1 and ALK inhibitors," Mol. Canc. Ther., 20(Supplement 12): P247 (2021).
Tangpeerachaikul et al., "Evaluating TRKB Activity of Novel Preclinical Brain-Penetrant ROS1 and ALK Inhibitors," AACR-NCI-EORTC Virtual International Conference on Molecular Targets and Cancer Therapeutics: 10 pages (Oct. 7-10, 2021).
Tangpeerachaikul et al., "NVL-655 Exhibits Antitumor Activity in Lorlatinib-Resistant Subcutaneous and Intracranial Models of ALK-Rearranged NSCLC," AACR-NCI-EORTC Virtual International Conference on Molecular Targets and Cancer Therapeutics: 9 pages (Oct. 7-10, 2021).
Tangpeerachaikul et al., "Preclinical activity of NVL-520 in ROS1-driven cancer models with diverse fusion partners and kinase-domain mutations," American Association for Cancer Research: Nuvalent Poster Abstract #3336 (Apr. 8, 2022).
Tangpeerachaikul et al., "Preclinical activity of NVL-655 in ALK-driven cancer models beyond non-small cell lung cancer," American Association for Cancer Research: Nuvalent Poster Abstract #3337 (Apr. 8, 2022).
Tangpeerachalkul et al., "NVL-66: a selective, potent 4G ALK TKI; NVL-655: dose-dependent in vivo anti-tumor activity against double mutant ALK; NVL-655: preclinical CNS penetrance and activity," 2022 Targeted Therapies of Lung Cancer Meeting: 3 pages (Feb. 22-26, 2022).

(56) References Cited

OTHER PUBLICATIONS

Trigg et al., "ALK in Neuroblastoma: Biological and Therapeutic Implications," Cancers, 10(113): pp. 1-26 (2018).
Tu et al., "Molecular inhibitory mechanism study on the potent inhibitor brigatinib against four crizotinib-resistant ALK mutations," Journal of Cellular Biochemistry, 120(1): 562-574 (Sep. 6, 2018).
Umapathy et al., "Targeting anaplastic lymphoma kinase in neuroblastoma," APMIS Journal of Pathology, Microbiology and Immunology, 127(5): 288-302 (2019).
Valery et al., "Cholangiocarcinoma with STRN-ALK translocation treated with ALK inhibitors," Digestive and Liver Disease: Article in Press pp. 1-2 (2021).
Weisner et al., "Alternative transcription initiation leads to expression of a novel ALK isoform in cancer," Nature, 56(7573): Author Manuscript pp. 1-35 (2015).
Yamazaki et al., "Mechanistic Understanding of Translational Pharmacokinetic-Pharmacodynamic Relationships in Nonclinical Tumor Models: A Case Study of Orally Available Novel Inhibitors of Anaplastic Lymphoma Kinase," Drug Metabolism and Disposition, 43: 54-62 (Jan. 2015).
Yamazaki et al., "Translational Pharmacokinetic-Pharmacodynamic Modeling for an Orally Available Novel Inhibitor of Anaplastic Lymphoma Kinase and c-Ros Oncogene 1," The Journal of Pharmacology and Experimental Therapeutics, 351: 67-76 (Oct. 2014).
Yoda et al., "Sequential ALK Inhibitors Can Select for Lorlatinib-Resistant Compound ALK Mutations in ALK-Positive Lung Cancer," Cancer Discovery, 8(6): 715-729 (Apr. 12, 2018).
Yoda et al., "Sequential ALK Inhibitors Can Select for Lorlatinib-Resistant Compound ALK Mutations in ALK-Positive Lung Cancer," Cancer Discovery, 8(6): Author Manuscript pp. 1-36 (2018).
Yoda et al., "Sequential ALK Inhibitors Can Select for Lorlatinib-Resistant Compound ALK Mutations in ALK-Positive Lung Cancer," Cancer Discovery, 8(6): Supplementary Figures pp. 1-11 (Apr. 12, 2018).
Yoda et al., "Sequential ALK Inhibitors Can Select for Lorlatinib-Resistant Compound ALK Mutations in ALK-Positive Lung Cancer," Cancer Discovery, 8(6): Supplementary Methods pp. 1-2 (Apr. 12, 2018).
Yun et al., "Repotrectinib Exhibits Potent Antitumor Activity in Treatment-Naïve and Solvent-Front-Mutant ROS1-Rearranged Non-Small Cell Lung Cancer," Clinical Cancer Research, 26(13): OF1-OF9 (Jul. 2020).
Zhang et al., "Determination of the mean pressure gradient in aortic stenosis by Doppler echocardiography," European Heart Journal, 6: 999-1005 (Dec. 1, 1985).
Zhang et al., "The Potent ALK Inhibitor Brigatinib (AP26113) Overcomes Mechanisms of Resistance to First- and Second-Generation ALK Inhibitors in Preclinical Models," Clinical Cancer Research, 22(22): 5527-5538 (Nov. 2016).
Zhao et al., "A Bayesian network meta-analysis regarding the comparative efficacy of therapeutics for ALK-positive, brain metastatic non-small cell lung cancer," Pharmacological Research, 174: 105931 (12 pages)(2021).
Zheng et al., "Investigation on the prognostic impact of concurrent genomic alterations in crizotinib-treated EML4-ALK-rearranged advanced non-small cell lung cancer patients," Lung Cancer, 146: 209-216 (Aug. 2020).
Zhu et al., "A Novel Sequentially Evolved EML4-ALK Variant 3 G1202R/S1206Y Double Mutation In Cis Confers Resistance to Lorlatinib: A Brief Report and Literature Review," JTO Clinical and Research Reports, 2(1): 27 pages (Oct. 25, 2020).
Zhu et al., "An International Real-World Analysis of the Efficacy and Safety of Lorlatinib Through Early or Expanded Access Programs in Patients With Tyrosine Kinase Inhibitor-Refractory ALK-Positive or ROS1-Positive NSCLC," Journal of Thoracic Oncology, 15(9): 1484-1496 (Sep. 2020).
Zou et al., "PF-06463922 is a potent and selective next-generation ROS1/ALK inhibitor capable of blocking crizotinib-resistant ROS1 mutations," PNAS, 112(11): 3493-3498 (Mar. 17, 2015).
Zou et al., "PF-06463922 is a potent and selective next-generation ROS1/ALK inhibitor capable of blocking crizotinib-resistant ROS1 mutations," PNAS, Supporting Information: 1-8 (Mar. 17, 2015).
Zou et al., "The ALK/ROS1 Inhibitor PF -06463922 Has Potency across Resistant ALK Mutants," Cancer Discovery, 5: 902 (Jul. 2, 2015).
Adjei, "JTO Clinical and Research Reports Is Born," JTO Clinical and Research Reports, 1(1):100014 (2020).
Anderson, 2000, Practical Process Research & Development, Chapter 11: "Tools for Purifying the Product: Column Chromatography, Crystallization and Reslurrying," pp. 223-224.
Basit et al., 2017, "First macrocyclic 3rd-generation ALK inhibitor for treatment of ALK/ROSI cancer: Clinical and designing strategy update of lorlatinib," European Journal of Medicinal Chemistry, 134:348-356.
Berge et al., 1977, "Pharmaceutical salts," Journal of Pharmaceutical Sciences, 66(1):1-19.
Byrn et al., 1995, "Pharmaceutical Solids: A Strategic Approach to Regulatory Considerations," Pharmaceutical Research, 12(7):945-954.
Caira, M, 1998, "Crystalline Polymorphism of Organic Compounds," Topics in Current Chemistry, 198:163-208.
Cazes et al., "Characterization of rearrangements involving the ALK gene reveals a novel truncated form associated with tumor aggressiveness in neuroblastoma," Cancer Research, 73(1):195-204 (2013).
Chen et al., 2022, "Single-cell DNA-seq depicts clonal evolution of multiple driver alterations in osimertinib-resistant patients," Annals of Oncology, 33(4):434-444.
Chou et al., 2010, "Drug combination studies and their synergy quantification using the Chou-Talalay method," Cancer Research, 70(2):440-446.
ClinicalTrials.gov Identifier: NCT03202940, "A Phase IB/II Study of Alectinib Combined With Cobimetinib in Advanced ALK-Rearranged (ALK+) NSCLC," Last Updated Mar. 9, 2021.
Cooper et al., 2022, "LTK fusions: A new target emerges in non-small cell lung cancer," Cancer Cell, 40(1):23-25.
Debruyne et al., "ALK inhibitor resistance in ALKF1174L-driven neuroblastoma is associated with AXL activation and induction of EMT," Oncogene, 35:3681-3691 (2016).
Eisenhauer et al., 2009, New response evaluation criteria in solid tumours: revised RECIST guideline (version 1.1), European Journal of Cancer, 45(2):228-247.
Fransson et al., "Intragenic anaplastic lymphoma kinase (ALK) rearrangements: translocations as a novel mechanism of ALK activation in neuroblastoma tumors," Genes, Chromosomes and Cancer, 54(2):99-109 (2014).
Fukuhara et al., "Partial deletion of the ALK gene in ALK-positive anaplastic large cell lymphoma," Hematological Oncology, 36(1):150-158 (2018).
Harwood and Moody, 1989, "Experimental Organic Chemistry—Principles and Practice," Blackwell Science, pp. 127-132.
Huang et al., "Extracellular domain shedding of the ALK receptor mediates neuroblastoma cell migration," Cell Reports, 36:109363 (2021).
Inamura et al., 2017, "Association of tumor TROP2 expression with prognosis varies among lung cancer subtypes," Oncotarget, 8(17):28725-28735.
International Search Report and Written Opinion dated Jan. 18, 2023 for PCT/US2022/077364 (13 pages).
International Search Report and Written Opinion dated Jan. 26, 2023 for PCT/US2022/077323 (13 pages).
International Search Report and Written Opinion dated Jun. 30, 2023 for PCT/US2023/065449 (11 pages).
International Search Report and Written Opinion dated Aug. 14, 2023 for PCT/US2023/065434 (30 pages).
Izumi et al., 2021, "The CLIP1-LTK fusion is an oncogenic driver in non-small-cell lung cancer," Nature, 600:319-323.
Kim et al., 2020, "Synergistic Effect of Alectinib and Everolimus on ALK-positive Anaplastic Large Cell Lymphoma Growth Inhibition," Anticancer Research, 40(3):1395-1403.

(56) References Cited

OTHER PUBLICATIONS

Lucken et al., 2022, "EML4-ALK Variant 3 Promotes Mitotic Errors and Spindle Assembly Checkpoint Deficiency Leading to Increased Microtubule Poison Sensitivity," Molecular Cancer Research, 20(6):854-866.
NCBI Reference Sequence: NP_004295.2, "ALK tyrosine kinase receptor isoform 1 precursor [*Homo sapiens*]".
Oken et al., 1982, "Toxicity and response criteria of the Eastern Cooperative Oncology Group," American Journal of Clinical Oncology, 5(6):649-655.
Parsons and Flack, "Precise Absolute-Structure Determination in Light-Atom Crystals," Acta Crystallographica, A60:s61 (2004).
Schrock et al., 2018, "Receptor Tyrosine Kinase Fusions and BRAF Kinase Fusions are Rare but Actionable Resistance Mechanisms to EGFR Tyrosine Kinase Inhibitors," Journal of Thoracic Oncology, 13(9):1312-1323.
Taniguchi et al., 2021, "Efficacy of combination treatment using YHO-1701, an orally active STAT3 inhibitor, with molecular-targeted agents on cancer cell lines," Scientific Reports, 11(1):6685.
Tanimoto et al., 2021, "Proteasome Inhibition Overcomes ALK-TKI Resistance in ALK-Rearranged/TP53-Mutant NSCLC via Noxa Expression," Clinical Cancer Research, 27(5):1410-1420.
Tanimura et al., 2021, "Inhibition of c-Jun N-terminal kinase signaling increased apoptosis and prevented the emergence of ALK-TKI-tolerant cells in ALK-rearranged non-small cell lung cancer," Cancer Letters, 522:119-128.
Tanizaki et al., 2012, "Combined effect of ALK and MEK inhibitors in EML4-ALK-positive non-small-cell lung cancer cells, " British Journal of Cancer, 106(4):763-767.
Tsui et al., 2022, "Tumor Shrinkage With Combination of Alectinib and Trastuzumab in a Patient With ALK-Rearranged Non-small Cell Lung Cancer Harboring HER2-Amplification as an Acquired Resistance Mechanism to ALK Inhibitor Therapy," Clinical Lung Cancer, 23(2):e99-e103.
Tsuji et al., 2020, "YAP1 mediates survival of ALK-rearranged lung cancer cells treated with alectinib via pro-apoptotic protein regulation," Nature Communications, 11:74.
Vippagunta et al., 2001, "Crystalline solids," Advanced Drug Delivery Reviews, 48(1):3-26.
Von Buttlar et al., 2021, "EML4-ALK Rearrangement as a Mechanism of Resistance to Osimertinib in Metastatic Lung Adenocarcinoma: A Case Report," JTO Clinical and Research Reports, 2(6):100179.
Wiesner et al., "Alternative transcription initiation leads to expression of a novel ALK isoform in cancer," Nature, 526(7573):453-457 (2015).
Wilen et al., "Strategies in optical resolutions," Tetrahedron, 33(21):2725-2736 (1977).
Xiao et al., 2022, "Inhibiting ALK-TOPK signaling pathway promotes cell apoptosis of ALK-positive NSCLC," Cell Death & Disease, 13(9):828.
Yu, L, 2001, "Amorphous pharmaceutical solids: preparation, characterization and stabilization," Advanced Drug Delivery Reviews, 48:27-42.
Zhong et al., 2021, "Small molecules in targeted cancer therapy: advances, challenges, and future perspectives," Signal Transduction and Targeted Therapy, 6(1):201.
Aldea et al., "ALK Inhibitors in ALK-positive NSCLC with Central Nervous System Metastases," Lung Cancer, 4 pages (Sep. 15, 2020).
Armstrong et al., 2004, "Differential effects of X-ALK fusion proteins of proliferation, transformation, and invasion properties of NIH3T3 cells," Oncgene, 23: 6071-6082.
Bauer et al., 2020, "Brain Penetration of Lorlatinib: Cumulative Incidences of CNS and Non-CNS Progression with Lorlatinib in Patients with Previously Treated ALK-Positive Non-Small-Cell Lung Cancer," Targeted Oncology, 15:55-65.
Bertrand et al., 2012, "The Crystal Structures of TrkA and TrkB Suggest Key Regions for Achieving Selective Inhibition," J. Mol. Biol., 423: 439-453.
Camidge et al., 2012, "Activity and safety of crizotinib in patients with ALK-positive non-small-cell lung cancer: updated results form a phase 1 study," Lancet Oncol., 13(10): 1011-1019.
Camidge et al., 2020, "Brigatinib Versus Crizotinib in Advanced ALK Inhibitor-Naive ALK-Positive Non-Small Cell Lung Cancer: Second Interim Analysis of the Phase III ALTA-1L Trial," J Clin Oncol, 38:3592-3603.
Camidge, 2021, "Lorlatinib Should Not be Considered as the Preferred First-Line Option in Patients With Advanced ALK Rearranged NSCLC," Journal of Thoracic Oncology, 16(4): 528-531.
Chen et al., 2018, "Molecular Mechanism Behind the Resistance of the G1202R-Mutated Anaplastic Lymphoma Kinase to the Approved Drug Ceritinib," J. Phys. Chem. B, 122:4680-4692.
Childress et al., 2018, "ALK Fusion Partners Impact Response to ALK Inhibition: Differential Effects on Sensitivity, Cellular Phenotypes, and Biochemical Properties," Mol Cancer Res, 16(11): 1724-1736.
Cho et al., "Pivotal topline data from the phase 1/2 TRIDENT-1 trial of repotrectinib in patients with ROS1+ advanced non-small cell lung cancer (NSCLC)," European Journal of Cancer 174S1 (2002) S1-S2.
Delsol et al., 1997, "A New Subtype of Large B-Cell Lymphoma Expressing the ALK Kinase and Lacking the 2; 5 Translocation," Blood, 89(5): 1483-1490.
Drilon et al., 2023, "NVL-520 Is a Selective, TRK-Sparing, and Brain-Penetrant Inhibitor of ROS1 Fusions and Secondary Resistance Mutations," Cancer Discovery, 13(3), 598-615.
Drilon, 2019, "TRK inhibitors in TRK fusion-positive cancers," Annals of Oncology, 30(8): viii23-viii30.
Enot et al., 2018, "TumGrowth: An open-access web tool for the statistical analysis of tumor growth curves," Oncoimmunology, 7(9) 3 pages.
Ertl et al., 2000, "Fast Calculation of Molecular Polar Surface Area as a Sum of Fragment-Based Contributions and Its Application to the Prediction of Drug Transport Properties," J. Med. Chem., 43: 3714-3717.
Fujino et al., "Preclinical activity of NVL-655 in patient-derived models of ALK cancers, including those with lorlatinib-resistant G1202R/L1196M compound mutation," Abstracts, 34th EORTC-NCI-AACR Symposium (Oct. 27, 2022).
Gadgeel et al., 2018, "Alectinib versus crizotinib in treatment-naïve anaplastic lymphoma kinase-positive (ALKP) non-small-cell lung cancer: CNS efficacy results from the ALEX study," Annals of Oncology, 29: 2214-2222.
Griffin et al., 1999, "Recurrent Involvement of 2p23 in Inflammatory Myofibroblastic Tumors," Cancer Research, 59: 2776-2780.
Guerreiro Stucklin et al., 2019, "Alterations in ALK/ROS1/NTRK/MET drive a group of infantile hemispheric gliomas," Nature Communications, 10:4343.
Hatcher et al., 2015, "Discovery of inhibitors that overcome the G1202R ALK Resistance Mutation," J Med Chem 58(23): 9296-9308.
Heuckmann et al., 2012, "Differential Protein Stability and ALK Inhibitor Sensitivity of EML4-ALK Fusion Variants," Clin Cancer Res, 18(17): 4682-4690.
Horn et al., 2018, "Ensartinib (X-396) in ALK-Positive Non-Small Cell Lung Cancer: Results from a First-in-Human Phase I/II, Multicenter Study," Clin Cancer Res, 24(12): 2771-2779.
Horn et al., 2021, "Ensartinib vs Crizotinib for Patients With Anaplastic Lymphoma Kinase-Positive Non-Small Cell Lung Cancer," JAMA Oncology, 7(11): 1617-1625.
Keldar et al., 1999, "Polar Molecular Surface as a Dominating Determinant for Oral Absorption and Brain Penetration of Drugs," Pharmaceutical Research, 16(10): 1514-1519.
Koopman et al., 2022, "Actionability of on-target ALK Resistance Mutations in Patients With Non-Small Cell Lung Cancer: Local Experience and Review of the Literature," Clinical Lung Cancer, 23(2): e104-e114.el.
Lee et al., 2023, "Abstract 4022: Preclinical intracranial activity of NVL-655 in an alectinib-resistant patient derived model harboring EML4-ALK fusion with G1202R mutation," Cancer Res, 23(7_ Suppl): Abstract nr 4022.

(56) References Cited

OTHER PUBLICATIONS

Lin et al., 2022, "Safety and activity of alectinib plus bevacizumab in patients with advanced ALK-rearranged non-small-cell lung cancer: a phase I/II study," ESMO Open, 7(1):100342.
Lin et al., 2023, "Safety and preliminary activity of the selective ALK inhibitor NVL-655 in patients with ALK fusion-positive solid tumors," AACR-EORTC-NCI International Conference on Molecular Targets and Cancer presentation.
Lu et al., 2020, "Medicinal Chemistry Strategies for the Development of Kinase Inhibitors Targeting Point Mutations, " J. Med. Chem., 63:10726-10741.
Mizuta et al., 2022, "Preclinical Activity of NVL-655 in a Patient-Derived NSCLC Model with Lorlatinib-Resistant Alk G1202R/T1151M Mutation," Journal of Thoracic Oncology, 17(95): S406.
Morris et al., 1994, "Fusion of Kinase Gene, ALK, to a Nucleolar Protein Gene, NPM, in Non-Hodgkin's Lymphoma," Science, 263: 1281-1284.
Mossé et al., 2008, "Identification of ALK as a major familial neuroblastoma predisposition gene," Nature, 455: 930-936.
Ou et al., 2020, "Catalog of 5' Fusion Partners in ALK-positive NSCLC Circa 2020," JTO Clinical and Research Reports, 1(1): 1-10.
Ayati et al., 2020, "A review on progression of epidermal growth factor receptor (ECFR) inhibitors as an efficient approach in cancer targeted therapy," Bioorganic Chemistry, 99:103811.
Pacheco et al., 2019, "Natural History and Factors Associated with Overall Survival in Stage IV ALK-Rearranged Non-Small Cell Lung Cancer," J Thorac Oncol., 14(4): 691-700.
Rossari et al., 2018, "Past, present, and future of Bcr-Abl inhibitors: from chemical development to clinical efficacy," Journal of Hematology & Oncology, 11:84.
Shaw et al., "Crizotinib versus Chemotherapy in Advanced ALK-Positive Lung Cancer," 2013, N Engl J Med, 368(25), 2385-2394.
Solomon et al., "Intracranial Efficacy of Crizotinib Versus Chemotherapy in Patients With Advanced ALK-Positive Non-Small-Cell Lung Cancer: Results From PROFILE 1014," 2016, J Clin Oncol 24:2858-2865.
Soria et al., "Osimertinib in Untreated EGFR-Mutated Advanced Non-Small-Cell Lung Cancer", 2018, N Engl J Med, 378(2), 113-125.
Wang, et al., 2010, "General Solution to the Synthesis of N-2-Substituted 1,2,3-Triazoles," Org. Lett. 12(20):4632-4635.
Robertson, et al., 2014, "Functionalized thienoacridines: synthesis, optoelectronic, and structural properties," Can. J. Chemistry, 92(11):1106-1110.
Gunasekera et al., 2007, "Practical synthesis and applications of benzoboroxoles," Tetrahedron, 63:9401-9405.
Pirali et al., 2019, "Applications of Deuterium in Medicinal Chemistry," Journal of Medicinal Chemistry, 62(11):5276-5297.
Drilon et al., "Safety and preliminary clinical activity of NVL-520, a highly selective ROS1 inhibitor, in patients with advanced ROS1 fusion-positive solid tumors," 2022, Plenary Session 6: New Drugs on the Horizon, vol. 174, Supplement 1, S6-S7.
Patil et al., 2018, "The incidence of brain metastases in stage IV ROS1-rearranged non-small cell lung cancer and rate of central nervous system progression on crizotinib," J. Thorac. Oncol., 13(11):1717-1726.
Lin et al., 2021, "Spectrum of Mechanisms of Resistance to Crizotinib and Lorlatinib in ROS1 Fusion-Positive Lung Cancer," Clin. Canc. Res., 27(10):2899-2909.
Xalkori Prescribing Information Label (crizotinib), U.S. Food and Drug Administration: 47 pages (Revised Sep. 2023).
Hamilton et al., 2015, "Pharmacokinetics of crizotinib in NSCLC patients," Pharmacokinetics of crizotinib in NSCLC patients, Expert Opinion on Drug Metabolism & Toxicology, 11:5, 835-842.
Entrectinib Prescribing Information Label., U.S. Food and Drug Administration: 33 pages (Revised Jan. 2024).
Repotrectinib Prescribing Information Label., U.S. Food and Drug Administration: 22 pages (Revised Nov. 2023).
Bradeen et al., 2006, "Comparison of imatinib mesylate, dasatinib (BMS-354825), and nilotinib (AMN107) in an N-ethyl-N-nitrosourea (ENU)-based mutagenesis screen: high efficacy of drug combinations," Blood, 108(7):2332-2338.
Davare et al., 2013, "Foretinib is a potent inhibitor of oncogenic ROS1 fusion proteins," PNAS, 110(48):19519-19524.
Katayama et al., 2015, "Cabozantinib Overcomes Crizotinib Resistance in ROS1 Fusion-Positive Cancer," Clin Cancer Res, 21(1): 166-174.
Drilon et al., 2024, "Repotrectinib in ROS1 Fusion-Positive Non-Small-Cell Lung Cancer," N Engl J Med, 390(2):118-131.
Ye et al., 2016, "ALK and ROSI as targeted therapy paradigms and clinical implications to overcome crizotinib resistance," Oncotarget. 7:12289-12304.
Hsiao et al., 2021, "Colorectal Cancer with EML4-ALK Fusion Gene Response to Alectinib: A Case Report and Review of the Literature," Case Rep. Oncol. 14:232-238.
Cognigni et al., 2022, "The Landscape of ALK-Rearranged Non-Small Cell Lung Cancer: A Comprehensive Review of Clinicopathologic, Genomic Characteristics, and Therapeutic Perspectives," Cancers 14:4765-4785.
Muminovic et al., 2022, "Importance of ROS1 gene fusions in non-small cell lung cancer," Cancer Drug Resist. 6:332-344.
International Search Report and Written Opinion for International Application No. PCT/US2023/071758 dated Jan. 23, 2024.
International Search Report and Written Opinion for International Application No. PCT/US2023/071759 dated Jan. 23, 2024.
International Search Report and Written Opinion for International Application No. PCT/US2023/077180 dated Jan. 30, 2024.
Mesaros et al., 2014, "Anaplastic lymphoma kinase inhibitors as anticancer therapeutics: a patent review," Expert Opin. Ther. Patents, 24(4):417-442.
International Search Report and Written Opinion for International Application No. PCT/US2024/048077 dated Mar. 21, 2025.
International Search Report and Written Opinion for International Application No. PCT/US2024/048087 dated Feb. 24, 2025.
Foster, 1985, "Deuterium isotope effects in the metabolism of drugs and xenobiotics: implications for drug design", Advances in Drug Research, Academic Press, London, GB, vol. 14, pp. 1-40.
International Search Report and Written Opinion for International Application No. PCT/US2025/022255 dated Sep. 1, 2025.
Iyer et al., 2023, "Discovery of oncogenic ROS1 missense mutations with sensitivity to tyrosine kinase inhibitors," EMBO Molecular Medicine, 15(10), e17367, 20 pages.
Drilon et al., 2022, "Safety and preliminary clinical activity of NVL-520, a highly selective ROS1 inhibitor, in patients with advanced ROS1 fusion-positive solid tumors," European Journal of Cancer, vol. 174, Supplement 1, S6-S7.
Tangpeerachaikul et al., 2022, "Abstract 3336: Preclinical activity of NVL-520 in ROS1-driven cancer models with diverse fusion partners and kinase-domain mutations," Cancer Research, 82(12), Supplement, 3336.
Hilfiker ed., Hilfiker et al., "Polymorphism in the Pharmaceutical Industry", Jan. 1, 2006, pp. 1-19.

* cited by examiner

Unit Cell b axis of Single Crystal XRD of Form 1 of Free Base of Compound 1

Unit Cell from Single Crystal XRD of Form 7 of Free Base of Compound 1

SOLID FORMS, PHARMACEUTICAL COMPOSITIONS AND PREPARATION OF HETEROAROMATIC MACROCYCLIC ETHER COMPOUNDS

This application is a divisional application of patent application Ser. No. 17/957,725, filed Sep. 30, 2022, which claims the benefit of priority to U.S. Ser. No. 63/251,514, filed Oct. 1, 2012, each of which is incorporated herein by reference in its entirety.

1. BACKGROUND

Receptor tyrosine kinases (RTKs) are cell surface enzymes that receive outside signals, such as whether to grow and divide, and transmit those signals in the cell through kinase activity. Many RTKs are proto-oncogenes; aberrant RTK activity can drive cell survival, growth and proliferation leading to cancer and related disorders. This aberrant kinase activity can be caused by mutations such as activating mutations in the kinase domain, gene rearrangements that result in fusion proteins containing the intact kinase domain, amplification and other means. RTK proto-oncogenes include ROS1, anaplastic lymphoma kinase (ALK), NTRK1 (encodes TRKA), NTRK2 (encodes TRKB), and NTRK3 (encodes TRKC).

ROS1 is an RTK proto-oncogene, with ROS1 rearrangements detected in non-small cell lung cancer (NSCLC), glioblastoma, inflammatory myofibroblastic tumor (IMT), cholangiocarcinoma, ovarian cancer, gastric cancer, colorectal cancer, angiosarcoma, and spitzoid melanoma. Oncogenic ROS1 gene fusions contain the kinase domain of ROS1 (3' region) fused to the 5' region of a variety of partner genes. Examples of ROS1 fusion partner genes observed in NSCLC include SLC34A2, CD74, TPM3, SDC4, EZR, LRIG3, KDELR2, CEP72, CLTL, CTNND2, GOPC, GPRC6A, LIMA1, LRIG3, MSN, MYO5C, OPRM1, SLC6A17 (putative), SLMAP, SRSF6, TFG, TMEM106B, TPD52L1, ZCCHC8 and CCDC6. Other fusion partners include CAPRIN1, CEP85, CHCHD3, CLIP1 (putative), EEF1G, KIF21A (putative), KLC1, SART3, ST13 (putative), TRIM24 (putative), ERC1, FIP1L1, HLAA, KIAA1598, MYO5A, PPFIBP1, PWWP2A, FN1, YWHAE, CCDC30, NCOR2, NFKB2, APOB, PLG, RBP4, and GOLGB1.

ALK is an RTK proto-oncogene, with ALK rearrangements detected in many cancers, including NSCLC, anaplastic large cell lymphoma (ALCL), IMT, diffuse large B-cell lymphoma (DLBCL), esophageal squamous cell carcinoma (ESCC), renal medullary carcinoma, renal cell carcinoma, breast cancer, colon cancer, serous ovarian carcinoma, papillary thyroid cancer, and spitzoid tumors, and ALK activating mutations detected in neuroblastoma. Oncogenic ALK gene fusions contain the kinase domain of ALK (3' region) fused to the 5' region of more than 20 different partner genes, the most common being EML4 in NSCLC and NPM in ALCL. Other partner genes include TMP1, WDCP, GTF2IRD1, TPM3, TPM4, CLTC, LMNA, PRKAR1A, RANBP2, TFG, FN1, KLC1, VCL, STRN, HIP1, DCTN1, SQSTM1, TPR, CRIM1, PTPN3, FBXO36, ATIC and KIF5B.kinases.

NTRK1, NTRK2 and NTRK3 are RTK proto-oncogenes that encode TRK-family kinases, with NTRK1, NTRK2 and NTRK3 chromosomal rearrangements detected at low frequency in many cancers. For treatment of ROS1-positive or ALK-positive patients, however, TRK inhibition, particularly in the central nervous system (CNS), has been associated with adverse reactions, including dizziness/ataxia/gait disturbance, paraesthesia, weight gain and cognitive changes.

Agents in the prior art used to treat oncogenic ROS1 and ALK have substantial deficiencies. These deficiencies may represent one or more of the following: associated TRK inhibition, limited CNS activity, and inadequate activity against resistance mutations. Treatment of ROS1-positive or ALK-positive patients accompanied by TRK inhibition is associated with adverse reactions, particularly in the CNS, including dizziness/ataxia/gait disturbance, paraesthesia, weight gain and cognitive changes. Additionally, there is a need for CNS-penetrant and TRK-sparing inhibitors of the wild type ROS1 kinase domain and ROS1 with acquired resistance mutations occurring either individually or in combination, including G2032R, D2033N, S1986F, S1986Y, L2026M, L1951R, E1935G, L1947R, G1971E, E1974K, L1982F, F2004C, F2004V, E2020K, C2060G, F2075V, V2089M, V2098I, G2101A, D2113N, D2113G, L2155S, L2032K, and L2086F. Likewise, there is a need for CNS-penetrant and TRK-sparing inhibitors of ALK with acquired resistance mutations. A variety of ALK drug resistance mutations, occurring either individually or in combination, have been reported, including G1202R, L1196M, G1269A, C1156Y, I1171T, I1171N, I1171S, F1174L, V1180L, S1206Y, E1210K, 1151Tins, F1174C, G1202del, D1203N, S1206Y, S1206C, L1152R, L1196Q, L1198P, L1198F, R1275Q, L1152P, C1156T, and F1245V.

In addition, for the production of a drug substance intended for use in humans, procedures need to be in place that can control the levels of impurities and ensure that API products are produced, which consistently meet their predetermined specifications. Thus, a need exists for a process to prepare ROS1 and ALK inhibitors suitable for human use, particularly on a commercial scale, that is, inter al/a, safe, scalable, efficient, economically viable, and/or having other desirable properties. Among other entities, disclosed herein are crystalline forms and pharmaceutical compositions comprising such crystalline forms to address these needs and provide exemplary advantages.

2. SUMMARY

Provided herein are solid forms comprising a compound of formula (I) (also referred as Compound 1) or a stereoisomer, or a mixture of stereoisomers thereof, or a pharmaceutically acceptable salt thereof:

(I)

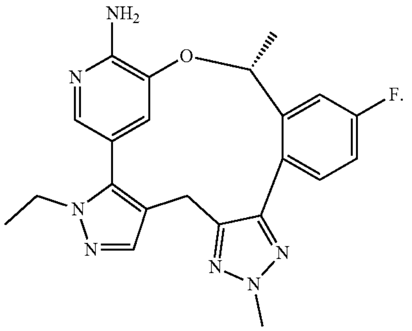

In some embodiments, the solid form is a crystalline form. In other embodiments, the solid form is an amorphous form. In some embodiments, the solid form is a solid form of a compound of formula (I). In some embodiments, the solid form is a solid form of a free base of a compound of formula (I). In some embodiments, the solid form is a solid form of a salt of a compound of formula (I). In some embodiments, the solid form is a crystalline form of a free base of a compound of formula (I). In some embodiments, the solid form is a crystalline form of a salt of a compound of formula (I).

Also provided herein are methods of preparing the solid forms. In some embodiments, provided herein are methods of preparing solid forms of a free base of a compound of formula (I). In some embodiments, provided herein are methods of preparing solid forms of a salt of a compound of formula (I).

Also provided herein are methods of treating cancer comprising administering a therapeutically effective amount of a solid form of a compound of formula (I) provided herein to a subject in need thereof.

Also provided herein are pharmaceutical compositions comprising a solid form of a compound of formula (I) and a pharmaceutically acceptable excipient. In some embodiments, the pharmaceutical composition comprises a solid form of a free base of a compound of formula (I). In some embodiments, the pharmaceutical composition comprises a solid form of a salt of a compound of formula (I).

Also provided herein are processes for preparing a compound of formula (I):

(I)

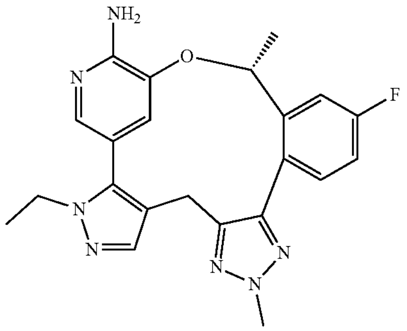

or a stereoisomer, or a mixture of stereoisomers thereof, or a pharmaceutically acceptable salt thereof, comprising:

(step 1.0) cyclizing a compound of Formula (II):

(II)

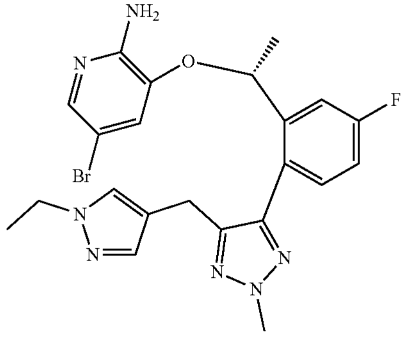

or a stereoisomer, or a mixture of stereoisomers thereof, or a pharmaceutically acceptable salt thereof, to provide a compound of Formula (I), or a stereoisomer, or a mixture of stereoisomers thereof, or a pharmaceutically acceptable salt thereof.

Also provided herein are pharmaceutical compositions comprising a compound of formula (I):

(I)

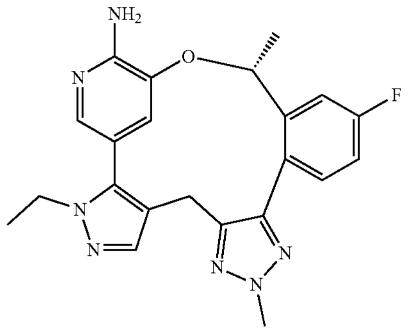

or a stereoisomer, or a mixture of stereoisomers thereof, or a pharmaceutically acceptable salt thereof, and a diluent, a binder, a disintegrant, and a lubricant.

Also provided herein are methods of treating cancer comprising administering a therapeutically effective amount of the pharmaceutical composition provided herein.

3. INCORPORATION BY REFERENCE

All publications, patents, and patent applications mentioned in this specification are herein incorporated by reference in their entireties and to the same extent as if each individual publication, patent, or patent application was specifically and individually indicated to be incorporated by reference.

4. BRIEF DESCRIPTION OF FIGURES

5. DETAILED DESCRIPTION

5.1 Definitions

Figure 1:
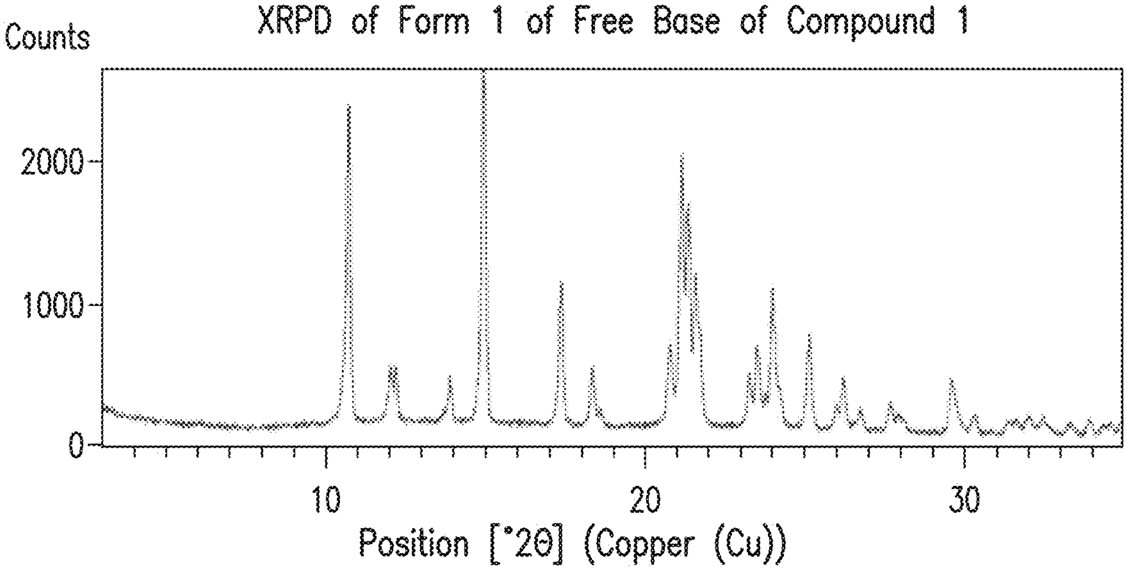
FIG. 1 is a representative X-ray powder diffraction (XRPD) pattern of Form 1 of free base of Compound 1.

Unless defined otherwise, all technical and scientific terms used herein have the meaning commonly understood by a person skilled in the art of the present disclosure. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

In some embodiments, chemical structures are disclosed with a corresponding chemical name. In case of conflict, the chemical structure controls the meaning, rather than the name.

As used herein, the terms “comprising” and “including” can be used interchangeably. The terms “comprising” and “including” are to be interpreted as specifying the presence of the stated features or components as referred to, but does not preclude the presence or addition of one or more features, or components, or groups thereof. Additionally, the terms “comprising” and “including” are intended to include examples encompassed by the term “consisting of”. Consequently, the term “consisting of” can be used in place of the terms “comprising” and “including” to provide for more specific embodiments of the invention.

The term “consisting of” means that a subject-matter has at least 90%, 95%, 97%, 98% or 99% of the stated features or components of which it consists. In another embodiment the term “consisting of” excludes from the scope of any succeeding recitation any other features or components, excepting those that are not essential to the technical effect to be achieved.

Unless specifically stated or obvious from context, as used herein, the term “or” is understood to be inclusive. Unless specifically stated or obvious from context otherwise, as used herein, the terms “a”, “an”, and “the” are understood to be singular or plural. For example, when a compound provided herein is administered to “a patient”, it includes administering the compound to an individual patient or a patient population.

As used herein and unless otherwise specified, “stereoisomers” refer to the various stereoisomeric forms of a compound that comprises one or more asymmetric centers or stereohindrance in the structure. In some embodiments, a stereoisomer is an enantiomer, a mixture of enantiomers, an atropisomer, or a tautomer thereof. For example, the compounds described herein can be in the form of an individual enantiomer, diastereomer or geometric isomer (e.g. an atropisomer), or can be in the form of a mixture of stereoisomers, including racemic mixtures and mixtures enriched in one or more stereoisomer. In some embodiments, compounds provided herein may be atropisomers. In certain embodiments, atropisomers are stereoisomers arising because of hindered rotation about a single bond, where energy differences due to steric strain or other contributors create a barrier to rotation that is high enough to allow for isolation of individual conformers. Stereoisomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. Tables of Resolving Agents and Optical Resolutions p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

In certain embodiments, compounds provided herein may be racemic. In certain embodiments, compounds provided herein may be enriched in one enantiomer. For example, a compound provided herein may have greater than about 30% ee, about 40% ee, about 50% ee, about 60% ee, about 70% ee, about 80% ee, about 90% ee, or even about 95% or greater ee. In certain embodiments, compounds provided herein may have more than one stereocenter. In certain such embodiments, compounds provided herein may be enriched in one or more diastereomer. For example, a compound provided herein may have greater than about 30% de, about 40% de, about 50% de, about 60% de, about 70% de, about 80% de, about 90% de, or even about 95% or greater de.

In certain embodiments, the therapeutic preparation may be enriched to provide predominantly one enantiomer of a compound. An enantiomerically enriched mixture may comprise, for example, at least about 60 mol percent of one enantiomer, or more particularly at least about 75, about 90, about 95, or even about 99 mol percent. In certain embodiments, the compound enriched in one enantiomer is substantially free of the other enantiomer, wherein substantially free means that the substance in question makes up less than about 10%, or less than about 5%, or less than about 4%, or less than about 3%, or less than about 2%, or less than about 1% as compared to the amount of the other enantiomer, e.g., in the composition or compound mixture. For example, if a composition or compound mixture contains about 98 grams of a first enantiomer and about 2 grams of a second enantiomer, it would be said to contain about 98 mol percent of the first enantiomer and only about 2% of the second enantiomer.

In certain embodiments, the therapeutic preparation may be enriched to provide predominantly one diastereomer of a compound. A diastereomerically enriched mixture may comprise, for example, at least about 60 mol percent of one diastereomer, or more particularly at least about 75, about 90, about 95, or even about 99 mol percent.

In some embodiments, a moiety in a compound exists as a mixture of tautomers. A "tautomer" is a structural isomer of a moiety or a compound that readily interconverts with another structural isomer. For example, a pyrazole ring has two tautomers:

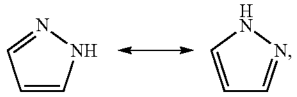 [SMILES: c1cn[nH]c1 ; c1cn[nH]c1]

which differ in the positions of the pi-bonds and a hydrogen atom. Unless explicitly stated otherwise, a drawing of one tautomer of a moiety or a compound encompasses all of the possible tautomers.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. In certain embodiments, the subject is a human. In certain embodiments, the subject is a human adult at least of 40 years old. In certain embodiments, the subject is a human adult at least of 50 years old. In certain embodiments, the subject is a human adult at least of 60 years old. In certain embodiments, the subject is a human adult at least of 70 years old. In certain embodiments, the subject is a human adult at least of 18 years old or at least of 12 years old. As used herein and unless otherwise specified, a human subject to which administration of a therapeutic (e.g., a compound as described herein) is contemplated in order to treat, prevent or manage a disease, disorder, or condition, or symptoms thereof, is also called a "patient".

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. These effects are also called "prophylactic" effects. Thus, as used herein and unless otherwise specified, the terms "prevention" and "preventing" refer to an approach for obtaining beneficial or desired results including, but not limited, to prophylactic benefit. For prophylactic benefit, a therapeutic can be administered to a patient at risk of developing a particular disease, or to a patient reporting one or more of the physiological symptoms of a disease, even though a diagnosis of this disease may not have been made. In one embodiment, a therapeutic is administered prior to clinical manifestation of the unwanted condition (e.g., disease or other unwanted state of the subject) for prophylactic benefit (e.g., it protects the subject against developing the unwanted condition).

As used herein and unless otherwise specified, the terms "treatment" and "treating" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable. "Treatment" can also mean prolonging survival as compared to expected survival if not receiving treatment. In one embodiment, "treatment" comprises administration of a therapeutic after manifestation of the unwanted condition (i.e., it is intended to diminish, ameliorate, or stabilize the existing unwanted condition or side effects thereof).

As used herein and unless otherwise indicated, the term "managing" encompasses preventing the recurrence of the particular disease or disorder in a patient who had suffered from it, lengthening the time a patient who had suffered from the disease or disorder remains in remission, reducing mortality rates of the patients, and/or maintaining a reduction in severity or avoidance of a symptom associated with the disease or condition being managed.

An "effective amount", as used herein, refers to an amount that is sufficient to achieve a desired biological effect. A "therapeutically effective amount", as used herein, refers to an amount that is sufficient to achieve a desired therapeutic effect. For example, a therapeutically effective amount can refer to an amount that is sufficient to improve at least one sign or symptom of cancer.

A "response" to a method of treatment can include a decrease in or amelioration of negative symptoms, a decrease in the progression of a disease or symptoms thereof, an increase in beneficial symptoms or clinical outcomes, a lessening of side effects, stabilization of disease, partial or complete remedy of disease, among others.

As used herein and unless otherwise indicated, the term "relapsed" refers to a disorder, disease, or condition that responded to prior treatment (e.g., achieved a complete response) then had progression. The prior treatment can include one or more lines of therapy.

As used herein and unless otherwise indicated, the term "refractory" refers to a disorder, disease, or condition that has not responded to prior treatment that can include one or more lines of therapy.

"Crystalline," as used herein, refers to a homogeneous solid formed by a repeating, three-dimensional pattern of atoms, ions or molecules having fixed distances between constituent parts. The unit cell is the simplest repeating unit in this pattern. Notwithstanding the homogenous nature of an ideal crystal, a perfect crystal rarely, if ever, exists. "Crystalline," as used herein, encompasses crystalline forms that include crystalline defects, for example, crystalline defects commonly formed by manipulating (e.g., preparing, purifying) the crystalline forms described herein. A person skilled in the art is capable of determining whether a sample of a compound is crystalline notwithstanding the presence of such defects. Crystalline forms can be characterized by analytical methods such as x-ray powder diffraction (XRPD), differential scanning calorimetry (DSC), thermogravimetric analysis (TGA), nuclear magnetic resonance spectroscopy (NMR), single crystal x-ray diffraction, Raman spectroscopy, Fourier transform infrared spectroscopy (FTIR) and/or any other suitable analytical techniques.

As used herein "solvate" refers to a crystalline form of a molecule, atom, and/or ions that further comprises molecules of a solvent or solvents incorporated into the crystalline lattice structure. The solvent molecules in the solvate may be present in a regular arrangement and/or a non-ordered arrangement. The solvate may comprise either a stoichiometric or nonstoichiometric amount of the solvent molecules. For example, a solvate with a nonstoichiometric amount of solvent molecules may result from partial loss of solvent from the solvate. Solvates may occur as dimers or oligomers comprising more than one molecule or Compound ABC within the crystalline lattice structure.

As used herein "amorphous" refers to a solid form of a molecule, atom, and/or ions that is not crystalline. In particular, the term "amorphous form" describes a disordered solid form, i.e., a solid form lacking long range crystalline order. An amorphous solid does not display a definitive X-ray diffraction pattern. In certain embodiments, an amorphous form of a substance may be substantially pure of other amorphous forms and/or crystal forms.

As used herein and unless otherwise specified, the term "solid form" and related terms refer to a physical form which is not predominantly in a liquid or a gaseous state. Solid forms may be crystalline, amorphous or mixtures thereof. As used herein and unless otherwise specified, the term "crystal forms" and related terms refer to solid forms that are crystalline. Crystal forms include, but are not limited to, non-solvates, non-hydrates, solvates, hydrates, and other molecular complexes, as well as salts, solvates of salts, hydrates of salts, and other molecular complexes of salts thereof. In certain embodiments, a solid form or crystal form of a substance may be substantially free of amorphous forms and/or other solid forms and/or crystal forms. In certain embodiments, a solid form and/or crystal form of a substance may contain less than about 1%, 2%, 3%, 4%, 5%, 6%, 7%, 8%, 9%, 10%, 15%, 20%, 25%, 30%, 35%, 40%, 45% or 50% of one or more amorphous forms and/or other solid forms and/or crystal forms on a weight basis. In certain embodiments, a solid form or crystal form of a substance may be physically and/or chemically pure. In certain embodiments, a solid form or crystal form of a substance may be about 99%, 98%, 97%, 96%, 95%, 94%, 93%, 92%, 91% or 90% physically and/or chemically pure. In certain embodiments, a solid form or crystal form of a substance may be at least about 99%, 98%, 97%, 96%, 95%, 94%, 93%, 92%, 91% or 90% physically and/or chemically pure. In one embodiment, a solid form or crystal form of a substance is about 97.0% physically and/or chemically pure on a weight basis. In one embodiment, a solid form or crystal form of a substance is about 98.0% physically and/or chemically pure on a weight basis. In one embodiment, a solid form or crystal form of a substance is about 99.0% physically and/or chemically pure on a weight basis. In one embodiment, a solid form or crystal form of a substance is about 99.9% physically and/or chemically pure on a weight basis. In certain embodiments, a solid form or crystal form may be substantially chemically pure and/or substantially physically pure.

"Substantially pure," when used without further qualification, means the compound has a purity greater than 90 weight percent, for example, greater than 90, 91, 92, 93, 94, 95, 96, 97, 98, or 99 weight percent, and also including a purity equal to about 100 weight percent, based on the weight of the compound. The remaining material may comprise other form(s) of the compound and/or reaction impurities and/or processing impurities arising from its preparation. Purity can be assessed using techniques known in the art, for example, using an HPLC assay.

"Substantially pure" can also be qualified. If the compound is "substantially pure" with respect to the presence of chemical impurities (e.g. reaction impurities and/or processing impurities arising from its preparation), it can be referred to as "substantially chemically pure". If the compound is "substantially pure" with respect to the presence of the other enantiomer, it can be referred to as "substantially enantiomerically pure". In some embodiments, the compound (e.g. Compound 1) is substantially enantiomerically pure with the other enantiomer (e.g. the S enanontiomer) present less than 10%, less than 5%, less than 3%, less than 1%, less than 0.5%, or less than 0.1% by weight. If the compound is "substantially pure" with respect to the presence of other physical forms of the compound having the indicated structure, it can be referred to as "substantially physically pure". When qualified, "substantially pure" means that the indicated compound contains less than 10%, less than 5%, less than 3%, less than 1%, less than 0.5%, or less than 0.1% by weight of the indicated impurity. In certain embodiments, the solid form of Compound 1 is substantially pure (e.g. having the purity of at least about 90 wt %, at least about 95 wt %, at least about 96 wt %, at least about 97 wt %, at least about 98 wt %, or at least about 99 wt %). In certain embodiments, the solid form of Compound 1 has the purity of at least about 95 wt %. In certain embodiments, the solid form of Compound 1 is substantially enantiomerically pure (e.g. having the enantiomeric purity of at least about 98.0 wt %, at least about 99.0 wt %, at least about 99.5 wt %, or at least about 99.9 wt %). In certain embodiments, the solid form of Compound 1 has the enantiomeric purity of at least about 99.5 wt %. In certain embodiments, the pharmaceutical composition comprising Compound 1 has the purity of at least about 95 wt %. In certain embodiments, the pharmaceutical composition comprising Compound 1 has the purity of at least about 96 wt %. In certain embodiments, the pharmaceutical composition comprising Compound 1 has the purity of at least about 97 wt %. In certain embodiments, the pharmaceutical composition comprising Compound 1 has the purity of at least about 98 wt %. In certain embodiments, the pharmaceutical composition comprising Compound 1 has the purity of at least about 99 wt %. In certain embodiments, the pharmaceutical composition comprising Compound 1 has the purity of at least about 95 wt % over 12 months.

Solid forms may exhibit distinct physical characterization data that are unique to a particular solid form, such as the crystal forms described herein. These characterization data may be obtained by various techniques known to those skilled in the art. The data provided by these techniques may be used to identify a particular solid form. For example, an XRPD pattern, DSC thermogram or TGA thermal curve that "matches" or, interchangeably, is "substantially in accordance" with one or more figures herein showing an XRPD pattern or DSC thermogram or TGA thermal curve, respectively, is one that would be considered by one skilled in the art to represent the same single crystalline form of the compound as the sample of the compound that provided the pattern or thermogram or thermal curve of one or more figures provided herein. Thus, an XRPD pattern or DSC thermogram or TGA thermal curve that matches or is substantially in accordance may be identical to that of one of the figures or, more likely, may be somewhat different from one or more of the figures. For example, an XRPD pattern that is somewhat different from one or more of the figures may not necessarily show each of the lines of the diffraction pattern presented herein and/or may show a slight change in appearance or intensity of the lines or a shift in the position of the lines. These differences typically result from differences in the conditions involved in obtaining the data or differences in the purity of the sample used to obtain the data. A person skilled in the art is capable of determining if a sample of a crystalline compound is of the same form as or a different form from a form disclosed herein by comparison of the XRPD pattern or DSC thermogram or TGA thermal curve of the sample and the corresponding XRPD pattern or DSC thermogram or TGA thermal curve disclosed herein.

As used herein, and unless otherwise specified, the terms “about” and “approximately,” when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms “about” and “approximately,” when used in this context, contemplate a dose, amount, or weight percent within 30%, within 20%, within 15%, within 10%, or within 5%, of the specified dose, amount, or weight percent.

As used herein and unless otherwise specified, the terms “about” and “approximately,” when used in connection with a numeric value or a range of values which is provided to characterize a particular solid form, e.g., a specific temperature or temperature range, such as, for example, that describing a melting, dehydration, desolvation or glass transition temperature; a mass change, such as, for example, a mass change as a function of temperature or humidity; a solvent or water content, in terms of, for example, mass or a percentage; or a peak position, such as, for example, in analysis by IR or Raman spectroscopy or XRPD; indicate that the value or range of values may deviate to an extent deemed reasonable to one of ordinary skill in the art while still describing the particular solid form. For example, in particular embodiments, the terms “about” and “approximately,” when used in this context, indicate that the numeric value or range of values may vary within 25%, 20%, 15%, 10%, 9%, 8%, 7%, 6%, 5%, 4%, 3%, 2%, 1.5%, 1%, 0.5%, or 0.25% of the recited value or range of values. For example, in some embodiments, the value of XRPD peak position may vary by up to ±0.2 degrees 2θ while still describing the particular XRPD peak. In one embodiment, he value of XRPD peak position may vary by up to ±0.1 degrees 2θ. In one embodiment, he value of XRPD peak position may vary by up to ±0.05 degrees 2θ.

The term “between” includes the endpoint numbers on both limits of the range. For example, the range described by “between 3 and 5” is inclusive of the numbers “3” and “5”.

As used herein and unless otherwise specified, the term “pharmaceutically acceptable salt” refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J. Pharmaceutical Sciences* (1977) 66:1-19. In certain embodiments, pharmaceutically acceptable salts include, but are not limited to, alkyl, dialkyl, trialkyl or tetra-alkyl ammonium salts. In certain embodiments, pharmaceutically acceptable salts include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, pharmaceutically acceptable salts include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Pharmaceutically acceptable anionic salts include, but are not limited to, acetate, aspartate, benzenesulfonate, benzoate, besylate, bicarbonate, bitartrate, bromide, camsylate, carbonate, chloride, citrate, decanoate, edetate, esylate, fumarate, gluceptate, gluconate, glutamate, glycolate, hexanoate, hydroxynaphthoate, iodide, isethionate, lactate, lactobionate, malate, maleate, mandelate, mesylate, methylsulfate, mucate, napsylate, nitrate, octanoate, oleate, pamoate, pantothenate, phosphate, polygalacturonate, propionate, salicylate, stearate, acetate, succinate, sulfate, tartrate, teoclate, and tosylate.

As used herein, and unless otherwise specified, the term “enantiomerically pure” refers to a composition comprising an enantiomeric excess of at least about 50%, at least about 75%, at least about 90%, at least about 95%, or at least about 99% of one enantiomer of a compound having one or more chiral center(s). In some embodiments, the composition may be “substantially enantiomerically pure”, which refers to preparations of compositions which have at least about 85% by weight of one enantiomer relative to the other enantiomer of a compound, such as at least about 90% by weight, and further such as at least 95% by weight. In certain embodiments, the compositions provided herein comprise an enantiomeric excess of at least about 90% by weight of one enantiomer of the compound. In other embodiments, the compositions comprises an enantiomeric excess of at least about 95%, at least about 98%, or at least about 99% by weight of one enantiomer of the compound.

As used herein and unless otherwise indicated, the term “process(es)” provided herein refers to the methods provided herein which are useful for preparing a compound as described herein or a solid form thereof (e.g. a crystalline form, partically crystalline form, or an amorphous form) provided herein. Modifications to the methods provided herein (e.g., starting materials, reagents, protecting groups, solvents, temperatures, reaction times, purification) are also provided herein. In general, the technical teaching of one embodiment provided herein can be combined with that disclosed in any other embodiments provided herein.

As used herein, and unless otherwise indicated, the term “adding,” “reacting,” “treating,” or the like means contacting one reactant, reagent, solvent, catalyst, reactive group or the like with another reactant, reagent, solvent, catalyst, reactive group or the like. Reactants, reagents, solvents, catalysts, reactive group or the like can be added individually, simultaneously or separately and can be added in any order. Reactants, reagents, solvents, catalysts, reactive group or the like can each respectively be added in one portion, which may be delivered all at once or over a period of time, or in discrete portions, which also may be delivered all at once or over a period of time. They can be added in the presence or absence of heat and can optionally be added under an inert atmosphere. "Reacting" can refer to in situ formation or intramolecular reaction where the reactive groups are in the same molecule.

As used herein, the term "combining" refers to bringing one or more chemical entities into association with another one or more chemical entities. Combining includes the processes of adding one or more compounds to a solid, liquid or gaseous mixture of one or more compounds (the same or other chemical entities), or a liquid solution or multiphasic liquid mixture. The act of combining includes the process or processes of one or more compounds reacting (e.g., bond formation or cleavage; salt formation, solvate formation, chelation, or other non-bond altering association) with one or more compounds (the same or other chemical entities). The act of combining can include alteration of one or more compounds, such as by isomerization (e.g., tautomerization, resolution of one isomer from another, or racemization).

As used herein, and unless otherwise indicated, the term "transforming" refers to subjecting the compound at hand to reaction conditions suitable to effect the formation of the desired compound at hand.

As used herein, the term "recovering" includes, but is not limited to, the action of obtaining one or more compounds by collection during and/or after a process step as disclosed herein, and the action of obtaining one or more compounds by separation of one or more compounds from one or more other chemical entities during and/or after a process step as disclosed herein. The term "collection" refers to any action(s) known in the art for this purpose, including, but not limited to, filtration, decanting a mother liquor from a solid to obtain one or more compounds, and evaporation of liquid media in a solution or other mixture to afford a solid, oil, or other residue that includes one or more compounds. The solid can be crystalline, acrystalline, partially crystalline, or amorphous, a powder, granular, of varying particle sizes, of uniform particle size, among other characteristics known in the art. An oil can vary in color and viscosity, and include one or more solid forms as a heterogeneous mixture, among other characteristics known in the art. The term "separation" refers to any action(s) known in the art for this purpose, including, but not limited to, isolating one or more compounds from a solution or mixture using, for example, seeded or seedless crystallization or other precipitation techniques (e.g., adding an anti-solvent to a solution to induce compound precipitation; heating a solution, then cooling to induce compound precipitation; scratching the surface of a solution with an implement to induce compound precipitation), and distillation techniques. Recovering one or more compounds can involve preparation of a salt, solvate, hydrate, chelate or other complexes of the same, then collecting or separating as described above.

As used herein, the term "catalyst precursor" refers to a chemical composition wherein one or more components of an active catalyst (e.g. metal center and supporting ligand) are added to the reaction mixture such that formation of an active catalyst occurs in situ. For example, a cataCXium A ligated palladium catalyst may be formed in situ by adding a catalyst precursor comprising a palladium source (e.g. $Pd(OAc)_2$) and a source of cataCXium A (e.g. cataCXium A). Those skilled in the art will recognize that even when the metal source and supporting ligand are added to a reaction mixture in the form of a single chemical entity (e.g. $Pd(dppf)Cl_2$), further activation and/or reaction in situ may be required to produce an active catalyst. Notwithstanding, as used herein, the term "catalyst" includes, but is not limited to a chemical composition wherein more than one component of an active catalyst (e.g. metal center and supporting ligand) is added to a reaction mixture in the form of a single chemical entity (e.g. $Pd(dppf)Cl_2$), even if further activation and/or reaction in situ is required to produce an active catalyst.

Although most embodiments and examples provided herein are directed to one enantiomer of a compound, it is to be understood that the opposite enantiomer of a compound can be prepared by the provided processes when the stereochemistry of chiral reactant, reagent, solvent, catalyst, ligand or the like is reversed.

As used herein, and unless otherwise specified, the terms "solvent," "organic solvent," or "inert solvent" each mean a solvent inert under the conditions of the reaction being described. Unless specified to the contrary, for each gram of a limiting reagent, one cc (or mL) of solvent constitutes a volume equivalent (or "vol.").

The disclosure can be understood more fully by reference to the following detailed description and illustrative examples, which are intended to exemplify non-limiting embodiments.

5.2 Solid Forms

Potential pharmaceutical solids include crystalline solids and amorphous solids. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability (see, e.g., S. R. Vippagunta et al., *Adv. Drug. Deliv. Rev.*, (2001) 48:3-26; L. Yu, *Adv. Drug. Deliv. Rev.*, (2001) 48:27-42). A change in solid form may affect a variety of physical and chemical properties, which may provide benefits or drawbacks in processing, formulation, stability and bioavailability, among other important pharmaceutical characteristics.

Whether crystalline or amorphous, potential solid forms of a pharmaceutical compound may include single-component and multiple-component solids. Single-component solids consist essentially of the pharmaceutical compound in the absence of other compounds. Variety among single-component crystalline materials may potentially arise from the phenomenon of polymorphism, wherein multiple three-dimensional arrangements exist for a particular pharmaceutical compound (see, e.g., S. R. Byrn et al., *Solid State Chemistry of Drugs*, (1999) SSCI, West Lafayette).

Additional diversity among the potential solid forms of a pharmaceutical compound may arise from the possibility of multiple-component solids. Crystalline solids comprising two or more ionic species are termed salts (see, e.g., *Handbook of Pharmaceutical Salts: Properties, Selection and Use*, P. H. Stahl and C. G. Wermuth, Eds., (2002), Wiley, Weinheim). Additional types of multiple-component solids that may potentially offer other property improvements for a pharmaceutical compound or salt thereof include, e.g., hydrates, solvates, co-crystals and clathrates, among others (see, e.g., S. R. Byrn et al., *Solid State Chemistry of Drugs*, (1999) SSCI, West Lafayette). Multiple-component crystal forms may potentially be susceptible to polymorphism, wherein a given multiple-component composition may exist in more than one three-dimensional crystalline arrangement. The discovery of solid forms is of great importance in the development of a safe, effective, stable and marketable pharmaceutical compound.

The solid forms provided herein are useful as active pharmaceutical ingredients for the preparation of formulations for use in animals or humans. Thus, embodiments herein encompass the use of these solid forms as a final drug product. Certain embodiments provide solid forms useful in making final dosage forms with improved properties, e.g., powder flow properties, compaction properties, tableting properties, stability properties, and excipient compatibility properties, among others, that are needed for manufacturing, processing, formulation and/or storage of final drug products. Certain embodiments herein provide pharmaceutical compositions comprising a single-component crystal form, and/or a multiple-component crystal form comprising the compound of formula (I) and a pharmaceutically acceptable excipient.

Solid form and related terms refer to a physical form which is not predominantly in a liquid or a gaseous state. Solid forms may be crystalline or mixtures of crystalline and amorphous forms. A "single-component" solid form comprising a particular compound consists essentially of that compound. A "multiple-component" solid form comprising a particular compound comprises that compound and a significant quantity of one or more additional species, such as ions and/or molecules, within the solid form. The solid forms provided herein may be crystalline or an intermediate form (e.g., a mixture of crystalline and amorphous forms). The crystal forms described herein, therefore, may have varying degrees of crystallinity or lattice order. The solid forms described herein are not limited to any particular degree of crystallinity or lattice order, and may be 0-100% crystalline. Methods of determining the degree of crystallinity are known to those of ordinary skill in the art, such as those described in Suryanarayanan, R., *X-Ray Powder Diffractometry*, Physical Characterization of Pharmaceutical Solids, H. G. Brittain, Editor, Marcel Dekker, Murray Hill, N.J., 1995, pp. 187-199, which is incorporated herein by reference in its entirety. In some embodiments, the solid forms described herein are about 0, 5, 10, 15, 20, 25, 30, 35, 40, 45, 50, 55, 60, 65, 70, 75, 80, 85, 90, 95 or 100% crystalline.

Solid forms may exhibit distinct physical characterization data that are unique to a particular solid form, such as the crystal forms described herein. These characterization data may be obtained by various techniques known to those skilled in the art, including for example X-ray powder diffraction, differential scanning calorimetry, thermal gravimetric analysis, and nuclear magnetic resonance spectroscopy. The data provided by these techniques may be used to identify a particular solid form. One skilled in the art can determine whether a solid form is one of the forms described herein by performing one of these characterization techniques and determining whether the resulting data is "substantially similar" to the reference data provided herein, which is identified as being characteristic of a particular solid form. Characterization data that is "substantially similar" to those of a reference solid form is understood by those skilled in the art to correspond to the same solid form as the reference solid form. In analyzing whether data is "substantially similar," a person of ordinary skill in the art understands that particular characterization data points may vary to a reasonable extent while still describing a given solid form, due to, for example, experimental error and routine sample-to-sample analysis.

In some embodiments, provided herein are solid forms comprising a compound of formula (I), or a pharmaceutically acceptable salt thereof:

(I)

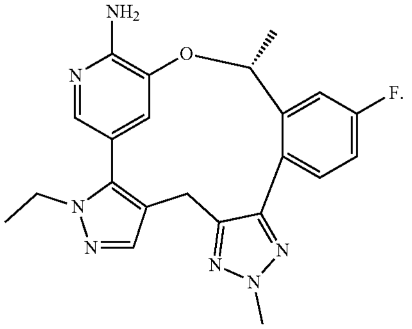

In one embodiment, the solid form comprising a compound of formula (I) can be a crystalline form, a partially crystalline form, or a mixture of crystalline form(s) and amorphous form(s). In one embodiment, provided herein is a solid form comprising a crystalline form of a compound of formula (I). In one embodiment, the solid form comprises a salt, solvate (e.g., hydrate), or solvate of a salt thereof, or a mixture thereof. In another embodiment, the solid form is an amorphous form. In one embodiment, the solid form is substantially pure. In one embodiment, the solid form is substantially chemically pure. In one embodiment, the solid form is substantially physically pure. In one embodiment, the solid form has a chemical and/or physical purity of at least about 95% w/w. In one embodiment, the solid form has a chemical and/or physical purity of at least about 96% w/w. In one embodiment, the solid form has a chemical and/or physical purity of at least about 97% w/w. In one embodiment, the solid form has a chemical and/or physical purity of about 99.71% w/w. In one embodiment, the solid form has a chemical and/or physical purity of about 99.9% w/w. In one embodiment, the solid form is substantially enantiomerically pure. In one embodiment, the solid form (e.g. Form 1) has an enantiomeric purity of at least about 98% (e.g. 99% or 99.5%). In one embodiment, the solid form (e.g. Form 1) has an enantiomeric purity of at least about 98.0%. In one embodiment, the solid form (e.g. Form 1) has an enantiomeric purity of at least about 98.5%. In one embodiment, the solid form (e.g. Form 1) has an enantiomeric purity of at least about 99.0%. In one embodiment, the solid form (e.g. Form 1) has an enantiomeric purity of at least about 99.5%. In one embodiment, the solid form (e.g. Form 1) has an enantiomeric purity of about 99.9%. In one embodiment, the solid form (e.g. Form 1) has an enantiomeric purity of about 100%. The compound of formula (I) is described in international patent application No. PCT/US2021/030842, the entirety of which is incorporated herein by reference.

5.2.1. Solid Forms of Free Base of Compound 1

Provided herein is a solid form comprising a compound of Formula (I):

(I)

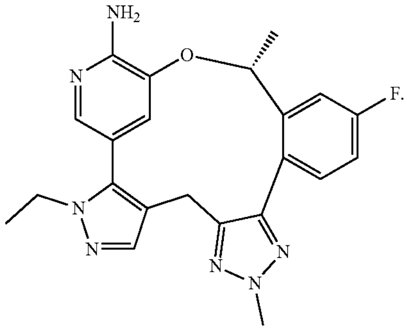

In one embodiment, provided herein is a solid form comprising a free base of Compound 1. In one embodiment, provided herein is a solid form comprising an anhydrous free base of Compound 1. In one embodiment, provided herein is a solid form comprising a solvate of a free base of Compound 1. In one embodiment, provided herein is a solid form comprising a hydrate of a free base of Compound 1. In one embodiment, provided herein is a solid form comprising a MTBE, MEK, ACN, or 1,4-dioxane solvate of a free base of Compound 1.

As used herein, "Compound 1," "free base of Compound 1," "free base of a compound of formula (I)," and "Compound 1 free base" are used interchangeably.

It is contemplated that Compound 1, or a stereoisomer, or a mixture of stereoisomers thereof, or a pharmaceutically acceptable salt thereof, can exist in a variety of solid forms. Such solid forms include crystalline solids (e.g., crystalline forms of anhydrous Compound 1, crystalline forms of hydrates of Compound 1, and crystalline forms of solvates of Compound 1), amorphous solids, or mixtures of crystalline and amorphous solids. In one embodiment, the solid form is substantially crystalline. In one embodiment, the solid form is crystalline.

In some embodiments, the molar ratio of Compound 1 to the solvent (e.g. water) in the solid form ranges from about 10:1 to about 1:10. In some embodiments, the molar ratio of Compound 1 to the solvent (e.g. water) in the solid form ranges from about 5:1 to about 1:5. In some embodiments, the molar ratio of Compound 1 to the solvent (e.g. water) in the solid form ranges from about 3:1 to about 1:3. In some embodiments, the molar ratio of Compound 1 to the solvent (e.g. water) in the solid form ranges from about 2:1 to about 1:2. In one embodiment, the molar ratio is about 1:2 (i.e., bis-solvate or dehydrate). In another embodiment, the molar ratio is about 1:1 (i.e., mono-solvate or mono-hydrate). In yet another embodiment, the molar ratio is about 2:1 (i.e., hemi-solvate or hemi-hydrate).

5.2.1.1 Form 1 of Compound 1

In one embodiment, provided herein is a Form 1 of Compound 1. A representative XRPD pattern of Form 1 of Compound 1 is provided in FIG. 1.

In one embodiment, provided herein is a solid form comprising a free base of Compound 1, characterized by 1, 2, 3, 4, 5, 6, 7, 8, 9, 10, 11, 12, 13, 14, 15, 16, 17, 18, 19, 20, 21, 22 or all of the XRPD peaks located at approximately the following positions (e.g., degrees 2θ±0.2) when measured using Cu Kα radiation: 10.7, 12.0, 12.2, 13.9, 15.0, 17.4, 18.4, 18.6, 20.8, 21.2, 21.3, 21.6, 21.7, 23.3, 23.5, 24.0, 25.2, 26.0, 26.2, 26.7, 27.7, 28.0, and 29.6° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form (e.g. a crystalline form) comprising a free base of Compound 1, characterized by an XRPD pattern, when measured using Cu Kα radiation, comprising at least three peaks selected from the group consisting of approximately (e.g., ±0.2°) 10.7, 15.0, 17.4, 20.8, 21.2, 21.3, 21.6, 24.0, and 25.2° 2θ. In one embodiment, the solid form is characterized by an XRPD pattern comprising at least four peaks selected from the group consisting of approximately (e.g., ±0.2°) 10.7, 15.0, 17.4, 20.8, 21.2, 21.3, 21.6, 24.0, and 25.2° 2θ. In one embodiment, the solid form is characterized by an XRPD pattern comprising at least five peaks selected from the group consisting of approximately (e.g., ±0.2°) 10.7, 15.0, 17.4, 20.8, 21.2, 21.3, 21.6, 24.0, and 25.2° 2θ.

In one embodiment, provided herein is a solid form (e.g. a crystalline form) comprising a free base of Compound 1, characterized by an XRPD pattern, when measured using Cu Kα radiation, comprising at least three peaks selected from the group consisting of approximately (e.g., ±0.2°) 10.7, 12.0, 12.2, 13.9, 15.0, 17.4, 18.4, 20.8, 21.2, 21.3, 21.6, 24.0, and 25.2° 2θ. In one embodiment, the solid form is characterized by an XRPD pattern comprising at least four peaks selected from the group consisting of approximately (e.g., ±0.2°) 10.7, 12.0, 12.2, 13.9, 15.0, 17.4, 18.4, 20.8, 21.2, 21.3, 21.6, 24.0, and 25.2° 2θ. In one embodiment, the solid form is characterized by an XRPD pattern comprising at least five peaks selected from the group consisting of approximately (e.g., ±0.2°) 10.7, 12.0, 12.2, 13.9, 15.0, 17.4, 18.4, 20.8, 21.2, 21.3, 21.6, 24.0, and 25.2° 2θ.

In one embodiment, provided herein is a solid form (e.g. a crystalline form) comprising a free base of Compound 1, characterized by an XRPD pattern comprising peaks at approximately (e.g., ±0.2°) 10.7, 15.0, and 21.2° 2θ. In one embodiment, the XRPD pattern further comprises peaks at approximately (e.g., ±0.2°) 17.4 and 21.3° 2θ. In one embodiment, the XRPD pattern further comprises peaks at approximately (e.g., ±0.2°) 12.0, 12.2, and 13.9° 2θ. In another embodiment, the XRPD pattern further comprises peaks at approximately (e.g., ±0.2°) 21.6 and 24.0° 2θ. In one embodiment, the XRPD pattern comprises peaks at approximately (e.g., ±0.2°) 10.7, 15.0, 17.4, 20.8, 21.2, 21.3, 21.6, 24.0 and 25.2° 2θ. In one embodiment, the XRPD pattern comprises peaks at approximately (e.g., ±0.2°) 10.7, 12.0, 12.2, 13.9, 15.0, 17.4, 18.4, 20.8, 21.2, 21.3, 21.6, 24.0 and 25.2°20.

In one embodiment, provided herein is a solid form comprising a free base of Compound 1, characterized by an XRPD pattern that matches the XRPD pattern depicted in FIG. 1.

In one embodiment, an XRPD pattern described herein is obtained using Cu Kα radiation. In one embodiment, the XRPD pattern is measured by XRPD using Cu Kα radiation comprising $K\alpha_1$ radiation having a wavelength of 1.5406 Å and $K\alpha_2$ radiation having a wavelength of 1.5444 Å, wherein the $K\alpha_1$:$K\alpha_2$ ratio is 0.5.

Figure 3:
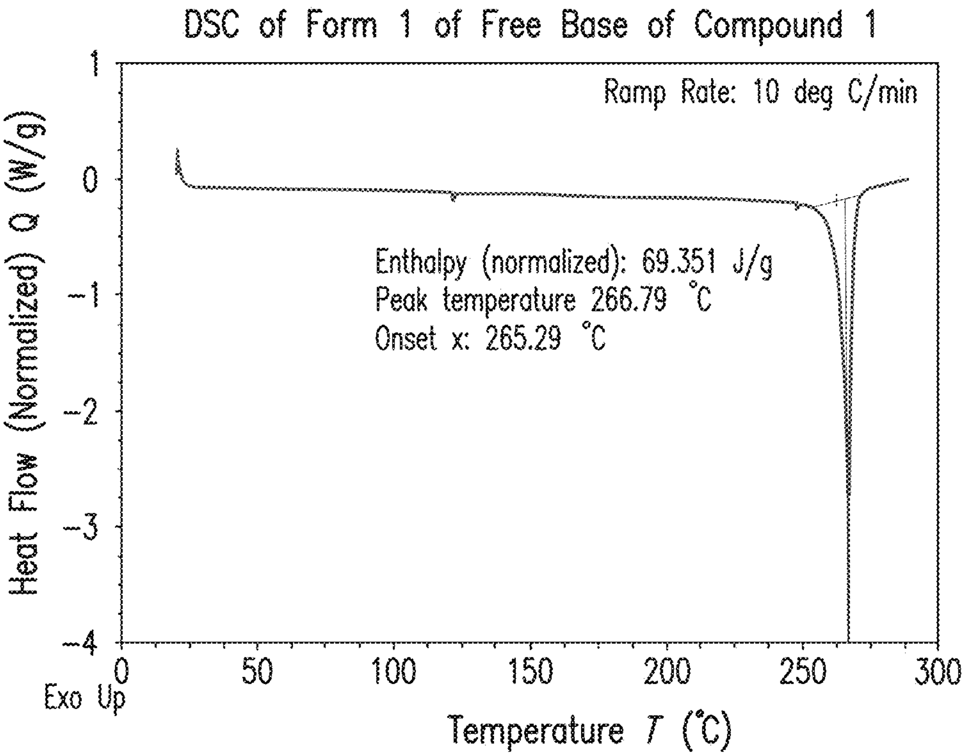
FIG. 3 is a representative and differential scanning calorimetry (DSC) thermogram of Form 1 of free base of Compound 1.

A representative DSC thermogram of Form 1 is provided in FIG. 3. In one embodiment, provided herein is a solid form comprising a free base of Compound 1, which exhibits, as characterized by DSC, a thermal event (endothermic) with an onset temperature of about 265° C. (e.g. ±2°). In one embodiment, the thermal event also has a peak temperature of about 267° C. (e.g. ±2°). In one embodiment, without being bound by a particular theory, the thermal event corresponds to melting. In one embodiment, the solid form is characterized by a DSC thermogram that matches the DSC thermogram depicted in FIG. 3. In one embodiment, the DSC thermogram is as measured by DSC using a scanning rate of about 10° C./minute.

In another embodiment, the solid form has a melting point at about 270° C. (e.g. ±2°).

Figure 2:
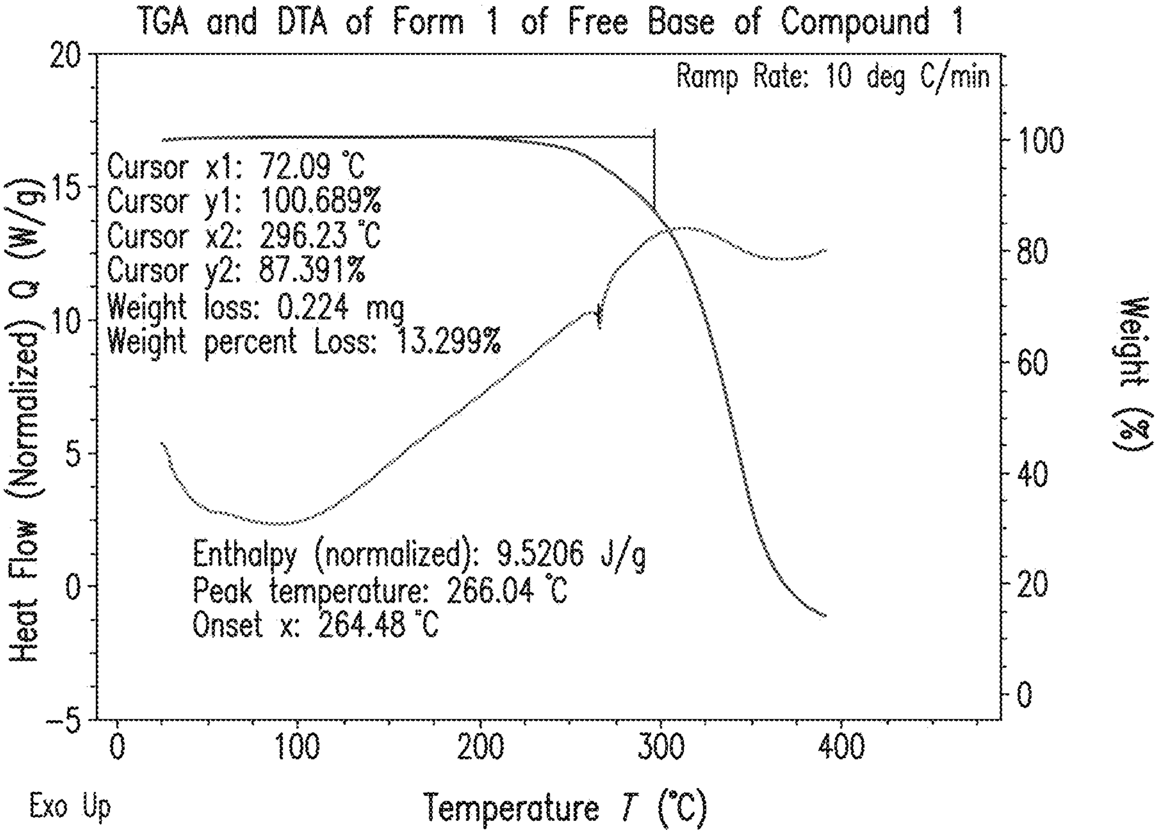
FIG. 2 is a representative integrated thermal gravimetric analysis (TGA) and differential thermal analysis (DTA) thermograms for Form 1 of free base of Compound 1.

A representative overlay of TGA/DSC thermograms of Form 1 is provided in FIG. 2. In one embodiment, provided herein is a solid form comprising a free base of Compound 1, which exhibits substantially no weight loss upon heating from about 20° C. to about 200° C. In one embodiment, provided herein is a solid form comprising a free base of Compound 1, which exhibits decomposition upon heating from about 200° C. (e.g. ±2°). In one embodiment, the solid form is characterized by a TGA thermogram that matches the TGA thermogram depicted in FIG. 2. In one embodiment, the TGA thermogram is as measured using a heating rate of about 10° C./minute.

Figure 4:
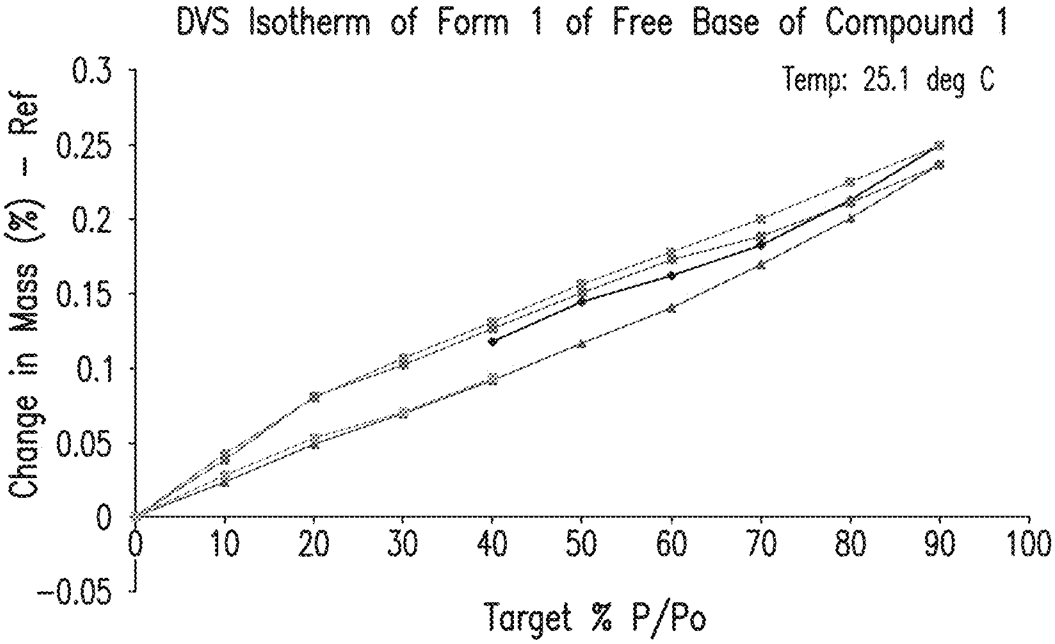
FIG. 4 is a representative dynamic vapor sorption (DVS) isotherm of Form 1 of free base of Compound 1.

A representative DVS isotherm of Form 1 is provided in FIG. 4. In one embodiment, provided herein is a solid form comprising a free base of Compound 1, which exhibits a weight increase of about 0.25% (e.g. ±0.05%) when subjected to an increase in relative humidity from about 0 to about 90% relative humidity. In one embodiment, the solid form is characterized by a DVS isotherm that matches the DVS isotherm depicted in FIG. 4. In one embodiment, the DVS isotherm is as measured at about 25° C.

Figure 5:
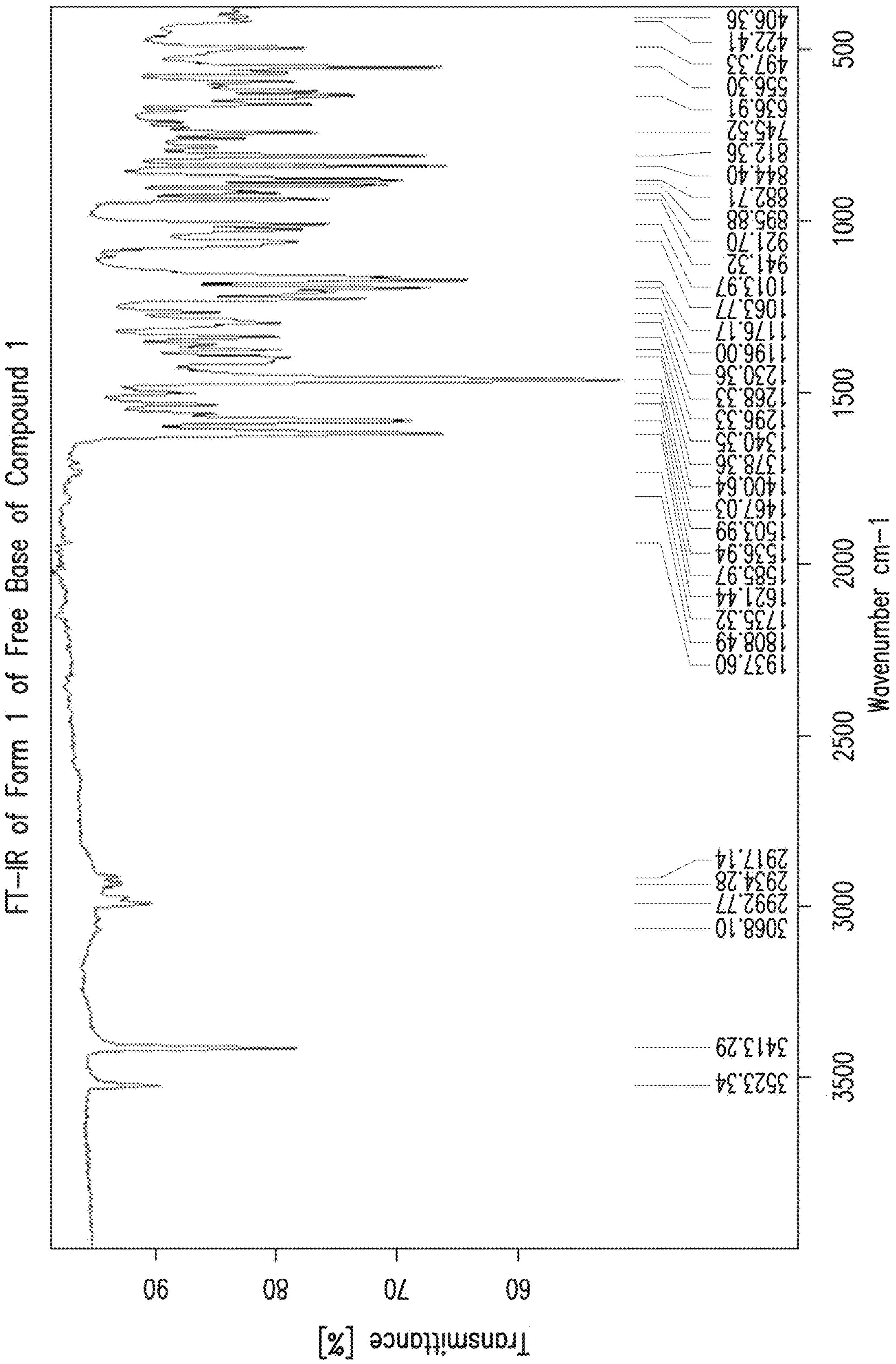
FIG. 5 is a representative fourier-transform infrared spectrum (FT-IR) spectrum of Form 1 of free base of Compound 1.

A representative FT-IR spectrum of Form 1 is provided in FIG. 5. In one embodiment, provided herein is a solid form comprising a free base of Compound 1, characterized by an FT-IR spectrum comprising resonances at approximately 1621, 3523, 3413 (e.g. ±5) $cm^{-1}$. In one embodiment, the FT-IR spectrum comprises resonances at approximately at least three peaks selected from the group consisting of 1176, 1400, 1537, 1621, 3413, and 3523 (e.g. ±5) $cm^{-1}$. In one embodiment, provided herein is a solid form comprising a free base of Compound 1, characterized by an FT-IR spectrum that matches the FT-IR spectrum depicted in FIG. 5.

In one embodiment, provided herein is a solid form comprising a free base of Compound 1 having approximately unit cell dimensions of: a=8.4 Å, b=8.4 Å, c=14.9 Å, α=90°, β=106°, and γ=90°. In one embodiment, Form 1 has approximately unit cell dimensions of: a=8.43 Å, b=8.44 Å, c=14.91 Å, α=90°, β=105.6°, and γ=90°. In one embodiment, Form 1 has approximately unit cell dimensions of: a=8.431 Å, b=8.441 Å, c=14.914 Å, α=90°, β=105.55°, and γ=90°. In one embodiment, Form 1 has a unit cell of a space group of $P2_1$. In one embodiment, Form 1 has a volume of about 1022.7 $Å^3$/cell. In one embodiment, Form 1 has a Z value of 2. In one embodiment, Form 1 has a density of about 1.362 $g/cm^3$.

In one embodiment, provided herein is a solid form comprising a free base of Compound 1 which is anhydrous. In one embodiment, the solid form is a crystalline anhydrous free base of Compound 1. In one embodiment, the solid form is substantially free of amorphous Compound 1. In one embodiment, the solid form is substantially free of other crystalline forms of Compound 1. In one embodiment, the solid form is substantially free of salts of Compound 1. In one embodiment, the solid form is not solvated. In one embodiment, one or more residual solvent (e.g., small amount of ethyl acetate) may be present in the solid form, but the residual solvent does not form a solvate of Compound 1. In one embodiment, the solid form is substantially pure. In one embodiment, the solid form is substantially chemically pure. In one embodiment, the solid form is substantially physically pure. In one embodiment, the solid form has a chemical and/or physical purity of at least about 97% w/w. In one embodiment, the solid form has a chemical and/or physical purity of at least about 98% w/w. In one embodiment, the solid form has a chemical and/or physical purity of at least about 99% w/w. In one embodiment, the solid form has a chemical and/or physical purity of about about 99.71% w/w. In one embodiment, the solid form has a chemical and/or physical purity of about 99.9% w/w. In one embodiment, the solid form has an enantiomeric purity of at least about 98% (e.g. 99% or 99.5%). In one embodiment, the solid form has an enantiomeric purity of at least about about 98.5%. In one embodiment, the solid form has an enantiomeric purity of at least about about 99.0%. In one embodiment, the solid form has an enantiomeric purity of at least about about 99.5%. In one embodiment, the solid form has an enantiomeric purity of about 99.9%. In one embodiment, the solid form (e.g. Form 1) has an enantiomeric purity of about 100%. In one embodiment, the purity is determined by HPLC or chiral HPLC (% area).

In one embodiment, the solid form is non-hygroscopic. In one embodiment, the solid form is stable after storage at 40° C./75% RH, 25° C./60% RH and/or 80° C. for at least 7 days. In embodiment, the solid form is stable to compression at about 100 MPa and/or about 250 MPa for at least about 60 seconds.

In one embodiment, provided herein is a solid form comprising Form 1 of a free base of Compound 1 and amorphous free base of Compound 1. In one embodiment, provided herein is a solid form comprising Form 1 of a free base Compound 1 and one or more other crystalline forms of a free base of Compound 1 provided herein. In one embodiment, provided herein is a solid form comprising Form 1 of a free base Compound 1 and Form 7 of a free base of Compound 1 provided herein.

All of the combinations of the above embodiments are encompassed by this application.

5.2.1.2 Form 2 of Compound 1

In one embodiment, provided herein is a Form 2 of Compound 1. A representative XRPD pattern of Form 2 of Compound 1 is provided in FIG. 7.

In one embodiment, provided herein is a solid form comprising a free base of Compound 1, characterized by 1, 2, 3, 4, 5, 6, 7, 8, 9, 10, 11, 12, 13, 14, 15, 16, 17, 18, 19, 20, 21, 22, 23 or all of the XRPD peaks located at approximately the following positions (e.g., degrees 2θ±0.2) when measured using Cu Kα radiation: 6.8, 8.6, 10.0, 10.7, 13.8, 14.0, 14.9, 15.9, 17.3, 18.3, 18.9, 19.4, 20.1, 20.4, 20.8, 21.2, 21.7, 22.9, 23.3, 23.8, 24.2, 24.8, 25.1, and 30.4° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a free base of Compound 1, characterized by an XRPD pattern, when measured using Cu Kα radiation, comprising at least three peaks selected from the group consisting of approximately (e.g., ±0.2°) 6.8, 8.6, 10.0, 13.8, 14.0, 20.1, 20.8, 21.2, and 22.9° 2θ. In one embodiment, the solid form is characterized by an XRPD pattern comprising at least four peaks selected from the group consisting of approximately (e.g., ±0.2°) 6.8, 8.6, 10.0, 13.8, 14.0, 20.1, 20.8, 21.2, and 22.9° 2θ. In one embodiment, the solid form is characterized by an XRPD pattern comprising at least five peaks selected from the group consisting of approximately (e.g., ±0.2°) 6.8, 8.6, 10.0, 13.8, 14.0, 20.1, 20.8, 21.2, and 22.9° 2θ.

In one embodiment, provided herein is a solid form comprising a free base of Compound 1, characterized by an XRPD pattern comprising peaks at approximately (e.g., ±0.2°) 8.6, 14.0, and 20.8° 2θ. In one embodiment, the solid form is characterized by an XRPD pattern further comprising peaks at approximately (e.g., 0.2°) 6.8 and 13.8° 2θ. In one embodiment, the solid form is characterized by an XRPD pattern further comprising peaks at approximately (e.g., ±0.2°) 10.0 and 21.2° 2θ. In one embodiment, the XRPD pattern comprises peaks at approximately (e.g., ±0.2°) 6.8, 8.6, 10.0, 13.8, 14.0, 20.1, 20.8, 21.2 and 22.9° 2θ.

Figure 7:
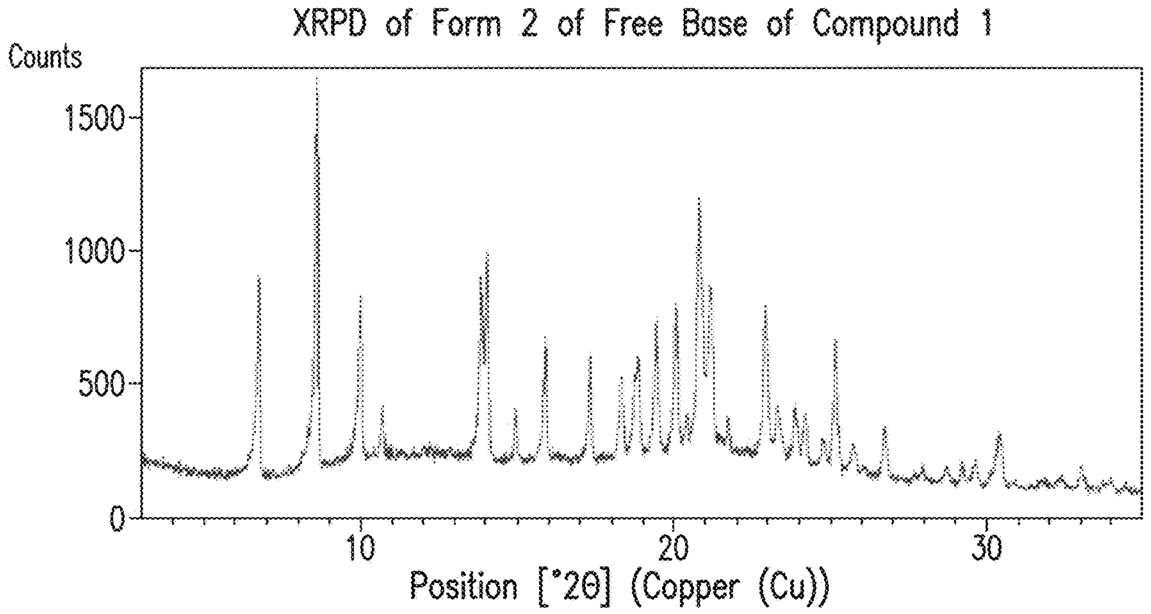
FIG. 7 is a representative XRPD pattern of Form 2 of free base of Compound 1.

In one embodiment, provided herein is a solid form comprising a free base of Compound 1, characterized by an XRPD pattern that matches the XRPD pattern depicted in FIG. 7.

In one embodiment, an XRPD pattern described herein is obtained using Cu Kα radiation. In one embodiment, the XRPD pattern is measured by XRPD using Cu Kα radiation comprising Kα, radiation having a wavelength of 1.5406 Å and $K\alpha_2$ radiation having a wavelength of 1.5444 Å, wherein the $K\alpha_1$:$K\alpha_2$ ratio is 0.5.

Figure 8:
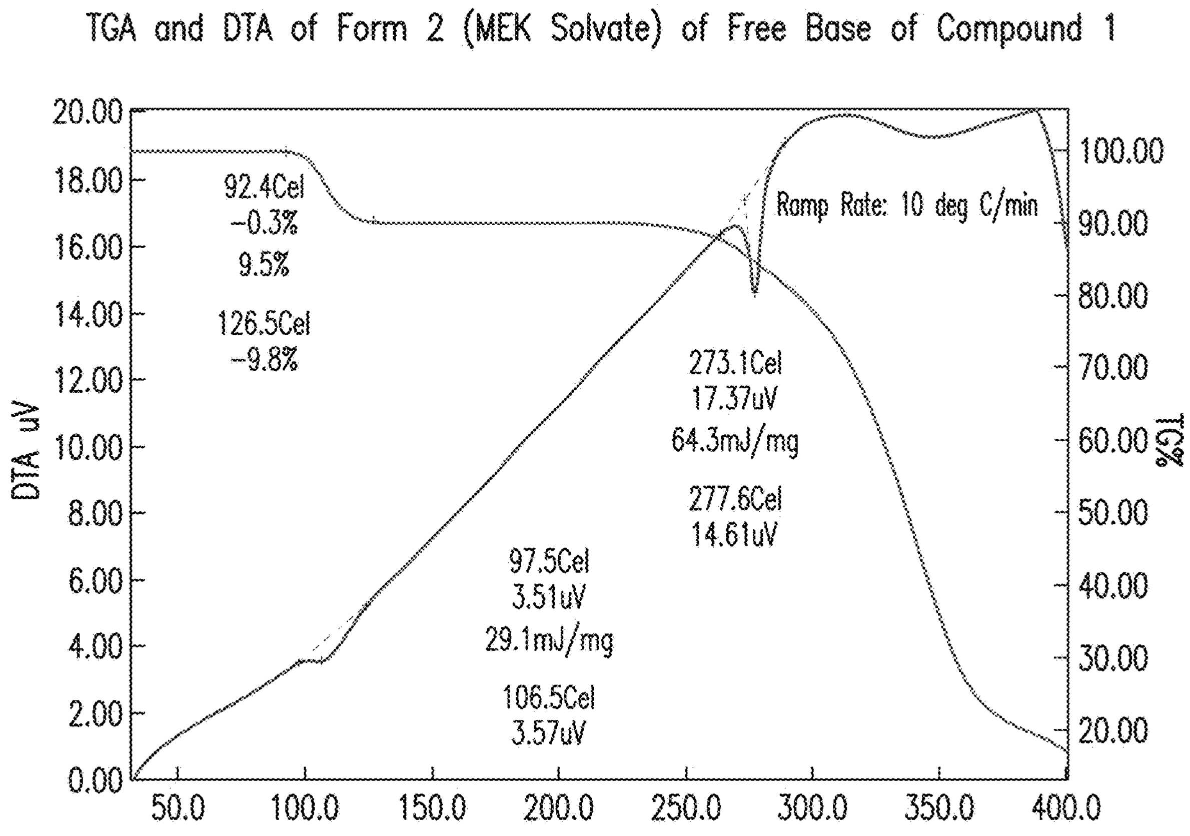
FIG. 8 is a representative overlay of TGA and differential thermal analysis (DTA) thermograms for Form 2 of free base of Compound 1.

A representative overlay of TGA/DTA thermograms of Form 2 is provided in FIG. 8. In one embodiment, provided herein is a solid form comprising a free base of Compound 1, which exhibits, as characterized by DTA, a thermal event (endo) with an onset temperature of about 98° C. (e.g. ±2°). In one embodiment, the solid form is characterized by a DTA thermogram that matches the DTA thermogram depicted in FIG. 8. In one embodiment, provided herein is a solid form comprising a free base of Compound 1, which exhibits a weight loss of about 9.8% upon heating from about 90° C. to about 130° C. In one embodiment, the solid form is characterized by a TGA thermogram that matches the TGA thermogram depicted in FIG. 8.

Figure 9:
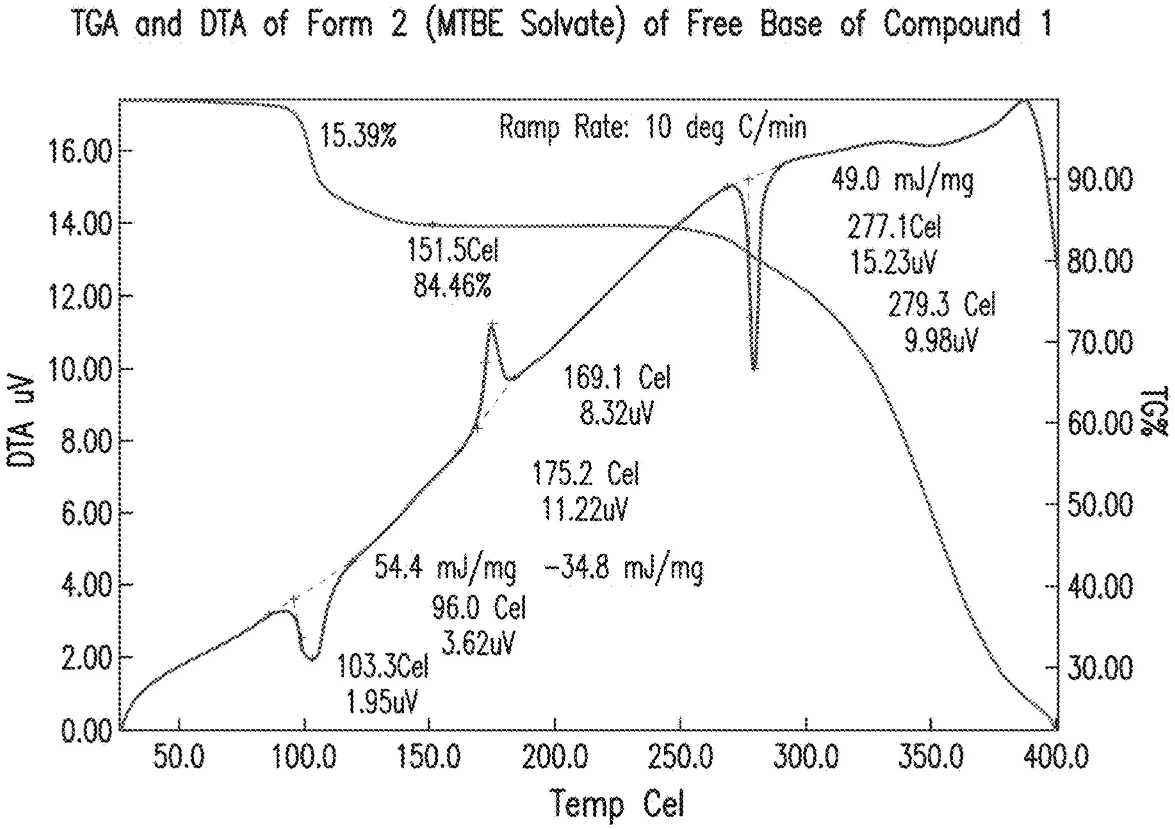
FIG. 9 is another representative overlay of TGA and differential thermal analysis (DTA) thermograms for of Form 2 of free base of Compound 1.

Another representative overlay of TGA/DTA thermograms of Form 2 is provided in FIG. 9. In one embodiment, provided herein is a solid form comprising a free base of Compound 1, which exhibits, as characterized by DTA, a thermal event (endo) with an onset temperature of about 96° C. (e.g. ±2°) and/or a thermal event (exo) with an onset temperature of about 169° C. (e.g. ±2°). In one embodiment, the solid form is characterized by a DTA thermogram is substantially in accordance with that depicted in FIG. 9. In another embodiment, provided herein is a solid form, which exhibits a weight loss of about 15.4% upon heating from about 50° C. to about 170° C. In one embodiment, the solid form is characterized by a TGA thermogram that matches the TGA thermogram depicted in FIG. 9.

In one embodiment, the DTA thermogram is as measured by DTA using a scanning rate of about 10° C./minute. In one embodiment, the TGA thermogram is as measured using a heating rate of about 10° C./minute.

Figure 10:
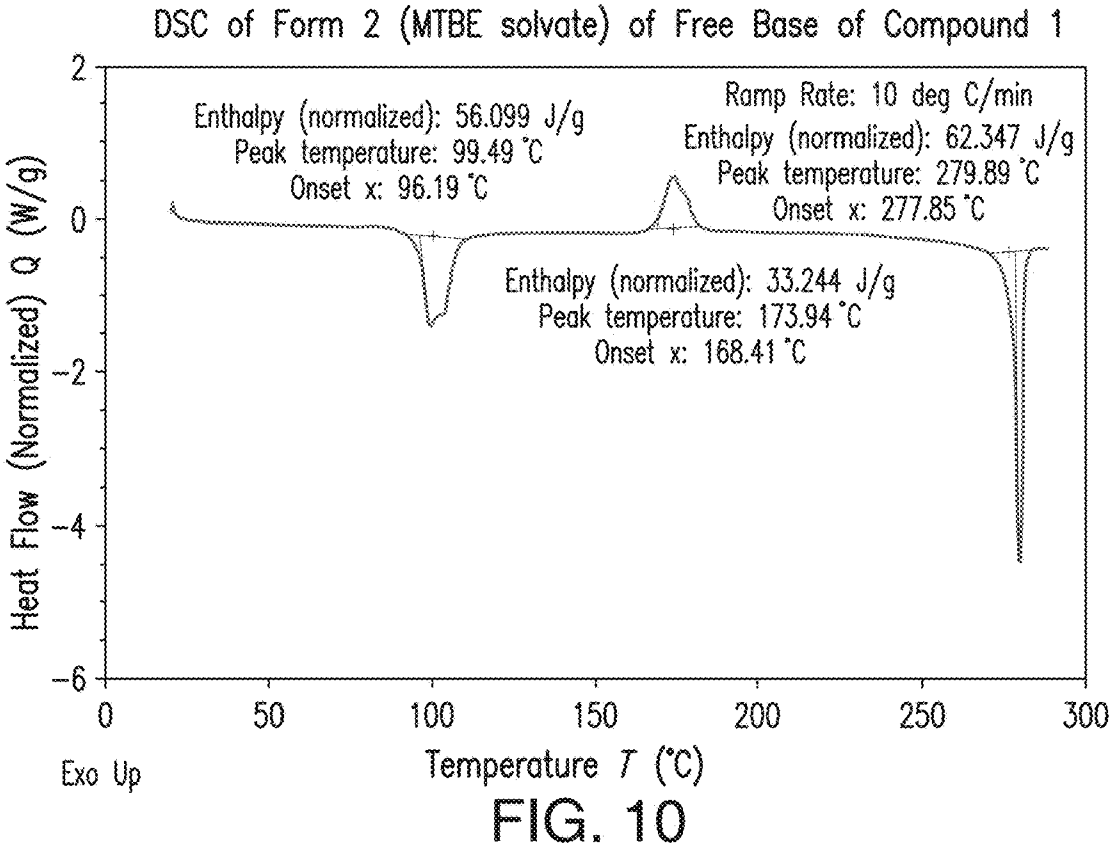
FIG. 10 is a representative DSC thermogram of Form 2 of free base of Compound 1.

A representative DSC thermograms of Form 2 is provided in FIG. 10. In one embodiment, provided herein is a solid form comprising a free base of Compound 1, which exhibits, as characterized by DSC, a thermal event (endo) with an onset temperature of about 96° C. (e.g. ±2°). In one embodiment, the thermal event also has a peak temperature of about 99° C. (e.g. ±2°). In one embodiment, provided herein is a solid form comprising a free base of Compound 1, which exhibits, as characterized by DSC, a thermal event (exo) with an onset temperature of about 168° C. (e.g. ±2°). In one embodiment, the thermal event also has a peak temperature of about 174° C. (e.g. ±2°). In one embodiment, the solid form is characterized by a DSC thermogram that matches the DSC thermogram depicted in FIG. 10. In one embodiment, the DSC thermogram is as measured by DSC using a scanning rate of about 10° C./minute.

Figure 11:
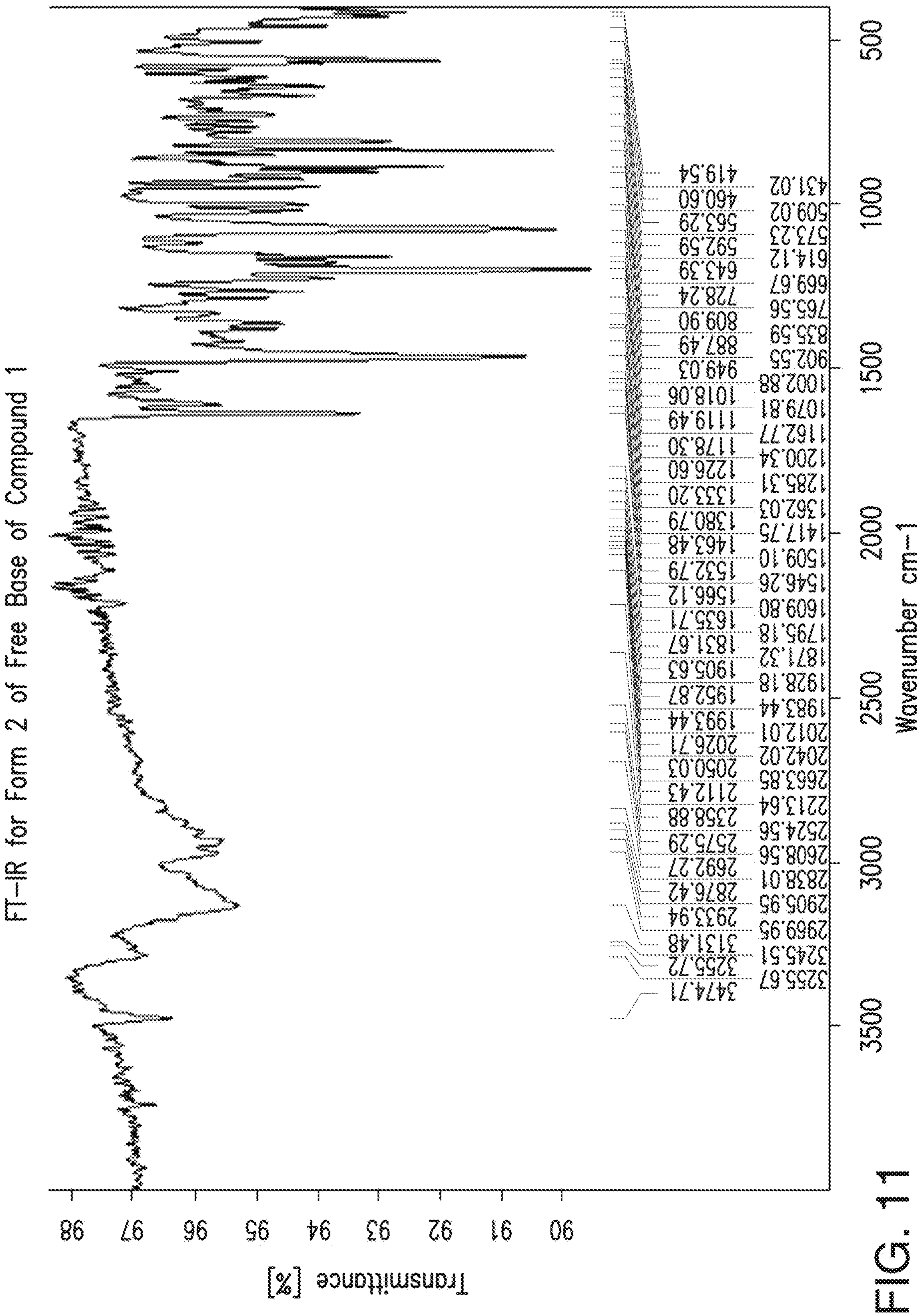
FIG. 11 is a representative FT-IR spectrum of Form 2 of free base of Compound 1.

A representative FT-IR spectrum of Form 2 is provided in FIG. 11. In one embodiment, provided herein is a solid form comprising a free base of Compound 1, characterized by an FT-IR spectrum that matches the FT-IR spectrum depicted in FIG. 11.

In some embodiments, provided herein is a solid form comprising a free base of Compound 1 which is a crystalline solvate of free base of Compound 1. In some embodiments, the solid form is substantially free of amorphous Compound 1. In some embodiments, the solid form is substantially free of other solid forms (e.g., crystalline forms) of Compound 1. In some embodiments, the solid form is substantially free of salts of Compound 1. In some embodiments, the solid form is provided as substantially pure. In some embodiments, the solid form is substantially chemically pure. In some embodiments, the solid form is substantially physically pure. In one embodiment, the solid form is non-hygroscopic.

In one embodiment, the solid form is stable after storage at 40° C./75% RH or 25° C./60% RH for at least 7 days. In one embodiment, the solid form undergoes a form change upon heating. In one embodiment, the solid form undergoes a form change after being stored at about 80° C. In one embodiment, the form change results in Form 7 of a free base of Compound 1.

In one embodiment, provided herein is a solid form comprising a free base of Compound 1, wherein the molar ratio of Compound 1 to the solvent ranges from about 1:0.5 to about 1:2. In one embodiment, the molar ratio of Compound 1 to the solvent ranges from about 1:0.6 to about 1:1.35. In one embodiment, the molar ratio of Compound 1 to the solvent ranges from about 1:0.75 to about 1:1. In one embodiment, the molar ratio of Compound 1 to the solvent is about 1:0.6. In one embodiment, the molar ratio of Compound 1 to the solvent is about 1:0.9. In one embodiment, the molar ratio of Compound 1 to the solvent is about 1:1.3. In one embodiment, the molar ratio of Compound 1 to the solvent is about 1:1.

In one embodiment, provided herein is a solid form comprising a free base of Compound 1 which is an isostructural solvate. In one embodiment, provided herein is a solid form comprising a free base of Compound 1 which is a methyl ethyl ketone (MEK) solvate of free base of Compound 1. In one embodiment, the molar ratio of Compound 1 to MEK is about 1:0.6. In another embodiment, the solid form is a methyl t-butyl ether solvate of free base of Compound 1. In one embodiment, the molar ratio of Compound 1 to methyl t-butyl ether is about 1:0.9. In one embodiment, the molar ratio of Compound 1 to methyl t-butyl ether is about 1:1.3. In another embodiment, the solid form is a 1-butanol, 2-methyl-1-propanol, 3-methyl-1-butanol, acetone, cyclopentyl methyl ether, or tAmyl alcohol solvate of free base of Compound 1.

In one embodiment, provided herein is a solid form comprising Form 2 of a free base of Compound 1 and amorphous free base of Compound 1. In one embodiment, provided herein is a solid form comprising Form 2 of a free base Compound 1 and one or more other crystalline forms of a free base of Compound 1 provided herein.

All of the combinations of the above embodiments are encompassed by this application.

5.2.1.3 Form 3 of Compound 1

In one embodiment, provided herein is a Form 3 of Compound 1. A representative XRPD pattern of Form 3 of Compound 1 is provided in FIG. 12.

In one embodiment, provided herein is a solid form comprising a free base of Compound 1, characterized by 1, 2, 3, 4, 5, 6, 7, 8, 9, 10, 11, 12, 13, 14, 15, 16 or all of the XRPD peaks located at approximately the following positions (e.g., degrees 2θ±0.2) when measured using Cu Kα radiation: 9.7, 11.4, 11.8, 12.5, 13.4, 14.7, 16.2, 16.9, 18.9, 19.3, 19.5, 20.9, 21.9, 22.5, 22.9, 23.3, and 24.3° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a free base of Compound 1, characterized by an XRPD pattern, when measured using Cu Kα radiation, comprising at least three peaks selected from the group consisting of approximately (e.g., ±0.2°) 9.7, 11.4, 13.4, 16.2, 18.9, 19.5, 20.9, 22.5, 22.9, and 23.3° 2θ. In one embodiment, the solid form is characterized by an XRPD pattern comprising at least four peaks selected from the group consisting of approximately (e.g., ±0.2°) 9.7, 11.4, 13.4, 16.2, 18.9, 19.5, 20.9, 22.5, 22.9, and 23.3° 2θ. In one embodiment, the solid form is characterized by an XRPD pattern comprising at least five peaks selected from the group consisting of approximately (e.g., ±0.2°) 9.7, 11.4, 13.4, 16.2, 18.9, 19.5, 20.9, 22.5, 22.9, and 23.3° 2θ.

In one embodiment, provided herein is a solid form comprising a free base of Compound 1, characterized by an XRPD pattern comprising peaks at approximately (e.g., ±0.2°) 13.4, 19.5, and 20.9° 2θ. In one embodiment, the solid form is characterized by an XRPD pattern further comprising peaks at approximately (e.g., ±0.2°) 11.4 and 22.9° 2θ. In one embodiment, the solid form is characterized by an XRPD pattern further comprising peaks at approximately (e.g., ±0.2°) 9.7 and 16.2° 2θ. In one embodiment, the XRPD pattern comprises peaks at approximately (e.g., ±0.2°) 9.7, 11.4, 13.4, 16.2, 18.9, 19.5, 20.9, 22.5, 22.9, and 23.3° 2θ.

Figure 12:
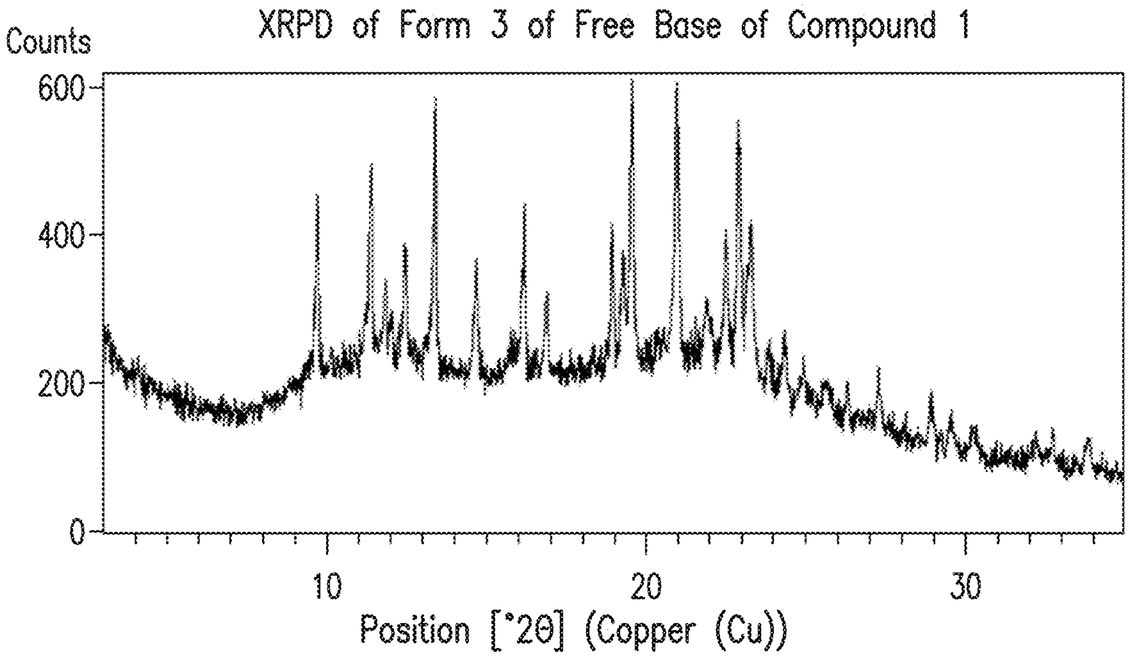
FIG. 12 is a representative XRPD pattern of Form 3 of free base of Compound 1.

In one embodiment, provided herein is a solid form comprising a free base of Compound 1, characterized by an XRPD pattern that matches the XRPD pattern depicted in FIG. 12.

In one embodiment, an XRPD pattern described herein is obtained using Cu Kα radiation. In one embodiment, the XRPD pattern is measured by XRPD using Cu Kα radiation comprising $K\alpha_1$ radiation having a wavelength of 1.5406 Å and $K\alpha_2$ radiation having a wavelength of 1.5444 Å, wherein the $K\alpha_1$:$K\alpha_2$ ratio is 0.5.

Figure 13:
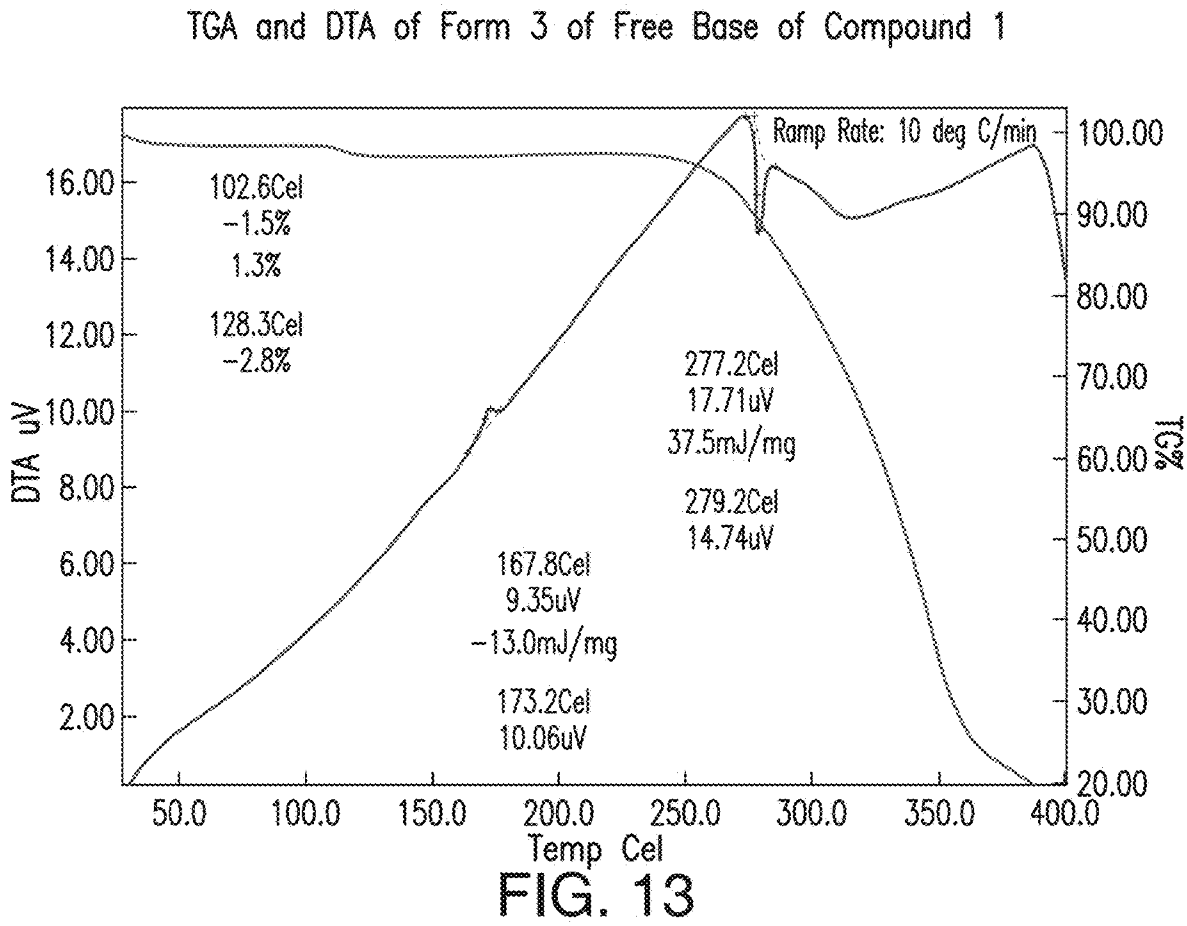
FIG. 13 is a representative overlay of TGA and DTA thermograms for Form 3 of free base of Compound 1.

A representative overlay of TGA/DTA thermograms of Form 3 is provided in FIG. 13. In one embodiment, provided herein is a solid form comprising a free base of Compound 1, which exhibits, as characterized by DTA, a thermal event with an onset temperature of about 168° C. (e.g. ±2°). In one embodiment, the solid form is characterized by a DTA thermogram that matches the DTA thermogram depicted in FIG. 13. In one embodiment, the DTA thermogram is as measured by DTA using a scanning rate of about 10° C./minute.

In one embodiment, provided herein is a solid form comprising a free base of Compound 1, which exhibits a weight loss of about 1.3% upon heating from about 100° C. to about 130° C. In one embodiment, the solid form is characterized by a TGA thermogram that matches the TGA thermogram depicted in FIG. 13. In one embodiment, the TGA thermogram is as measured using a heating rate of about 10° C./minute.

In some embodiments, provided herein is a solid form comprising a free base of Compound 1, which is a crystalline solvate of free base of Compound 1. In some embodiments, the solid form is substantially free of amorphous Compound 1. In some embodiments, the solid form is substantially free of other solid forms (e.g., crystalline forms) of Compound 1. In some embodiments, the solid form is substantially free of salts of Compound 1. In some embodiments, the solid form is provided as substantially pure. In some embodiments, the solid form is substantially chemically pure. In some embodiments, the solid form is substantially physically pure.

In one embodiment, provided herein is a solid form comprising a free base of Compound 1 which is an isostructural solvate. In one embodiment, provided herein is a solid form comprising a free base of Compound 1, wherein the molar ratio of Compound 1 to the solvent ranges from about 1:0.2 to about 1:1. In one embodiment, the solid form is a hydrate of free base of Compound 1. In one embodiment, the solid form is a hemihydrate of free base of Compound 1. In another embodiment, the solid form is a methanol solvate of a free base of Compound 1. In yet another embodiment, the solid form is an isopropyl acetate solvate of a free base of Compound 1.

In one embodiment, provided herein is a solid form comprising Form 3 of a free base of Compound 1 and amorphous free base of Compound 1. In one embodiment, provided herein is a solid form comprising Form 3 of a free base Compound 1 and one or more other crystalline forms of a free base of Compound 1 provided herein.

All of the combinations of the above embodiments are encompassed by this application.

5.2.1.4 Form 4 of Compound 1

In one embodiment, provided herein is a Form 4 of Compound 1. A representative XRPD pattern of Form 4 of Compound 1 is provided in FIG. 14.

In one embodiment, provided herein is a solid form comprising a free base of Compound 1, characterized by 1, 2, 3, 4, 5, 6, 7, 8, 9, 10, 11, 12, 13, 14, 15, 16, 17, 18, 19, 20, 21, 22, 23, 24, 25, 26, 27, 28 or all of the XRPD peaks located at approximately the following positions (e.g., degrees 2θ±0.2) when measured using Cu Kα radiation: 7.5, 7.6, 10.8, 12.0, 12.1, 12.7, 12.8, 15.0, 15.7, 18.4, 19.0, 19.3, 19.7, 20.0, 21.4, 21.8, 21.9, 22.0, 22.8, 23.9, 24.1, 24.3, 24.8, 25.1, 25.7, 29.1, and 30.2° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, solid form is characterized by 11 of the peaks. In one embodiment, solid form is characterized by all of the peaks.

In one embodiment, provided herein is a solid form comprising a free base of Compound 1, characterized by an XRPD pattern, when measured using Cu Kα radiation, comprising at least three peaks selected from the group consisting of approximately (e.g., ±0.2°) 12.0, 12.1, 12.7, 12.8, 15.0, 15.7, 18.4, 21.4, 21.9, 23.9 and 24.3° 2θ. In one embodiment, the solid form is characterized by an XRPD pattern comprising at least four peaks selected from the group consisting of approximately (e.g., ±0.2°) 12.0, 12.1, 12.7, 12.8, 15.0, 15.7, 18.4, 21.4, 21.9, 23.9 and 24.3° 2θ. In one embodiment, the solid form is characterized by an XRPD pattern comprising at least five peaks selected from the group consisting of approximately (e.g., ±0.2°) 12.0, 12.1, 12.7, 12.8, 15.0, 15.7, 18.4, 21.4, 21.9, 23.9 and 24.3° 2θ.

In one embodiment, provided herein is a solid form comprising a free base of Compound 1, characterized by an XRPD pattern comprising peaks at approximately (e.g., ±0.2°) 12.1, 12.7, and 18.4° 2θ. In one embodiment, the solid form is characterized by an XRPD pattern further comprising peaks at approximately (e.g., ±0.2°) 15.0 and 21.9° 2θ. In one embodiment, the solid form is characterized by an XRPD pattern further comprising peaks at approximately (e.g., ±0.2°) 23.9 and 24.3° 2θ. In one embodiment, the XRPD pattern comprises peaks at approximately (e.g., ±0.2°) 12.1, 12.7, 15.0, 15.7, 18.4, 21.4, 21.9, 23.9 and 24.3° 2θ.

Figure 14:
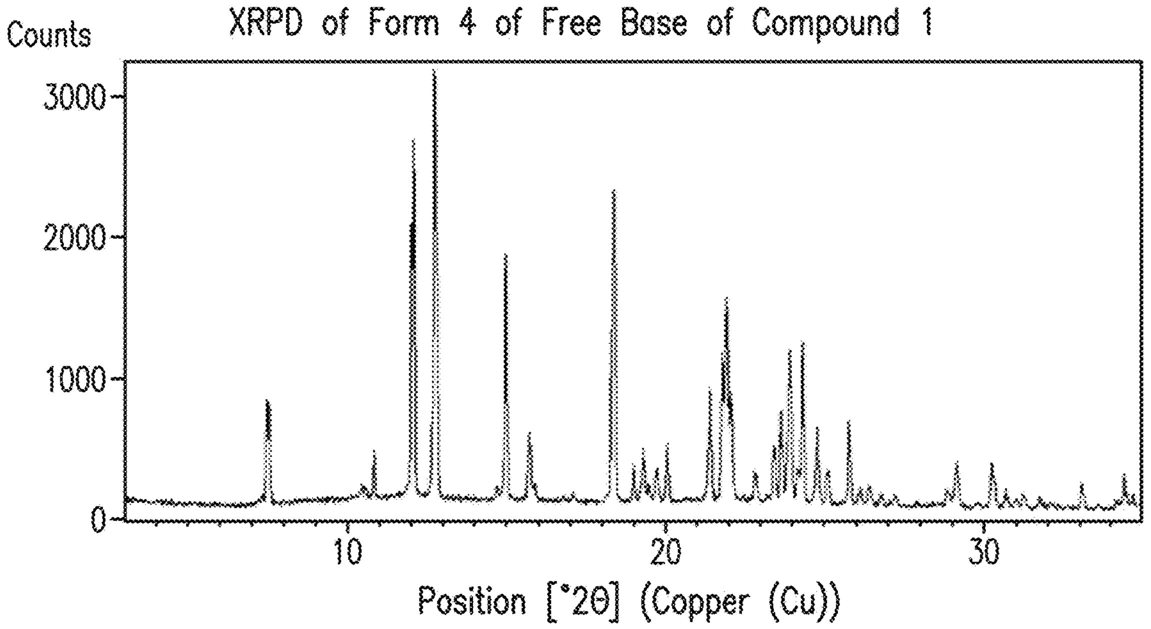
FIG. 14 is a representative XRPD pattern of Form 4 of free base of Compound 1.

In one embodiment, provided herein is a solid form comprising a free base of Compound 1, characterized by an XRPD pattern that matches the XRPD pattern depicted in FIG. 14.

In one embodiment, an XRPD pattern described herein is obtained using Cu Kα radiation. In one embodiment, the XRPD pattern is measured by XRPD using Cu Kα radiation comprising $K\alpha_1$ radiation having a wavelength of 1.5406 Å and $K\alpha_2$ radiation having a wavelength of 1.5444 Å, wherein the $K\alpha_1$:$K\alpha_2$ ratio is 0.5.

Figure 15:
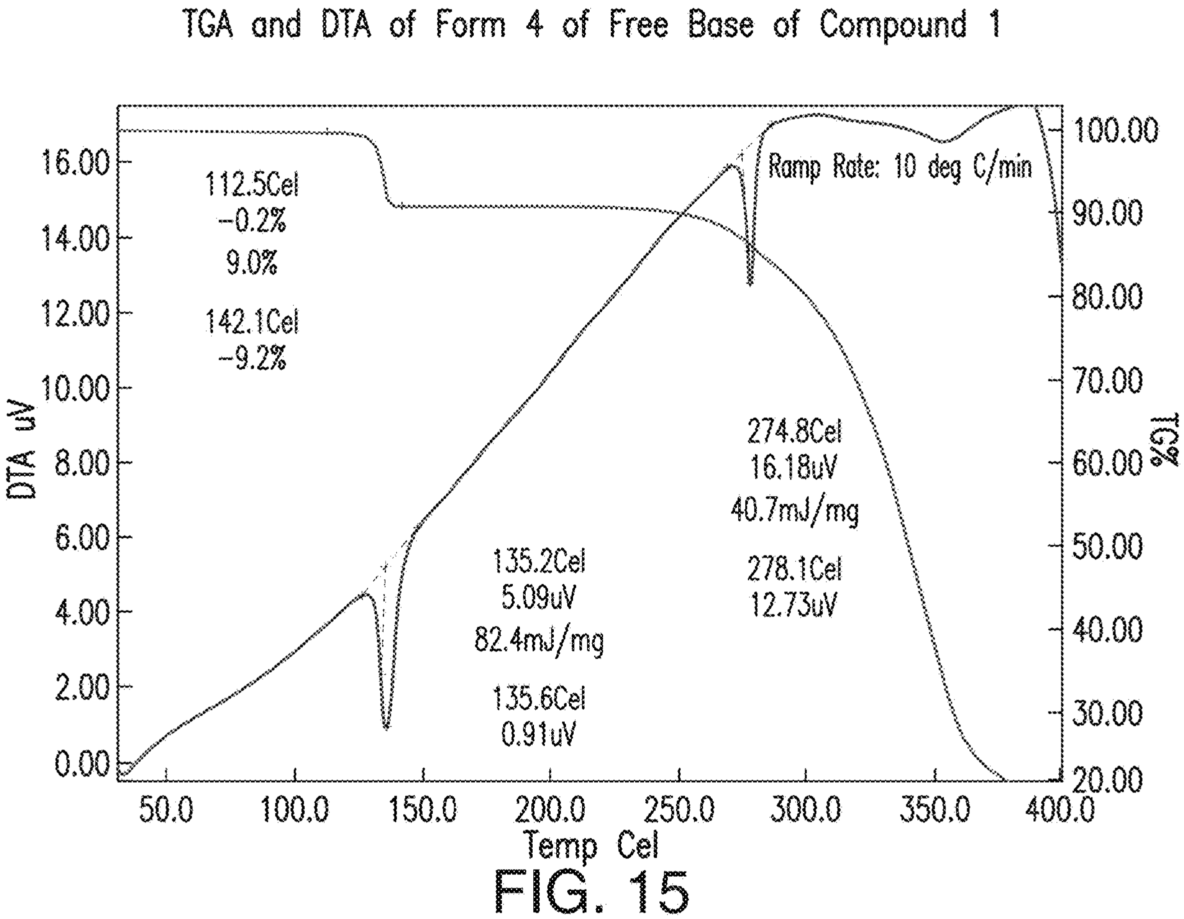
FIG. 15 is a representative overlay of TGA and DTA thermograms for Form 4 of free base of Compound 1.

A representative overlay of TGA/DTA thermograms of Form 4 is provided in FIG. 15. In one embodiment, provided herein is a solid form comprising a free base of Compound 1, which exhibits, as characterized by DTA, a thermal event (endo) with an onset temperature of about 135° C. (e.g. ±2°). In one embodiment, the solid form is characterized by a DTA thermogram that matches the DTA therogram depicted in FIG. 15. In one embodiment, the DTA thermogram is as measured by DTA using a scanning rate of about 10° C./minute.

In one embodiment, provided herein is a solid form comprising a free base of Compound 1, which exhibits a weight loss of about 9.0% upon heating from about 110° C. to about 145° C. In one embodiment, the solid form is characterized by a TGA thermogram that matches the TGA thermogram depicted in FIG. 15. In one embodiment, the TGA thermogram is as measured using a heating rate of about 10° C./minute.

In some embodiments, provided herein is a solid form comprising a free base of Compound 1 which is a crystalline solvate of free base of Compound 1. In some embodiments, the solid form is substantially free of amorphous Compound 1. In some embodiments, the solid form is substantially free of other solid forms (e.g., crystalline forms) of Compound 1. In some embodiments, the solid form is substantially free of salts of Compound 1. In some embodiments, the solid form is provided as substantially pure. In some embodiments, the solid form is substantially chemically pure. In some embodiments, the solid form is substantially physically pure.

In one embodiment, provided herein is a solid form comprising a free base of Compound 1, wherein the molar ratio of Compound 1 to the solvent ranges from about 1:0.5 to about 1:1.5. In one embodiment, the molar ratio of Compound 1 to the solvent ranges from about 1:0.8 to about 1:1.1. In one embodiment, the solid form is an acetonitrile solvate of free base of Compound 1. In one embodiment, the molar ratio of Compound 1 to acetonitrile is about 1:0.9.

In one embodiment, provided herein is a solid form comprising Form 4 of a free base of Compound 1 and amorphous free base of Compound 1. In one embodiment, provided herein is a solid form comprising Form 4 of a free base Compound 1 and one or more other crystalline forms of a free base of Compound 1 provided herein.

All of the combinations of the above embodiments are encompassed by this application.

5.2.1.5 Form 5 of Compound 1

In one embodiment, provided herein is a Form 5 of Compound 1. A representative XRPD pattern of Form 4 of Compound 1 is provided in FIG. 16.

In one embodiment, provided herein is a solid form comprising a free base of Compound 1, characterized by 1, 2, 3, 4, 5, 6, 7, 8, 9, 10, 11, 12, 13, 14, 15, 16, 17, 18, or all of the XRPD peaks located at approximately the following positions (e.g., degrees 2θ±0.2) when measured using Cu Kα radiation: 7.6, 10.5, 10.8, 12.1, 12.8, 13.4, 15.0, 15.8, 16.4, 18.3, 18.9, 19.3, 19.7, 20.3, 21.9, 22.7, 23.6, 23.9, and 28.9° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a free base of Compound 1, characterized by an XRPD pattern, when measured using Cu Kα radiation, comprising at least three peaks selected from the group consisting of approximately (e.g., ±0.2°) 7.6, 10.5, 10.8, 12.1, 12.8, 15.0, 15.8, 19.7, 21.9, 22.7, and 23.9° 2θ. In one embodiment, the solid form is characterized by an XRPD pattern comprising at least four peaks selected from the group consisting of approximately (e.g., ±0.2°) 7.6, 10.5, 10.8, 12.1, 12.8, 15.0, 15.8, 19.7, 21.9, 22.7, and 23.9° 2θ. In one embodiment, the solid form is characterized by an XRPD pattern comprising at least five peaks selected from the group consisting of approximately (e.g., ±0.2°) 7.6, 10.5, 10.8, 12.1, 12.8, 15.0, 15.8, 19.7, 21.9, 22.7, and 23.9° 2θ.

In one embodiment, provided herein is a solid form comprising a free base of Compound 1, characterized by an XRPD pattern comprising peaks at approximately (e.g., ±0.2°) 10.5, 10.8, and 21.9° 2θ. In one embodiment, the solid form is characterized by an XRPD pattern further comprising peaks at approximately (e.g., ±0.2°) 12.1 and 12.8° 2θ. In one embodiment, the solid form is characterized by an XRPD pattern further comprising peaks at approximately (e.g., ±0.2°) 7.6 and 15.0° 2θ. In one embodiment, the XRPD pattern comprises peaks at approximately (e.g., ±0.2°) 7.6, 10.5, 10.8, 12.1, 12.8, 15.0, 15.8, 19.7 and 21.9° 2θ.

Figure 16:
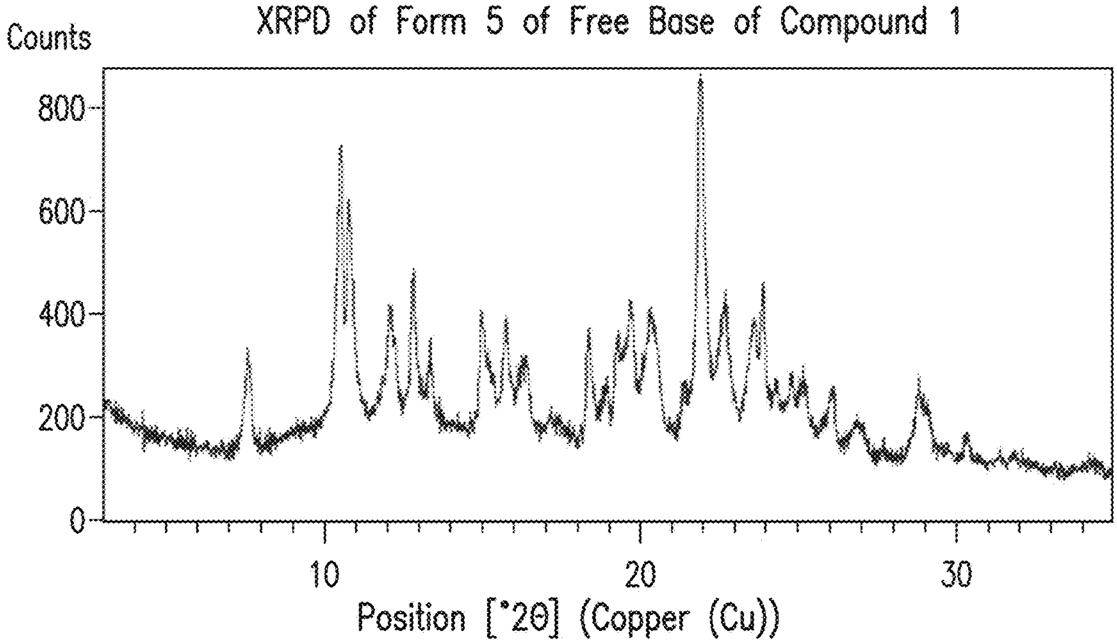
FIG. 16 is a representative XRPD pattern of Form 5 of free base of Compound 1.

In one embodiment, provided herein is a solid form comprising a free base of Compound 1, characterized by an XRPD pattern that matches the XRPD pattern depicted in FIG. 16.

In one embodiment, an XRPD pattern described herein is obtained using Cu Kα radiation. In one embodiment, the XRPD pattern is measured by XRPD using Cu Kα radiation comprising $K\alpha_1$ radiation having a wavelength of 1.5406 Å and $K\alpha_2$ radiation having a wavelength of 1.5444 Å, wherein the $K\alpha_1$:$K\alpha_2$ ratio is 0.5.

In some embodiments, provided herein is a solid form comprising a free base of Compound 1 which is a crystalline solvate of free base of Compound 1. In some embodiments, the solid form is substantially free of amorphous Compound 1. In some embodiments, the solid form is substantially free of other solid forms (e.g., crystalline forms) of Compound 1. In some embodiments, the solid form is substantially free of salts of Compound 1. In some embodiments, the solid form is provided as substantially pure. In some embodiments, the solid form is substantially chemically pure. In some embodiments, the solid form is substantially physically pure.

In one embodiment, provided herein is a solid form comprising a free base of Compound 1, wherein the molar ratio of Compound 1 to the solvent ranges from about 1:0.5 to about 1:1.5. In one embodiment, the molar ratio of Compound 1 to the solvent ranges from about 1:0.6 to about 1:0.8. In one embodiment, the solid form is an acetonitrile solvate of free base of Compound 1. In one embodiment, the molar ratio of Compound 1 to acetonitrile is about 1:0.7.

In one embodiment, provided herein is a solid form comprising Form 5 of a free base of Compound 1 and amorphous free base of Compound 1. In one embodiment, provided herein is a solid form comprising Form 5 of a free base Compound 1 and one or more other crystalline forms of a free base of Compound 1 provided herein.

All of the combinations of the above embodiments are encompassed by this application.

5.2.1.6 Form 6 of Compound 1

In one embodiment, provided herein is a Form 6 of Compound 1. A representative XRPD pattern of Form 6 of Compound 1 is provided in FIG. 17.

In one embodiment, provided herein is a solid form comprising a free base of Compound 1, characterized by 1, 2, 3, 4, 5, 6, 7, 8, 9, 10, 11, 12, 13, 14, 15, 16, 17, 18, 19, 20, 21, 22, 23, 24, 25, or all of the XRPD peaks located at approximately the following positions (e.g., degrees 2θ±0.2) when measured using Cu Kα radiation: 6.7, 6.8, 8.3, 8.5, 8.6, 10.0, 13.8, 13.9, 14.1, 15.9, 17.3, 18.3, 18.7, 18.9, 19.3, 20.1, 20.5, 20.8, 21.2, 22.9, 23.9, 24.2, 24.8, 25.2, and 26.8° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a free base of Compound 1, characterized by an XRPD pattern, when measured using Cu Kα radiation, comprising at least three peaks selected from the group consisting of approximately (e.g., ±0.2°) 8.4, 8.6, 10.0, 15.9, 18.7, 20.5, 20.8, 21.2 and 22.9° 2θ. In one embodiment, the solid form is characterized by an XRPD pattern comprising at least four peaks selected from the group consisting of approximately (e.g., ±0.2°) 8.4, 8.6, 10.0, 15.9, 18.7, 20.5, 20.8, 21.2 and 22.9° 2θ. In one embodiment, the solid form is characterized by an XRPD pattern comprising at least five peaks selected from the group consisting of approximately (e.g., ±0.2°) 8.4, 8.6, 10.0, 15.9, 18.7, 20.5, 20.8, 21.2 and 22.9° 2θ.

In one embodiment, provided herein is a solid form comprising a free base of Compound 1, characterized by an XRPD pattern comprising peaks at approximately (e.g., ±0.2°) 8.6, 18.7, and 20.5° 2θ. In one embodiment, the solid from is characterized by an XRPD pattern further comprising peaks at approximately (e.g., 0.2°) 15.9 and 20.8° 2θ. In one embodiment, the solid form is characterized by an XRPD pattern further comprising peaks at approximately (e.g., ±0.2°) 10.0 and 14.1° 2θ. In one embodiment, the XRPD pattern comprises peaks at approximately (e.g., ±0.2°) 8.6, 10.0, 15.9, 18.7, 20.5, 20.8, 21.2 and 22.9° 2θ.

Figure 17:
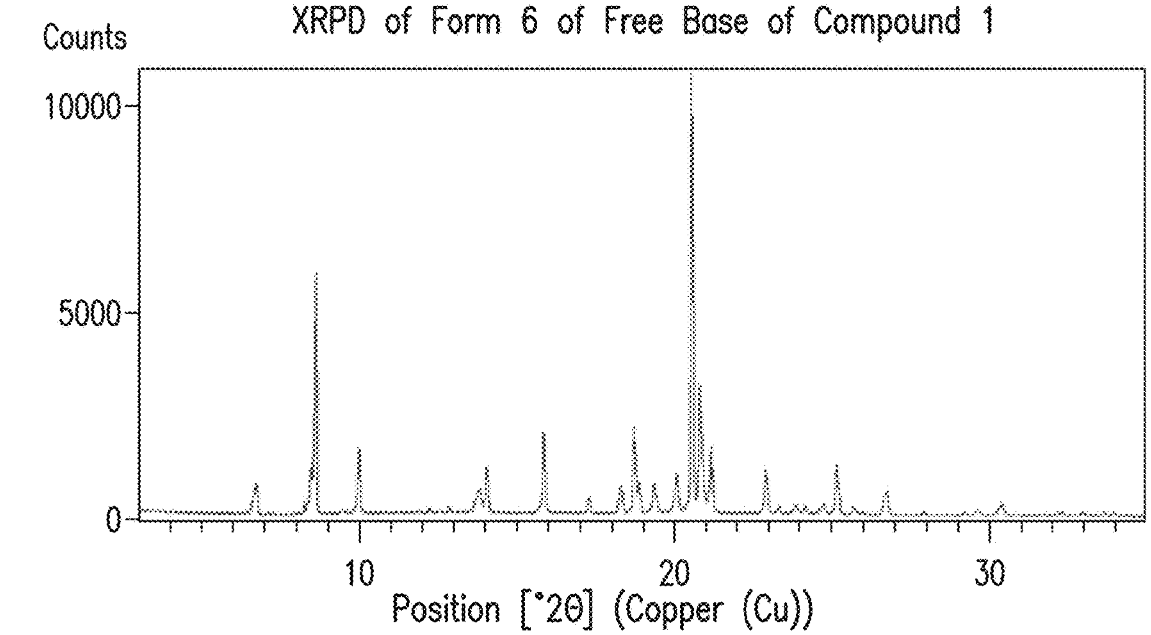
FIG. 17 is a representative XRPD pattern of Form 6 of free base of Compound 1.

In one embodiment, provided herein is a solid form comprising a free base of Compound 1, characterized by an XRPD pattern that matches the XRPD pattern depicted in FIG. 17.

In one embodiment, an XRPD pattern described herein is obtained using Cu Kα radiation. In one embodiment, the XRPD pattern is measured by XRPD using Cu Kα radiation comprising $K\alpha_1$ radiation having a wavelength of 1.5406 Å and $K\alpha_2$ radiation having a wavelength of 1.5444 Å, wherein the $K\alpha_1$:$K\alpha_2$ ratio is 0.5.

Figure 18:
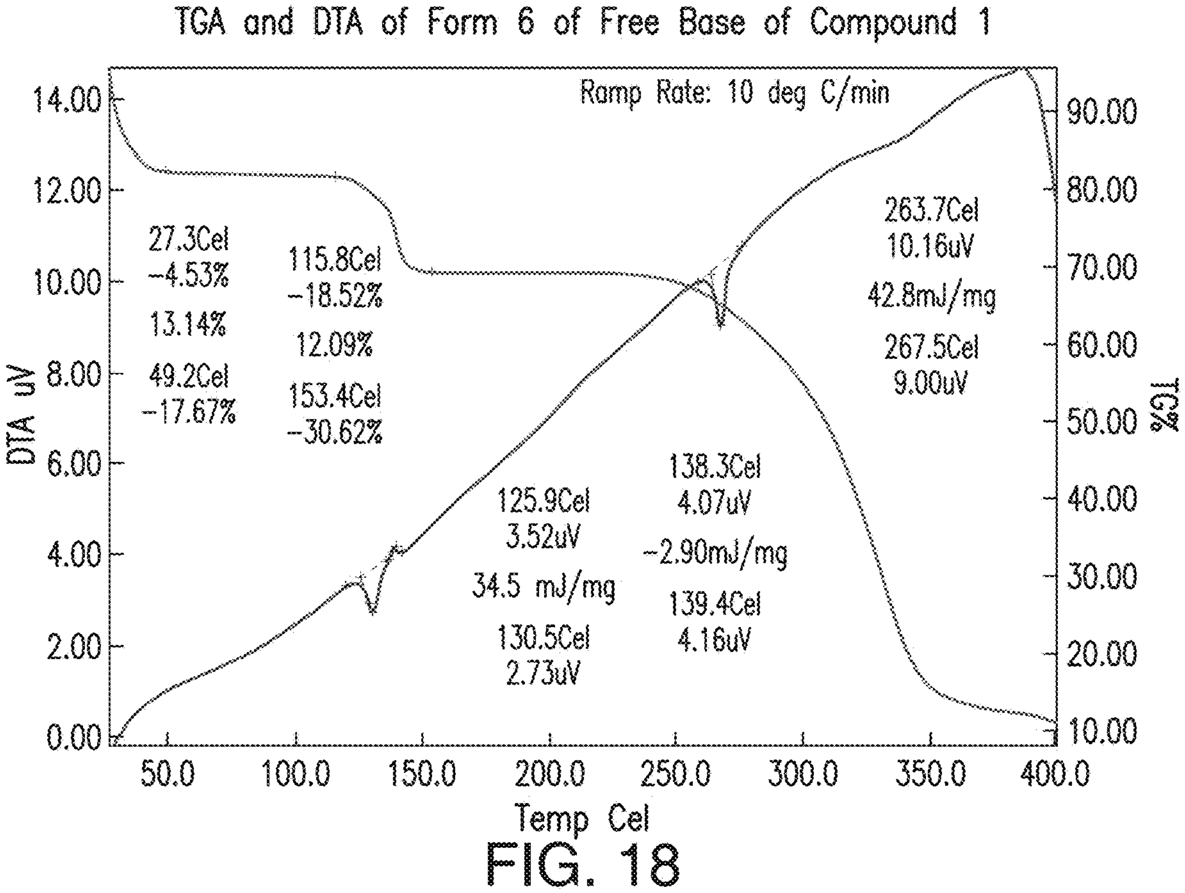
FIG. 18 is a representative overlay of TGA and DTA thermograms for Form 6 of free base of Compound 1.

A representative overlay of TGA/DTA thermograms of Form 6 is provided in FIG. 18. In one embodiment, provided herein is a solid form comprising a free base of Compound 1, which exhibits, as characterized by DTA, a thermal event (endo) with an onset temperature of about 126° C. (e.g. ±2°). In one embodiment, the solid form is characterized by a DTA thermogram that matches the DTA thermogram depicted in FIG. 18. In one embodiment, the DTA thermogram is as measured by DTA using a scanning rate of about 10° C./minute.

In one embodiment, provided herein is a solid form comprising a free base of Compound 1, which exhibits a weight loss of about 13.1% upon heating from about 25° C. to about 50° C. and/or a weight loss of about 12.1% upon heating from about 115° C. to about 155° C. In one embodiment, the solid form is characterized by a TGA thermogram that matches the TGA thermogram depicted in FIG. 18. In one embodiment, the TGA thermogram is as measured using a heating rate of about 10° C./minute.

In some embodiments, provided herein is a solid form comprising a free base of Compound 1 which is a crystalline solvate of free base of Compound 1. In some embodiments, the solid form is substantially free of amorphous Compound 1. In some embodiments, the solid form is substantially free of other solid forms (e.g., crystalline forms) of Compound 1. In some embodiments, the solid form is substantially free of salts of Compound 1. In some embodiments, the solid form is provided as substantially pure. In some embodiments, the solid form is substantially chemically pure. In some embodiments, the solid form is substantially physically pure.

In one embodiment, provided herein is a solid form comprising a free base of Compound 1, wherein the molar ratio of Compound 1 to the solvent ranges from about 1:0.2 to about 1:1.5. In one embodiment, the molar ratio of Compound 1 to the solvent ranges from about 1:0.5 to about 1:1.3. In one embodiment, the solid form is a 1,4-dioxane solvate of free base of Compound 1. In one embodiment, the molar ratio of Compound 1 to 1,4-dioxane is about 1:0.7. In another embodiment, the molar ratio of Compound 1 to 1,4-dioxane is about 1:1.2.

In one embodiment, provided herein is a solid form comprising Form 6 of a free base of Compound 1 and amorphous free base of Compound 1. In one embodiment, provided herein is a solid form comprising Form 6 of a free base Compound 1 and one or more other crystalline forms of a free base of Compound 1 provided herein.

All of the combinations of the above embodiments are encompassed by this application.

5.2.1.7 Form 7 of Compound 1

In one embodiment, provided herein is a Form 7 of Compound 1. A representative XRPD pattern of Form 7 of Compound 1 is provided in FIG. 19.

In one embodiment, provided herein is a solid form comprising a free base of Compound 1, characterized by 1, 2, 3, 4, 5, 6, 7, 8, 9, 10, 11, 12, 13, 14, 15, 16, 17, 18, 19, 20, 21, 22, 23 or all of the XRPD peaks located at approximately the following positions (e.g., degrees 2θ±0.2) when measured using Cu Kα radiation: 9.5, 9.7, 11.1, 11.4, 12.3, 12.5, 13.4, 14.6, 14.7, 15.8, 16.2, 16.9, 18.4, 18.8, 19.3, 19.5, 20.9, 21.5, 22.5, 22.8, 23.2, 24.9, 25.1, and 29.5° 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a free base of Compound 1, characterized by an XRPD pattern, when measured using Cu Kα radiation, comprising at least three peaks selected from the group consisting of approximately (e.g., ±0.2°) 9.5, 9.7, 11.4, 12.3, 12.5, 13.4, 14.6, 14.7, 15.8, 20.9, 22.8 and 23.2° 2θ. In one embodiment, the solid form is characterized by an XRPD pattern comprising at least four peaks selected from the group consisting of approximately (e.g., ±0.2°) 9.5, 9.7, 11.4, 12.3, 12.5, 13.4, 14.6, 14.7, 15.8, 20.9, 22.8 and 23.2° 2θ. In one embodiment, the solid form is characterized by an XRPD pattern comprising at least five peaks selected from the group consisting of approximately (e.g., ±0.2°) 9.5, 9.7, 11.4, 12.3, 12.5, 13.4, 14.6, 14.7, 15.8, 20.9, 22.8 and 23.2° 2θ.

In one embodiment, provided herein is a solid form comprising a free base of Compound 1, characterized by an XRPD pattern comprising peaks at approximately (e.g., ±0.2°) 12.5, 13.4, and 14.6° 2θ. In one embodiment, the solid form is characterized by an XRPD pattern further comprising peaks at approximately (e.g., ±0.2°) 20.9 and 22.8° 2θ. In one embodiment, the solid form is characterized by an XRPD pattern further comprising peaks at approximately (e.g., ±0.2°) 11.4 and 15.8° 2θ. In one embodiment, the XRPD pattern comprises peaks at approximately (e.g., ±0.2°) 9.5, 11.4, 12.5, 13.4, 14.6, 15.8, 20.9, 22.8 and 23.2° 2θ.

Figure 19:
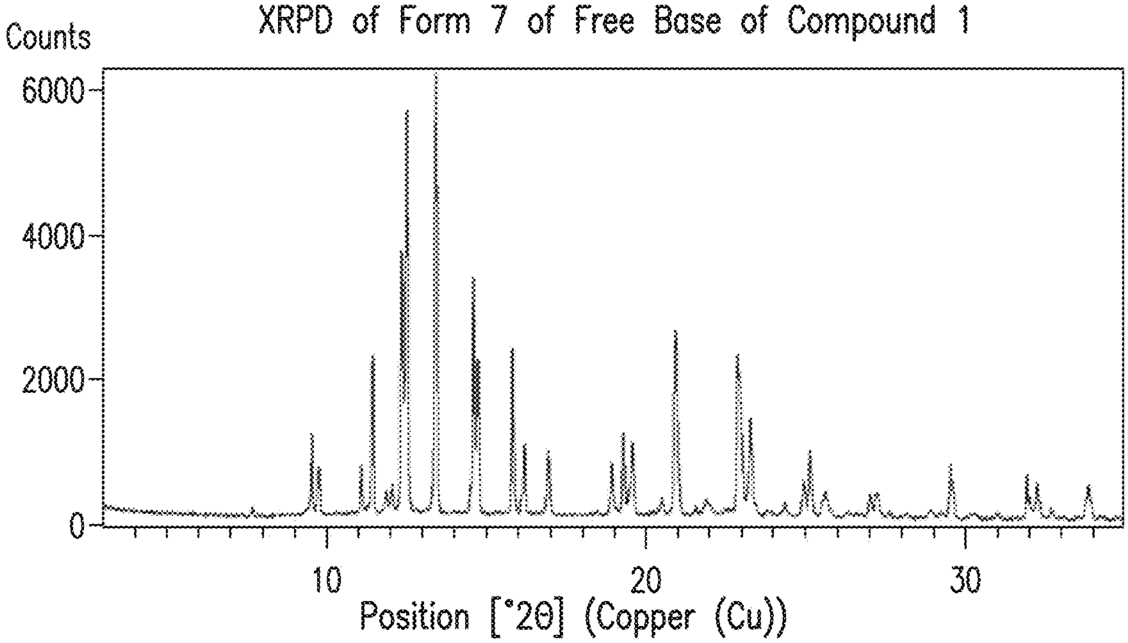
FIG. 19 is a representative XRPD pattern of Form 7 of free base of Compound 1.

In one embodiment, provided herein is a solid form comprising a free base of Compound 1, characterized by an XRPD pattern that matches the XRPD pattern depicted in FIG. 19.

In one embodiment, an XRPD pattern described herein is obtained using Cu Kα radiation. In one embodiment, the XRPD pattern is measured by XRPD using Cu Kα radiation comprising $K\alpha_1$ radiation having a wavelength of 1.5406 Å and $K\alpha_2$ radiation having a wavelength of 1.5444 Å, wherein the $K\alpha_1$:$K\alpha_2$ ratio is 0.5.

Figure 20:
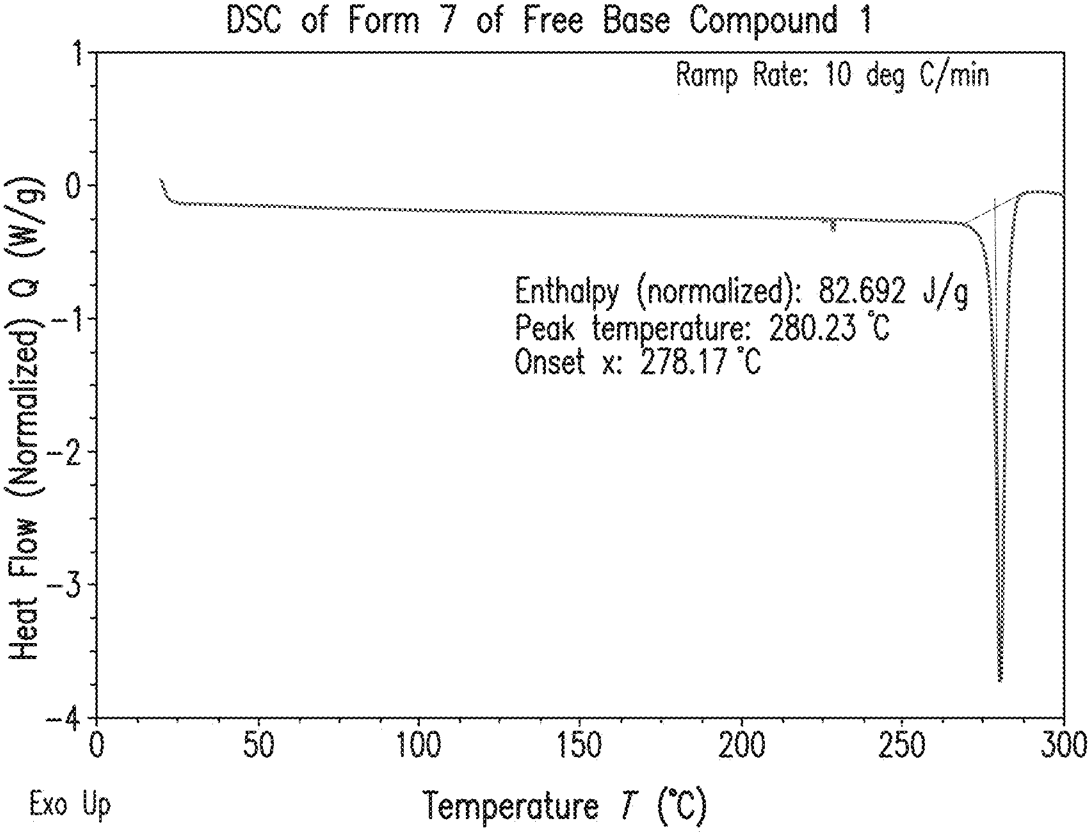
FIG. 20 is a representative DSC thermogram of Form 7 of free base of Compound 1.

A representative DSC thermograms of Form 7 is provided in FIG. 20. In one embodiment, provided herein is a solid form comprising a free base of Compound 1, which exhibits, as characterized by DSC, a thermal event (endo) with an onset temperature of about 278° C. (e.g. ±2°). In one embodiment, the thermal event also has a peak temperature of about 280° C. (e.g. ±2°). In one embodiment, without being bound by a particular theory, the thermal event corresponds to melting. In one embodiment, the solid form is characterized by a DSC thermogram that matches the DSC thermogram depicted in FIG. 20. In one embodiment, the DSC thermogram is as measured by DSC using a scanning rate of about 10° C./minute.

Figure 21:
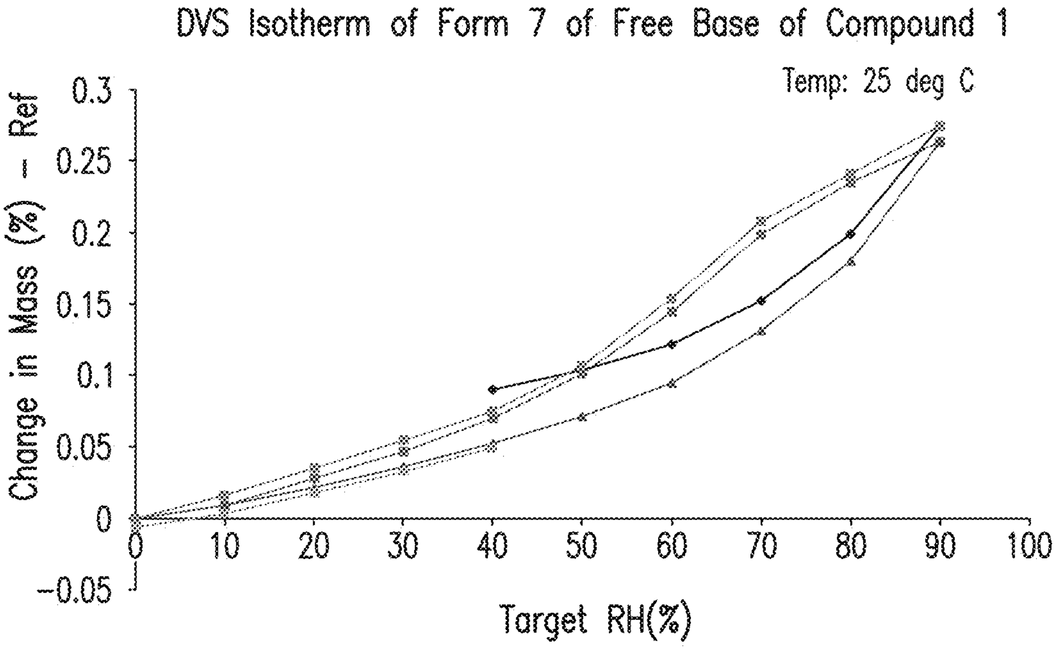
FIG. 21 is a representative DVS isotherm of Form 7 of free base of Compound 1.

A representative DVS isotherm of Form 7 is provided in FIG. 21. In one embodiment, provided herein is a solid form comprising a free base of Compound 1, which exhibits a weight increase of about 0.27% (e.g. ±0.05%) when subjected to an increase in relative humidity from about 0 to about 90% relative humidity. In one embodiment, the solid form is characterized by a DVS isotherm that matches the DVS isotherm depicted in FIG. 21. In one embodiment, the DVS isotherm is as measured at about 25° C.

Figure 22:
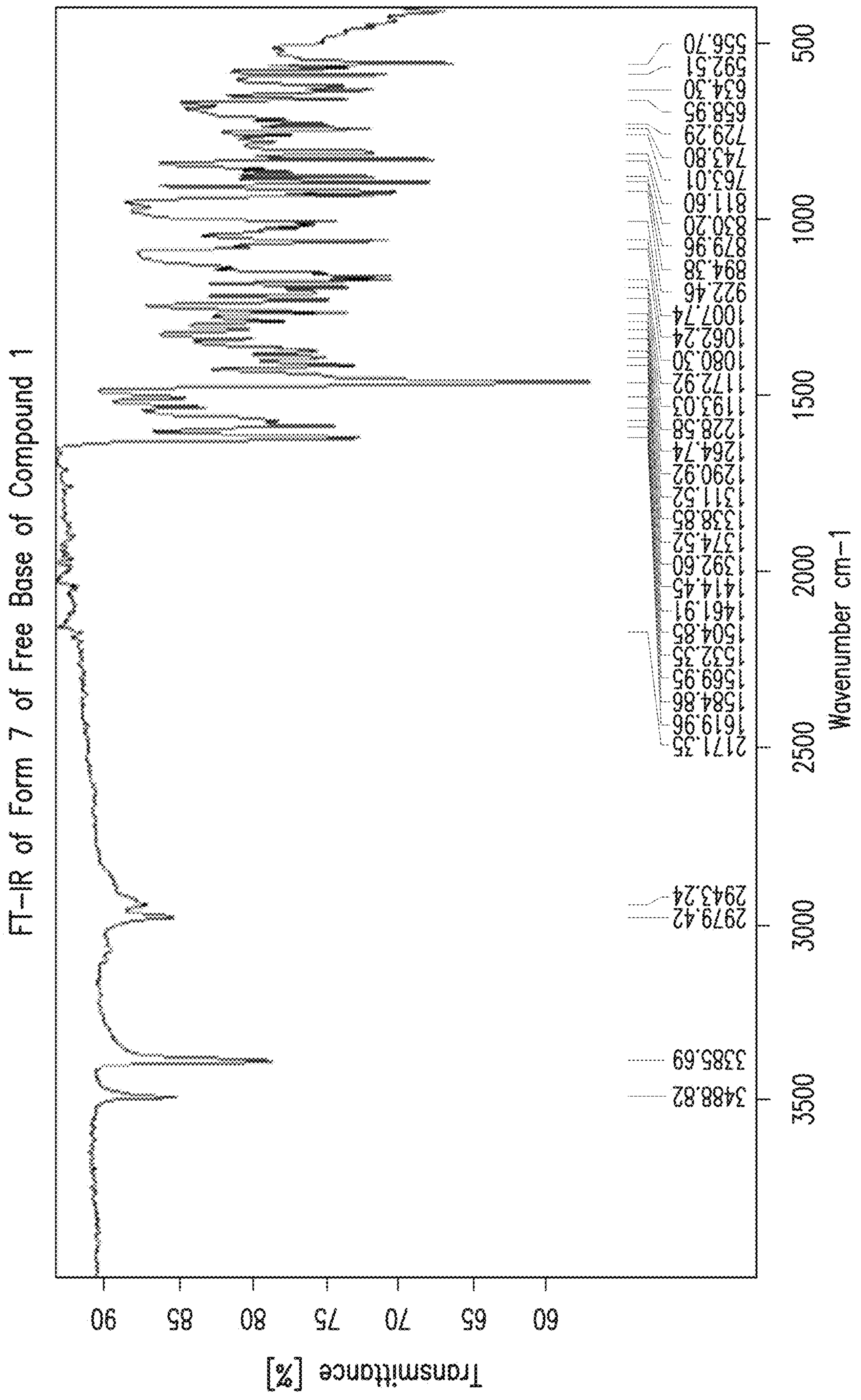
FIG. 22 is a representative FT-IR spectrum of Form 7 of free base of Compound 1.

A representative FT-IR spectrum of Form 7 is provided in FIG. 22. In one embodiment, provided herein is a solid form comprising a free base of Compound 1, characterized by an FT-IR spectrum comprising resonances at approximately 3386 and 3489 (e.g. ±5) $cm^{-1}$. In one embodiment, the FT-IR spectrum comprises at least three resonances selected from the group approximately 1461, 1584, 1619, 3386 and 3489 (e.g. ±5) $cm^{-1}$. In one embodiment, provided herein is a solid form comprising a free base of Compound 1, characterized by an FT-IR spectrum that matches the FT-IR spectrum depicted in FIG. 22.

In one embodiment, provided herein is a solid form comprising a free base of Compound 1, having approximately unit cell dimensions of: a=8.0 Å, b=14.8 Å, c=18.0 Å, α=90°, β=90°, and γ=90°. In one embodiment, the solid form is characterized by approximate unit cell dimensions of: a=7.95 Å, b=14.8 Å, c=18.0 Å, α=90°, β=90°, and γ=90°. In one embodiment, the solid form has approximately unit cell dimensions of: a=7.954 Å, b=14.82 Å, c=18.02 Å, α=90°, β=90°, and γ=90°. In one embodiment, the solid form has a unit cell of a space group of $P2_12_12_1$. In one embodiment, the solid form has a volume of about 2124.1 $Å^3$/cell. In one embodiment, the solid form has a Z value of 4. In one embodiment, the solid form has a density of about 1.312 $g/cm^3$.

In one embodiment, provided herein is a solid form comprising a free base of Compound 1 which is anhydrous. In one embodiment, the solid form is a crystalline anhydrous free base of Compound 1. In some embodiments, the solid form is substantially free of amorphous Compound 1. In some embodiments, the solid form is substantially free of other solid forms (i.e., crystalline forms) of Compound 1. In some embodiments, the solid form is substantially free of salts of Compound 1. In some embodiments, the solid form is provided as substantially pure. In some embodiments, one or more residual solvent (e.g., small amount of ethyl acetate) may be present in the solid form, but the residual solvent does not form a solvate of Compound 1. In some embodiments, the solid form is not solvated. In some embodiments, the solid form is substantially chemically pure. In some embodiments, the solid form is substantially physically pure.

In one embodiment, provided herein is a solid form comprising Form 7 of a free base of Compound 1 and amorphous free base of Compound 1. In one embodiment, provided herein is a solid form comprising Form 7 of a free base Compound 1 and one or more other crystalline forms of a free base of Compound 1 provided herein.

All of the combinations of the above embodiments are encompassed by this application.

5.2.2. Process of Preparing Solid Forms of Compound 1

In one embodiment, provided herein is a process for preparing Form 1 of a compound of Formula (I) comprising:

(i) exposing a composition comprising at least one non-Form 1 solid form of a compound of Formula (I) to one or more solvent for a period of time sufficient to convert at least about 50% of the total amount of the non-Form 1 solid form(s) into Form 1; and (ii) recovering said Form 1.

In one embodiment, the solvent is 2-MeTHF, isopropyl acetate, acetone, anisole, ethanol, ethyl acetate, isopropyl acetate, methyl ethyl ketone, or a mixture thereof. In one embodiment, the solvent is ethyl acetate. In one embodiment, the anti-solvent is water. In one embodiment, the anti-solvent is a non-polar organic solvent. In one embodiment, the non-polar organic solvent is a hydrocarbon solvent. In one embodiment, the anti-solvent is heptane. In one embodiment, the solvent is ethyl acetate and the anti-solvent is heptane. In one embodiment, the final ratio of solvent to anti-solvent is from about 1:2 to about 1:6. In one embodiment, the final ratio of solvent to anti-solvent is from about 1:3 to about 1:5. In one embodiment, the final ratio of solvent to anti-solvent is about 1:4. In one embodiment, the anti-solvent is added to the solvent at a temperature above room temperature. In one embodiment, the anti-solvent is added at a temperature of from about 30° C. to about 60° C. In one embodiment, the temperature is about 50° C.

As used herein, all solvents ratios are meant for volume ratios.

In one embodiment, the non-Form 1 solid form is exposed to one solvent. In one embodiment, the non-Form 1 solid form is exposed to a mixture of two solvents. In one embodiment, the non-Form 1 solid form is exposed to one or more solvents. In one embodiment, the solvent is an organic solvent. In one embodiment, the solvent is an alcohol. In one embodiment, the solvent is 1-butanol, 1-propanol, 2-methyl-1-propanol, 2-butanol, ethanol, or tAmyl alcohol. In one embodiment, the solvent is tetrahydrofuran, 2-methyltetrahydrofuran (2-MeTHF), butyl acetate, cyclopentyl methyl ether (CPME), ethyl acetate, isopropyl acetate, methyl ethyl ketone, toluene, methylisobutyl ketone or methyl acetate. In one embodiment, the solvent is ethyl acetate. In one embodiment, the solvent system comprises a mixture of two solvents. In one embodiment, the solvent system is a mixture of two solvents. In one embodiment, the mixture of two solvents is a mixture of 1-butanol and heptane, a mixture of 1-propanol and heptane, a mixture of 2-MeTHF and heptane, a mixture of 2-propanol and heptane, a mixture of ethanol and water, a mixture of acetone and water, a mixture of butyl acetate and heptane, a mixture of dimethylsulfoxide and water, a mixture of ethyl acetate and heptane, a mixture of isopropyl acetate and heptane, or a mixture of methyl ethyl ketone and heptane. In one embodiment, the mixture of two solvents is a mixture of 1-butanol and heptane. In one embodiment, the volume ratio of 1-butanol to heptane is from about 1:10 to about 1:5. In one embodiment, the volume ratio of 1-butanol to heptane is about 2:9. In one embodiment, the mixture of two solvents is a mixture of 1-propanol and heptane. In one embodiment, the volume ratio of 1-propanol to heptane is from about 1:5 to about 1:2. In one embodiment, the volume ratio of 1-propanol to heptane is about 1:4. In one embodiment, the mixture of two solvents is a mixture of 2-MeTHF and heptane. In one embodiment, the volume ratio of 2-MeTHF to heptane is from about 1:3 to about 1:3. In one embodiment, the volume ratio of 2-MeTHF to heptane is about 1:1. In one embodiment, the mixture of two solvents is a mixture of 2-propanol and heptane. In one embodiment, the volume ratio of 2-propanol to heptane is from about 1:5 to about 1:2. In one embodiment, the volume ratio of 2-propanol to heptane is about 1:3. In one embodiment, the mixture of two solvents is a mixture of 98.5% ethanol/1.5% water and water. In one embodiment, the volume ratio of 98.5% ethanol/1.5% water to water is from about 1:6 to about 1:2. In one embodiment, the volume ratio of 98.5% ethanol/1.5% water to water is about 2:5. In one embodiment, the mixture of two solvents is a mixture of acetone and water. In one embodiment, the volume ratio of acetone to water is from about 1:3 to about 2:1. In one embodiment, the volume ratio of acetone to water is about 1:1. In one embodiment, the mixture of two solvents is a mixture of butyl acetate and heptane. In one embodiment, the volume ratio of butyl acetate and heptane is from about 1:4 to about 2:1. In one embodiment, the volume ratio of butyl acetate and heptane is about 2:3. In one embodiment, the mixture of two solvents is a mixture of dimethylsulfoxide and water. In one embodiment, the volume ratio of dimethylsulfoxide and water is from about 1:1 to about 1:3. In one embodiment, the volume ratio of dimethylsulfoxide and water is about 1:2. In one embodiment, the mixture of two solvents is a mixture of ethanol and water. In one embodiment, the volume ratio of ethanol and water is from about 1:1 to about 1:3. In one embodiment, the volume ratio of ethanol and water is about 2:3. In one embodiment, the mixture of two solvents is a mixture of ethyl acetate and heptane. In one embodiment, the volume ratio of ethyl acetate and heptane is from about 1:1 to about 1:3. In one embodiment, the volume ratio of ethyl acetate and heptane is about 1:2. In one embodiment, the mixture of two solvents is a mixture of isopropyl acetate and heptane. In one embodiment, the volume ratio of isopropyl acetate and heptane is from about 1:1 to about 1:3. In one embodiment, the volume ratio of isopropyl acetate and heptane is about 2:3. In one embodiment, the mixture of two solvents is a mixture of methyl ethyl ketone and heptane. In one embodiment, the volume ratio of methyl ethyl ketone and heptane is from about 1:1 to about 1:3. In one embodiment, the volume ratio of methyl ethyl ketone and heptane is about 2:3. In one embodiment, the mixture of two solvents is a mixture of ethanol and heptane. In one embodiment, the volume ratio of ethanol and heptane is from about 1:10 to about 1:5. In one embodiment, the mixture of two solvents is a mixture of acetone and heptane. In one embodiment, the mixture of two solvents is a mixture of ethanol and heptane. In one embodiment, the volume ratio of acetone and heptane is from about 1:10 to about 1:5. In one embodiment, the mixture of two solvents is a mixture of tetrahydrofuran and heptane. In one embodiment, the mixture of two solvents is a mixture of ethanol and heptane. In one embodiment, the volume ratio of tetrahydrofuran and heptane is from about 1:10 to about 1:5.

In one embodiment, the non-Form 1 solid form is an amorphous solid form of a compound of Formula (I). In one embodiment, the non-Form 1 solid form is any one of Form 2 to Form 7 of a compound of Formula (I). In one embodiment, the non-Form 1 solid form is Form 6. In one embodiment, the non-Form 1 solid form is Form 7. In one embodiment, the period of time sufficient to convert at least about 50% of the total amount of the non-Form 1 solid form into Form 1 is about 1 hr, about 2 hr, about 5 hr, about 10 hr, about 12 hr, about 20 hr, about 24 hr, about 30 hr, about 40 hr, about 48 hr, about 72 hr, about 97 hours, about 121 hours, or greater than 121 hours.

Form 1 of a compound of Formula (I) may be prepared by exposing a composition comprising a compound of Formula (I) to one or more solvent as described in the experiments provided herein, including but not limited to evaporation, anti-solvent addition, slow cooling, crash cooling, temperature cycling or solvent drop grinding.

In one embodiment, Form 1 of a compound of Formula (I) is prepared by crystallization or recrystallization of a compound of Formula (I), or a stereoisomer, or a mixture of stereoisomers thereof, or a pharmaceutically acceptable salt thereof, from one or more solvents. In one embodiment, the solvent is an organic solvent. In one embodiment, the solvent is an alcohol. In one embodiment, the solvent is 1-butanol, 1-propanol, 2-methyl-1-propanol, 2-butanol, ethanol, or tAmyl alcohol. In one embodiment, the solvent is tetrahydrofuran, 2-methyltetrahydrofuran (2-MeTHF), butyl acetate, cyclopentyl methyl ether (CPME), ethyl acetate, isopropyl acetate, methyl ethyl ketone, toluene, or methyl acetate.

In one embodiment, Form 1 of a compound of Formula (I) is prepared by crystallization or recrystallization of a compound of Formula (I) from a solvent comprising a mixture of two solvents. In one embodiment, the mixture of two solvents is a mixture of 1-butanol and heptane, a mixture of 1-propanol and heptane, a mixture of 2-MeTHF and heptane, a mixture of 2-propanol and heptane, a mixture of ethanol and water, a mixture of acetone and water, a mixture of butyl acetate and heptane, a mixture of dimethylsulfoxide and water, a mixture of ethyl acetate and heptane, a mixture of isopropyl acetate and heptane, or a mixture of methyl ethyl ketone and heptane. In one embodiment, the mixture of two solvents is a mixture of 1-butanol and heptane. In one embodiment, the volume ratio of 1-butanol to heptane is from about 1:10 to about 1:5. In one embodiment, the volume ratio of 1-butanol to heptane is about 2:9. In one embodiment, the mixture of two solvents is a mixture of 1-propanol and heptane. In one embodiment, the volume ratio of 1-propanol to heptane is from about 1:5 to about 1:2. In one embodiment, the volume ratio of 1-propanol to heptane is about 1:4. In one embodiment, the mixture of two solvents is a mixture of 2-MeTHF and heptane. In one embodiment, the volume ratio of 2-MeTHF to heptane is from about 1:3 to about 1:3. In one embodiment, the volume ratio of 2-MeTHF to heptane is about 1:1. In one embodiment, the mixture of two solvents is a mixture of 2-propanol and heptane. In one embodiment, the volume ratio of 2-propanol to heptane is from about 1:5 to about 1:2. In one embodiment, the volume ratio of 2-propanol to heptane is about 1:3. In one embodiment, the mixture of two solvents is a mixture of 98.5% ethanol 1.5% water and water. In one embodiment, the volume ratio of 98.5% ethanol 1.5% water to water is from about 1:6 to about 1:2. In one embodiment, the volume ratio of 98.5% ethanol/1.5% water to water is about 2:5. In one embodiment, the mixture of two solvents is a mixture of acetone and water. In one embodiment, the volume ratio of acetone to water is from about 1:3 to about 2:1. In one embodiment, the volume ratio of acetone to water is about 1:1. In one embodiment, the mixture of two solvents is a mixture of butyl acetate and heptane. In one embodiment, the volume ratio of butyl acetate and heptane is from about 1:4 to about 2:1. In one embodiment, the volume ratio of butyl acetate and heptane is about 2:3. In one embodiment, the mixture of two solvents is a mixture of dimethylsulfoxide and water. In one embodiment, the volume ratio of dimethylsulfoxide and water is from about 1:1 to about 1:3. In one embodiment, the volume ratio of dimethylsulfoxide and water is about 1:2. In one embodiment, the mixture of two solvents is a mixture of ethanol and water. In one embodiment, the volume ratio of ethanol and water is from about 1:1 to about 1:3. In one embodiment, the volume ratio of ethanol and water is about 2:3. In one embodiment, the mixture of two solvents is a mixture of ethyl acetate and heptane. In one embodiment, the volume ratio of ethyl acetate and heptane is from about 1:1 to about 1:3. In one embodiment, the volume ratio of ethyl acetate and heptane is about 1:2. In one embodiment, the mixture of two solvents is a mixture of isopropyl acetate and heptane. In one embodiment, the volume ratio of isopropyl acetate and heptane is from about 1:1 to about 1:3. In one embodiment, the volume ratio of isopropyl acetate and heptane is about 2:3. In one embodiment, the mixture of two solvents is a mixture of methyl ethyl ketone and heptane. In one embodiment, the volume ratio of methyl ethyl ketone and heptane is from about 1:1 to about 1:3. In one embodiment, the volume ratio of methyl ethyl ketone and heptane is about 2:3.

In one embodiment, Form 1 of a compound of Formula (I) is prepared by crystallization or recrystallization as described in the experiments provided herein, including but not limited to evaporation, anti-solvent addition, slow cooling, or crash cooling.

In one embodiment, provided herein is a process for preparing Form 1 of a compound of Formula (I), comprising (i) dissolving the compound of Formula (I) in an solvent;
(ii) adding an anti-solvent; and
(iii) recovering said Form 1.

In one embodiment, Form 1 of a compound of Formula (I) is prepared by crystallization or recrystallization of a compound of Formula (I), or a stereoisomer, or a mixture of stereoisomers thereof, or a pharmaceutically acceptable salt thereof, from 2-MeTHF, isopropyl acetate, acetone, anisole, ethanol, ethyl acetate, isopropyl acetate, methyl ethyl ketone, or a mixture thereof, by addition of an anti-solvent. In one embodiment, the solvent is ethyl acetate. In one embodiment, the anti-solvent is water. In one embodiment, the anti-solvent is a non-polar organic solvent. In one embodiment, the non-polar organic solvent is a hydrocarbon solvent. In one embodiment, the anti-solvent is heptane. In one embodiment, the solvent is ethyl acetate and the anti-solvent is heptane. In one embodiment, the final ratio of solvent to anti-solvent is from about 1:2 to about 1:6. In one embodiment, the final ratio of solvent to anti-solvent is from about 1:3 to about 1:5. In one embodiment, the final ratio of solvent to anti-solvent is about 1:4. In one embodiment, the anti-solvent is added to the solvent at a temperature above room temperature. In one embodiment, the anti-solvent is added at a temperature of from about 30° C. to about 60° C. In one embodiment, the temperature is about 50° C.

In one embodiment, provided herein is a process for preparing Form 2 of a compound of Formula (I), comprising:

(i) exposing a composition comprising at least one non-Form 2 solid form of a compound of Formula (I) to one or more solvent for a period of time sufficient to convert at least about 50% of the total amount of the non-Form 2 solid form(s) into Form 2; and
(ii) recovering said Form 2.

In one embodiment, the non-Form 2 solid form is exposed to one solvent. In one embodiment, the non-Form 2 solid form is exposed to a mixture of two solvents. In one embodiment, the non-Form 2 solid form is exposed to one or more solvents. In one embodiment, the solvent is an organic solvent. In one embodiment, the solvent is MTBE, MEK, 1-butanol, 2-methyl-1-propanol, 3-methyl-1-butanol acetone, cyclopentyl methyl ether, or tAmyl alcohol. In one embodiment, the solvent is MEK. In one embodiment, the solvent is MTBE. In one embodiment, the solvent is 1-butanol. In one embodiment, the non-Form 2 solid form is an amorphous form of a compound of Formula (I). In one embodiment, the period of time sufficient to convert at least about 50% of the total amount of the non-Form 2 solid form into Form 2 is about 1 hr, about 2 hr, about 5 hr, about 10 hr, about 12 hr, about 20 hr, about 24 hr, about 30 hr, about 40 hr, about 48 hr, about 72 hr, about 97 hours, about 121 hours, or greater than 121 hours.

In one embodiment, Form 2 of a compound of Formula (I) is prepared by exposing a composition comprising a compound of Formula (I) to one or more solvent as described in the experiments provided herein, including but not limited to evaporation, anti-solvent addition, slow cooling, crash cooling, temperature cycling or solvent drop grinding.

In one embodiment, Form 2 of a compound of Formula (I) is obtained by evaporation from 1-butanol. In one embodiment, Form 2 of a compound of Formula (I) is prepared by temperature cycling a slurry of amorphous Compound 1 in MTBE in an incubator shaker. In some embodiments, the temperature is cycled between ambient temperature and an elevated temperature of about 30~60° C. In some embodiments, the temperature is cycled at intervals of between about 2 and about 6 hours for a period of about 24 hr, about 30 hr, about 40 hr, about 48 hr, about 72 hr, about 97 hours, about 121 hours, or greater than 121 hours. In one embodiment, Form 2 of a compound of Formula (I) is prepared by temperature cycling a slurry of amorphous Compound 1 in MTBE in an incubator shaker between ambient temperature and a temperature of about 40° C. at intervals of about 4 hours for a period of about 24 hours.

In one embodiment, provided herein is a process for preparing Form 3 of a compound of Formula (I), comprising:

(i) exposing a composition comprising at least one non-Form 3 solid form of a compound of Formula (I) to one or more solvent for a period of time sufficient to convert at least about 50% of the total amount of the non-Form 3 solid form(s) into Form 3; and (ii) recovering said Form 3.

In one embodiment, the non-Form 3 solid form is exposed to one solvent. In one embodiment, the non-Form 3 solid form is exposed to a mixture of two solvents. In one embodiment, the non-Form 3 solid form is exposed to one or more solvents. In one embodiment, the solvent is water. In one embodiment, the solvent is an organic solvent. In one embodiment, the solvent is methanol or isopropyl acetate. In one embodiment, the mixture of two solvents is a mixture of acetonitrile and heptane. In one embodiment, the non-Form 3 solid form is an amorphous form of a compound of Formula (I). In one embodiment, the period of time sufficient to convert at least about 50% of the total amount of the non-Form 3 solid form into Form 3 is about 1 hr, about 2 hr, about 5 hr, about 10 hr, about 12 hr, about 20 hr, about 24 hr, about 30 hr, about 40 hr, about 48 hr, about 72 hr, about 97 hours, about 121 hours, or greater than 121 hours.

In one embodiment, Form 3 of a compound of Formula (I) is prepared by exposing a composition comprising a compound of Formula (I) to one or more solvent as described in the experiments provided herein, including but not limited to evaporation, anti-solvent addition, slow cooling, crash cooling, temperature cycling or solvent drop grinding.

In one embodiment, provided herein is a process for preparing Form 4 of a compound of Formula (I) comprising:

(i) exposing a composition comprising at least one non-Form 4 solid form of a compound of Formula (I) to one or more solvent for a period of time sufficient to convert at least about 50% of the total amount of the non-Form 4 solid form(s) into Form 4; and (ii) recovering said Form 4.

In one embodiment, the non-Form 4 solid form is exposed to one solvent. In one embodiment, the non-Form 4 solid form is exposed to a mixture of two solvents. In one embodiment, the non-Form 4 solid form is exposed to one or more solvents. In one embodiment, the solvent is an organic solvent. In one embodiment, the solvent is acetonitrile. In one embodiment, the non-Form 4 solid form is an amorphous form of a compound of Formula (I). In one embodiment, the period of time sufficient to convert at least about 50% of the total amount of the non-Form 4 solid form into Form 4 is about 1 hr, about 2 hr, about 5 hr, about 10 hr, about 12 hr, about 20 hr, about 24 hr, about 30 hr, about 40 hr, about 48 hr, about 72 hr, about 97 hours, about 121 hours, or greater than 121 hours.

In one embodiment, Form 4 of a compound of Formula (I) is prepared by exposing a composition comprising a compound of Formula (I) to one or more solvent as described in the experiments provided herein, including but not limited to evaporation, anti-solvent addition, slow cooling, crash cooling, temperature cycling or solvent drop grinding.

In one embodiment, Form 4 of a compound of Formula (I) is obtained from addition of heptane anti-solvent to a composition comprising amorphous Compound 1 and acetonitrile. In one embodiment, Form 4 of a compound of Formula (I) is prepared by temperature cycling a slurry of amorphous Compound 1 in acetonitrile in an incubator shaker. In some embodiments, the temperature is cycled between ambient temperature and an elevated temperature of about 30~60° C. In some embodiments, the temperature is cycled at intervals of between about 2 and about 6 hours for a period of about 24 hr, about 30 hr, about 40 hr, about 48 hr, about 72 hr, about 97 hours, about 121 hours, or greater than 121 hours. In one embodiment, Form 4 of a compound of Formula (I) is prepared by temperature cycling a slurry of amorphous Compound 1 in acetonitrile in an incubator shaker between ambient temperature and a temperature of about 40° C. at intervals of about 4 hours for a period of about 72 hours.

In one embodiment, provided herein is a process for preparing Form 5 of a compound of Formula (I), comprising:

(i) exposing a composition comprising at least one non-Form 5 solid form of a compound of Formula (I) to one or more solvent for a period of time sufficient to convert at least about 50% of the total amount of the non-Form 5 solid form(s) into Form 5; and (ii) recovering said Form 5.

In one embodiment, the non-Form 5 solid form is exposed to one solvent. In one embodiment, the non-Form 5 solid form is exposed to a mixture of two solvents. In one embodiment, the non-Form 5 solid form is exposed to one or more solvents. In one embodiment, the solvent is an organic solvent. In one embodiment, the solvent is acetonitrile. In one embodiment, the non-Form 5 solid form is an amorphous form of a compound of Formula (I). In one embodiment, the period of time sufficient to convert at least about 50% of the total amount of the non-Form 5 solid form into Form 5 is about 1 hr, about 2 hr, about 5 hr, about 10 hr, about 12 hr, about 20 hr, about 24 hr, about 30 hr, about 40 hr, about 48 hr, about 72 hr, about 97 hours, about 121 hours, or greater than 121 hours.

In one embodiment, Form 5 of a compound of Formula (I) is prepared by exposing a composition comprising a compound of Formula (I) to one or more solvent as described in the experiments provided herein, including but not limited to evaporation, anti-solvent addition, slow cooling, crash cooling, temperature cycling or solvent drop grinding.

In some embodiments, Form 5 of a compound of Formula (I) is obtained from solvent drop grinding amorphous Compound 1 in acetonitrile. In one embodiment, provided herein is a process for preparing Form 6 of a compound of Formula (I), comprising:

(i) exposing a composition comprising at least one non-Form 6 solid form of a compound of Formula (I) to one or more solvent for a period of time sufficient to convert at least about 50% of the total amount of the non-Form 6 solid form(s) into Form 6; and (ii) recovering said Form 6.

In one embodiment, the non-Form 6 solid form is exposed to one solvent. In one embodiment, the non-Form 6 solid form is exposed to a mixture of two solvents. In one embodiment, the non-Form 6 solid form is exposed to one or more solvents. In one embodiment, the solvent is an organic solvent. In one embodiment, the solvent is 1,4-dioxane. In one embodiment, the non-Form 6 solid form is an amorphous form of a compound of Formula (I). In one embodiment, the period of time sufficient to convert at least about 50% of the total amount of the non-Form 6 solid form into Form 6 is about 1 hr, about 2 hr, about 5 hr, about 10 hr, about 12 hr, about 20 hr, about 24 hr, about 30 hr, about 40 hr, about 48 hr, about 72 hr, about 97 hours, about 121 hours, or greater than 121 hours.

In one embodiment, Form 6 of a compound of Formula (I) is prepared by exposing a composition comprising a compound of Formula (I) to one or more solvent as described in the experiments provided herein, including but not limited to evaporation, anti-solvent addition, slow cooling, crash cooling, temperature cycling or solvent drop grinding.

In one embodiment, Form 6 of a compound of Formula (I) is prepared by temperature cycling a slurry of amorphous Compound 1 in 1,4-dioxane in an incubator shaker. In some embodiments, the temperature is cycled between ambient temperature and an elevated temperature of about 30~60° C. In some embodiments, the temperature is cycled at intervals of between about 2 and about 6 hours for a period of about 24 hr, about 30 hr, about 40 hr, about 48 hr, about 72 hr, about 97 hours, about 121 hours, or greater than 121 hours. In one embodiment, Form 6 of a compound of Formula (I) is prepared by temperature cycling a slurry of amorphous Compound 1 in 1,4-dioxane in an incubator shaker between ambient temperature and a temperature of about 40° C. at intervals of about 4 hours for a period of about 72 hours.

In one embodiment, provided herein is a process for preparing Form 7 of a compound of Formula (I) comprising:

(i) exposing a composition comprising at least one non-Form 7 solid form of a compound of Formula (I) to one or more solvent for a period of time sufficient to convert at least about 50% of the total amount of the non-Form 7 solid form(s) into Form 7; and (ii) recovering said Form 7.

In one embodiment, the non-Form 7 solid form is exposed to one solvent. In one embodiment, the non-Form 7 solid form is exposed to a mixture of two solvents. In one embodiment, the non-Form 7 solid form is exposed to one or more solvents. In one embodiment, the solvent is an organic solvent. In one embodiment, the solvent is a mixture of 2-butanol and octane, a mixture of methylisobutyl ketone and octane, a mixture of isopropyl acetate and octane, or a mixture of 1,2-dimethoxyethane and octane. In one embodiment, the non-Form 7 solid form is Form 1. In one embodiment, the period of time sufficient to convert at least about 50% of the total amount of the non-Form 7 solid form into Form 7 is about 1 hr, about 2 hr, about 5 hr, about 10 hr, about 12 hr, about 20 hr, about 24 hr, about 30 hr, about 40 hr, about 48 hr, about 72 hr, about 97 hours, about 121 hours, or greater than 121 hours.

In one embodiment, Form 7 of a compound of Formula (I) is prepared by exposing a composition comprising a compound of Formula (I) to one or more solvent as described in the experiments provided herein, including but not limited to evaporation, anti-solvent addition, slow cooling, crash cooling, temperature cycling or solvent drop grinding.

In one embodiment, Form 7 of a compound of Formula (I) is prepared by slurrying Form 1 in a solvent at elevated temperature. In one embodiment, the solvent is a mixture of 2-butanol and octane, a mixture of methylisobutyl ketone and octane, a mixture of isopropyl acetate and octane, or a mixture of 1,2-dimethoxyethane and octane. In one embodiment, the temperature is greater than about 60° C. In one embodiment, the temperature is about 60° C. In one embodiment, the temperature is greater than about 80° C. or higher. In one embodiment, the temperature is about 80° C.

Also provided herein is a process of preparing Form 7 of a compound of Formula (I); and the process comprises heating a solid form of Form 1 to Form 6, optionally under vacuum. In some embodiments, Form 7 of a compound of Formula (I) is prepared by heating Form 2 in a reaction vessel under vacuum. In some embodiments, the reaction vessel is a glass vial, wherein Form 2 is spread over one of the vial walls so as to have a large surface area to promote the homogeneous desolvation. In some embodiments, the vacuum pressure is between about 2 mbar and about 50 mbar. In some embodiments, the vacuum pressure is about 10 mbar. In some embodiments, Form 7 of a compound of Formula (I) is prepared by heating Form 2 under vacuum at a reaction temperature between about 200° C. and about 300° C. In some embodiments, the reaction temperature is about 250° C. In some embodiments, the reaction vessel is maintained at the reaction temperature for a time of between about 3 and about 10 minutes. In some embodiments, the time is about 6 minutes. In some embodiments, the reaction temperature is reached by heating the reaction vessel at a rate of between about 10° C./min and about 30° C./min. In some embodiments, the rate is about 20° C./min. In some embodiments, after the reaction vessel has been heated under vacuum for the desired time, the reaction vessel and/or the solids contained therein are actively cooled. In some embodiments, the active cooling involves use of wet towels.

5.2.3. Salts of a Compound of Formula (I)

In certain embodiments, provided herein is a solid form comprising a salt of a compound of Formula (I):

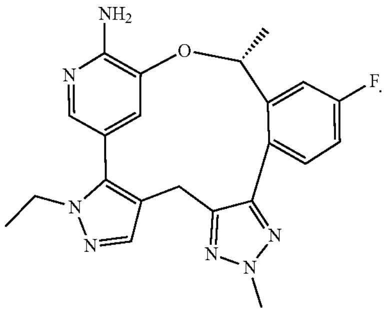
(I)

The molar ratio of Compound 1 to a counterion of the salt of Compound 1 may be about 1:1, about 1:2, about 1:3, or about 1:4. In one embodiment, the molar ratio of Compound 1 to counterion is about 1:1. In one embodiment, the molar ratio of Compound 1 to a counterion is about 1:2. In one embodiment, the molar ratio of Compound 1 to a counterion is about 1:3. In one embodiment, the molar ratio of Compound 1 to a counterion is about 1:4.

In one embodiment, the counterion is chloride, phosphate, besylate, mesylate, citrate or maleate. In one embodiment, the salt of Compound 1 is a besylate salt of Compound 1. In one embodiment, the salt of Compound 1 is a phosphate salt of Compound 1.

In one embodiment, provided herein a solid form comprising a salt of Compound 1. In one embodiment, provided herein is an unsolvated solid form comprising a salt of Compound 1. In one embodiment, provided herein is an anhydrous solid form comprising a salt of Compound 1. In one embodiment, provided herein is a solvated solid form comprising a salt of Compound 1. In one embodiment, provided herein is a hydrate solid form comprising a salt of Compound 1.

It is contemplated that a salt of Compound 1 can exist in a variety of solid forms. Such solid forms include crystalline solids or mixtures of crystalline and amorphous solids. In one embodiment, the solid form is substantially crystalline. In one embodiment, the solid form is crystalline.

In some embodiments, the molar ratio of the salt of Compound 1 to the solvent (e.g. water) in the solid form ranges from about 10:1 to about 1:10. In some embodiments, the molar ratio of the salt of Compound 1 to the solvent (e.g. water) in the solid form ranges from about 5:1 to about 1:5. In some embodiments, the molar ratio of the salt of Compound 1 to the solvent (e.g. water) in the solid form ranges from about 3:1 to about 1:3. In some embodiments, the molar ratio of the sale of Compound 1 to the solvent (e.g. water) in the solid form ranges from about 2:1 to about 1:2. In one embodiment, the molar ratio is about 1:1 (i.e., mono-solvate or mono-hydrate).

5.2.3.1 Form A of a Besylate Salt of Compound 1

In one embodiment, provided herein is a Form A of a besylate salt of Compound 1. A representative XRPD pattern of Form A of a besylate salt of Compound 1 is provided in FIG. 24.

In one embodiment, provided herein is a solid form comprising a besylate salt of Compound 1, characterized by 1, 2, 3, 4, 5, 6, 7, 8, 9, 10, 11, 12, 13, or all of the XRPD peaks located at approximately the following positions (e.g., degrees 2θ±0.2) when measured using Cu Kα radiation: 4.6, 10.7, 11.5, 14.6, 15.0, 17.9, 19.4, 20.4, 21.0, 21.3, 21.4, 23.0, 23.4, and 25.7 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a besylate salt of Compound 1, characterized by an XRPD pattern, when measured using Cu Kα radiation, comprising at least three peaks selected from the group consisting of approximately (e.g., ±0.2°) 4.6, 10.7, 11.5, 14.6, 15.0, 17.9, 19.4, 21.0, 21.4, 23.0, and 25.7 2θ. In one embodiment, the solid form is characterized by an XRPD pattern comprising at least four peaks selected from the group consisting of approximately (e.g., ±0.2°) 4.6, 10.7, 11.5, 14.6, 15.0, 17.9, 19.4, 21.0, 21.4, 23.0, and 25.7 2θ. In one embodiment, the solid form is characterized by an XRPD pattern comprising at least five peaks selected from the group consisting of approximately (e.g., ±0.2°) 4.6, 10.7, 11.5, 14.6, 15.0, 17.9, 19.4, 21.0, 21.4, 23.0, and 25.7 2θ.

In one embodiment, provided herein is a solid form comprising a besylate salt of Compound 1, characterized by an XRPD pattern comprising peaks at approximately (e.g., ±0.2°) 15.0, 17.9 and 23.0° 2θ. In one embodiment, the solid form is characterized by an XRPD pattern further comprising peaks at approximately (e.g., ±0.2°) 10.7 and 14.6° 2θ. In one embodiment, the solid form is characterized by an XRPD pattern further comprising peaks at approximately (e.g., ±0.2°) 4.6 and 25.7° 2θ. In one embodiment, the XRPD pattern comprises peaks at approximately (e.g., ±0.2°) 4.6, 10.7, 11.5, 14.6, 15.0, 17.9, 21.4, 23.0, and 25.7° 2θ.

Figure 24:
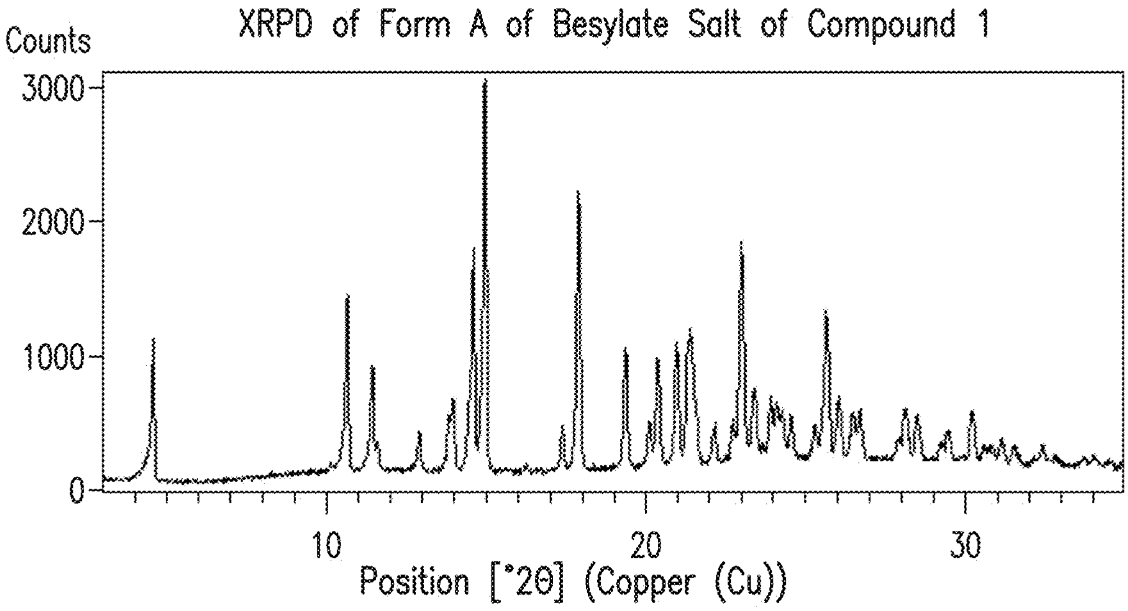
FIG. 24 is a representative XRPD pattern of Form A of a besylate salt of Compound 1.

In one embodiment, provided herein is a solid form comprising a besylate salt of Compound 1, characterized by an XRPD pattern that matches the XRPD pattern depicted in FIG. 24.

In one embodiment, an XRPD pattern described herein is obtained using Cu Kα radiation. In one embodiment, the XRPD pattern is measured by XRPD using Cu Kα radiation comprising Kα, radiation having a wavelength of 1.5406 Å and $K\alpha_2$ radiation having a wavelength of 1.5444 Å, wherein the $K\alpha_1$:$K\alpha_2$ ratio is 0.5.

Figure 25:
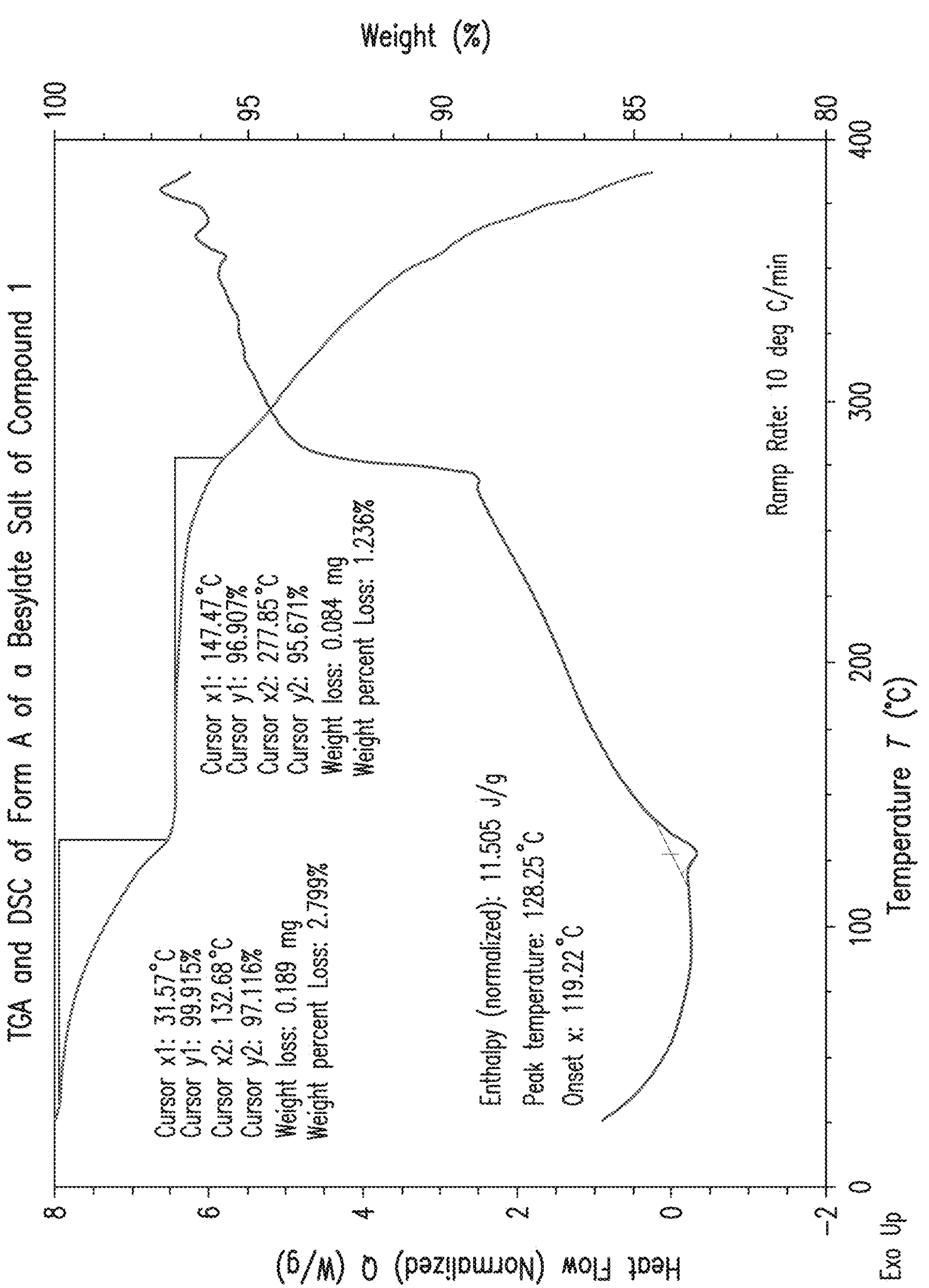
FIG. 25 is a representative overlay of TGA and DSC thermograms for Form A of a besylate salt of Compound 1.

A representative overlay of TGA/DSC thermograms of Form A of a besylate salt of Compound 1 is provided in FIG. 25. In one embodiment, provided herein is a solid form comprising a besylate salt of Compound 1, which exhibits a weight loss of about 2.8% upon heating from about 25° C. to about 125° C., and/or a weight loss of about 1.2% upon heating from about 125° C. to about 275° C. In one embodiment, provided herein is a solid form comprising a besylate salt of Compound 1, which exhibits a decomposition upon heating from about 25° C. (e.g. ±2°) and/or a decomposition upon heating from about 125° C. (e.g. ±2°). In one embodiment, the solid form is characterized by a TGA thermogram that matches the TGA thermogram depicted in FIG. 25. In one embodiment, the TGA thermogram is as measured using a heating rate of about 10° C./minute.

Figure 26:
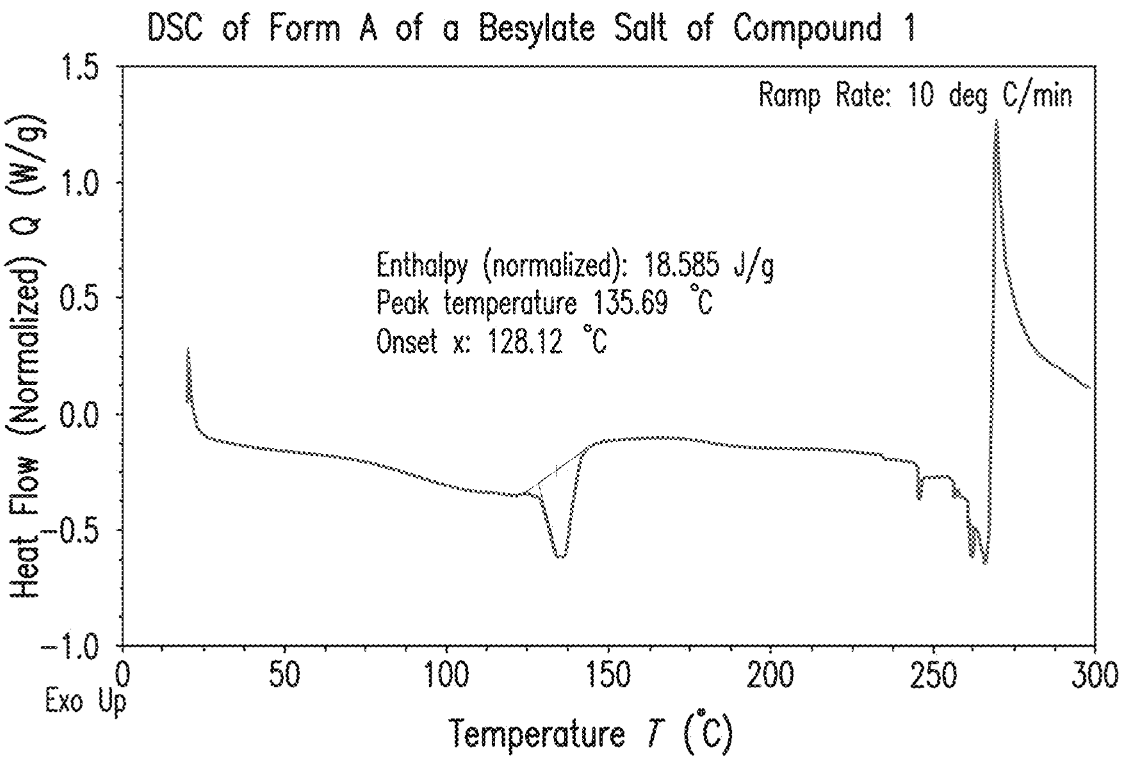
FIG. 26 is a representative DSC thermogram for Form A of a besylate salt of Compound 1.

A representative DSC thermograms of Form A of a besylate salt of Compound 1 is provided in FIG. 26. In one embodiment, provided herein is a solid form comprising a besylate salt of Compound 1, which exhibits, as characterized by DSC, a thermal event (endo) with an onset temperature at about 128° C. (e.g. ±2°). In one embodiment, the thermal event also has a peak temperature of about 136° C. (e.g. ±2°). In one embodiment, without being limited by a particular theory, the thermal event corresponds to melting. In one embodiment, the solid form is characterized by a DSC thermogram that matches the DSC thermogram depicted in FIG. 26. In one embodiment, the DSC thermogram is as measured by DSC using a scanning rate of about 10° C./minute.

Figure 27:
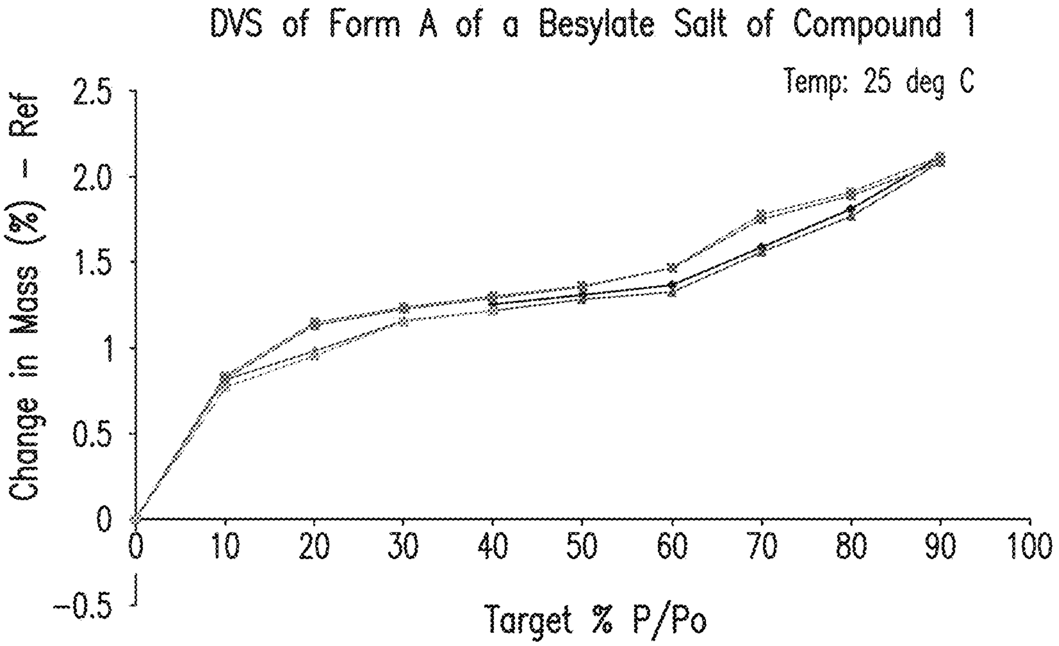
FIG. 27 is a representative DVS isotherm of Form A of a besylate salt of Compound 1.

A representative DVS isotherm of Form A of a besylate salt of Compound 1 is provided in FIG. 27. In one embodiment, provided herein is a solid form comprising a besylate salt of Compound 1 which exhibits a weight increase of about 2% (e.g. ±0.05%) when subjected to an increase in relative humidity from about 0 to about 90% relative humidity. In one embodiment, the solid form is characterized by a DVS isotherm that matches the DVS isotherm depicted in FIG. 27. In one embodiment, the DVS isotherm is as measured at about 25° C.

In some embodiments, provided herein is a solid form comprising a besylate salt of Compound 1. In one embodiment, the solid form is a monobesylate salt of Compound 1. In one embodiment, the solid form is a hydrate of a besylate salt of Compound 1. In one embodiment, the solid form is a monohydrate of a besylate salt of Compound 1.

In one embodiment, the solid form is a crystalline solid form comprising a besylate salt of Compound 1. In some embodiments, the solid form is substantially free of amorphous Compound 1 and/or an amorphous form of a salt of Compound 1. In some embodiments, the solid form comprising a besylate salt of Compound 1 is substantially free of other solid forms (i.e., crystalline forms) of Compound 1. In some embodiments, the solid form is provided as substantially pure. In some embodiments, the solid form is substantially chemically pure. In some embodiments, the solid form is substantially chemically pure.

In one embodiment, provided herein is a solid form comprising Form A of a besylate salt of Compound 1 and amorphous free base of Compound 1. In one embodiment, provided herein is a solid form comprising Form A of a besylate salt of Compound 1 and amorphous besylate salt of Compound 1. In one embodiment, provided herein is a solid form comprising Form A of a besylate salt of Compound 1 and one or more other crystalline forms of a besylate salt of Compound 1.

All of the combinations of the above embodiments are encompassed by this application.

5.2.3.2 Form A of a Phosphate Salt of Compound 1

In one embodiment, provided herein is a Form A of a phosphate salt of Compound 1. A representative XRPD pattern of Form A of a phosphate salt of Compound 1 is provided in FIG. 28.

In one embodiment, provided herein is a solid form comprising a phosphate salt of Compound 1, characterized by 1, 2, 3, 4, 5, 6, 7, 8, 9, 10, 11, 12, 13, or all of the XRPD peaks located at approximately the following positions (e.g., degrees 2θ±0.2) when measured using Cu Kα radiation: 10.8, 14.2, 15.0, 15.9, 17.7, 18.5, 19.4, 20.1, 20.7, 21.6, 22.3, 24.1, 24.8, and 25.8 2θ. In one embodiment, the solid form is characterized by 3 of the peaks. In one embodiment, the solid form is characterized by 5 of the peaks. In one embodiment, the solid form is characterized by 7 of the peaks. In one embodiment, the solid form is characterized by 9 of the peaks. In one embodiment, the solid form is characterized by 11 of the peaks. In one embodiment, the solid form is characterized by all of the peaks.

In one embodiment, provided herein is a solid form comprising a phosphate salt of Compound 1, characterized by an XRPD pattern, when measured using Cu Kα radiation, comprising at least three peaks selected from the group consisting of approximately (e.g., ±0.2°) 10.8, 14.2, 15.0, 15.9, 17.7, 18.5, 19.4, 22.3, 24.1, 24.8, and 25.8. In one embodiment, the solid form is characterized by an XRPD pattern comprising at least four peaks selected from the group consisting of approximately (e.g., ±0.2°) 10.8, 14.2, 15.0, 15.9, 17.7, 18.5, 19.4, 22.3, 24.1, 24.8, and 25.8. In one embodiment, the solid form is characterized by an XRPD pattern comprising at least five peaks selected from the group consisting of approximately (e.g., ±0.2°) 10.8, 14.2, 15.0, 15.9, 17.7, 18.5, 19.4, 22.3, 24.1, 24.8, and 25.8.

In one embodiment, provided herein is a solid form comprising a phosphate salt of Compound 1, characterized by an XRPD pattern comprising peaks at approximately (e.g., ±0.2°) 10.8, 18.5, and 24.8° 2θ. In one embodiment, the solid form is characterized by an XRPD pattern further comprising peaks at approximately (e.g., ±0.2°) 22.3 and 24.10 2θ. In one embodiment, the solid form is characterized by an XRPD pattern further comprising peaks at approximately (e.g., ±0.2°) 14.2 and 17.7° 2θ. In one embodiment, the XRPD pattern comprises peaks at approximately (e.g., ±0.2°) 10.8, 14.2, 15.9, 17.7, 18.5, 22.3, 24.1, and 24.8° 2θ.

Figure 28:
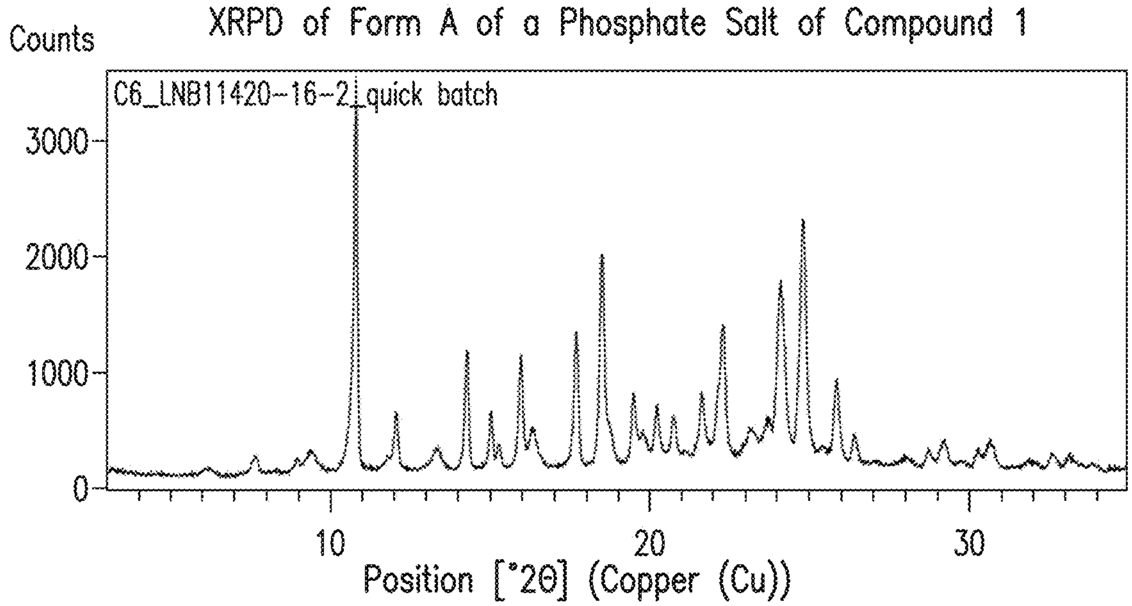
FIG. 28 is a representative XRPD pattern of Form A of a phosphate salt of Compound 1.

In one embodiment, provided herein is a solid form comprising a phosphate salt of Compound 1, characterized by an XRPD pattern that matches the XRPD pattern depicted in FIG. 28.

In one embodiment, an XRPD pattern described herein is obtained using Cu Kα radiation. In one embodiment, the XRPD pattern is measured by XRPD using Cu Kα radiation comprising Kα, radiation having a wavelength of 1.5406 Å and $K\alpha_2$ radiation having a wavelength of 1.5444 Å, wherein the $K\alpha_1$:$K\alpha_2$ ratio is 0.5.

Figure 29:
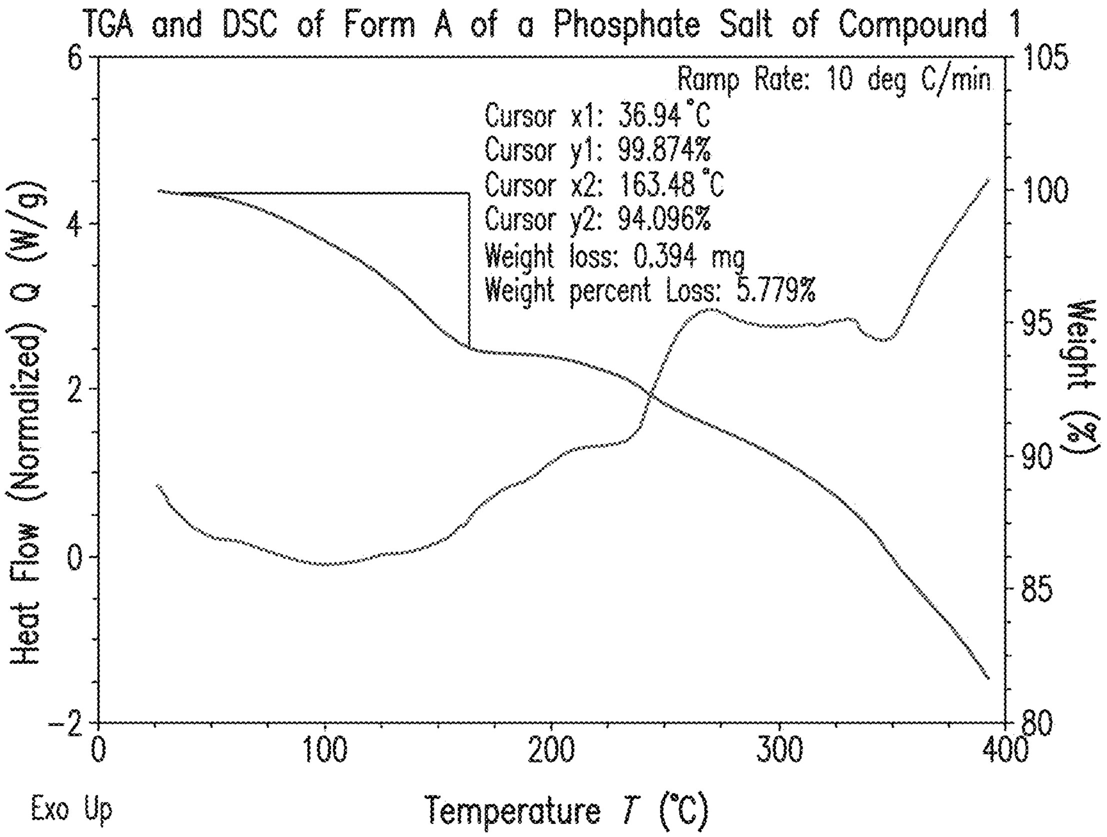
FIG. 29 is a representative overlay of TGA and DSC thermograms of Form A of a phosphate salt of Compound 1.

A representative overlay of TGA/DSC thermograms of Form A of a phosphate salt of Compound 1 is provided in FIG. 29. In one embodiment, provided herein is a solid form comprising a phosphate salt of Compound 1, which exhibits a weight loss of about 5.8% upon heating from about 25° C. to about 175° C. In one embodiment, provided herein is a solid form comprising a phosphate salt of Compound 1, which exhibits decomposition upon heating from about 25° C. (e.g. ±2°). In one embodiment, the solid form comprising a phosphate salt of Compound 1 is characterized by a TGA thermogram that matches the TGA thermogram depicted in FIG. 29. In one embodiment, the TGA thermogram is as measured using a heating rate of about 10° C./minute.

In some embodiments, provided herein is solid form comprising a phosphate salt of Compound 1. In one embodiment, the solid form comprises a single phosphate counterion. In one embodiment, the solid form is a hydrate of a phosphate salt of Compound 1. In one embodiment, the solid form is a solvate of a phosphate salt of Compound 1.

In one embodiment, the solid form is a crystalline solid form comprising a phosphate salt of Compound 1. In some embodiments, the solid form is substantially free of amorphous Compound 1 and/or an amorphous form of a salt of Compound 1. In some embodiments, the solid form comprising a phosphate salt of Compound 1 is substantially free of other solid forms (e.g., crystalline forms) of Compound 1. In some embodiments, the solid form is provided as substantially pure. In some embodiments, the solid form is substantially chemically pure. In some embodiments, the solid form is substantially physically pure.

In one embodiment, provided herein is a solid form comprising Form A of a phosphate salt of Compound 1 and amorphous free base of Compound 1. In one embodiment, provided herein is a solid form comprising Form A of a phosphate salt of Compound 1 and amorphous phosphate salt of Compound 1. In one embodiment, provided herein is a solid form comprising Form A of a phosphate salt of Compound 1 and one or more other crystalline forms of a phosphate salt of Compound 1.

All of the combinations of the above embodiments are encompassed by this application.

5.2.4. Process of Preparing Solid Forms of a Salt of Compound 1

Provided herein is a process of preparing a solid form of Compound 1, wherein the solid form is a solid form of a besylate salt of Compound 1; and the process comprises:

(i) exposing a composition comprising Compound 1 to benezenesulfonic acid in one or more solvents for a period of time sufficient to convert at least about 50% of the total amount of Compound 1 into a solid form of a besylate salt of Compound 1; and (ii) recovering said solid form.

In one embodiment, Form 1 of a free base of Compound 1 is exposed to benezenesulfonic acid in one or more solvents. In one embodiment, amorphous Compound 1 is exposed to benezenesulfonic acid in one or more solvents. In one embodiment, mostly amorphous Compound 1 is exposed to benezenesulfonic acid in one or more solvents. In one embodiment, Compound 1 is exposed an aqueous benzenesulfonic acid solution. In one embodiment, the benesulfonic acid solution has a concentration of between about 0.1M and 5M benezenesulfonic acid. In one embodiment, the benesulfonic acid solution has a concentration of 1M benezenesulfonic acid. In one embodiment, Compound 1 is exposed about 0.8 to about 1.3 molar equivalents of benzenesulfonic acid. In one embodiment, Compound 1 is exposed about 1.1 molar equivalents of benzenesulfonic acid. In one embodiment, benezenesulfonic acid is added to Compound 1 in a one or more solvents. In one embodiment, Compound 1 is dissolved in a solvent. In one embodiment, Compound 1 is dissolved in a solvent at a concentration of between about 10 and about 200 mg/ml of Compound 1. In one embodiment, Compound 1 is dissolved in a solvent at a concentration of about 100 mg/ml of Compound 1. In one embodiment, the solvent is an organic solvent. In one embodiment, the solvent is an alcohol. In one embodiment, the solvent is 1-butanol, 1-propanol, 2-methyl-1-propanol, 2-butanol, ethanol, or tAmyl alcohol. In one embodiment, the solvent is tetrahydrofuran, 2-methyltetrahydrofuran (2-MeTHF), butyl acetate, cyclopentyl methyl ether (CPME), ethyl acetate, isopropyl acetate, methyl ethyl ketone, toluene, methylisobutyl ketone or methyl acetate. In one embodiment, the solvent is 2-MeTHF. In one embodiment, the composition comprising Compound 1 is agitated following exposure to benezenesulfonic acid in one or more solvents. In one embodiment, the period of time sufficient to convert at least about 50% of the total amount of Compound 1 into a solid form of a besylate salt of Compound 1 is less than 1 hr, about 1 hr, about 2 hr, about 5 hr, about 10 hr, about 12 hr, about 20 hr, about 24 hr, about 30 hr, about 40 hr, about 48 hr, about 72 hr, about 97 hours, about 121 hours, or greater than 121 hours.

In one embodiment, the process of preparing a solid form of a besylate salt of Compound 1 further comprises a step of crystallizing or recrystallizing from a solvent after exposing a composition comprising Compound 1 to benezenesulfonic acid. In one embodiment, the crystallization or recrystallization step includes but not limited to evaporation, anti-solvent addition, slow cooling, crash cooling, temperature cycling or solvent drop grinding. In one embodiment, the process of preparing the solid form of a besylate salt of Compound 1 further comprises a step of evaporating solvent after exposing a composition comprising Compound 1 to benezenesulfonic acid. In one embodiment, the process comprises a step of evaporating 2-MeTHF solvent.

Provided herein is a process of preparing a solid form of Compound 1, wherein the solid form is a solid form of a phosphate salt of Compound 1; and the process comprises:

(i) exposing a composition comprising Compound 1 to phosphoric acid in one or more solvents for a period of time sufficient to convert at least about 50% of the total amount of Compound 1 into a solid form of a phosphate salt of Compound 1; and (ii) recovering said solid form.

In one embodiment, Form 1 of a free base of Compound 1 is exposed to phosphoric acid in one or more solvents. In one embodiment, amorphous Compound 1 is exposed to phosphoric acid in one or more solvents. In one embodiment, mostly amorphous Compound 1 is exposed to phosphoric acid in one or more solvents. In one embodiment, Compound 1 is exposed an aqueous phosphoric acid solution. In one embodiment, the phosphoric acid solution has a concentration of between about 0.1M and 15M phosphoric acid. In one embodiment, the phosphoric acid solution has a concentration of 1M phosphoric acid. In one embodiment, Compound 1 is exposed about 0.8 to about 1.3 molar equivalents of phosphoric acid. In one embodiment, Compound 1 is exposed about 1.1 molar equivalents of phosphoric acid. In one embodiment, phosphoric acid is added to Compound 1 in a one or more solvents. In one embodiment, Compound 1 is dissolved in a solvent. In one embodiment, Compound 1 is dissolved in a solvent at a concentration of between about 10 and about 200 mg/ml of Compound 1. In one embodiment, Compound 1 is dissolved in a solvent at a concentration of about 100 mg/ml of Compound 1. In one embodiment, the solvent is an organic solvent. In one embodiment, the solvent is an alcohol. In one embodiment, the solvent is 1-butanol, 1-propanol, 2-methyl-1-propanol, 2-butanol, ethanol, or tAmyl alcohol. In one embodiment, the solvent is tetrahydrofuran, 2-methyltetrahydrofuran (2-MeTHF), butyl acetate, cyclopentyl methyl ether (CPME), ethyl acetate, isopropyl acetate, methyl ethyl ketone, toluene, methylisobutyl ketone or methyl acetate. In one embodiment, the solvent is 2-MeTHF. In one embodiment, the composition comprising Compound 1 is agitated following exposure to phosphoric acid in one or more solvents. In one embodiment, the period of time sufficient to convert at least about 50% of the total amount of Compound 1 into a solid form of a phosphate salt of Compound 1 is less than 1 hr, about 1 hr, about 2 hr, about 5 hr, about 10 hr, about 12 hr, about 20 hr, about 24 hr, about 30 hr, about 40 hr, about 48 hr, about 72 hr, about 97 hours, about 121 hours, or greater than 121 hours.

In one embodiment, the process of preparing a solid form of a phosphate salt of Compound 1 further comprises a step of crystallizing or recrystallizing from a solvent after exposing a composition comprising Compound 1 to phosphoric acid. In one embodiment, the crystallization or recrystallization step includes but not limited to evaporation, anti-solvent addition, slow cooling, crash cooling, temperature cycling or solvent drop grinding. In one embodiment, the process of preparing the solid form of a phosphate salt of Compound 1 further comprises a step of evaporating solvent after exposing a composition comprising Compound 1 to phosphoric acid. In one embodiment, the process comprises a step of evaporating 2-MeTHF solvent.

5.3 Process for Preparation of Compound 1

In certain embodiments, provided herein is a process of preparing a compound of Formula (I):

(I)

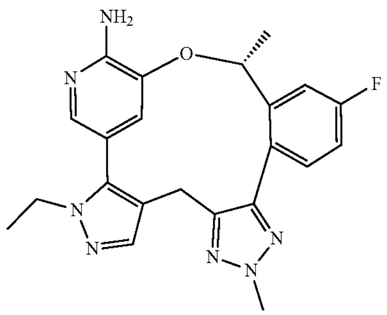

or a stereoisomer, or a mixture of stereoisomers thereof, or a pharmaceutically acceptable salt thereof, comprising:

(step 1.0) cyclizing a compound of Formula (II):

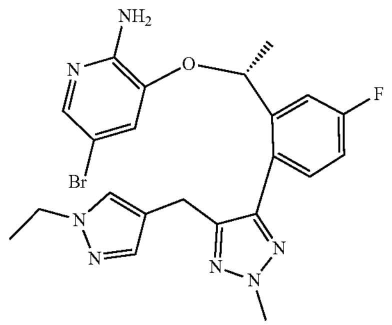

(II)

or a stereoisomer, or a mixture of stereoisomers thereof, or a pharmaceutically acceptable salt thereof, to provide a compound of Formula (I), or a stereoisomer, or a mixture of stereoisomers thereof, or a pharmaceutically acceptable salt thereof.

In some embodiments, step 1.0 occurs in the presence of a base. In some embodiments, the base is an organic base. In some embodiments, the organic base is a carboxylate base. In some embodiments, the carboxylate base is lithium acetate, sodium acetate, potassium acetate, lithium pivalate, sodium pivalate, potassium pivalate, cesium acetate, or cesium pivalate. In one embodiment, the base is potassium acetate. In one embodiment, the base is potassium pivalate.

In some embodiments, the molar ratio of the compound of Formula (II) to base in step 1.0 is from about 1:2 to about 1:6. In one embodiment, the molar ratio of the compound of Formula (II) to base in step 1.0 is about 1:5. In one embodiment, the molar ratio of the compound of Formula (II) to base in step 1.0 is about 1:3.

In some embodiments, step 1.0 occurs in the presence of a catalyst precursor. In some embodiments, the catalyst precursor comprises a palladium source. In some embodiments, the palladium source is Pd-G3, $Pd_2(dba)_3$, $PdCl_2(MeCN)_2$, $Pd(OAc)_2$, $Pd(PPh_3)_4$, $PdCl_2(PPh_3)_2$, $PdCl_2(PCy_3)_2$, $PdCl_2$(dtbpf), $PdCl_2$(dppf), $PdCl_2$(Amphos), $\{Pd(\mu\text{-Br})[P(tBu)_3]\}_2$, $PdCl_2[P(Cy)_3]_2$, $Pd[P(tBu)_3]_2$, $PdCl_2$(dtbpf), $Pd[P(Cy)_3]_2$, or $PdCl_2[P(tBu)(Cy)_2]_2$. In one embodiment, the palladium source is $Pd(OAc)_2$. In one embodiment, the catalyst precursor comprises $Pd(OAc)_2$. In some embodiments, the catalysts precursor comprises a ligand. In some embodiments, the ligand is a phosphine ligand or bisphosphine ligand. In some embodiments, the ligand is phosphine or bisphosphine ligand commonly used in the art. In one embodiment, the ligand is a cataCXium ligand. In one embodiment, the cataCXium ligand is cataCXium A, cataCXium ABn, cataCXium AHI, cataCXium PIntB, cataCXium PICy, cataCXium PtB, cataCXium POmeB, or cataCXium C. In one embodiment, the cataCXium ligand is cataCXium A. In one embodiment, the catalyst precursor comprises cataCXium A. In one embodiment, use of a cataCXium A results in improved conversion in step 1.0. In some embodiments, the catalyst precursor comprises a palladium source and a ligand. In some embodiments, the catalyst precursor and the ligand are pre-formed palladium ligand complexes such as cataCXium A Pd G2, cataCXium A Pd G3, or bis(butyldi-1-adamantylphosphine) palladium diacetate. In one embodiment, the catalyst precursor comprises $Pd(OAc)_2$ and cataCXium A. In one embodiment, when using a catalyst precursor comprising $Pd(OAc)_2$ and cataCXium A, step 1.0 proceeds to greater than 90%, greater than 95%, greater than 96%, greater than 97%, greater than 98%, or greater than 99% conversion within about 22-24 hours, as determined by HPLC.

In some embodiments, the molar ratio of the compound of Formula (II) to palladium source in step 1.0 is from about 1:0.01 (i.e. 1 mol %) to about 1:0.15 (i.e. 15 mol %). In some embodiments, the molar ratio of the compound of Formula (II) to palladium source in step 1.0 is about 1:0.02, about 1:0.03, about 1:0.04, about 1:0.05, about 1:0.06, about 1:0.07, about 1:0.08, about 1:0.09, about 1:0.10, about 1:0.11, or about 1:0.12. In one embodiment, the molar ratio of the compound of Formula (II) to palladium source in step 1.0 is about 1:0.02 (i.e. 2 mol %). In one embodiment, the molar ratio of the compound of Formula (II) to palladium source in step 1.0 is about 1:0.03 (i.e. 3 mol %). In one embodiment, the molar ratio of the compound of Formula (II) to palladium source in step 1.0 is about 1:0.04 (i.e. 4 mol %). In one embodiment, a palladium loading of less than about 10 mol %, less than about 5 mol %, or about 4 mol %, is employed in step 1.0.

In some embodiments, the molar ratio of the compound of Formula (II) to ligand in step 1.0 is from about 1:0.01 (i.e. 1 mol %) to about 1:0.15 (i.e. 15 mol %). In some embodiments, the molar ratio of the compound of Formula (II) to ligand in step 1.0 is about 1:0.03, about 1:0.04, about 1:0.05, about 1:0.06, about 1:0.07, about 1:0.08, about 1:0.09, about 1:0.10, about 1:0.11, or about 1:0.12. In one embodiment, the molar ratio of the compound of Formula (II) to ligand in step 1.0 is about 1:0.04 (i.e. 4 mol %). In one embodiment, the molar ratio of the compound of Formula (II) to ligand in step 1.0 is about 1:0.08 (i.e. 8 mol %). In one embodiment, a ligand loading of less than about 10 mol % is employed in step 1.0.

In one embodiment, the molar ratio of the ligand to the palladium source is from about 5:1 about 1:5. In one embodiment, the molar ratio of the ligand to the palladium source is from about 2:1 to about 1:2. In one embodiment, the molar ratio of the ligand to the palladium source is from about 2:1 to about 1:1. In one embodiment, the ligand is a monodentate ligand and the molar ratio of the ligand to the palladium source is about 2:1. In one embodiment, the ligand is a monodentate ligand and the molar ratio of the ligand to the palladium source is about 1:1. In one embodiment, the ligand is a bidentate ligand and the molar ratio of the ligand to the palladium source is about 1:1. In one embodiment, the ligand is a bidentate ligand and the molar ratio of the ligand to the palladium source is about 1:2.

Step 1.0 may occur in a solvent suitable for the reaction. In some embodiments, the solvent is an organic solvent or a mixture of organic solvents. In one embodiment, the solvent is a high-boiling solvent, including but not limited to $C_{4-12}$ aliphatic alcohol (branched or unbranched), toluene, anisole, 2-MeTHF, DMF, NMP, DMA or tAmOH. In one embodiment, the solvent is an alcohol. In one embodiment, the solvent is t-amyl alcohol (tAmOH). In one embodiment, the solvent is n-BuOH, s-BuOH, or t-BuOH.

In some embodiments, the volume of solvent in step 1.0 is from about 10 vol to about 30 vol. In one embodiment, the volume of the solvent in step 1.0 is about 20 vol. In some embodiments, the volume of solvent in step 1.0 is from about 5 vol to about 10 vol. In one embodiment, the volume of solvent in step 1.0 is about 8 vol.

As used herein, vol refers to the volume (L or mL) of a solvent relevant to the weight (kg or g respectively) of the limiting reagent. In some embodiments, step 1.0 occurs in an inert atmosphere (i.e. under conditions which eliminate or substantially reduce the presence of atmospheric oxygen). In one embodiment, the solvent is sparged with an inert gas (e.g. dinitrogen or argon) in step 1.0.

In some embodiments, step 1.0 occurs at a reaction temperature of from about 90° C. to about 120° C. In one embodiment, the reaction temperature is the boiling temperature of the solvent. In one embodiment, the reaction temperature is from about 100° C. to about 110° C. In one embodiment, the reaction temperature is about 102° C. In one embodiment, the reaction temperature is about 105° C.

In some embodiments, step 1.0 occurs at a reaction time from about 16 hours to about 30 hours. In one embodiment, the reaction time is from about 22 hours to about 24 hours.

In one embodiment, step 1.0 occurs in the presence of potassium pivalate base and a catalyst precursor comprising $Pd(OAc)_2$ and cataCXium A. In one embodiment, the molar ratios of the compound of Formula (I) to potassium pivalate, $Pd(OAc)_2$ and cataCXium A are 1:3, 1:0.04, and 1:0.08, respectively. In one embodiment, step 1.0 occurs in a solvent of t-amyl alcohol and a solvent volume of 20 vol at a reaction temperature of about 102° C. In one embodiment, the molar ratios of the compound of Formula (I) to potassium pivalate, $Pd(OAc)_2$ and cataCXium A are 1:3, 1:0.02, and 1:0.04, respectively. In one embodiment, step 1.0 occurs in a solvent of t-amyl alcohol and a solvent volume of 8 vol at a reaction temperature of about 105° C. In one embodiment, the solvent is sparged with dinitrogen gas in step 1.0.

In some embodiments, step 1.0 proceeds to greater than 90%, greater than 95%, greater than 96%, greater than 97%, greater than 98%, or greater than 99% conversion within about 22-24 hours, as determined by HPLC and/or NMR. In some embodiments, step 1.0 provides less than about 10%, less than about 5%, less than about 4%, less than about 3%, less than about 2%, or less than about 1% of an impurity distinct from the compound of Formula (I). Impurities provided in step 1.0 may include, but are not limited to, starting material, a debrominated species of Formula (SP-1), a dimer of Formula (SP-2), a t-butyl carbonylated species of Formula (SP-3), a regioisomer of Formula (SP-7), and/or the compound of Formula (V) described herein below.

(SP-1)

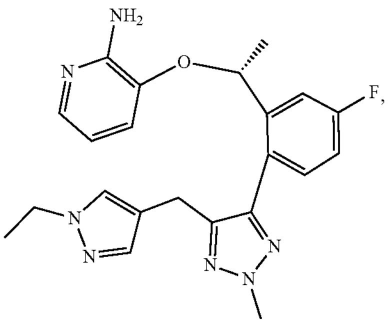

-continued (SP-2)

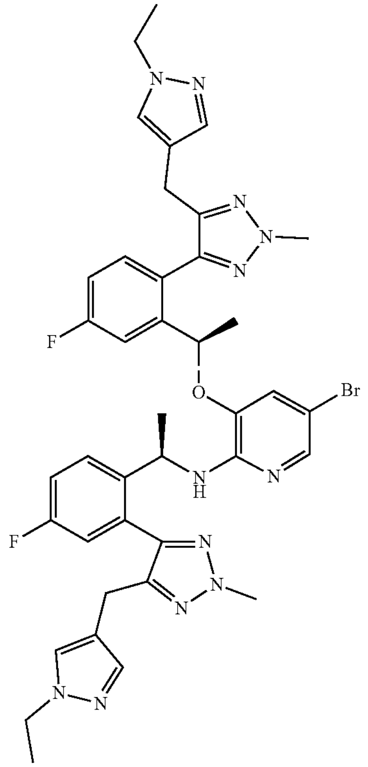

(SP-3)

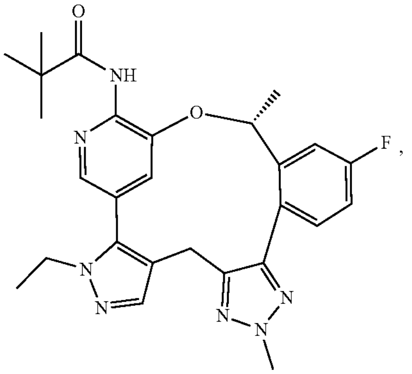

(SP-4)

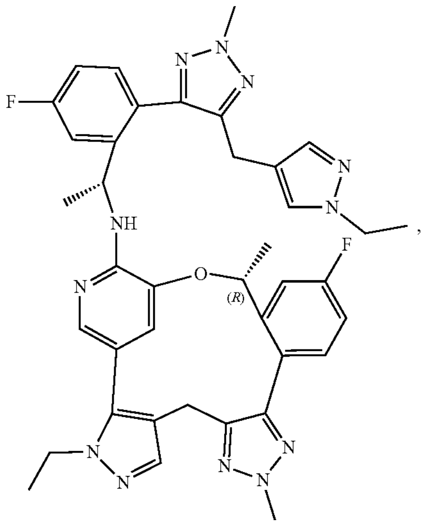

-continued (SP-7)

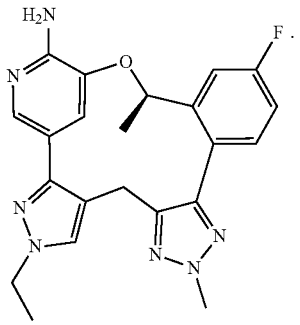

In one embodiment, the total amount of impurities provided in step 1.0 is less than less than about 10 wt %, less than about 5 wt %, less than about 4 wt %, less than about 3 wt %, less than about 2 wt %, less than about 1 wt %, less than about 0.5 wt %, less than about 0.1 wt %, or less than about 0.05 wt %.

In some embodiments, step 1.0 further comprises purification of the compound of Formula (I). In certain embodiments, the compound of Formula (I) produced in step 1.0 is purified by palladium remediation, precipitation from a solvent by an anti-solvent, and/or (re)crystallization.

In one embodiment, the palladium remediation comprises treatment with any palladium scavenger known in the art. In one embodiment, the palladium scavenger is a thiopropyl silica scavenger. In one embodiment, the palladium remediation occurs at a temperature above room temperature, e.g., from about 40° C. to about 80° C., e.g., about 60° C. In one embodiment, the palladium remediation comprises treatment with a palladium scavenger for a period of greater than 1 hour, greater than 4 hours, greater than 10 hours, greater than 14 hours, greater than 16 hours, or about 18 hours. In one embodiment, the palladium remediation comprises more than one treatment with a palladium scavenger, e.g., two treatments with a palladium scavenger.

In another embodiment, the palladium remediation comprises purifying the compound of Formula (I) by functionalized silica treatment. In one embodiment, a thiol functionalized silica gel is used to scavenge palladium from the reaction mixture. In some embodiments, this is done at room temperature. In other embodiments, it is performed at elevated temperatures (60-100° C.). In some embodiments, the scavenger loading is up to 60% by wt relative to the product mass. In other embodiments it is 0-30% by wt relative to the product mass. In some embodiments, the palladium remediation comprises purifying the compound of Formula (I) by silica gel chromatography. In yet another embodiment, the palladium remediation comprises washing an organic solution of the compound of Formula (I) with aqueous L-cysteine. In some embodiments, the aqueous L-cysteine is 5 w % aqueous solution of L-cysteine. In some embodiments, the washing is conducted at elevated temperatures (i.e. at a temperature above room temperature), for example at a temperature of about 35 to about 50° C., or about 40 to about 45° C. In one embodiment, the palladium remediation comprises purifying the compound of Formula (I) by silica gel chromatography and washing an organic solution of the compound of Formula (I) with aqueous L-cysteine.

In one embodiment, the compound of Formula (I) is precipitated from a high-boiling organic solvent. In one embodiment, the compound of Formula (I) is precipitated from anisole. In one embodiment, the compound of Formula (I) is precipitated from a solvent by addition of a non-polar organic anti-solvent. In one embodiment, the non-polar organic anti-solvent is a hydrocarbon solvent. In one embodiment, the anti-solvent is heptane. In one embodiment, the final ratio of solvent to anti-solvent is from about 1:2 to about 1:6. In one embodiment, the final ratio of solvent to anti-solvent is from about 1:4 to about 1:6. In one embodiment, the final ratio of solvent to anti-solvent is about 1:5. In one embodiment, the final ratio of solvent to anti-solvent is about 1:5.5.

In one embodiment, the compound of Formula (I) is crystallized or recrystallized from an organic solvent or a mixture of organic solvents. In one embodiment, crystallization or recrystallization of the compound of Formula (I) provides Form 1 of Compound 1. In one embodiment, the compound of Formula (I) is crystallized or recrystallized from 2-MeTHF, isopropyl acetate, acetone, anisole, ethanol, ethyl acetate, isopropyl acetate, methyl ethyl ketone, or a mixture thereof, optionally by addition of an anti-solvent. In one embodiment, the anti-solvent is water. In one embodiment, the anti-solvent is a non-polar organic solvent. In one embodiment, the non-polar organic solvent is a hydrocarbon solvent. In one embodiment, the anti-solvent is heptane. In one embodiment, the solvent is ethyl acetate and the anti-solvent is heptane. In one embodiment, the final ratio of solvent to anti-solvent is from about 1:2 to about 1:6. In one embodiment, the final ratio of solvent to anti-solvent is from about 1:3 to about 1:5. In one embodiment, the final ratio of solvent to anti-solvent is about 1:4. In one embodiment, the anti-solvent is added to the solvent at a temperature above room temperature. In one embodiment, the anti-solvent is added at a temperature of from about 30° C. to about 60° C. In one embodiment, the temperature is about 50° C.

In certain embodiments, step 1.0 provides a compound of Formula (I) in a substantially pure form. In certain embodiments, step 1.0 provides a compound of Formula (I) in a substantially chemically pure form. In certain embodiments, step 1.0 provides a compound of Formula (I) having a chemical and/or physical purity of at least about 97% w/w. In certain embodiments, step 1.0 provides a compound of Formula (I) having a chemical and/or physical purity of at least about 98% w/w. In certain embodiments, step 1.0 provides a compound of Formula (I) having a chemical and/or physical purity of at least about 99% w/w. In certain embodiments, step 1.0 provides a compound of Formula (I) having a chemical and/or physical purity of about 99.71% w/w. In certain embodiments, step 1.0 provides a compound of Formula (I) having a chemical and/or physical purity of about 99.9% w/w. In certain embodiments, step 1.0 provides a compound of Formula (I) having an enantiomeric purity of at least about 98% (e.g. 99% or 99.5%). In certain embodiments, step 1.0 provides a compound of Formula (I) having an enantiomeric purity of at least about 99.5%. In certain embodiments, step 1.0 provides a compound of Formula (I) having an enantiomeric purity of about 99.9%. In certain embodiments, step 1.0 provides a compound of Formula (I) having an enantiomeric purity of about 100%. In certain embodiments, step 1.0 provides a compound of Formula (I) substantially free of impurities. In certain embodiments, step 1.0 provides a composition comprising Compound 1 having a residual palladium content of less than about 200 ppm, less than about 100 ppm, less than about 50 ppm, less than about 40 ppm, less than about 30 ppm, less than about 20 ppm, or less than about 10 ppm. In certain embodiments, step 1.0 provides a compound of Formula (I) in a substantially enantiomerically pure form. In certain embodiments, step 1.0 provides a compound of Formula (I) in a substantially physically pure form. In certain embodiments, step 1.0 provides a compound of Formula (I) in a solid form having a desired morphology (e.g. a specific crystalline form, such as Form 1 of Compound 1) or advantageous rheological properties.

In certain embodiments, also provided herein is a process of preparing a compound of Formula (II), or a stereoisomer, or a mixture of stereoisomers thereof, or a pharmaceutically acceptable salt thereof, comprising:

(step 2.0) reacting a compound of Formula (III)

(III)

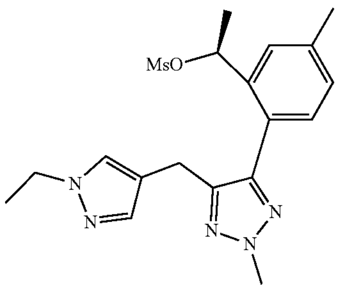

or a stereoisomer, or a mixture of stereoisomers thereof, or a pharmaceutically acceptable salt thereof, with a compound of Formula (IV):

(IV)

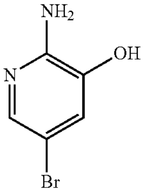

or a stereoisomer, or a mixture of stereoisomers thereof, or a pharmaceutically acceptable salt thereof.

In some embodiment, the molar ratio of the compound of Formula (III) to the compound of Formula (IV) in step 2.0 is from about 1:1 to about 1:1.5. In one embodiment, the molar ratio of the compound of Formula (III) to the compound of Formula (IV) in step 2.0 is about 1.2. In one embodiment, the molar ratio of the compound of Formula (III) to the compound of Formula (IV) in step 2.0 is about 1.1. In one embodiment, the molar ratio of the compound of Formula (III) to the compound of Formula (IV) in step 2.0 is about 1.14.

In some embodiments, step 2.0 occurs in the presence of a base. In some embodiments, step 2.0 occurs in the presence of an alkali metal base. In some embodiments, the base is an alkali metal hydroxide, carbonate, hydrogencarbonate, phosphate, hydrogenphosphate, or dihydrogenphosphate. In some embodiments, the base is LiOH, $Li_2CO_3$, NaOH, KOH, tBuOK, $Na_2CO_3$, $K_2CO_3$, $Cs_2CO_3$, $NaHCO_3$, $KHCO_3$, $Na_3PO_4$, $K_3PO_4$, $Na_2HPO_4$, $K_2HPO_4$, $NaH_2PO_4$, or $KH_2PO_4$. In one embodiment, the base is sodium carbonate ($Na_2CO_3$). In some embodiments, the base is cesium carbonate ($Cs_2CO_3$). In one embodiment, the base is potassium phosphate ($K_3PO_4$). In some embodiments, step 2.0 occurs in the presence of a nitrogen containing base. In some embodiments, step 2.0 occurs in the presence of 1,8-diazabicyclo[5.4.0]undec-7-ene (DBU), 1,1,3,3-tetramethylguanidine (TMG), triazabicyclodecene (TBD), or potassium bis(trimethylsilyl)amide (KHMDS).

In some embodiments, the molar ratio of the compound of Formula (III) to base in step 2.0 is from about 1:1 to about 1:5. In some embodiments, the molar ratio of the compound of Formula (III) to base in step 2.0 is from about 1:1 to about 1:3. In one embodiment, the molar ratio of the compound of Formula (III) to base in step 2.0 is about 1:1. In one embodiment, the molar ratio of the compound of Formula (III) to base in step 2.0 is about 1:2. In one embodiment, the molar ratio of the compound of Formula (III) to base in step 2.0 is about 1:2.2. In one embodiment, the molar ratio of the compound of Formula (III) to base in step 2.0 is about 1:4.1.

Step 2.0 may occur in a solvent suitable for the reaction. In some embodiments, the solvent is an organic solvent or a mixture of organic solvents. In one embodiment, the solvent is a polar organic solvent. In one embodiment, the solvent is DMF, DCM, IPAc, ehyl acetate, t-amyl alcohol, 1,4-dioxane, DMA, NMP, ACN, or DMSO. In one embodiment, step 2.0 occurs in a solvent of N-methyl-2-pyrrolidone (NMP). In one embodiment, step 2.0 occurs in a solvent of dimethyl acetamide (DMA). In one embodiment, step 2.0 occurs in a solvent of dimethyl formamide (DMF).

In some embodiments, the volume of solvent in step 2.0 is from about 4 vol to about 20 vol. In one embodiment, the volume of the solvent in step 2.0 is about 16 vol. In some embodiments, the volume of solvent in step 2.0 is from about 4 vol to about 15 vol. In one embodiment, the volume of the solvent in step 2.0 is 15 vol. In one embodiment, the volume of the solvent in step 2.0 is about 13 vol. In one embodiment, the volume of the solvent in step 2.0 is about 8 vol. In one embodiment, the volume of the solvent in step 2.0 is about 6 vol. In one embodiment, the volume of the solvent in step 2.0 is about 5.6 vol.

In some embodiments, step 2.0 occurs in an inert atmosphere (i.e. under conditions which eliminate or substantially reduce the presence of atmospheric oxygen). In one embodiment, the solvent is sparged with an inert gas (e.g. dinitrogen or argon) in step 2.0.

In some embodiments, step 2.0 occurs at a reaction temperature of from about 20° C. to about 60° C. In some embodiments, step 2.0 occurs at a reaction temperature of from about 35° C. to about 45° C. In some embodiments, step 2.0 occurs at a reaction temperature of from about 20° C. to about 30° C. In one embodiment, the reaction temperature is about 20° C. In one embodiment, the reaction temperature is about 25° C. In one embodiment, step 2.0 is conducted at room temperature. In one embodiment, step 2.0 is conducted at a temperature that minimizes decomposition of the compound of Formula (III).

In some embodiments, step 2.0 occurs at a reaction time from about 10 hours to about 30 hours. In one embodiment, the reaction time is about 22 hours.

In one embodiment, the molar ratio of the compound of Formula (III) to the compound of Formula (IV) in step 2.0 is about 1:1. In one embodiment, step 2.0 occurs in the presence of cesium carbonate ($Cs_2CO_3$) and the molar ratio of the compound of Formula (III) to $Cs_2CO_3$ in step 2.0 is about 1:2.2. In one embodiment, step 2.0 occurs in a solvent of DMA. In one embodiment, step 2.0 occurs in a solvent of NMP. In one embodiment, step 2.0 occurs in a solvent of N-methyl-2-pyrrolidone (NMP) and a solvent volume of 6 vol. at room temperature. In one embodiment, the solvent is sparged with nitrogen gas in step 2.0.

In one embodiment, the molar ratio of the compound of Formula (III) to the compound of Formula (IV) in step 2.0 is about 1:1. In one embodiment, step 2.0 occurs in the presence of potassium phosphate ($K_3PO_4$) and the molar ratio of the compound of Formula (III) to $K_3PO_4$ in step 2.0 is about 1:4.1. In one embodiment, step 2.0 occurs in a solvent of dimethyl formamide (DMA) and a solvent volume of 16 vol. at about 35° C. to about 45° C. In one embodiment, the solvent is sparged with dinitrogen gas in step 2.0.

In one embodiment, the molar ratio of the compound of Formula (III) to the compound of Formula (IV) in step 2.0 is about 1:14. In one embodiment, step 2.0 occurs in the presence of cesium carbonate ($Cs_2CO_3$) and the molar ratio of the compound of Formula (III) to $Cs_2CO_3$ in step 2.0 is about 1:2.2. In one embodiment, step 2.0 occurs in a solvent of N-methyl-2-pyrrolidone (NMP) and a solvent volume of 5.6 vol. at about 20° C. to about 30° C. In one embodiment, the solvent is sparged with dinitrogen gas in step 2.0.

In some embodiments, step 2.0 proceeds to greater than 90%, greater than 95%, greater than 96%, greater than 97%, greater than 98%, or greater than 99% conversion within about 22-24 hours, as determined by HPLC and/or NMR. In some embodiments, step 2.0 provides less than about 10%, less than about 5%, less than about 4%, less than about 3%, less than about 2%, or less than about 1% of an impurity distinct from the compound of Formula (II). Impurities provided in step 2.0 may include, but are not limited to, starting material, an elimination product of Formula (SP-5) and/or the compound of Formula (V) described herein below.

(SP-5)

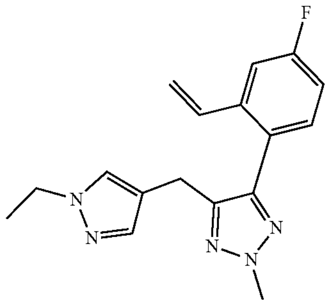

In one embodiment, the total amount of impurities provided in step 2.0 is less than less than about 10%, less than about 5 wt %, less than about 4 wt %, less than about 3 wt %, less than about 2 wt %, or less than about 1 wt %.

In some embodiments, step 2.0 further comprises purification of the compound of Formula (II). In certain embodiments, the compound of Formula (II) produced in step 2.0 is purified by precipitation from a solvent by an anti-solvent and/or (re)crystallization.

In one embodiment, the compound of Formula (II) is precipitated from an organic solvent. In one embodiment, the compound of Formula (II) is precipitated from NMP. In one embodiment, the compound of Formula (II) is precipitated from a solvent by addition of an anti-solvent. In one embodiment, the anti-solvent is water. In one embodiment, the final volume ratio of solvent to anti-solvent is from about 1:1 to about 1:4. In one embodiment, the final volume ratio of solvent to anti-solvent is about 1:1.5. In one embodiment, the final volume ratio of solvent to anti-solvent is about 1:2. In one embodiment, the final volume ratio of solvent to anti-solvent is about 1:3.

In one embodiment, the compound of Formula (II)

(II)

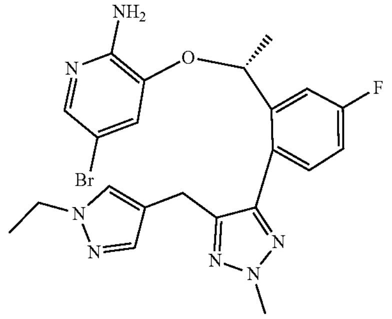

is crystallized or recrystallized from an organic solvent or a mixture of organic solvents. In one embodiment, the compound of Formula (II) is crystallized or recrystallized from 2-MeTHF, isopropyl acetate, acetone, anisole, toluene, t-butanol, acetonitrile, ethanol, ethyl acetate, isopropyl acetate, methyl ethyl ketone, or a mixture thereof, optionally by addition of an anti-solvent. In one embodiment, the anti-solvent is water. In one embodiment, the anti-solvent is a non-polar organic solvent. In one embodiment, the non-polar organic solvent is a hydrocarbon solvent. In one embodiment, the anti-solvent is heptane. In one embodiment, the anti-solvent is methylcyclohexane. In one embodiment, the solvent is ethyl acetate, toluene, anisole, t-butanol, acetonitrile, isopropyl acetate, or EtOH, and the anti-solvent is water, heptane or methylcyclohexane. In one embodiment, the solvent is ethyl acetate and the anti-solvent is heptane. In one embodiment, the solvent is toluene and the anti-solvent is heptane. In one embodiment, the solvent is a mixture of ethyl acetate and toluene, and the anti-solvent is heptane. In one embodiment, the final volume ratio of solvent to anti-solvent is from about 1:2 to about 1:6. In one embodiment, the final volume ratio of solvent to anti-solvent is from about 1:3 to about 1:5. In one embodiment, the final volume ratio of solvent to anti-solvent is about 1:3. In one embodiment, the final volume ratio of solvent to anti-solvent is about 1:4. In one embodiment, the final volume ratio of solvent to anti-solvent is about 1:5. In one embodiment, the anti-solvent is added to the solvent at a temperature above room temperature. In one embodiment, the anti-solvent is added at a temperature of from about 30° C. to about 60° C. In one embodiment, the temperature is about 40° C.

In certain embodiments, step 2.0 provides a compound of Formula (II) in a substantially pure form. In certain embodiments, step 2.0 provides a compound of Formula (II) in a substantially chemically pure form. In certain embodiments, step 2.0 provides a compound of Formula (II) in a substantially enantiomerically pure form. In certain embodiments, step 2.0 provides a compound of Formula (II) substantially free of impurities and easy scale up. In certain embodiments, step 2.0 reduces, eliminates or minimizes the amount of impurities carried forward into step 1.0.

In certain embodiments, also provided herein is a process for preparing a compound of Formula (III), or a stereoisomer, or a mixture of stereoisomers thereof, or a pharmaceutically acceptable salt thereof, comprising:

(step 3.0) reacting a compound of Formula (V):

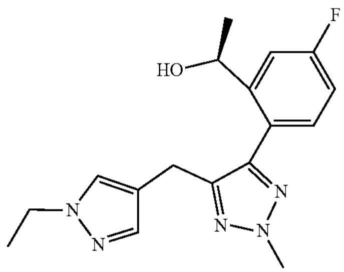 [SMILES: CCn1cc(Cc2nn(C)nc2-c2ccc(F)cc2[C@H](C)O)cn1]

or a stereoisomer, or a mixture of stereoisomers thereof, or a pharmaceutically acceptable salt thereof, with a mesylating reagent.

In some embodiments, the mesylating reagent in step 3.0 is mesyl chloride (MsCl) or methanesulfonic anhydride ($Ms_2O$). In one embodiment, the mesylating reagent is methanesulfonic anhydride ($Ms_2O$).

In some embodiments, the molar ratio of the compound of Formula (V) to mesylating reagent in step 3.0 is from about 1:1 to about 1:2. In one embodiment, the molar ratio of the compound of Formula (V) to mesylating reagent is 1:2. In one embodiment, the molar ratio of the compound of Formula (V) to mesylating reagent is about 1:1.2.

In some embodiments, step 3.0 occurs in the presence of a base. In some embodiments, step 3.0 occurs in the presence of a nitrogen containing base. In some embodiments, step 3.0 occurs in the presence of $NH_4OH$, triethylamine, diisopropylethylamine (DIEA or DIPEA), pyridine, lutidine, 4-dimethylaminopyridine, imidazole, or 1,8-diazabicyclo [5.4.0]undec-7-ene (DBU). In one embodiment, the base is triethylamine (TEA).

In some embodiments, the molar ratio of the compound of Formula (V) to base in step 3.0 is from about 1:1 to about 1:4. In one embodiment, the molar ratio of the compound of Formula (V) to base is about 1:4. In one embodiment, the molar ratio of the compound of Formula (V) to base is about 1:1.3.

Step 3.0 may occur in a solvent suitable for the reaction. In some embodiments, the solvent is an organic solvent or a mixture of organic solvents. In one embodiment, step 3.0 occurs in a solvent of dichloromethane (DCM). In one embodiment, step 3.0 occurs in a solvent of 2-methyl THF.

In some embodiments, the volume of solvent in step 3.0 is from about 4 vol to about 20 vol. In one embodiment, the volume of the solvent in step 3.0 is about 20 vol. In one embodiment, the volume of the solvent in step 3.0 is about 15 vol. In one embodiment, the volume of the solvent in step 3.0 is about 10 vol.

In some embodiments, step 3.0 occurs at a reaction temperature of less than 5° C. In some embodiments, step 3.0 occurs at a reaction temperature of from about 0° C. to about 5° C. In one embodiment, the reaction temperature is about 0° C. In one embodiment, the reaction temperature is about 5° C.

In some embodiments, step 3.0 occurs at a reaction time from about 10 minutes to about 2 hours. In one embodiment, the reaction time is about 30 minutes.

In one embodiment, the mesylating reagent in step 3.0 is methanesulfonic anhydride ($Ms_2O$) and the base is triethylamine. In one embodiment, the molar ratios of the compound of Formula (V) to mesylating reagent and base are 1.2 and 1.3, respectively. In one embodiment, step 3.0 occurs in a solvent of DCM and a solvent volume of 10 vol. at 0° C. to room temperature. In one embodiment, step 3.0 occurs in a solvent of DCM and a solvent volume of 10 vol. at room temperature. In one embodiment, step 3.0 occurs in a solvent of 2-methyl THF and a solvent volume of 10 vol. at room temperature. In one embodiment, the compound of Formula (V) is purified by an aqueous extraction and/or precipitation from ethyl acetate with added heptane. In one embodiment, the compound of Formula (V) is purified by an aqueous extraction and/or precipitation from DCM with added heptane.

In some embodiments, step 3.0 proceeds to greater than 90%, greater than 95%, greater than 96%, greater than 97%, greater than 98%, or greater than 99% conversion within about 1 hour, as determined by HPLC and/or NMR. In some embodiments, step 3.0 provides less than about 10%, less than about 5%, less than about 4%, less than about 3%, less than about 2%, or less than about 1% of an impurity distinct from the compound of Formula (III). Impurities provided in step 3.0 may include, but are not limited to, starting materials. In some embodiments, the exemplified impurities observed in this step are elimination impurity (SP-3) and the starting material. In one embodiment, the total amount of impurities provided in step 3.0 is less than less than about 10%, less than about 5%, less than about 4%, less than about 3%, less than about 2%, or less than about 1%.

In some embodiments, step 3.0 further comprises purification of the compound of Formula (III). In certain embodiments, the compound of Formula (III) produced in step 3.0 is purified by aqueous extraction, and/or precipitation from a solvent by an anti-solvent. In one embodiment, the compound of Formula (III) is purified by aqueous extraction with dilute sodium bicarbonate. In one embodiment, extraction with sodium bicarbonate maintains the pH of the reaction mixture at about pH 7 or above. In one embodiment, extraction with sodium bicarbonate quenches resident methanesulfonic anhydride.

In one embodiment, the compound of Formula (III) is precipitated from an organic solvent. In one embodiment, the compound of Formula (III) is precipitated from ethyl acetate. In one embodiment, the compound of Formula (III) is precipitated from DCM. In one embodiment, the compound of Formula (III) is precipitated from a solvent by addition of an anti-solvent. In one embodiment, the anti-solvent is heptane. In one embodiment, the final volume ratio of solvent to anti-solvent is from about 1:1 to about 1:4. In one embodiment, the final volume ratio of solvent to anti-solvent is about 1:3.

In certain embodiments, step 3.0 provides a compound of Formula (III) in a substantially pure form. In certain embodiments, step 3.0 provides a compound of Formula (III) in a substantially chemically pure form. In certain embodiments, step 3.0 provides a compound of Formula (III) substantially free of impurities. In certain embodiments, step 3.0 provides a compound of Formula (III) in a substantially enantiomerically pure form. In certain embodiments, step 3.0 provides a compound of Formula (III) in a solid form having a desired morphology or advantageous rheological properties.

In certain embodiments, also provided herein is a process for preparing a compound of Formula (V), or a stereoisomer, or a mixture of stereoisomers thereof, or a pharmaceutically acceptable salt thereof, comprising:

(step 4.0) reacting a compound of Formula (VI):

(VI)

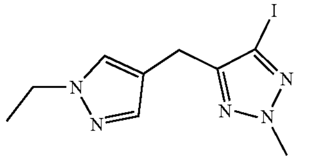

or a stereoisomer, or a mixture of stereoisomers thereof, or a pharmaceutically acceptable salt thereof, with a compound of Formula (VII):

(VII)

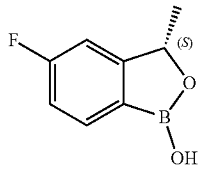

or a stereoisomer, or a mixture of stereoisomers thereof, or a pharmaceutically acceptable salt thereof.

In some embodiments, the molar ratio of the compound of formula (VI) to the compound of Formula (VII) in step 4.0 is from about 1:1 to about 1:1.2. In one embodiment, the molar ratio of the compound of formula (VI) to the compound of Formula (VII) in step 4.0 is about 1:2. In one embodiment, the molar ratio of the compound of formula (VI) to the compound of Formula (VII) in step 4.0 is about 1:1.05. In one embodiment, the molar ratio of the compound of formula (VI) to the compound of Formula (VII) in step 4.0 is about 1:1.02.

In some embodiments, step 4.0 occurs in the presence of a catalyst. In one embodiment, the catalyst is a palladium catalyst. In one embodiment, the palladium catalyst is $Pd_2(dba)_3$, $Pd(PPh_3)_4$, $PdCl_2(PPh_3)_2$, $PdCl_2(PCy_3)_2$, $PdCl_2(dppf)$, $PdCl_2(dtbpf)$, or $Pd(Amphos)Cl_2$. In one embodiment, the catalyst is $PdCl_2(dppf)$. In one embodiment, the catalyst is $Pd(Amphos)Cl_2$.

In some embodiments, the molar ratio of the compound of Formula (VI) to catalyst in step 4.0 is from about 1:0.001 (i.e. 0.1 mol %) to about 1:0.04 (i.e. 4 mol %). In some embodiments, the molar ratio of the compound of Formula (VI) to catalyst in step 4.0 is about 1:0.001, about 1:0.002, about 1:0.003, about 1:0.004, about 1:0.005, about 1:0.006, about 1:0.007, about 1:0.008, about 1:0.009, or about 1:0.01. In one embodiment, the molar ratio of the compound of Formula (VI) to catalyst in step 4.0 is about 1:0.04 (i.e. 4 mol %). In one embodiment, the molar ratio of the compound of Formula (VI) to catalyst in step 4.0 is about 1:0.005 (i.e. 0.5 mol %). In one embodiment, the molar ratio of the compound of Formula (VI) to catalyst in step 4.0 is about 1:0.002 (i.e. 0.2 mol %). In one embodiment, a catalyst loading of less than about 4 mol %, less than about 1 mol %, or about 0.5 mol %, is employed in step 4.0.

In some embodiments, step 4.0 occurs in the presence of a base. In some embodiments, step 2.0 occurs in the presence of an alkali metal base. In some embodiments, the base is an alkali metal hydroxide, carbonate, hydrogencarbonate, phosphate, hydrogenphosphate, or dihydrogenphosphate. In some embodiments, the base is LiOH, NaOH, KOH, $Na_2CO_3$, $K_2CO_3$, $Cs_2CO_3$, $NaHCO_3$, $KHCO_3$, $Na_3PO_4$, $K_3PO_4$, $Na_2HPO_4$, $K_2HPO_4$, $NaH_2PO_4$, or $KH_2PO_4$. In one embodiment, the base is potassium carbonate ($K_2CO_3$). In one embodiment, the base is potassium phosphate ($K_3PO_4$). In one embodiment, the base is potassium phosphate trihydrate ($K_3PO_4 \cdot 3\ H_2O$).

In some embodiments, the molar ratio of the compound of Formula (VI) to base in step 4.0 is from about 1:2 to about 1:4. In one embodiment, the molar ratio of the compound of Formula (VI) to base in step 4.0 is about 1:3. In one embodiment, the molar ratio of the compound of Formula (VI) to base in step 4.0 is about 1:3.05.

Step 4.0 may occur in a solvent suitable for the reaction. In one embodiment, the solvent is CPME, MeTHF, DME, DMAc, IPA, MeOH, DMF, DMA, NMP, ACN, DMSO, 1,4-dioxane, tetrahydrofuran, or water, or a mixture thereof. In one embodiment, the solvent is a mixture of an organic solvent and water. In one embodiment, step 4.0 occurs in a mixture of 1,4-dioxane and water. In one embodiment, step 4.0 occurs in a mixture of tetrahydrofuran and water. In one embodiment, step 4.0 occurs in a mixture of dimethyl formamide (DMF) and water. In one embodiment, step 4.0 occurs in a mixture of toluene and water. In one embodiment, the mixture an organic solvent and water has a ratio of organic solvent to water of from about 10:1 to about 3:1. In one embodiment, the ratio of organic solvent to water is about 10:1. In one embodiment, the ratio of organic solvent to water is about 5:1. In one embodiment, the mixture an organic solvent and water has a ratio of organic solvent to water of from about 1:2 to about 1:5. In one embodiment, the ratio of organic solvent to water is about 1:4.

In some embodiments, the volume of solvent in step 4.0 is from about 2 vol to about 15 vol. In some embodiments, the volume of solvent in step 4.0 is from about 4 vol to about 15 vol. In one embodiment, the volume of the solvent in step 4.0 is about 11 vol. In one embodiment, the volume of the solvent in step 4.0 is about 6 vol. In one embodiment, the volume of the solvent in step 4.0 is about 2.5 vol.

In some embodiments, step 4.0 occurs at a reaction temperature of from about 40° C. to about 90° C. In some embodiments, step 4.0 occurs at a reaction temperature of from about 40° C. to about 70° C. In some embodiments, step 4.0 occurs at a reaction temperature of from about 60° C. to about 70° C. In one embodiment, the reaction temperature is about 65° C. In one embodiment, the reaction temperature is about 50° C.

In some embodiments, step 4.0 occurs at a reaction time from about 1 hour to about 4 hours. In one embodiment, the reaction time is from about 2 to about 3 hours. In one embodiment, the purity of the compound of Formula (V) provided in step 4.0 decreases with longer reaction times.

In one embodiment, the molar ratio of the compound of formula (VI) to the compound of Formula (VII) in step 4.0 is about 1:1.2. In one embodiment, the catalyst is $Pd(dppf)Cl_2$ and the catalyst loading is 4 mol %. In one embodiment, the base is potassium carbonate ($K_2CO_3$) and the molar ratio of the compound of Formula (VI) to potassium carbonate in step 4.0 is about 1:3. In one embodiment, the solvent in step 4.0 is an about 10:1 mixture of THE and water. In one embodiment, step 4.0 occurs at a reaction temperature of about 60 to about 65° C.

In one embodiment, the molar ratio of the compound of formula (VI) to the compound of Formula (VII) in step 4.0 is about 1:1.05. In one embodiment, the catalyst is $Pd(Amphos)Cl_2$ and the catalyst loading is 0.05 mol %. In one embodiment, the catalyst is $Pd(Amphos)Cl_2$ and the catalyst loading is 0.5 mol %. In one embodiment, the catalyst is $Pd(Amphos)Cl_2$ and the catalyst loading is 0.4 mol %. In one embodiment, the catalyst is Pd(Amphos)$Cl_2$ and the catalyst loading is 0.3 mol %. In one embodiment, the catalyst is Pd(Amphos)$Cl_2$ and the catalyst loading is 0.2 mol %. In one embodiment, the base is potassium carbonate ($K_2CO_3$) and the molar ratio of the compound of Formula (VI) to potassium carbonate in step 4.0 is about 1:3. In one embodiment, the solvent in step 4.0 is an about 5:1 mixture of dimethylformamide and water. In one embodiment, step 4.0 occurs at a reaction temperature of about 65° C. and a reaction time of about 2 to about 3 hours.

In one embodiment, the molar ratio of the compound of formula (VI) to the compound of Formula (VII) in step 4.0 is about 1:1.02. In one embodiment, the catalyst is Pd(Amphos)$Cl_2$ and the catalyst loading is 0.2 mol %. In one embodiment, the base is potassium phosphate trihydrate ($K_3PO_4.3H_2O$) and the molar ratio of the compound of Formula (VI) to potassium phosphate trihydrate in step 4.0 is about 1:3.05. In one embodiment, the solvent in step 4.0 is an about 1:4 mixture of toluene and water. In one embodiment, step 4.0 occurs at a reaction temperature of about 50° C.

In some embodiments, step 4.0 proceeds to greater than 90%, greater than 95%, greater than 96%, greater than 97%, greater than 98%, or greater than 99% conversion within about 2-3 hours, as determined by HPLC and/or NMR. In some embodiments, step 4.0 provides less than about 10%, less than about 5%, less than about 4%, less than about 3%, less than about 2%, or less than about 1% of an impurity distinct from the compound of Formula (V). Impurities provided in step 4.0 may include, but are not limited to, starting materials and a compound of Formula (SP-6):

(SP-6)

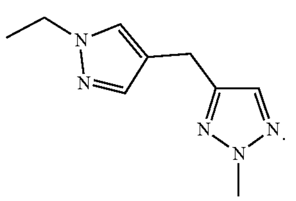

In one embodiment, the total amount of impurities provided in step 3.0 is less than less than about 10%, less than about 5%, less than about 4%, less than about 3%, less than about 2%, or less than about 1%.

In some embodiments, step 4.0 further comprises purification of the compound of Formula (V). In certain embodiments, the compound of Formula (V) produced in step 4.0 is purified by aqueous extraction, palladium remediation, and/or precipitation from a solvent by an anti-solvent.

In one embodiment, aqueous extraction comprises extraction of a composition comprising a compound of Formula (V) dissolved in an organic solvent with water. In one embodiment, the organic solvent is ethyl acetate. In one embodiment, aqueous extraction comprises extraction of a composition comprising a compound of Formula (V) dissolved in an organic solvent with an aqueous lithium chloride solution. In one embodiment, the aqueous lithium chloride solution is a 5% aqueous lithium chloride solution. In one embodiment, the aqueous lithium chloride solution is a 15% aqueous lithium chloride solution. In one embodiment, the organic solvent is ethyl acetate, DMF, MTBE, 2-MeTHF, or CPME, or a mixture thereof. In one embodiment, the organic solvent is a mixture of MTBE and DMF. In one embodiment the organic solvent is MTBE. In one embodiment, the organic solvent is a mixture of MTBE and isopropyl ether.

In one embodiment, the palladium remediation comprises treatment with any palladium scavenger known in the art. In one embodiment, the palladium scavenger is a thiopropyl silica scavenger. In one embodiment, the palladium remediation occurs at a temperature above room temperature, e.g., from about 40° C. to about 80° C., e.g., about 65° C. In one embodiment, the palladium remediation comprises treatment with a palladium scavenger for a period of about 1 hour to about 18 hours. In certain embodiments, the palladium remediation comprises treatment with a palladium scavenger for a period of about 1 hour, about 3 hours, greater than about 3 hours, greater than 10 hours, greater than 14 hours, greater than 16 hours, or about 18 hours.

In another embodiment, the palladium remediation comprises purifying the compound of Formula (V) by silica gel chromatography. In yet another embodiment, the palladium remediation comprises washing an organic solution of the compound of Formula (V) with aqueous L-cysteine. In some embodiments, the aqueous L-cysteine is 5 w % aqueous solution of L-cysteine. In some embodiments, the washing is conducted at elevated temperatures, (i.e. at a temperature above room temperature), for example at a temperature of about 35~50° C., or 40~45° C. In one embodiment, the palladium remediation comprises purifying the compound of Formula (V) by silica gel chromatography and washing an organic solution of the compound of Formula (V) with aqueous L-cysteine.

In yet another embodiment, the palladium remediation comprises treating a solution of the compound of Formula (V) with activated carbon (e.g., via a CUNO filter).

In one embodiment, the compound of Formula (V) is precipitated from an organic solvent. In one embodiment, the compound of Formula (V) is precipitated from MTBE. In one embodiment, the compound of Formula (V) is precipitated from a mixture of MTBE and isopropyl ether. In one embodiment, the compound of Formula (V) is precipitated from a solvent by addition of an anti-solvent. In one embodiment, the anti-solvent is isopropyl ether. In one embodiment, the anti-solvent is heptane. In one embodiment, the final ratio of solvent to anti-solvent is from about 1:1 to about 1:4. In one embodiment, the final ratio of solvent to anti-solvent is about 1:3. In one embodiment, the anti-solvent is added to the solvent at a temperature below 0° C. In one embodiment, the compound of Formula (V) is crystallized or recrystallized from an organic solvent or a mixture of organic solvents. In one embodiment, the compound of Formula (II) is crystallized or recrystallized from ethyl acetate, CPME, MTBE, toluene, or a mixture thereof, optionally by addition of an anti-solvent. In one embodiment, the anti-solvent is water. In one embodiment, the anti-solvent is a non-polar organic solvent. In one embodiment, the non-polar organic solvent is a hydrocarbon solvent. In one embodiment, the anti-solvent is heptane. In one embodiment, the solvent is ethyl acetate and the anti-solvent is heptane. In one embodiment, the solvent is toluene and the anti-solvent is heptane. In one embodiment, the final volume ratio of solvent to anti-solvent is from about 1:2 to about 1:6.

In certain embodiments, step 4.0 provides a compound of Formula (V) in a substantially pure form. In certain embodiments, step 4.0 provides a compound of Formula (V) in a substantially chemically pure form. In certain embodiments, step 4.0 provides a compound of Formula (V) substantially free of impurities. In certain embodiments, step 4.0 provides a compound of Formula (V) in a substantially enantiomerically pure form. In certain embodiments, step 4.0 provides a compound of Formula (V) in a solid form having a desired morphology or advantageous rheological properties.

In certain embodiments, also provided herein is a process for preparing a compound of Formula (I), or a stereoisomer, or a mixture of stereoisomers thereof, or a pharmaceutically acceptable salt thereof, is prepared by a process comprising:

(step 1.0) cyclizing a compound of Formula (II) or a stereoisomer, or a mixture of stereoisomers thereof, or a pharmaceutically acceptable salt thereof, to provide a compound of Formula (I), or an enantiomer, a mixture of enantiomers, or a tautomer thereof, or a pharmaceutically acceptable salt thereof, wherein the compound of Formula (II) is prepared by a process comprising:

(step 2.0) reacting a compound of Formula (III) or a stereoisomer, or a mixture of stereoisomers thereof, or a pharmaceutically acceptable salt thereof, with a compound of Formula (IV), or a pharmaceutically acceptable salt thereof, wherein the compound of Formula (III) is prepared by a process comprising:

(step 3.0) reacting a compound of Formula (V) or a stereoisomer, or a mixture of stereoisomers thereof, or a pharmaceutically acceptable salt thereof, with a mesylating reagent; and wherein the compound of Formula (V) is prepared by a process comprising:

(step 4.0) reacting a compound of Formula (VI) or or a stereoisomer, or a mixture of stereoisomers thereof, or a pharmaceutically acceptable salt thereof, with a compound of Formula (VII) or a stereoisomer, or a mixture of stereoisomers thereof, or a pharmaceutically acceptable salt thereof.

In one embodiment, the processes provided herein further comprise a step of providing the compound of Formula (I), or a stereoisomer, or a mixture of stereoisomers thereof, or a pharmaceutically acceptable salt thereof, in a solid form. In one embodiment, the solid form is a crystalline form. In one embodiment, provided herein is a crystalline form of a compound of Formula (I), or a stereoisomer, or a mixture of stereoisomers thereof, or a pharmaceutically acceptable salt thereof, prepared by the process.

In one embodiment, also provided herein is a compound of Formula (II), (III), (V), or (VI):

(II)

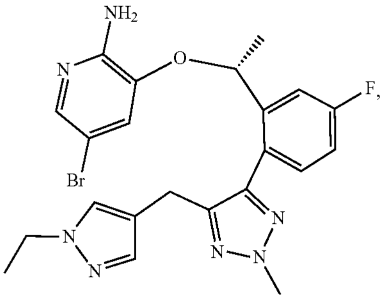

(III)

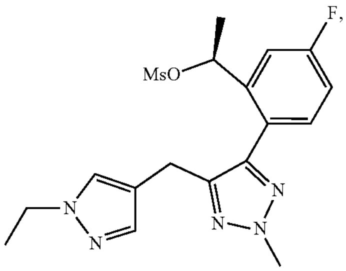

-continued (V)

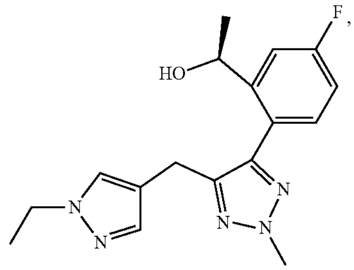

, or (VI)

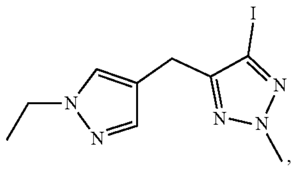

or a stereoisomer, or a mixture of stereoisomers thereof, or a pharmaceutically acceptable salt thereof.

5.4. Pharmaceutical Compositions

In one embodiment, provided herein is a pharmaceutical composition comprising a compound of Formula (I):

(I)

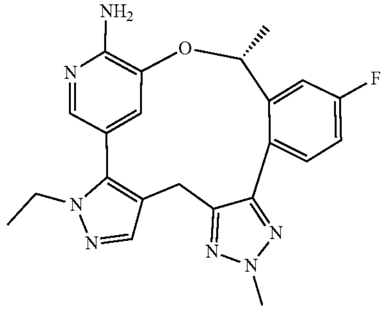

or a stereoisomer, or a mixture of stereoisomers thereof, or a pharmaceutically acceptable salt thereof, and a diluent, a binder, a disintegrant, and a lubricant.

In one embodiment, Compound 1, or a stereoisomer, or a mixture of stereoisomers thereof, or a pharmaceutically acceptable salt thereof, in the pharmaceutical composition is free base of Compound 1. In one embodiment, the free base of Compound 1 is amorphous. In one embodiment, the free base of Compound 1 is one of the solid forms of free base of Compound 1 provided herein. In one embodiment, the free base of Compound 1 is Form 1 of the free base of Compound 1.

In one embodiment, Compound 1, or a stereoisomer, or a mixture of stereoisomers thereof, or a pharmaceutically acceptable salt thereof, in the pharmaceutical composition is a pharmaceutically acceptable salt of Compound 1. In one embodiment, the salt is a chloride, phosphate, besylate, mesylate, citrate or maleate salt of Compound 1. In one embodiment, the salt is a besylate salt of Compound 1 provided herein. In one embodiment, the salt is a phosphate salt of Compound 1 provided herein. In one embodiment, the salt is amorphous. In one embodiment, the salt is one of the crystalline forms of a salt of Compound 1 provided herein.

As used herein and unless otherwise specified, the total weight of the pharmaceutical composition (or the w/w based on the total weight of the pharmaceutical composition) does not include coating of the pharmaceutical composition (e.g., an Opadry II coat of a tablet pharmaceutical composition provided herein). In one embodiment, the amount of Compound 1, or a stereoisomer, or a mixture of stereoisomers thereof, or a pharmaceutically acceptable salt thereof, in the pharmaceutical composition is from about 1% to about 30% w/w. In one embodiment, the amount is from about 3% to about 20% w/w. In one embodiment, the amount is from about 5% to about 17% w/w. In one embodiment, the amount is from about 3% to about 7% w/w. In one embodiment, the amount is from about 4% to about 6% w/w. In one embodiment, the amount is about 3, about 4, about 5, about 6, or about 7% w/w. In one embodiment, the amount is about 5% w/w. In one embodiment, the amount is from about 15% to about 20% w/w. In one embodiment, the amount is from about 10% to about 17% w/w. In one embodiment, the amount is from about 15% to about 17% w/w. In one embodiment, the amount is from about 16% to about 18% w/w. In one embodiment, the amount is from about 16% to about 17% w/w. In one embodiment, the amount is about 15, about 16, about 17, about 18, about 19, or about 20% w/w. In one embodiment, the amount is about 17% w/w. In one embodiment, the amount is about 16.7% w/w. In one embodiment, the amount is about 16.67% w/w.

In one embodiment, the diluent is mannitol. In one embodiment, the diluent is Pearlitol 100SD, Pearlitol 110 C, Pearlitol 160 C, Pearlitol 25 C, Pearlitol 300 DC, Pearlitol 400 DC, Pearlitol 500 DC, Pearlitol SW-F 200, Parteck M 100, Parteck M 200, or lactose monohydrate. In one embodiment, the diluent can be a saccharide, e.g., selected from the group consisting of sucrose, dextrose, lactose, fructose, mannitol, a cellulosic derivative, calcium phosphate, calcium carbonate, and a mixture thereof. In another embodiments, the diluent can be mannitol or microcrystalline cellulose (e.g., SMCC 90). In one embodiment, the diluent is mannitol Pearlitol 50C. In one embodiment, the diluent is mannitol Pearlitol 200SD.

In one embodiment, the amount of the diluent in the pharmaceutical composition is from about 50% to about 95% w/w. In one embodiment, the amount is from about 60% to about 90% w/w. In one embodiment, the amount is from about 65% to about 87% w/w. In one embodiment, the amount is from about 62% to about 68% w/w. In one embodiment, the amount is from about 64% to about 66% w/w. In one embodiment, the amount is about 62, about 63, about 64, about 65, about 66, about 67, or about 68% w/w. In one embodiment, the amount is about 65% w/w. In one embodiment, the amount is from about 85% to about 90% w/w. In one embodiment, the amount is from about 86% to about 88% w/w. In one embodiment, the amount is about 85, about 86, about 87, about 88, about 89, or about 90% w/w. In one embodiment, the amount is about 87% w/w. In some embodiments, the diluent is mannitol, starch, SMCC, lactose, dibasic calcium phosphate (DCP). In some embodiments, the diluent is mannitol. In some embodiments, the diluent is SMCC. In some embodiments, the diluent is a mixture of mannitol and SMCC. In some embodiments, the weight ratio of mannitol to SMCC is in a range of about 1:5 to about 35:1. In some embodiments, the weight ratio of mannitol to SMCC is in a range of about 1:1 to about 35:1. In some embodiments, the weight ratio of mannitol to SMCC is in a range of about 3:1 to about 30:1. In some embodiments, the weight ratio of mannitol to SMCC is in a range of about 6:1 to about 1:1. In some embodiments, the weight ratio of mannitol to SMCC is in a range of about 1:5 to about 1:1. In some embodiment, the weight ratio of mannitol to SMCC is about 5:1. In some embodiment, the weight ratio of mannitol to SMCC is about 5.3:1.

Silicified microcrystalline cellulose (SMCC), is a unique combination of microcrystalline cellulose (MCC) and colloidal silicon dioxide (CSD) as a high functionality and multifunctional excipient, SMCC is unique in that it imparts both optimum compaction and superior flow to formulations as a diluent. It also exhibits both brittle fracture and plastic deformation characteristics, leading to good binding properties. Given the binding property of SMCC, it can be used as a dry binder alone or together with other binder(s), for example, in a direct compression process. In one embodiment, the binder is hydroxypropyl cellulose (HPC), silicified microcrystalline cellulose (SMCC), or a mixture thereof. In one embodiment, the binder is HPC. In one embodiment, the binder is SMCC. In one embodiment, the binder is a mixture of HPC and SMCC. In one embodiment, the weight ratio of HPC to SMCC is from about 1:8 to about 1:14. In one embodiment, the weight ratio of HPC to SMCC is about 1:8, about 1:9, about 1:10, about 1:11, about 1:12, about 1:13, or about 1:14. In one embodiment, the weight ratio of HPC to SMCC is about 1:11. In one embodiment, the amount of HPC in the pharmaceutical composition is about 1.1% w/w. In one embodiment, the amount of SMCC in the pharmaceutical composition is about 12.2% w/w. In certain embodiments, the binder is carboxymethylcellulose, alginates, gelatin, polyvinyl pyrrolidone, sucrose and/or acacia, or a mixture thereof. In certain embodiments, the binder is one or more polysaccharides and their derivatives such as starches, cellulose or modified cellulose such as MCC and cellulose ethers such as hydroxypropyl cellulose (HPC); sodium alginate, gelatin, polyvinyl pyrrolidone (PVP), methylcellulose, hydroxy propyl methyl cellulose (HPMC), polymethacrylates, sodium carboxy methyl cellulose, polyethylene glycol (PEG), or a mixture thereof.

In one embodiment, the amount of the binder in the pharmaceutical composition is from about 1% to about 20% w/w. In one embodiment, the amount is from about 2% to about 16% w/w. In one embodiment, the amount is from about 2% to about 14% w/w. In one embodiment, the amount is from about 4% to about 14% w/w. In one embodiment, the amount is from about 2% to about 6% w/w. In one embodiment, the amount is from about 2% to about 5% w/w. In one embodiment, the amount is from about 3% to about 5% w/w. In one embodiment, the amount is about 2, about 3, about 4, about 5, or about 6% w/w. In one embodiment, the amount is about 4% w/w. In one embodiment, the amount is from about 12% to about 16% w/w. In one embodiment, the amount is from about 13% to about 15% w/w. In one embodiment, the amount is about 12, about 13, about 14, about 15, or about 16% w/w. In one embodiment, the amount is about 14% w/w. In one embodiment, the amount is about 13.3% w/w. In one embodiment, the amount is about 1, about 1.1, about 1.2, about 1.3, about 1.4, about 1.5, about 1.6, about 1.7, about 1.8, about 1.9, or about 2% w/w. In one embodiment, the amount of binder is about 1.1% w/w.

In one embodiment, the disintegrant is sodium starch glycolate (SSG). In one embodiment, the disintegrant is cross-linked sodium carboxymethyl cellulose. In one embodiment, the disintegrant is one or more selected from the group consisting of cross-linked sodium carboxymethylcellulose, starch, sodium starch glycolate, cross-linked polyvinylpyrrolidone, crospovidone and a mixture thereof.

In one embodiment, the amount of the disintegrant in the pharmaceutical composition is from about 1% to about 8% w/w. In one embodiment, the amount is from about 2% to about 5% w/w. In one embodiment, the amount is from about 2% to about 4% w/w. In one embodiment, the amount is from about 2.9% to about 4% w/w. In one embodiment, the amount is about 2, about 2.1, about 2.2, about 2.3, about 2.4, about 2.5, about 2.6, about 2.7, about 2.8, about 2.9, about 3, about 3.1, about 3.2, about 3.3, about 3.4, about 3.5, about 3.6, about 3.7, about 3.8, about 3.9, about 4, about 4.1, about 4.2, about 4.3, about 4.4, about 4.5, about 4.6, about 4.7, about 4.8, about 4.9, or about 5% w/w. In one embodiment, the amount is about 2.9% w/w. In one embodiment, the amount is about 3.9% w/w. In one embodiment, the amount is about 4% w/w.

In one embodiment, the lubricant is magnesium stearate. In another embodiment, the lubricant is sodium lauryl sulfate. In one embodiment, the lubricant is one or more metallic salts of fatty acids such as magnesium stearate and steric acid, Carbowax (PEG) 4000/6000, sodium oleate, sterotex, sodium benzoate, Talc, sodium acetate, waxes, sodium lauryl sulfate, Stear-O-Wet, Mg-lauryl sulfate, and glyceryl behenate (Compritol 888).

In one embodiment, the amount of the lubricant in the pharmaceutical composition is from about 0.1% to about 3% w/w. In one embodiment, the amount is from about 0.8% to about 1.4% w/w. In one embodiment, the amount is from about 1% to about 1.2% w/w. In one embodiment, the amount is about 0.8, about 0.9, about 1, about 1.1, about 1.2, about 1.3, or about 1.4% w/w. In one embodiment, the amount is about 1% w/w. In one embodiment, the amount is about 1.1% w/w. In one embodiment, the amount is about 1.2% w/w.

In one embodiment, the pharmaceutical composition is a tablet comprising: Compound 1 at an amount of from about 4.0% to about 5.5% w/w of the total weight of the pharmaceutical composition; mannitol at an amount of from about 80% to about 88% w/w of the total weight of the pharmaceutical composition; silicified microcrystalline cellulose at an amount of from about 3.0% to about 4.0% w/w of the total weight of the pharmaceutical composition; hydroxypropyl cellulose at an amount of from about 0.2% to about 0.4% w/w of the total weight of the pharmaceutical composition; sodium starch glycolate at an amount of from about 2.2% to about 3.5% w/w of the total weight of the pharmaceutical composition; and magnesium stearate at an amount of from about 0.5% to about 1.5% w/w of the total weight of the pharmaceutical composition. In one embodiment, the tablet composition comprises: Compound 1 at an amount of about 5% w/w of the total weight of the pharmaceutical composition; mannitol at an amount of about 84% w/w of the total weight of the pharmaceutical composition; silicified microcrystalline cellulose at an amount of about 3.5% w/w of the total weight of the pharmaceutical composition; hydroxypropyl cellulose at an amount of about 0.3% w/w of the total weight of the pharmaceutical composition; sodium starch glycolate at an amount of about 2.8% w/w of the total weight of the pharmaceutical composition; and magnesium stearate at an amount of about 1.0% w/w of the total weight of the pharmaceutical composition. In one embodiment, the tablet composition has a total weight of about 100 mg with about 5 mg of a solid form (e.g. Form 1) of Compound 1.

In one embodiment, the pharmaceutical composition is a tablet comprising: Compound 1 at an amount of from about 15.0% to about 17.5% w/w of the total weight of the pharmaceutical composition; mannitol at an amount of from about 60% to about 66% w/w of the total weight of the pharmaceutical composition; silicified microcrystalline cellulose at an amount of from about 10% to about 13% w/w of the total weight of the pharmaceutical composition; hydroxypropyl cellulose at an amount of from about 0.5 to about 1.5% w/w of the total weight of the pharmaceutical composition; sodium starch glycolate at an amount of from about 3.0% to about 4.5% w/w of the total weight of the pharmaceutical composition; and magnesium stearate at an amount of from about 0.8 to about 1.5% w/w of the total weight of the pharmaceutical composition. In one embodiment, the tablet composition comprises: Compound 1 at an amount of about 16.67% w/w of the total weight of the pharmaceutical composition; mannitol at an amount of about 62% w/w of the total weight of the pharmaceutical composition; silicified microcrystalline cellulose at an amount of about 11.7% w/w of the total weight of the pharmaceutical composition; hydroxypropyl cellulose at an amount of about 1.0% w/w of the total weight of the pharmaceutical composition; sodium starch glycolate at an amount of about 3.7% w/w of the total weight of the pharmaceutical composition; and magnesium stearate at an amount of about 1.1% w/w of the total weight of the pharmaceutical composition. In one embodiment, the tablet composition has a total weight of about 150 mg. In one embodiment, the tablet composition has a total weight of about 150 mg with about 25 mg of a solid form (e.g. Form 1) of Compound 1.

In one embodiment, the tablet composition comprises: Compound 1 at an amount of about 16.7% w/w of the total weight of the pharmaceutical composition; mannitol at an amount of about 65% w/w of the total weight of the pharmaceutical composition; silicified microcrystalline cellulose at an amount of about 12.2% w/w of the total weight of the pharmaceutical composition; hydroxypropyl cellulose at an amount of about 1.1% w/w of the total weight of the pharmaceutical composition; sodium starch glycolate at an amount of about 3.9% w/w of the total weight of the pharmaceutical composition; and magnesium stearate at an amount of about 1.1% w/w of the total weight of the pharmaceutical composition. In one embodiment, the tablet composition comprises: Compound 1 at an amount of about 16.67% w/w of the total weight of the pharmaceutical composition; mannitol at an amount of about 64.97% w/w of the total weight of the pharmaceutical composition; silicified microcrystalline cellulose at an amount of about 12.22% w/w of the total weight of the pharmaceutical composition; hydroxypropyl cellulose at an amount of about 1.11% w/w of the total weight of the pharmaceutical composition; sodium starch glycolate at an amount of about 3.89% w/w of the total weight of the pharmaceutical composition; and magnesium stearate at an amount of about 1.14% w/w of the total weight of the pharmaceutical composition. In one embodiment, the tablet composition has a total weight of about 150 mg. In one embodiment, the tablet composition has a total weight of about 150 mg with about 25 mg of a solid form (e.g. Form 1) of Compound 1. In one embodiment, the tablet composition has a total weight of about 300 mg. In one embodiment, the tablet composition has a total weight of about 300 mg with about 50 mg of a solid form (e.g. Form 1) of Compound 1. In one embodiment, the tablet composition has a total weight of about 450 mg. In one embodiment, the tablet composition has a total weight of about 450 mg with about 75 mg of a solid form (e.g. Form 1) of Compound 1. In one embodiment, the tablet composition has a total weight of about 600 mg. In one embodiment, the tablet composition has a total weight of about 600 mg with about 100 mg of a solid form (e.g. Form 1) of Compound 1.

The pharmaceutical compositions may conveniently be presented in unit dosage form. In certain embodiments, the unit dosage form is a tablet. In certain embodiments, the unit dosage form is a tablet of 5 mg (by weight of free base Compound 1) dose strength. In certain embodiments, the unit dosage form is a tablet of 25 mg (by weight of free base Compound 1) dose strength. The amount of active ingredient which can be combined with a carrier material to produce a single dosage form will vary depending upon the subject being treated, the particular mode of administration.

In one embodiment, the pharmaceutical composition provided herein comprises (i) a granular formulation comprising Compound 1, or a stereoisomer, or a mixture of stereoisomers thereof, or a pharmaceutically acceptable salt thereof, (ii) extragranular diluent, (iii) extragranular disintegrant, and (iv) extragranular lubricant.

In one embodiment, the amount of the granular formulation in the pharmaceutical composition is from about 10% to about 65% w/w. In one embodiment, the amount is from about 13% to about 60% w/w. In one embodiment, the amount is from about 16% to about 56% w/w. In one embodiment, the amount is from about 13% to about 20% w/w. In one embodiment, the amount is from about 15% to about 18% w/w. In one embodiment, the amount is about 13, about 14, about 15, about 16, about 17, about 18, about 19, or about 20% w/w. In one embodiment, the amount is about 16% w/w. In one embodiment, the amount is about 17% w/w. In one embodiment, the amount is about 16.7% w/w. In one embodiment, the amount is about 16.67% w/w. In one embodiment, the amount is from about 50% to about 60% w/w. In one embodiment, the amount is from about 54% to about 57% w/w. In one embodiment, the amount is about 50, about 51, about 52, about 53, about 54, about 55, about 56, about 57, about 58, about 59, or about 60% w/w. In one embodiment, the amount is about 55% w/w. In one embodiment, the amount is about 56% w/w. In one embodiment, the amount is about 55.6% w/w. In one embodiment, the amount is about 55.55% w/w.

In one embodiment, the amount of the extragranular diluent in the pharmaceutical composition is from about 30% to about 85% w/w. In one embodiment, the amount is from about 35% to about 85% w/w. In one embodiment, the amount is from about 40% to about 80% w/w. In one embodiment, the amount is from about 35% to about 45% w/w. In one embodiment, the amount is from about 40% to about 42% w/w. In one embodiment, the amount is about 35, about 36, about 37, about 38, about 39, about 40, about 41, about 42, about 43, about 44, or about 45% w/w. In one embodiment, the amount is about 41% w/w. In one embodiment, the amount is about 40.95% w/w. In one embodiment, the amount is from about 75% to about 85% w/w. In one embodiment, the amount is from about 79% to about 81% w/w. In one embodiment, the amount is about 75, about 76, about 77, about 78, about 79, about 80, about 81, about 82, about 83, about 84, or about 85% w/w. In one embodiment, the amount is about 80% w/w. In one embodiment, the amount is about 79.8% w/w. In one embodiment, the amount is about 79.83% w/w.

In one embodiment, the amount of the extragranular disintegrant in the pharmaceutical composition is from about 1% to about 4% w/w. In one embodiment, the amount is from about 2% to about 3% w/w. In one embodiment, the amount is about 2, about 2.1, about 2.2, about 2.3, about 2.4, about 2.5, about 2.6, about 2.7, about 2.8, about 2.9, or about 3% w/w. In one embodiment, the amount is about 2.5% w/w.

In one embodiment, the amount of the extragranular lubricant in the pharmaceutical composition is from about 0.1% to about 2.5% w/w. In one embodiment, the amount is from about 0.5% to about 1.5% w/w. In one embodiment, the amount is about 0.5, about 0.6, about 0.7, about 0.8, about 0.9, about 1, about 1.1, about 1.2, about 1.3, about 1.4, or about 1.5% w/w. In one embodiment, the amount is about 1% w/w.

In one embodiment, the granular formulation comprising Compound 1, or a stereoisomer, or a mixture of stereoisomers thereof, or a pharmaceutically acceptable salt thereof, the binder, intragranular diluent which is optional, intragranular disintegrant, and intragranular lubricant. In certain embodiments, the granular formulation comprising a solid form (e.g. Form 1) of Compound 1.

In one embodiment, the amount of Compound 1, or a stereoisomer, or a mixture of stereoisomers thereof, or a pharmaceutically acceptable salt thereof, in the granular formulation is from about 20% to about 80% w/w. In one embodiment, the amount is from about 30% to about 70% w/w. In one embodiment, the amount is from about 30% to about 50% w/w. In one embodiment, the amount is from about 30% to about 40% w/w. In one embodiment, the amount is about 20, about 25, about 30, about 35, about 40, about 45, about 50, about 55, about 60, about 65, about 70, about 75, or about 80% w/w. In one embodiment, the amount is about 30% w/w. In one embodiment, the amount is about 40% w/w. In one embodiment, the amount is about 50% w/w.

In one embodiment, the amount of the binder in the granular formulation is from about 15% to about 35% w/w. In one embodiment, the amount is from about 20% to about 30% w/w. In one embodiment, the amount is about 20, about 21, about 22, about 23, about 24, about 25, about 26, about 27, about 28, about 29, or about 30% w/w. In one embodiment, the amount is about 24% w/w.

In one embodiment, the amount of the intragranular disintegrant in the granular formulation is from about 1% to about 4% w/w. In one embodiment, the amount is from about 2% to about 3% w/w. In one embodiment, the amount is about 2, about 2.1, about 2.2, about 2.3, about 2.4, about 2.5, about 2.6, about 2.7, about 2.8, about 2.9, or about 3% w/w. In one embodiment, the amount is about 2.5% w/w.

In one embodiment, the amount of the intragranular lubricant in the granular formulation is from about 0.1% to about 0.5% w/w. In one embodiment, the amount is about 0.1, about 0.15, about 0.2, about 0.25, about 0.3, about 0.35, about 0.4, about 0.45, or about 0.5% w/w. In one embodiment, the amount is about 0.25% w/w.

In one embodiment, the amount of the intragranular diluent in the granular formulation is from about 0% to about 60% w/w. In one embodiment, the amount is from about 35% to about 50% w/w. In one embodiment, the amount is from about 40% to about 45% w/w. In one embodiment, the amount is about 35, about 36, about 37, about 38, about 39, about 40, about 41, about 42, about 43, about 44, about 45, about 46, about 47, about 48, about 49, or about 50% w/w. In one embodiment, the amount is about 43% w/w. In one embodiment, the amount is about 43.2% w/w. In one embodiment, the amount is about 43.3% w/w. In one embodiment, the amount is about 43.25% w/w. In one embodiment, the amount of the intragranular diluent in the granular formulation is the balance of the granular formulation.

In one embodiment, the pharmaceutical composition comprises: (i) a granular formulation at an amount of from about 16% to about 17.5% w/w of the total weight of the pharmaceutical composition; (ii) mannitol at an amount of from about 79% to about 80.5% w/w of the total weight of the pharmaceutical composition; (iii) sodium starch glycolate at an amount of about 2.5% w/w of the total weight of the pharmaceutical composition; and (iv) magnesium stearate at an amount of about 1% w/w of the total weight of the pharmaceutical composition; wherein the granular formulation comprises: (i.a) Compound 1 at an amount of from about 30% to about 30.5% w/w in the granular formulation; (i.b) mannitol at an amount of from about 42.75% to about 43.25% w/w of the total weight of the granular formulation; (i.c) silicified microcrystalline cellulose at an amount of about 22% w/w of the total weight of the granular formulation; (i.d) hydroxypropyl cellulose at an amount of about 2% w/w of the total weight of the granular formulation; (i.e) sodium starch glycolate at an amount of about 2.5% w/w of the total weight of the granular formulation; and (i.f) magnesium stearate at an amount of about 0.25% w/w of the total weight of the granular formulation. In one embodiment, the pharmaceutical composition comprises: (i) a granular formulation at an amount of about 16.7% (in one embodiment, about 16.67%) w/w of the total weight of the pharmaceutical composition; (ii) mannitol at an amount of about 79.8% (in one embodiment, about 79.83%) w/w of the total weight of the pharmaceutical composition; (iii) sodium starch glycolate at an amount of about 2.5% w/w of the total weight of the pharmaceutical composition; and (iv) magnesium stearate at an amount of about 1% w/w of the total weight of the pharmaceutical composition; wherein the granular formulation comprises: (i.a) Compound 1 at an amount of about 30% w/w in the granular formulation; (i.b) mannitol at an amount of about 43.25% w/w of the total weight of the granular formulation; (i.c) silicified microcrystalline cellulose at an amount of about 22% w/w of the total weight of the granular formulation; (i.d) hydroxypropyl cellulose at an amount of about 2% w/w of the total weight of the granular formulation; (i.e) sodium starch glycolate at an amount of about 2.5% w/w of the total weight of the granular formulation; and (i.f) magnesium stearate at an amount of about 0.25% w/w of the total weight of the granular formulation. In one embodiment, the pharmaceutical composition has a total weight of about 100 mg.

In one embodiment, the pharmaceutical composition comprises: (i) a granular formulation at the amount of from about 55% to about 56.5% w/w of the total weight of the pharmaceutical composition; (ii) mannitol at the amount of from about 40% to about 41.5% w/w of the total weight of the pharmaceutical composition; (iii) sodium starch glycolate at the amount of about 2.5% w/w of the total weight of the pharmaceutical composition; and (iv) magnesium stearate at the amount of about 1% w/w of the total weight of the pharmaceutical composition; wherein the granular formulation comprises: (i.a) Compound 1 at an amount of from about 30% to about 30.5% w/w in the granular formulation; (i.b) mannitol at an amount of from about 42.75% to about 43.25% w/w of the total weight of the granular formulation; (i.e) silicified microcrystalline cellulose at an amount of about 22% w/w of the total weight of the granular formulation; (id) hydroxypropyl cellulose at an amount of about 2% w/w of the total weight of the granular formulation; (i.e) sodium starch glycolate at an amount of about 2.5% w/w of the total weight of the granular formulation; and (if) magnesium stearate at an amount of about 0.25% w/w of the total weight of the granular formulation. In one embodiment, the pharmaceutical composition comprises: (i) a granular formulation at the amount of about 55.6% w/w of the total weight of the pharmaceutical composition; (ii) mannitol at the amount of about 40.9% w/w of the total weight of the pharmaceutical composition; (iii) sodium starch glycolate at the amount of about 2.5% w/w of the total weight of the pharmaceutical composition; and (iv) magnesium stearate at the amount of about 1% w/w of the total weight of the pharmaceutical composition; wherein the granular formulation comprises: (i.a) Compound 1 at an amount of about 30% w/w in the granular formulation; (i.b) mannitol at an amount of about 43.25% w/w of the total weight of the granular formulation; (i.e) silicified microcrystalline cellulose at an amount of about 22% w/w of the total weight of the granular formulation; (id) hydroxypropyl cellulose at an amount of about 2% w/w of the total weight of the granular formulation; (i.e) sodium starch glycolate at an amount of about 2.5% w/w of the total weight of the granular formulation; and (if) magnesium stearate at an amount of about 0.25% w/w of the total weight of the granular formulation. In one embodiment, the pharmaceutical composition has a total weight of about 150 mg.

In one embodiment, the pharmaceutical composition provided herein is an oral dosage form. In one embodiment, the oral dosage form is a tablet. In one embodiment, the oral dosage form is an immediate release tablet.

In one embodiment, the pharmaceutical composition is prepared by a process comprising blending a granule formulation comprising Compound 1, or a stereoisomer, or a mixture of stereoisomers thereof, or a pharmaceutically acceptable salt thereof, with one or more extragranular excipient(s). In one embodiment, the one or more extragranular excipient(s) comprises an extragranular diluent (e.g., mannitol), an extragranular disintegrant (e.g., sodium starch glycolate), and an extragranular lubricant (e.g., magnesium stearate). In one embodiment, the extragranular lubricant (e.g., magnesium stearate) is blended after the other components are blended first.

In one embodiment, the granule formulation is prepared by a process feeding an intragranular blend comprising Compound 1, or a stereoisomer, or a mixture of stereoisomers thereof, or a pharmaceutically acceptable salt thereof, through a roller compactor and optionally a comil to provide the granule formulation. In one embodiment, the intragranular blend is prepared by a process comprising blending Compound 1, or a stereoisomer, or a mixture of stereoisomers thereof, or a pharmaceutically acceptable salt thereof, with one or more intragranular excipient(s). In one embodiment, the one or more intragranular excipient(s) comprises an intragranular diluent (e.g., mannitol), an intragranular binder (e.g., a mixture of silicified microcrystalline cellulose and hydroxypropyl cellulose), an intragranular disintegrant (e.g., sodium starch glycolate), and an intragranular lubricant (e.g., magnesium stearate). In one embodiment, the intragranular lubricant (e.g., magnesium stearate) is blended after the other components are blended first.

In one embodiment, the pharmaceutical composition provided herein has a particle size of between about 10 μm and about 500 μm. In one embodiment, the particle size is between about 10 μm and about 50 μm. In one embodiment, the particle size is between about 25 μm and about 35 μm. In one embodiment, the particle size is between about 50 μm and about 150 μm. In one embodiment, the particle size is between about 120 μm and about 140 μm. In one embodiment, the particle size is between about 150 μm and about 400 μm. In one embodiment, the particle size is between about 320 μm and about 360 μm.

In one embodiment, the pharmaceutical composition provided herein comprises a population of particles having an average particle size of between about 10 μm and about 150 μm. In one embodiment, the average particle size (e.g., D10) is between about 10 μm and about 50 μm. In one embodiment, the average particle size (e.g., D10) is between about 10 μm and about 30 μm. In one embodiment, the average particle size (e.g., D10) is between about 10 μm and about 20 μm. In one embodiment, the average particle size (e.g., D50) is between about 50 μm and about 100 μm. In one embodiment, the average particle size (e.g., D50) is between about 50 μm and about 100 μm. In one embodiment, the average particle size (e.g., D50) is between about 60 μm and about 90 μm. In one embodiment, the average particle size (e.g., D50) is between about 70 μm and about 80 μm. In one embodiment, the average particle size (e.g., D90) is between about 100 μm and about 150 μm. In one embodiment, the average particle size (e.g., D90) is between about 110 μm and about 150 μm. In one embodiment, the average particle size (e.g., D90) is between about 110 μm and about 120 μm. In one embodiment, the average particle size (e.g., D10) is about 10 μm, about 11 μm, about 12 μm, about 13 μm, about 14 μm, about 15 μm, about 16 μm, about 17 μm, about 18 μm, about 19 μm, or about 20 μm. In one embodiment, the average particle size (e.g., D50) is about 50 μm, about 55 μm, about 60 μm, about 65 μm, about 70 μm, about 75 μm, about 80 μm, about 85 μm, about 90 μm, about 95 μm, or about 100 μm. In one embodiment, the average particle size (e.g., D90) is about 110 μm, about 115 μm, about 120 μm, about 125 μm, about 130 μm, about 135 μm, about 140 μm, about 145 μm, or about 150 μm.

In one embodiment, the particles having the particle size or the population of particles having the average particle size is obtained by milling a solid form of Compound 1 (e.g. Form 1). In one embodiment, the milling is wet milling. In one embodiment, the wet milling is conducted according to means described herein or known in the art. In one embodiment, the milling is dry milling. In one embodiment, the dry milling is conducted according to means described herein or known in the art.

In one embodiment, the particle size or average particle size is determined using any means known in the art, for example using a Malvern Mastersizer 3000 or analogous instrument.

In certain embodiments, the pharmaceutical composition comprising Compound 1 (e.g. in a solid dosage form such as a tablet comprising Compound 1) has a chemical and/or physical purity of at least about 90%. As used herein and unless otherwise specified, the chemical and/or physical purity of Compound 1 in a pharmaceutical composition is the amount of Compound 1 detected in a representative sample of the pharmaceutical composition (e.g., the amount detected by HPLC or other analytical technique) divided by the theoretical amount of Compound 1 in the formulation. In certain embodiments, the pharmaceutical composition comprising Compound 1 has a chemical and/or physical purity of at least about 95%. In certain embodiments, the pharmaceutical composition comprising Compound 1 has a chemical and/or physical purity of at least about 96%. In certain embodiments, the pharmaceutical composition comprising Compound 1 has a chemical and/or physical purity of at least about 97%. In certain embodiments, the pharmaceutical composition comprising Compound 1 has a chemical and/or physical purity of at least about 98%. In certain embodiments, the pharmaceutical composition comprising Compound 1 has a chemical and/or physical purity of at least about 99%. In certain embodiments, the pharmaceutical composition comprising Compound 1 has a chemical and/or physical purity of about 99.4%. In certain embodiments, the pharmaceutical composition comprising Compound 1 has a chemical and/or physical purity of about 101.1%. In certain embodiments, the pharmaceutical composition comprising Compound 1 has an enantiomeric purity of at least about 99.5%. In certain embodiments, the pharmaceutical composition comprising Compound 1 has an enantiomeric purity of about 100%. In certain embodiments, the pharmaceutical composition comprising Compound 1 has a chemical, physical, and/or enantiomeric purity of at least about 95% over 12 months.

In certain embodiments, after preparation of the pharmaceutical composition comprising Compound 1 (e.g. preparation of a solid dosage form such as a tablet comprising Compound 1), the chemical and/or physical purity of the Compound 1 in the pharmaceutical composition is at least about 90 wt %. In certain embodiments, the chemical and/or physical purity of the Compound 1 in the pharmaceutical composition is at least about 95 wt %. In certain embodiments, the chemical and/or physical purity of the Compound 1 in the pharmaceutical composition is at least about 96 wt %. In certain embodiments, the chemical and/or physical purity of the Compound 1 in the pharmaceutical composition is at least about 97 wt %. In certain embodiments, the chemical and/or physical purity of the Compound 1 in the pharmaceutical composition is at least about 98 wt %. In certain embodiments, the chemical and/or physical purity of the Compound 1 in the pharmaceutical composition is at least about 99 wt %. In certain embodiments, the chemical and/or physical purity of the Compound 1 in the pharmaceutical composition is about 99.4 wt %. In certain embodiments, the chemical and/or physical purity of the Compound 1 in the pharmaceutical composition is about 101.1 wt %. In certain embodiments, the enantiomeric purity of the Compound 1 in the pharmaceutical composition is at least about 99.5 wt %. In certain embodiments, the enantiomeric purity of the Compound 1 in the pharmaceutical composition is about 100 wt %.

In certain embodiments, the pharmaceutical composition comprising Compound 1 (e.g. in a solid dosage form such as a tablet comprising Compound 1) has less than about 3% by area of degradation products. In certain embodiments, the pharmaceutical composition comprising Compound 1 (e.g. in a solid dosage form such as a tablet comprising Compound 1) has less than about 2% by area of degradation products. In certain embodiments, the pharmaceutical composition comprising Compound 1 (e.g. in a solid dosage form such as a tablet comprising Compound 1) has less than about 1% by area of degradation products. In certain embodiments, the pharmaceutical composition comprising Compound 1 (e.g. in a solid dosage form such as a tablet comprising Compound 1) has less than about 0.5% by area of degradation products. In certain embodiments, the pharmaceutical composition comprising Compound 1 (e.g. in a solid dosage form such as a tablet comprising Compound 1) has less than about 0.1% by area of degradation products. In certain embodiments, the pharmaceutical composition comprising Compound 1 (e.g. in a solid dosage form such as a tablet comprising Compound 1) has about 0.1% by area of degradation products.

In certain embodiments, the pharmaceutical composition comprising Compound 1 (e.g. in a solid dosage form such as a tablet comprising Compound 1) has less than about 0.5% by area of one or more degradation product, respectively. In certain embodiments, the pharmaceutical composition comprising Compound 1 (e.g. in a solid dosage form such as a tablet comprising Compound 1) has less than about 0.4% by area of one or more degradation product, respectively. In certain embodiments, the pharmaceutical composition comprising Compound 1 (e.g. in a solid dosage form such as a tablet comprising Compound 1) has less than about 0.3% by area of one or more degradation product, respectively. In certain embodiments, the pharmaceutical composition comprising Compound 1 (e.g. in a solid dosage form such as a tablet comprising Compound 1) has less than about 0.2% by area of one or more degradation product, respectively. In certain embodiments, the pharmaceutical composition comprising Compound 1 (e.g. in a solid dosage form such as a tablet comprising Compound 1) has less than about 0.1% by area of one or more degradation product, respectively. In certain embodiments, the pharmaceutical composition comprising Compound 1 (e.g. in a solid dosage form such as a tablet comprising Compound 1) has less than about 0.05% by area of one or more degradation product, respectively.

In certain embodiments, provided herein is a pharmaceutical preparation suitable for use in a human patient, comprising a compound provided herein (e.g., a compound of Formula (I), and one or more pharmaceutically acceptable excipients. In certain embodiments, the pharmaceutical preparations may be for use in treating or preventing a condition or disease as described herein. A compound provided herein may be used in the manufacture of medicaments for the treatment of any diseases or conditions disclosed herein.

The compositions and methods provided herein may be utilized to treat a subject in need thereof. In certain embodiments, the subject is a mammal such as a human, or a non-human mammal. When administered to subject, such as a human, the composition or the compound is preferably administered as a pharmaceutical composition comprising, for example, a compound provided herein and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound provided herein. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound provided herein. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the subject being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound provided herein, with the carrier and, optionally, one or more accessory ingredients. In general, the formulations are prepared by uniformly and intimately bringing into association a compound provided herein with liquid carriers, or finely divided solid carriers, or both, and then, if necessary, shaping the product.

Formulations provided herein suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound provided herein as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound provided herein to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this disclosure. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions provided herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods provided herein, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the subject being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the subject's condition, the disorder being treated, the stability of the compound, and, if desired, another type of therapeutic agent being administered with the compound provided herein. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods provided herein will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments provided herein, the active compound may be administered two or three times daily. In preferred embodiments, the active compound will be administered once daily.

In certain embodiments, compounds provided herein may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, a subject who receives such treatment can benefit from a combined effect of different therapeutic compounds.

In certain embodiments, conjoint administration of compounds provided herein with one or more additional therapeutic agent(s) (e.g., one or more additional chemotherapeutic agent(s)) provides improved efficacy relative to each individual administration of the compound provided herein or the one or more additional therapeutic agent(s). In certain such embodiments, the conjoint administration provides an additive effect, wherein an additive effect refers to the sum of each of the effects of individual administration of the compound provided herein and the one or more additional therapeutic agent(s).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

5.5. Therapeutic Methods

In one embodiment, provided herein are methods of treating cancer comprising administering a solid form or pharmaceutical composition provided herein. In one embodiment, provided herein are methods of using a solid form or pharmaceutical composition provided herein for treating, preventing or managing solid tumor. In one embodiment, provided herein is a method of treating solid tumor, comprising administering to a patient in need thereof a solid form or pharmaceutical composition provided herein.

In one embodiment, the cancer is anaplastic large cell lymphoma (ALCL), atypical meningioma, breast cancer, cholangiocarcinoma, gastric cancer, glioblastoma, inflammatory myofibroblastic tumor (IMT), inflammatory hepatocellular adenoma (HCA), melanoma, pancreatic cancer, papillary thyroid carcinoma, salivary gland carcinoma, serous ovarian carcinoma, or spitzoid neoplasm.

In one embodiment, the solid tumor is advanced solid tumor. In one embodiment, the advanced solid tumor is relapsed after, refractory to, or resistant to the prior treatment by a tyrosine kinase inhibitor (TKI). In one embodiment, the solid tumor is non-small cell lung cancer (NSCLC). In one embodiment, the solid tumor is advanced NSCLC. In one embodiment, the solid tumor is locally advanced NSCLC. In one embodiment, the solid tumor is metastatic. In one embodiment, the solid tumor is CNS metastatic. In one embodiment, the solid tumor is metastatic NSCLC. In one embodiment, the solid tumor is CNS metastatic NSCLC. As used herein and unless otherwise specified, "advanced tumor" refers to a tumor that cannot be cured or grows beyond the initial site of origin, either locally advanced or metastatic.

In one embodiment, the solid tumor (or cancer) is ROS1 positive. In one embodiment, the solid tumor is ROS1 positive NSCLC. In one embodiment, the solid tumor is advanced ROS1 positive solid tumor. In one embodiment, the solid tumor is locally advanced ROS1 positive solid tumor. In one embodiment, the solid tumor is advanced ROS1 positive NSCLC. In one embodiment, the solid tumor is locally advanced ROS1 positive NSCLC. In one embodiment, the solid tumor is metastatic ROS1 positive solid tumor. In one embodiment, the solid tumor is CNS metastatic ROS1 positive solid tumor. In one embodiment, the solid tumor is metastatic ROS1 positive NSCLC. In one embodiment, the solid tumor is CNS metastatic ROS1 positive NSCLC. In one embodiment, the solid tumor (or cancer) has a ROS1 mutation. In one embodiment, the ROS1 mutation is G2032R. In one embodiment, the ROS1 mutation comprise G2032R and one or more of S1986F, 51986Y, F2004C, F2004V, L2026M, D2033N, or G2101A. In one embodiment, the solid tumor (or cancer) has a ROS1 fusion.

In one embodiment, the solid tumor (or cancer) is ALK positive. As used herein and unless otherwise specified, an "ALK positive" (ALK+) cancer, disease, or disorder refers to a cancer, disease, or disorder characterized by inappropriately high expression of an ALK gene and/or the presence of a mutation in an ALK gene and/or the presence of a partially deleted ALK protein. In one embodiment, the solid tumor is ALK positive NSCLC. In one embodiment, the solid tumor is advanced ALK positive solid tumor. In one embodiment, the solid tumor is locally advanced ALK positive solid tumor. In one embodiment, the solid tumor is advanced ALK positive NSCLC. In one embodiment, the solid tumor is locally advanced ALK positive NSCLC. In one embodiment, the solid tumor is metastatic ALK positive solid tumor. In one embodiment, the solid tumor is CNS metastatic ALK positive solid tumor. In one embodiment, the solid tumor is metastatic ALK positive NSCLC. In one embodiment, the solid tumor is CNS metastatic ALK positive NSCLC. In one embodiment, the solid tumor (or cancer) has an ALK mutation.

In one embodiment, the ALK mutation comprises one or more ALK rearrangements (in one embodiment, one rearrangement). In one embodiment, the ALK mutation comprises one or more ALK fusions (in one embodiment, one fusion). In some embodiments, cancers treated by methods of the present disclosure include ALK fusions. In one embodiment, the ALK fusion is with one of the fusion partners described in Ou et al., *JTO Clinical and Research Reports,* 1(1): 1-10, the entirety of which is incorporated herein by reference. In one embodiment, the ALK fusion is with one of the fusion partners selected from the group consisting of EML4, TFG, KIF5B, KLC1, STRN, HIP1, TPR, BIRC6, DCTN1, SQSTM1, SOCS5, SEC31A, CLTC, PRKAR1A, PPM1B, EIF2AK3, CRIM1, CEBPZ, PICALM, CLIP1, BCL11A, GCC2, LMO7, PHACTR1, CMTR1, VIT, DYSF, ITGAV, PLEKHA7, CUX1, VKORCIL1, FBXO36, SPTBN1, EML6, FBXO11, CLIP4, CAMKMT, NCOA1, MYT1L, SRBD1, SRD5A2, NYAP2, MPRIP, ADAM17, ALK, LPIN1, WDPCP, CEP55, ERC1, SLC16A7, TNIP2, ATAD2B, SLMAP, FBN1, SWAP70, TCF12, TRIM66, WNK3, AKAP8L, SPECC1L, PRKCB, CDK15, LCLAT1, YAP1, PLEKHM2, DCHS1, PPFIBP1, ATP13A4, C12orf75, EPAS1, FAM179A, FUT8, LIMD1, LINC00327, LOC349160, LYPD1, RBM20, TACR1, TANC1, TTC27, TUBBB, SMPD4, SORCS1, LINC00211, SOS1, C9orf3, CYBRD1, MTA3, THADA, TSPYL6, WDR37, and PLEKHH2. In one embodiment, the ALK fusion is with one of the fusion partners selected from the group consisting of EML4, TMP1, WDCP, GTF21RD1, TPM3, TPM4, CLTC, LMNA, PRKAR1A, RANBP2, TFG, FN1, KLC1, VCL, STRN, HIP1, NPM1, DCTN1, SQSTM1, TPR, CRIM1, PTPN3, FBXO36, ATIC and KIF5B. In one embodiment, the ALK mutation is EML4-ALK, a fusion between the echinoderm microtubule-associated protein-like 4 (EML4) gene and the ALK tyrosine kinase domain. There are many variants of EML4-ALK that differ by breakpoint junctions, with variant 1 (v1) and variant 3 (v3) being the most prevalent clinically. In one embodiment, the ALK mutation is NPM1-ALK. In one embodiment, the ALK mutation is STRN-ALK.

In one embodiment, the solid tumor (or cancer) is leukocyte receptor tyrosine kinase (LTK) positive. As used herein and unless otherwise specified, an “LTK positive” (LTK+) cancer, disease, or disorder refers to a cancer, disease, or disorder characterized by inappropriately high expression of an LTK gene and/or the presence of a mutation in an LTK gene, including LTK gene rearrangements resulting in LTK fusion proteins. In one embodiment, the solid tumor is LTK positive breast invasive ductal carcinoma, prostate adenocarcinoma, pancreatic adenocarcinoma, adenocarcinoma of unknown primary, or bladder urothelial carcinoma. In one embodiment, the cancer is LTK positive leukemia. In one embodiment, the solid tumor is LTK positive lung cancer. In one embodiment, the solid tumor is LTK positive NSCLC. In one embodiment, the solid tumor (or cancer) has an LTK mutation. In one embodiment, the LTK mutation is G269A, F218I, N257T, A13fs, or A214fs. In one embodiment, the solid tumor (or cancer) has an LTK fusion. In one embodiment, the LTK fusion is CLIP1-LTK. See Cooper A J, Sequist L V, Johnson T W, Lin J J. LTK fusions: A new target emerges in non-small cell lung cancer. Cancer Cell. 2022 Jan. 10; 40(1):23-25; and Izumi, H., Matsumoto, S., Liu, J. et al. The CLIP1-LTK fusion is an oncogenic driver in non-small-cell lung cancer. Nature 600, 319-323 (2021), each of which are incorporated herein by reference in their entirety.

In one embodiment, the patient has not been treated with a prior therapy. In one embodiment, the patient is naïve to (i.e. not receiving) any tyrosine kinase inhibitor (TKI) therapy.

In one embodiment, the patient has been treated with one or more prior therapies. In one embodiment, the patient has been treated with at least one prior TKI therapy. In one embodiment, the patient has been treated with at least two prior TKI therapies. In one embodiment, the patient has been treated with one prior TKI therapy. In one embodiment, the patient has been treated with two prior TKI therapies. In one embodiment, the patient’s tumor does not have a known oncogenic driver alteration other than ROS1. In one embodiment, the TKI is ROS1 TKI (e.g. crizotinib or entrectinib). In one embodiment, the prior TKI therapy is one or more selected from the group consisting of crizotinib, entrectinib, repotrectinib, taletrectinib, and lorlatinib.

In one embodiment, the patient has not been treated with prior platinum-based chemotherapy. In one embodiment, the patient has been treated with up to one prior platinum-based chemotherapy. In one embodiment, the patient has been treated with at least one prior platinum-based chemotherapy. In one embodiment, the patient has been treated with at least two prior platinum-based chemotherapies. In one embodiment, the patient has been treated with one prior platinum-based chemotherapy. In one embodiment, the patient has been treated with two prior platinum-based chemotherapies.

As used herein, “platinum-based chemotherapy” refers to chemotherapeutic agents that are coordination complexes of platinum. Exemplified platinum-based chemotherapy includes but not limited to cisplatin, oxaliplatin, nedaplatin, or carboplatin.

In one embodiment, the patient has not been treated with immunotherapy. In one embodiment, the patient has been treated with immunotherapy. In one embodiment, the patient has been treated with at least one prior immunotherapy. In one embodiment, the patient has been treated with at least two prior immunotherapies. In one embodiment, the patient has been treated with one prior immunotherapy. In one embodiment, the patient has been treated with two immunotherapies.

As used herein, “immunotherapy” refers to the treatment of a disease by activating or suppressing the immune system. Immunotherapies designed to elicit or amplify an immune response are classified as activation immunotherapies, while immunotherapies that reduce or suppress are classified as suppression immunotherapies. The immunotherapy can regulate the immune effector cells (e.g. lymphocytes, macrophages, dendritic cells, natural killer cells (NK Cell), cytotoxic T lymphocytes (CTL), etc.) to work together against cancer by targeting abnormal antigens expressed on the surface of tumor cells. Exemplified immunotherapy includes but not limited to checkpoint inhibitors (e.g. anti-cytotoxic T-lymphocyte-associated protein 4 (CTLA-4) and anti-programmed cell death protein 1 (PD-1) antibodies). Exemplified PD-1 inhibitors include but are not limited to pembrolizumab (Keytruda), nivolumab (Opdivo), and cemiplimab (Libtayo). Exemplified PD-L1 inhibitors include but are not limited to atezolizumab (Tecentriq), avelumab (Bavencio), durvalumab (Imfinzi). Exemplified CTLA-4 inhibitor includes but is not limited to ipilimumab (Yervoy).

In one embodiment, the patient has not been treated with chemotherapy. In one embodiment, the patient has been treated with at least one prior line of chemotherapy. In one embodiment, the patient has been treated with at least two prior lines of chemotherapy.

In one embodiment, the patient has been treated with at least three prior lines of anticancer therapy. In one embodiment, the patient has been treated with at least two prior lines of anticancer therapy selected from the group consisting of ROS1 TKI (e.g., investigational ROS1 TKI, crizotinib, lorlatinib, entrectinib, taletrectinib, repotrectinib) and chemotherapy. In one embodiment, the patient has been treated with at least one line of ROS1 TKI and one line of chemotherapy. In one embodiment, the patient has been treated with at least two lines of ROS1 TKI and one line of chemotherapy. In one embodiment, the patient has been treated with at least three lines of ROS1 TKI and one line of chemotherapy. In one embodiment, the patient has been treated with at least two lines of chemotherapy. In one embodiment, the patient has been treated with at least one line of ROS1 TKI and two lines of chemotherapy. In one embodiment, the patient has been treated with at least two lines of ROS1 TKI and two lines of chemotherapy. In one embodiment, the patient has been treated with at least three lines of ROS1 TKI and two lines of chemotherapy.

In one embodiment, the ROS1 TKI is crizotinib. In one embodiment, the ROS1 TKI is entrectinib. In one embodiment, the ROS1 TKI is lorlatinib. In one embodiment, the ROS1 TKI is repotrectinib. In one embodiment, the patient has been treated with lorlatinib and repotrectinib. In one embodiment, the ROS1 TKI is taletrectinib.

In one embodiment, the solid tumor is metastatic ROS1-positive solid tumor, and the patient has been treated with at least one prior ROS1 TKI therapy.

In one embodiment, the solid tumor is metastatic ROS1-positive NSCLC, and the patient is naïve to TKI therapy and has been treated with up to one prior platinum-based chemotherapy with or without immunotherapy.

In one embodiment, the solid tumor is metastatic ROS1-positive NSCLC, and the patient has been treated with one prior ROS1 TKI therapy and has not been treated with prior platinum-based chemotherapy or immunotherapy.

In one embodiment, the solid tumor is metastatic ROS1-positive NSCLC, and the patient has been treated with one prior ROS1 TKI therapy and one prior platinum-based chemotherapy with or without immunotherapy.

In one embodiment, the solid tumor is metastatic ROS1-positive NSCLC, and the patient has been treated with at least two prior ROS1 TKI therapies and up to one prior platinum-based chemotherapy with or without immunotherapy.

In one embodiment, the solid tumor is metastatic ROS1-positive solid tumor, and the patient has progressed on a prior therapy. In one embodiment, the prior therapy is a prior ROS1 TKI therapy. In one embodiment, the prior therapy is a prior chemotherapy (e.g., platinum-based chemotherapy). In one embodiment, the prior therapy is a prior immunotherapy.

In one embodiment, the solid tumor is advanced ROS1-positive NSCLC, and the patient is naïve to TKI therapy and has been treated with up to one prior platinum-based chemotherapy with or without immunotherapy.

In one embodiment, the solid tumor is advanced ROS1-positive NSCLC, and the patient has been treated with one prior ROS1 TKI therapy and has not been treated with prior platinum-based chemotherapy or immunotherapy.

In one embodiment, the solid tumor is advanced ROS1-positive NSCLC, and the patient has been treated with one prior ROS1 TKI therapy and one prior platinum-based chemotherapy with or without immunotherapy.

In one embodiment, the solid tumor is advanced ROS1-positive NSCLC, and the patient has been treated with at least two prior ROS1 TKI therapies and up to one prior platinum-based chemotherapy with or without immunotherapy.

In one embodiment, the solid tumor is advanced ROS1-positive solid tumor, and the patient has progressed on a prior therapy. In one embodiment, the prior therapy is a prior ROS1 TKI therapy.

In one embodiment, the ROS1 TKI is crizotinib. In one embodiment, the ROS1 TKI is entrectinib.

In one embodiment, the prior therapy is a prior ROS1 TKI therapy. In one embodiment, the ROS1 TKI is crizotinib, entrectinib, taletrectinib, or repotrectinib.

In one embodiment, the compound used herein (Compound 1 or a stereoisomer, or a mixture of stereoisomers thereof, or a pharmaceutically acceptable salt thereof) is administered once daily (QD). In one embodiment, the compound is administered twice daily (BID). In certain embodiments, the compound used herein is Compound 1.

In one embodiment, the compound used herein (Compound 1 or a stereoisomer, or a mixture of stereoisomers thereof, or a pharmaceutically acceptable salt thereof) is administered at an amount of from about 5 mg to about 500 mg (by weight of the free base Compound 1) per day. In one embodiment, the compound is administered at an amount of from about 25 mg to about 250 mg per day. In one embodiment, the compound is administered at an amount of from about 25 mg to about 200 mg per day. In one embodiment, the compound is administered at an amount of from about 50 mg to about 200 mg per day. In one embodiment, the compound is administered at an amount of from about 5 mg to about 150 mg per day. In one embodiment, the compound is administered at an amount of from about 25 mg to about 150 mg per day. In one embodiment, the compound is administered at an amount of from about 25 mg to about 125 mg per day. In one embodiment, the compound is administered at an amount of from about 25 mg to about 100 mg per day. In one embodiment, the compound is administered at an amount of from about 50 mg to about 125 mg per day. In one embodiment, the compound is administered at an amount of from about 50 mg to about 100 mg per day. In one embodiment, the compound is administered at an amount of about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, or about 200 mg per day. In one embodiment, the amount is about 5 mg per day. In one embodiment, the amount is about 10 mg per day. In one embodiment, the amount is about 15 mg per day. In one embodiment, the amount is about 20 mg per day. In one embodiment, the amount is about 25 mg per day. In one embodiment, the amount is about 30 mg per day. In one embodiment, the amount is about 35 mg per day. In one embodiment, the amount is about 40 mg per day. In one embodiment, the amount is about 45 mg per day. In one embodiment, the amount is about 50 mg per day. In one embodiment, the amount is about 75 mg per day. In one embodiment, the amount is about 100 mg per day. In one embodiment, the amount is about 125 mg per day. In one embodiment, the amount is about 150 mg per day. As used herein, the weight amount refers to the weight amount of the free base Compound 1. In certain embodiments, the compound used herein is Compound 1.

In one embodiment, the compound used herein (Compound 1 or a stereoisomer, or a mixture of stereoisomers thereof, or a pharmaceutically acceptable salt thereof) is administered at an amount of from about 5 mg to about 500 mg (by weight of the free base, Compound 1) once daily. In one embodiment, the compound is administered at an amount of from about 25 mg to about 250 mg once daily. In one embodiment, the compound is administered at an amount of from about 25 mg to about 200 mg once daily. In one embodiment, the compound is administered at an amount of from about 50 mg to about 200 mg once daily. In one embodiment, the compound is administered at an amount of from about 5 mg to about 150 mg once daily. In one embodiment, the compound is administered at an amount of from about 25 mg to about 150 mg once daily. In one embodiment, the compound is administered at an amount of from about 25 mg to about 125 mg once daily. In one embodiment, the compound is administered at an amount of from about 25 mg to about 100 mg once daily. In one embodiment, the compound is administered at an amount of from about 50 mg to about 125 mg once daily. In one embodiment, the compound is administered at an amount of from about 50 mg to about 100 mg once daily. In one embodiment, the compound is administered at an amount of about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, or about 200 mg once daily. In one embodiment, the amount is about 5 mg once daily. In one embodiment, the amount is about 10 mg once daily. In one embodiment, the amount is about 15 mg once daily. In one embodiment, the amount is about 20 mg once daily. In one embodiment, the amount is about 25 mg once daily. In one embodiment, the amount is about 30 mg once daily. In one embodiment, the amount is about 35 mg once daily. In one embodiment, the amount is about 40 mg once daily. In one embodiment, the amount is about 45 mg once daily. In one embodiment, the amount is about 50 mg once daily. In one embodiment, the amount is about 75 mg once daily. In one embodiment, the amount is about 100 mg once daily. In one embodiment, the amount is about 125 mg once daily. In one embodiment, the amount is about 150 mg once daily. As used herein, the weight amount refers to the weight amount of the free base Compound 1. In certain embodiments, the compound used herein is Compound 1.

In one embodiment, the compound used herein (Compound 1 or a stereoisomer, or a mixture of stereoisomers thereof, or a pharmaceutically acceptable salt thereof) is administered at an amount of from about 5 mg to about 500 mg (by weight of the free base, Compound 1) twice daily. In one embodiment, the compound is administered at an amount of from about 5 mg to about 250 mg twice daily. In one embodiment, the compound is administered at an amount of from about 25 mg to about 250 mg twice daily. In one embodiment, the compound is administered at an amount of from about 25 mg to about 200 mg twice daily. In one embodiment, the compound is administered at an amount of from about 5 mg to about 100 mg twice daily. In one embodiment, the compound is administered at an amount of from about 10 mg to about 50 mg twice daily. In one embodiment, the compound is administered at an amount of from about 10 mg to about 100 mg twice daily. In one embodiment, the compound is administered at an amount of from about 25 mg to about 100 mg twice daily. In one embodiment, the compound is administered at an amount of from about 50 mg to about 100 mg twice daily. In one embodiment, the compound is administered at an amount of from about 5 mg to about 150 mg twice daily. In one embodiment, the compound is administered at an amount of from about 25 mg to about 150 mg twice daily. In one embodiment, the compound is administered at an amount of about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, or about 200 mg twice daily. In one embodiment, the amount is about 5 mg twice daily. In one embodiment, the amount is about 10 mg twice daily. In one embodiment, the amount is about 15 mg twice daily. In one embodiment, the amount is about 20 mg twice daily. In one embodiment, the amount is about 25 mg twice daily. In one embodiment, the amount is about 30 mg twice daily. In one embodiment, the amount is about 35 mg twice daily. In one embodiment, the amount is about 40 mg twice daily. In one embodiment, the amount is about 45 mg twice daily. In one embodiment, the amount is about 50 mg twice daily. In one embodiment, the amount is about 75 mg twice daily. In one embodiment, the amount is about 100 mg twice daily. In one embodiment, the amount is about 125 mg twice daily. In one embodiment, the amount is about 150 mg twice daily. As used herein, the weight amount refers to the weight amount of the free base Compound 1. In certain embodiments, the compound used herein is Compound 1.

In one embodiment, the compound is administered orally.

In one embodiment, the compound is administered in the form of one or more tablets. In one embodiment, the tablet has a unit dose strength of about 5 mg by weight of the free base Compound 1. In one embodiment, the table has a unit dose strength of about 25 mg by weight of the free base Compound 1.

In one embodiment, the compound is administered to a subject with an empty stomach. In one embodiment, the compound is administered to a subject at fasted status. In one embodiment, the compound is administered to a subject without food. In one embodiment, the compound is administered to a subject at least 1 hour before and no sooner than 2 hours after ingestion of food and/or beverages other than water. In one embodiment, the compound is administered to a subject with a full stomach. In one embodiment, the compound is administered to a subject at fed status. In one embodiment, the compound is administered to a subject with food. In one embodiment, the compound is administered with the ingestion of food and/or beverages.

In one embodiment, the patient experiences improvement in one or more symptoms selected from the group consisting of cognitive impairment, mood disorders, sleep disturbances, dizziness, ataxia, and weight gain, after the administration of the compound. In one embodiment, the patient does not experience one or more symptoms selected from the group consisting of cognitive impairment, mood disorders, sleep disturbances, dizziness, ataxia, and weight gain, after the administration of the compound. In one embodiment, the patient experiences reduced levels of one or more of pROS1, ROS1, pAKT, and pERK, after the administration of the compound. In one embodiment, the patient experiences reduced expression level of one or more MAP kinase pathway genes in tumor, after the administration of the compound. In one embodiment, the patient experiences reduced expression level of one or more MAP kinase pathway genes in solid tumor, after the administration of the compound. In one embodiment, the one or more MAP kinase pathway genes are selected from the group consisting of DUSP6, FOS, IL1R1, and SPRY4.

In one embodiment, provided herein are methods of treating cancer comprising administering a therapeutically effective amount of a solid form or pharmaceutical composition provided herein, such as Form 1 of a compound of Formula (I), or a stereoisomer, or a mixture of stereoisomers thereof, or a pharmaceutically acceptable salt thereof.

Cancer is a disease of uncontrolled cell proliferation that results from alterations in certain genes. Some of these alterations occur in genes that encode receptor tyrosine kinases (RTKs), a family of membrane-bound proteins that transmit signals from outside the cell to promote cell survival, growth, and proliferation. Aberrant RTK activation can lead to excessive cell growth and hence cancer. Generally, RTKs contain an N-terminal domain that binds extracellular ligands, a transmembrane domain, and a C-terminal kinase domain that catalyzes intracellular signal transduction.

In some embodiments, the compound of Formula (I) is an inhibitor of human ROS1. ROS1 is an RTK encoded by the ROS1 gene. The ligands and biological functions of human ROS1 are unknown, but its homologs in some other species have been shown to bind extracellular ligands and stimulate cell differentiation. For example, mouse ROS1 is essential for male gamete maturation and reproduction. In humans, ROS1 chromosomal rearrangements are a well-documented cause of cancer, representing 1-2% of non-small cell lung cancer (NSCLC) and a subset of many other cancers. These rearrangements result in the fusion of the C-terminus of ROS1 with the N-terminus of various partner proteins, the most common of which is CD74. ROS1 fusions have constitutive kinase activity that drives tumor growth through MAPK, PI3K, and JAK/STAT signaling pathways. Small-molecule tyrosine kinase inhibitors (TKIs) have been used to target ROS1 fusions in cancer, including crizotinib and entrectinib. Crizotinib was the first FDA-approved TKI for the treatment of ROS1-positive NSCLC. Despite an initial response, most patients acquire resistance to crizotinib and relapse. The predominant mechanism of resistance is the G2032R mutation in the solvent front, which dramatically reduces crizotinib affinity. No inhibitors with activity against ROS1-G2032R fusions have been FDA-approved, indicating a need in the art.

In one embodiment, a compound provided herein selectively inhibits ROS1. In one embodiment, the compound selectively inhibits ROS1 over ALK. By way of non-limiting example, the ratio of selectivity can be greater than a factor of about 1.5, greater than a factor of about 2, greater than a factor of about 3, greater than a factor of about 4, greater than a factor of about 5, greater than a factor of about 10, greater than a factor of about 20, greater than a factor of about 30, greater than a factor of about 50, or greater than a factor of about 100, where selectivity can be measured by ratio of $IC_{50}$ values, among other means. In one embodiment, the selectivity of ROS1 over ALK is measured by the ratio of the $IC_{50}$ value against ALK to the $IC_{50}$ value against ROS1.

In one embodiment, the compound selectively inhibits ROS1 over TRK (e.g., TRKA, TRKB, and/or TRBC). By way of non-limiting example, the ratio of selectivity can be greater than a factor of about 5, greater than a factor of about 10, greater than a factor of about 50, greater than a factor of about 100, greater than a factor of about 200, greater than a factor of about 400, greater than a factor of about 600, greater than a factor of about 800, greater than a factor of about 1000, greater than a factor of about 1500, greater than a factor of about 2000, greater than a factor of about 5000, greater than a factor of about 10,000, or greater than a factor of about 20,000, where selectivity can be measured by ratio of $IC_{50}$ values, among other means. In one embodiment, the selectivity of ROS1 over TRK is measured by the ratio of the $IC_{50}$ value against TRK to the $IC_{50}$ value against ROS1.

In one embodiment, provided herein is a method for selectively inhibiting ROS1 over ALK wherein the inhibition takes place in a cell. In one embodiment, provided herein is a method for selectively inhibiting ROS1 over TRK (e.g., TRKA, TRKB, and/or TRBC) wherein the inhibition takes place in a cell. In one embodiment, the method comprises contacting ROS1 with an effective amount of a solid form or a pharmaceutical composition provided herein. In an embodiment, such contact occurs in a cell. In an embodiment, such contact occurs in a cell in a mammal such as a human. In an embodiment, such contact occurs in a cell in human patient having a cancer provided herein.

In one embodiment, provided herein is a method for selectively inhibiting ROS1 over ALK wherein the inhibition takes place in a subject suffering from cancer, said method comprising administering an effective amount of a solid form or a pharmaceutical composition provided herein to said subject. In certain embodiments, provided herein is a method of treating a subject suffering from a cancer associated with ROS1, said method comprising selectively inhibiting ROS1 over ALK by administering an amount of a solid form or a pharmaceutical composition provided herein to said subject, wherein said amount is sufficient for selective inhibiting ROS1 over ALK.

In one embodiment, provided herein is a method for selectively inhibiting ROS1 over TRK (e.g., TRKA, TRKB, and/or TRBC) wherein the inhibition takes place in a subject suffering from cancer, said method comprising administering an effective amount of a solid form or a pharmaceutical composition provided herein to said subject. In certain embodiments, provided herein is a method of treating a subject suffering from a cancer associated with ROS1, said method comprising selectively inhibiting ROS1 over TRK (e.g., TRKA, TRKB, and/or TRBC) by administering an amount of a solid form or a pharmaceutical composition provided herein to said subject, wherein said amount is sufficient for selective inhibiting ROS1 over TRK (e.g., TRKA, TRKB, and/or TRBC).

As used herein and unless otherwise specified, inhibition of ROS1 includes inhibition of wild type ROS1, or a mutation thereof, inhibition of ALK includes inhibition of wild type ALK, or a mutation thereof, and inhibition of TRK includes inhibition of wild type TRK, or a mutation thereof.

Cancers treated by methods provided herein include, but are not limited to, lung cancer, e.g., non-small cell lung cancer, inflammatory myofibroblastic tumor, ovarian cancer, e.g., serous ovarian carcinoma, melanoma, e.g., spitzoid melanoma, glioblastoma, bile duct cancer, e.g., cholangiocarcinoma, gastric cancer, colorectal cancer, angiosarcoma, anaplastic large cell lymphoma, diffuse large B-cell lymphoma, large B-cell lymphoma, esophageal cancer, e.g., esophageal squamous cell carcinoma, kidney cancer, e.g., renal medullary carcinoma or renal cell carcinoma, breast cancer, e.g., triple negative breast cancer, thyroid cancer, e.g., papillary thyroid cancer, neuroblastoma, epithelioid hemangioendothelioma, colon cancer, and spitzoid tumor.

Cancers treated by methods provided herein include cancers originating from one or more oncogenic proteins selected from ROS1, ALK, TRKA, TRKB, and TRKC. In certain embodiments, cancers treated by methods provided herein include cancers that are drug resistant to treatments directed at one or more oncogenic proteins selected from ROS1, ALK, TRKA, TRKB, and TRKC.

In one embodiment, the cancer in a method provided herein is ROS1 positive (ROS1+). As used herein and unless otherwise specified, a "ROS1 positive" (ROS1+) cancer, disease, or disorder refers to a cancer, disease, or disorder characterized by inappropriately high expression of a ROS1 gene and/or the presence of a mutation in a ROS1 gene. In one embodiment, the mutation alters the biological activity of a ROS1 nucleic acid molecule or polypeptide. As used herein and unless otherwise specified, a "mutation" or "mutant" of ROS1 comprises one or more deletions, substitutions, insertions, inversions, duplications, translocations, or amplifications in the amino acid or nucleotide sequences of ROS1, or fragments thereof. As used herein and unless otherwise specified, a ROS1 "rearrangement" refers to genetic translocations involving the ROS1 gene that may result in ROS1 fusion genes and/or ROS1 fusion proteins. The ROS1 fusion can also include one or more deletions, substitutions, insertions, inversions, duplications, translocations, or amplifications or a fragment thereof, as long as the mutant retains kinase phosphorylation activity.

In one embodiment, the ROS1 mutation comprises one or more ROS1 point mutations. In some embodiments, cancers treated by methods provided herein include one or more mutations in ROS1 kinase. In one embodiment, the one or more ROS1 point mutations are selected from point mutations at E1935, L1947, L1951, G1971, E1974, L1982, S1986, F2004, E2020, L2026, G2032, D2033, C2060, F2075, L2086, V2089, V2098, G2101, D2113, 1981Tins, M2001T, and L2155. In one embodiment, the one or more ROS1 point mutations are selected from G2032R, G2032K, D2033N, S1986F, S1986Y, L2026M, L1951R, E1935G, L1947R, G1971E, E1974K, L1982F, F2004C, F2004V, E2020K, C2060G, F2075V, V2089M, V2098I, G2101A, D2113N, D2113G, L2155S, and L2086F. In one embodiment, the ROS1 mutation is G2032R. In one embodiment, the ROS1 mutation is S1986F. In one embodiment, the ROS1 mutation is S1986Y. In one embodiment, the ROS1 mutation is L2026M. In one embodiment, the ROS1 mutation is D2033N. In one embodiment, the ROS1 mutation is L2086F. In one embodiment, the ROS1 mutation is F2004C. In one embodiment, the ROS1 mutation is F2004V. In one embodiment, the ROS1 mutation is G2101A. In one embodiment, the ROS1 mutation is L1982F. In one embodiment, the ROS1 mutation is co-mutation of G2032R and one or more of S1986F, S1986Y, F2004C, F2004V, L2026M, or D2033N.

In one embodiment, the ROS1 mutation comprises one or more ROS1 rearrangements (in one embodiment, one rearrangement). In one embodiment, the ROS1 mutation comprises one or more ROS1 fusions (in one embodiment, one fusion). In some embodiments, cancers treated by methods provided herein include ROS1 fusions. In one embodiment, the ROS1 fusion is with one of the fusion partners selected from SLC34A2, CD74, TPM3, SDC4, EZR, LRIG3, KDELR2, CEP72, CLTL, CTNND2, GOPC (e.g., GOPC-S, GOPC-L), GPRC6A, LIMA1, LRIG3, MSN, MYO5C, OPRM1, SLC6A17 SLMAP, SRSF6, TFG, TMEM106B, TPD52L1, ZCCHC8, CCDC6, CAPRIN1, CEP85L, CHCHD3, CLIP1, EEF1G, KIF21A, KLC1, SART3, ST13, TRIM24, ERC1, FIP1L1, HLAA, KIAA1598, MYO5A, PPFIBP1, PWWP2A, FN1, YWHAE, CCDC30, NCOR2, NFKB2, APOB, PLG, RBP4, and GOLGB1. In one embodiment, the ROS1 fusion is CD74-ROS1 fusion. In one embodiment, the ROS1 fusion is SDC4-ROS1 fusion. In one embodiment, the ROS1 fusion is EZR-ROS1 fusion. In one embodiment, the ROS1 fusion is SLC34A2-ROS1 fusion. In one embodiment, the ROS1 fusion is GOPC-ROS1 fusion (e.g., GOPC-ROS1-S, GOPC-ROS1-L). In one embodiment, the ROS1 fusion is CEP85L-ROS1 fusion.

In one embodiment, the ROS1 mutation comprises one ROS1 rearrangement and one or more ROS1 point mutations. In one embodiment, the ROS1 mutation comprises one or more ROS1 rearrangements from CD74-ROS1, EZR-ROS1, SLC34A2-ROS1, GOPC-ROS1 (e.g., GOPC-ROS1-S, GOPC-ROS1-L), and CEP85L-ROS1, and one or more ROS1 point mutations selected from F2004C, F2004V, and G2032R. In one embodiment, the ROS1 mutation comprises one or more ROS1 rearrangements from CD74-ROS1, EZR-ROS1, and SLC34A2-ROS1, and ROS1 point mutation of G2101A.

In one embodiment, the ROS1 mutation is CD74-ROS1 F2004C. In one embodiment, the ROS1 mutation is CD74-ROS1 F2004V. In one embodiment, the ROS1 mutation is CD74-ROS1 G2101A. In one embodiment, the ROS1 mutation is CD74-ROS1 G2032R. In one embodiment, the ROS1 mutation is CD74-ROS1 S1986F. In one embodiment, the ROS1 mutation is CD74-ROS1 L2026M. In one embodiment, the ROS1 mutation is CD74-ROS1 D2033N. In one embodiment, the ROS1 mutation is EZR-ROS1 F2004C. In one embodiment, the ROS1 mutation is EZR-ROS1 F2004V. In one embodiment, the ROS1 mutation is EZR-ROS1 G2101A. In one embodiment, the ROS1 mutation is EZR-ROS1 G2032R. In one embodiment, the ROS1 mutation is SLC34A2-ROS1 F2004C. In one embodiment, the ROS1 mutation is SLC34A2-ROS1 F2004V. In one embodiment, the ROS1 mutation is SLC34A2-ROS1 G2101A. In one embodiment, the ROS1 mutation is SLC34A2-ROS1 G2032R. In one embodiment, the ROS1 mutation is GOPC-ROS1 F2004C (e.g., GOPC-ROS1-S F2004C, GOPC-ROS1-L F2004C). In one embodiment, the ROS1 mutation is GOPC-ROS1 F2004V (e.g., GOPC-ROS1-S F2004V, GOPC-ROS1-L F2004V). In one embodiment, the ROS1 mutation is GOPC-ROS1 G2032R (e.g., GOPC-ROS1-S G2032R, GOPC-ROS1-L G2032R). In one embodiment, the ROS1 mutation is CEP85L-ROS1 F2004C. In one embodiment, the ROS1 mutation is CEP85L-ROS1 F2004V. In one embodiment, the ROS1 mutation is CEP85L-ROS1 G2032R. In one embodiment, the ROS1 mutation is GOPC-ROS1 L1982F (e.g., GOPC-ROS1-S L1982F, GOPC-ROS1-L L1982F). In one embodiment, the ROS1 mutation is CD74-ROS1 L1982F.

In one embodiment, the ROS1+ cancer is determined by an FDA-approved test or other tests known in the art. The tests that can be used include, e.g., Oncomine™ Dx Target Test by Thermo Fisher Scientific. (a qualitative in vitro diagnostic test that uses targeted high-throughput, parallel-sequencing technology to detect sequence variations in 23 genes in DNA and RNA isolated from formalin-fixed, paraffin-embedded tumor (FFPE) tissue samples from patients with non-small cell lung cancer (NSCLC) using the Ion PGM Dx System); Vysis ROS1 Break Apart FISH Probe Kit (a qualitative test to detect rearrangements involving ROS1 gene rearrangements at 6q22 via fluorescence in situ hybridization (FISH) in formalin-fixed, paraffin-embedded (FFPE) non-small cell lung cancer (NSCLC) tissue specimens) or Reverse transcription-Polymerase Chain Reaction (RT-PCR) or Next Generation Sequencing (NGS) via a local diagnostic test.

Also provided are methods of treating a subject having a cancer (e.g., a ROS1 positive cancer) that include: determining whether a cancer cell in a sample obtained from a subject having a cancer and previously administered a first ROS1 inhibitor, has one or more ROS1 inhibitor resistance mutations; and administering a solid form or a pharmaceutical composition provided herein as a monotherapy or in conjunction with another anticancer agent to the subject if the subject has a cancer cell that has one or more ROS1 inhibitor resistance mutations. In some embodiments, the one or more ROS1 inhibitor resistance mutations confer increased resistance to a cancer cell or tumor to treatment with the first ROS1 inhibitor. In some embodiments, the one or more ROS1 inhibitor resistance mutations include one or more ROS1 inhibitor resistance mutations. For example, the one or more ROS1 inhibitor resistance mutations can include a substitution at one or more of amino acid positions 2032, 2033, 1986, 2026, 1951, 1935, 1947, 1971, 1974, 1982, 2004, 2020, 2060, 2075, 2089, 2098, 2101, 2113, 2155, 2032, and 2086, e.g., G2032R, D2033N, 51986F, 51986Y, L2026M, L1951R, E1935G, L1947R, G1971E, E1974K, L1982F, F2004C, F2004V, E2020K, C2060G, F2075V, V2089M, V2098I, G2101A, D2113N, D2113G, L2155S, L2032K, and L2086F. In some embodiments, another anticancer agent is any anticancer agent known in the art. For example, another anticancer agent can be another ROS1 inhibitor (e.g., a second ROS1 inhibitor).

In one embodiment, a compound provided herein is a CNS-penetrating compound. In one embodiment, after the administration of an effective amount of a solid form or a pharmaceutical composition provided herein (e.g., orally or intravenously), the compound is able to penetrate CNS (e.g., blood-brain barrier) and achieve a concentration in CNS (e.g., brain) that is still sufficient to inhibit (e.g., selectively inhibit) ROS1.

In one embodiment, provided herein is a method for treating CNS metastases of a cancer, comprising administering to a subject in need thereof an effective amount of a solid form or a pharmaceutical composition provided herein, e.g., Form 1 of a compound of Formula (I), or a stereoisomer, or a mixture of stereoisomers thereof, or a pharmaceutically acceptable salt thereof. In one embodiment, the CNS metastases is brain metastases. In one embodiment, the cancer is a ROS1+ cancer.

In some embodiments, the compound is an inhibitor of human tropomyosin receptor kinase A, B, or C. In certain embodiments, the $IC_{50}$ of the compound for inhibition of mutant or non-mutant ROS1 or ALK is no more than one-fifth of the $IC_{50}$ of the compound for inhibition of wild-type tropomyosin receptor kinase A, B, or C. TRK inhibition, particularly in the central nervous system (CNS), has been associated with adverse reactions, including dizziness/ataxia/gait disturbance, paraesthesia, weight gain and cognitive changes.

In some embodiments, provided is a method of minimizing adverse events in a subject in need of treatment for cancer (e.g., a ROS1 positive cancer), the method comprising administering to the subject a therapeutically effective amount of a solid form or a pharmaceutical composition provided herein, e.g., Form 1 of a compound of Formula (I), a stereoisomer, or a mixture of stereoisomers thereof, or a pharmaceutically acceptable salt thereof, and wherein the method minimizes adverse events associated with TRK inhibitors. In some embodiments, the cancer is a ROS1-associated cancer. In some embodiments, the adverse events are one or more of TRK-related CNS adverse events.

As used herein "minimizing" adverse events refers to a reduction in the incidence of adverse events in a subject or patient population compared to the paradigmatic incidence of adverse events in a subject or patient population treated with TRK inhibitors (e.g., entrectinib, repotrectinib, or lorlatinib). In some embodiments, the incidence of an adverse event refers to the frequency or percentage of a specific adverse event over a subject or patient population. In some embodiments, the incidence of an adverse event refers to the total number of adverse events experienced by an individual subject. In some embodiments, minimizing adverse events refers to minimizing TRK-related CNS adverse events. In some embodiments, minimizing TRK-related CNS adverse events means less than 40% of the patient population has a TRK-related CNS adverse event. In some embodiments, minimizing TRK-related CNS adverse events means less than 35%, less than 30%, less than 25%, less than 20%, less than 15%, less than 10% or less than 5% of the patient population has a TRK-related CNS adverse event. In some embodiments, minimizing TRK-related CNS adverse events means less than 12% of the patient population have more than one TRK-related CNS adverse event. In some embodiments, minimizing TRK-related CNS adverse events means less than 11%, less than 10%, less than 9%, less than 8%, less than 7%, less than 6%, less than 5%, less than 4%, or less than 3% of the patient population have more than one TRK-related CNS adverse event.

In some embodiments, TRK-related CNS adverse events refers to one or more of the following: dizziness, ataxia, gait disturbance, paraesthesia, weight gain, hyperphagia, paresthesias, abnormal movement, cognitive changes, speech effects (e.g, dysarthria, slow speech, or speech disorder), mood disorder (e.g., irritability, anxiety, depression, affect lability, personality change, mood swings, affective disorder, aggression, agitation, mood altered, depressed mood, euphoric mood, or mania), and cognitive disorder (e.g., memory impairment, cognitive disorder, amnesia, confusion, disturbance in attention, delirium, mental impairment, attention deficit/hyperactivity disorder, dementia, sleep disturbance, or reading disorder).

In one embodiment, provided herein is a method for preventing or limiting TRK-related CNS side effect or adverse event in a cancer treatment, comprising administering to a subject in need thereof an effective amount of a solid form or a pharmaceutical composition provided herein, e.g., Form 1 of a compound of Formula (I), or a stereoisomer, or a mixture of stereoisomers thereof, or a pharmaceutically acceptable salt thereof. In one embodiment, the method prevents the occurrence of the TRK-related CNS adverse event. In one embodiment, the method limits the frequency of occurrence of the TRK-related CNS adverse event. In one embodiment, the method limits the severity of the TRK-related side effect. In one embodiment, provided herein is a method for treating CNS metastases of a cancer with reduced TRK-related side effect, comprising administering to a subject in need thereof an effective amount of a solid form or a pharmaceutical composition provided herein, e.g., Form 1 of a compound of Formula (I), or a stereoisomer, or a mixture of stereoisomers thereof, or a pharmaceutically acceptable salt thereof. In one embodiment, the reduction/limiting/prevention in CNS side effect or adverse event is determined in a statistical sample, as compared to a standard of care treatment, e.g., an approved ROS1 and/or ALK inhibitor (e.g., crizotinib, entrectinib, lorlatinib, or repotrectinib) for ROS1+ and/or ALK+ cancer. In one embodiment, the TRK-related side effect is a TRKB-related CNS side effect. In one embodiment, the TRK-related CNS side effect or adverse event is dizziness, ataxia, gait disturbance, paraesthesia, weight gain, cognitive impairment, a mood disorder, or sleep disturbance.

In one embodiment, provided herein is a method for treating cancer, comprising administering to a subject in need thereof a therapeutically effective amount of a solid form or a pharmaceutical composition provided herein, e.g., Form 1 of a compound of Formula (I), or a stereoisomer, or a mixture of stereoisomers thereof, or a pharmaceutically acceptable salt thereof. In one embodiment, the cancer is a ROS1-associated cancer. In one embodiment, the cancer is a ROS1+ cancer. In one embodiment, the cancer is identified to be ROS1

In one embodiment, provided herein is a method for treating a ROS1+ cancer, comprising administering to a subject in need thereof a therapeutically effective amount of a solid form or a pharmaceutical composition provided herein, e.g., Form 1 of a compound of Formula (I), or a stereoisomer, or a mixture of stereoisomers thereof, or a pharmaceutically acceptable salt thereof.

In one embodiment, provided herein is a method for treating cancer in a subject, comprising: (i) identifying the cancer in the subject to be ROS1+, and (ii) administering to the subject a therapeutically effective amount of a solid form or a pharmaceutical composition provided herein, e.g., Form 1 of a compound of Formula (I), or a stereoisomer, or a mixture of stereoisomers thereof, or a pharmaceutically acceptable salt thereof.

In one embodiment, the cancer (or ROS1+ cancer) is a solid tumor. In one embodiment, the cancer (or ROS1+ cancer) is an advanced solid tumor. In one embodiment, the cancer (or ROS1+ cancer) is a locally advanced solid tumor. In one embodiment, the cancer (or ROS1+ cancer) is lung cancer, e.g., non-small cell lung cancer (NSCLC), glioblastoma, inflammatory myofibroblastic tumor (IMT), bile duct cancer, e.g., cholangiocarcinoma, ovarian cancer, e.g., serous ovarian carcinoma, gastric cancer, colorectal cancer, angiosarcoma, melanoma, e.g., spitzoid melanoma, epithelioid hemangioendothelioma, esophageal cancer, e.g., esophageal squamous cell carcinoma (ESCC), kidney cancer, e.g., renal medullary carcinoma or renal cell carcinoma, breast cancer, e.g., triple negative breast cancer, colon cancer, thyroid cancer, e.g., papillary thyroid cancer, spitzoid tumor, pancreatic cancer, inflammatory hepatocellular adenoma, or neuroblastoma.

In one embodiment, the cancer is lung cancer. In one embodiment, the cancer is non-small cell lung cancer. In one embodiment, the cancer is ROS1+ non-small cell lung cancer. In one embodiment, the cancer is relapsed or refractory non-small cell lung cancer. In one embodiment, the cancer is relapsed or refractory ROS1+ non-small cell lung cancer. In one embodiment, the cancer is newly diagnosed non-small cell lung cancer. In one embodiment, the cancer is newly diagnosed ROS1+ non-small cell lung cancer. In one embodiment, the cancer is bronchus cancer. In one embodiment, the cancer is ROS1+ bronchus cancer. In one embodiment, the cancer is relapsed or refractory bronchus cancer. In one embodiment, the cancer is relapsed or refractory ROS1+ bronchus cancer. In one embodiment, the cancer is newly diagnosed bronchus cancer. In one embodiment, the cancer is newly diagnosed ROS1+ bronchus cancer.

In one embodiment, the cancer is glioblastoma. In one embodiment, the cancer is relapsed or refractory glioblastoma. In one embodiment, the cancer is relapsed or refractory ROS1+ glioblastoma. In one embodiment, the cancer is newly diagnosed glioblastoma. In one embodiment, the cancer is newly diagnosed ROS1+ glioblastoma.

In one embodiment, the cancer is IMT. In one embodiment, the cancer is ROS1+ IMT. In one embodiment, the cancer is relapsed or refractory IMT. In one embodiment, the cancer is relapsed or refractory ROS1+ IMT. In one embodiment, the cancer is newly diagnosed IMT. In one embodiment, the cancer is newly diagnosed ROS1+ IMT.

In one embodiment, the cancer is bile duct cancer. In one embodiment, the cancer is cholangiocarcinoma. In one embodiment, the cancer is ROS1+ cholangiocarcinoma. In one embodiment, the cancer is relapsed or refractory cholangiocarcinoma. In one embodiment, the cancer is relapsed or refractory ROS1+ cholangiocarcinoma. In one embodiment, the cancer is newly diagnosed cholangiocarcinoma. In one embodiment, the cancer is newly diagnosed ROS1+ cholangiocarcinoma.

In one embodiment, the cancer is ovarian cancer. In one embodiment, the cancer is ROS1+ ovarian cancer. In one embodiment, the cancer is relapsed or refractory ovarian cancer. In one embodiment, the cancer is relapsed or refractory ROS1+ ovarian cancer. In one embodiment, the cancer is newly diagnosed ovarian cancer. In one embodiment, the cancer is newly diagnosed ROS1+ ovarian cancer. In one embodiment, the ovarian cancer is serous ovarian carcinoma. In one embodiment, the ovarian cancer is high grade serous ovarian carcinoma.

In one embodiment, the cancer is gastric cancer. In one embodiment, the cancer is ROS1+ gastric cancer. In one embodiment, the cancer is relapsed or refractory gastric cancer. In one embodiment, the cancer is relapsed or refractory ROS1+ gastric cancer. In one embodiment, the cancer is newly diagnosed gastric cancer. In one embodiment, the cancer is newly diagnosed ROS1+ gastric cancer.

In one embodiment, the cancer is colorectal cancer. In one embodiment, the cancer is ROS1+ colorectal cancer. In one embodiment, the cancer is relapsed or refractory colorectal cancer. In one embodiment, the cancer is relapsed or refractory ROS1+ colorectal cancer. In one embodiment, the cancer is newly diagnosed colorectal cancer. In one embodiment, the cancer is newly diagnosed ROS1+ colorectal cancer.

In one embodiment, the cancer is angiosarcoma. In one embodiment, the cancer is ROS1+ angiosarcoma. In one embodiment, the cancer is relapsed or refractory angiosarcoma. In one embodiment, the cancer is relapsed or refractory ROS1+ angiosarcoma. In one embodiment, the cancer is newly diagnosed angiosarcoma. In one embodiment, the cancer is newly diagnosed ROS1+ angiosarcoma.

In one embodiment, the cancer is melanoma. In one embodiment, the cancer is spitzoid tumor. In one embodiment, the cancer is spitzoid melanoma. In one embodiment, the cancer is ROS1+ spitzoid melanoma. In one embodiment, the cancer is relapsed or refractory spitzoid melanoma. In one embodiment, the cancer is relapsed or refractory ROS1+ spitzoid melanoma. In one embodiment, the cancer is newly diagnosed spitzoid melanoma. In one embodiment, the cancer is newly diagnosed ROS1+ spitzoid melanoma.

In one embodiment, the cancer is epithelioid hemangioendothelioma. In one embodiment, the cancer is ROS1+ epithelioid hemangioendothelioma. In one embodiment, the cancer is relapsed or refractory epithelioid hemangioendothelioma. In one embodiment, the cancer is relapsed or refractory ROS1+ epithelioid hemangioendothelioma. In one embodiment, the cancer is newly diagnosed epithelioid hemangioendothelioma. In one embodiment, the cancer is newly diagnosed ROS1+ epithelioid hemangioendothelioma.

In one embodiment, the cancer is esophageal cancer. In one embodiment, the cancer is ESCC. In one embodiment, the cancer is ROS1+ ESCC. In one embodiment, the cancer is relapsed or refractory ESCC. In one embodiment, the cancer is relapsed or refractory ROS1+ ESCC. In one embodiment, the cancer is newly diagnosed ESCC. In one embodiment, the cancer is newly diagnosed ROS1+ ESCC.

In one embodiment, the cancer is kidney cancer. In one embodiment, the cancer is renal medullary carcinoma. In one embodiment, the cancer is ROS1+ renal medullary carcinoma. In one embodiment, the cancer is relapsed or refractory renal medullary carcinoma. In one embodiment, the cancer is relapsed or refractory ROS1+ renal medullary carcinoma. In one embodiment, the cancer is newly diagnosed renal medullary carcinoma. In one embodiment, the cancer is newly diagnosed ROS1+ renal medullary carcinoma. In one embodiment, the cancer is renal cell carcinoma. In one embodiment, the cancer is ROS1+ renal cell carcinoma. In one embodiment, the cancer is relapsed or refractory renal cell carcinoma. In one embodiment, the cancer is relapsed or refractory ROS1+ renal cell carcinoma. In one embodiment, the cancer is newly diagnosed renal cell carcinoma. In one embodiment, the cancer is newly diagnosed ROS1+ renal cell carcinoma.

In one embodiment, the cancer is breast cancer. In one embodiment, the cancer is ROS1+ breast cancer. In one embodiment, the cancer is relapsed or refractory breast cancer. In one embodiment, the cancer is relapsed or refractory ROS1+ breast cancer. In one embodiment, the cancer is newly diagnosed breast cancer. In one embodiment, the cancer is newly diagnosed ROS1+ breast cancer. In one embodiment, the breast cancer is triple negative breast cancer.

In one embodiment, the cancer is colon cancer. In one embodiment, the cancer is ROS1+ colon cancer. In one embodiment, the cancer is relapsed or refractory colon cancer. In one embodiment, the cancer is relapsed or refractory ROS1+ colon cancer. In one embodiment, the cancer is newly diagnosed colon cancer. In one embodiment, the cancer is newly diagnosed ROS1+ colon cancer.

In one embodiment, the cancer is thyroid cancer. In one embodiment, the cancer is papillary thyroid cancer. In one embodiment, the cancer is ROS1+ papillary thyroid cancer. In one embodiment, the cancer is relapsed or refractory papillary thyroid cancer. In one embodiment, the cancer is relapsed or refractory ROS1+ papillary thyroid cancer. In one embodiment, the cancer is newly diagnosed papillary thyroid cancer. In one embodiment, the cancer is newly diagnosed ROS1+ papillary thyroid cancer.

In one embodiment, the cancer is ROS1+ glioma (e.g. Grade 1, Grade 2, Grade 3, or Grade 4). In one embodiment, the cancer is relapsed or refractory glioma. In one embodiment, the cancer is relapsed or refractory ROS1+ glioma. In one embodiment, the cancer is newly diagnosed ROS1+ glioma. In one embodiment, the cancer is ROS1+ glioblastoma. In one embodiment, the cancer is newly diagnosed ROS1+ glioblastoma. In one embodiment, the cancer is relapsed or refractory glioblastoma. In one embodiment, the cancer is relapsed or refractory ROS1+ glioblastoma. In one embodiment, the cancer is neuroblastoma. In one embodiment, the cancer is ROS1+ neuroblastoma. In one embodiment, the cancer is relapsed or refractory neuroblastoma. In one embodiment, the cancer is relapsed or refractory ROS1+ neuroblastoma. one embodiment, the cancer is newly diagnosed neuroblastoma. In one embodiment, the cancer is newly diagnosed ROS1+ neuroblastoma.

In one embodiment, the cancer is ROS1+ pancreatic cancer. In one embodiment, the cancer is relapsed or refractory pancreatic cancer. In one embodiment, the cancer is relapsed or refractory ROS1+ pancreatic cancer. one embodiment, the cancer is newly diagnosed neuroblastoma. In one embodiment, the cancer is newly diagnosed ROS1+ pancreatic cancer.

In one embodiment, the cancer is ROS1+ inflammatory hepatocellular adenoma. In one embodiment, the cancer is relapsed or refractory inflammatory hepatocellular adenoma. In one embodiment, the cancer is relapsed or refractory ROS1+ inflammatory hepatocellular adenoma. one embodiment, the cancer is newly diagnosed neuroblastoma. In one embodiment, the cancer is newly diagnosed ROS1+ inflammatory hepatocellular adenoma.

In one embodiment, the cancer (or ROS1+ cancer, or ALK+ cancer) is a hematological cancer. In one embodiment, the cancer (or ROS1+ cancer, or ALK+ cancer) is lymphoma. In one embodiment, the lymphoma is non-Hodgkin lymphoma. In one embodiment, the lymphoma is anaplastic large cell lymphoma (ALCL), diffuse large B-cell lymphoma (DLBCL), or large B-cell lymphoma. In addition to hematological cancer, methods for treating other blood disorder or hematologic malignancy that is ROS1+ or ALK+ are also provided herein.

In one embodiment, the cancer is ALCL. In one embodiment, the cancer is ROS1+ ALCL. In one embodiment, the cancer is ALK+ ALCL. In one embodiment, the cancer is relapsed or refractory ALCL. In one embodiment, the cancer is relapsed or refractory ROS1+ ALCL. In one embodiment, the cancer is relapsed or refractory ALK+ ALCL. In one embodiment, the cancer is newly diagnosed ALCL. In one embodiment, the cancer is newly diagnosed ROS1+ ALCL. In one embodiment, the cancer is newly diagnosed ALK+ ALCL.

In one embodiment, the cancer is DLBCL. In one embodiment, the cancer is ROS1+ DLBCL. In one embodiment, the cancer is ALK+ DLBCL. In one embodiment, the cancer is relapsed or refractory DLBCL. In one embodiment, the cancer is relapsed or refractory ROS1+ DLBCL. In one embodiment, the cancer is relapsed or refractory ALK+ DLBCL. In one embodiment, the cancer is newly diagnosed DLBCL. In one embodiment, the cancer is newly diagnosed ROS1+ DLBCL. In one embodiment, the cancer is newly diagnosed ALK+ DLBCL.

In one embodiment, the cancer is large B-cell lymphoma. In one embodiment, the cancer is ROS1+ large B-cell lymphoma. In one embodiment, the cancer is ALK+ large B-cell lymphoma. In one embodiment, the cancer is relapsed or refractory large B-cell lymphoma. In one embodiment, the cancer is relapsed or refractory ROS1+ large B-cell lymphoma. In one embodiment, the cancer is relapsed or refractory ALK+ large B-cell lymphoma. In one embodiment, the cancer is newly diagnosed large B-cell lymphoma. In one embodiment, the cancer is newly diagnosed ROS1+ large B-cell lymphoma. In one embodiment, the cancer is newly diagnosed ALK+ large B-cell lymphoma. In one embodiment, the cancer (or ROS1+ cancer) is new diagnosed. In one embodiment, the cancer (or ROS1+ cancer) is previously untreated.

In one embodiment, the cancer (or ROS1+ cancer) is relapsed or refractory. In one embodiment, the cancer is relapsed. In one embodiment, the cancer (or ROS1+ cancer) is refractory.

In one embodiment, the subject is previously untreated. In one embodiment, the subject is treatment naïve to tyrosine kinase inhibitor (TKI) therapy. In one embodiment, the subject has received one or more prior lines of therapy. In one embodiment, the subject has received two or more prior lines of therapy. In one embodiment, the subject has developed resistance to one or more of the prior lines of therapy. In one embodiment, the prior therapy comprises a tyrosine kinase inhibitor (TKI). In one embodiment, the prior TKI therapy comprises a treatment with one or more of crizotinib, ceritinib, alectinib, brigatinib, lorlatinib, entrectinib, repotrectinib, cabozantinib, foretinib, taletrectinib, merestinib, masitinib, and ensartinib. In one embodiment, the prior therapy comprises one or more chemotherapies. In one embodiment, the one or more chemotherapies are in addition to the TKI therapy.

In one embodiment, the cancer is advanced cancer, e.g. relapsed after, refractory to, or resistant to the prior treatment by a TKI.

In one embodiment, the cancer (or ROS1+ cancer) is resistant to a tyrosine kinase inhibitor (TKI).

In one embodiment, the cancer is resistant lung cancer. In one embodiment, the cancer is resistant non-small cell lung cancer. In one embodiment, the cancer is non-small cell lung cancer resistant to a TKI. In one embodiment, the cancer is ROS1+ non-small cell lung cancer resistant to a TKI.

In one embodiment, the cancer is lung cancer (e.g., NSCLC). In one embodiment, the cancer is advanced lung cancer, e.g. relapsed after, or refractory to, prior treatment by a TKI.

In one embodiment, a compound provided herein is administered as first-line treatment. In one embodiment, a compound provided herein is administered as second-line treatment. In one embodiment, a compound provided herein is administered as third or fourth-line treatment.

In one embodiment, the cancer (or ROS1+ cancer) is metastatic. In one embodiment, the cancer has CNS metastases. In one embodiment, the cancer has brain metastases. In one embodiment, the cancer is metastatic non-small cell lung cancer (NSCLC). In one embodiment, the cancer is metastatic ROS1+ NSCLC.

In one embodiment, provided herein is a method for treating a patient with metastatic ROS1+ non-small cell lung cancer (NSCLC), comprising administering to the patient a therapeutically effective amount of a solid form or a pharmaceutical composition provided herein, e.g., Form 1 of a compound of Formula (I), or a stereoisomer, or a mixture of stereoisomers thereof, or a pharmaceutically acceptable salt thereof.

In one embodiment, the patient is an adult patient. In one embodiment, the patient is a pediatric patient.

In one embodiment, provided herein is a method for treating an adult patient with metastatic ROS1+ NSCLC, comprising administering to the patient a therapeutically effective amount of a solid form or a pharmaceutical composition provided herein, e.g., Form 1 of a compound of Formula (I), or a stereoisomer, or a mixture of stereoisomers thereof, or a pharmaceutically acceptable salt thereof.

In one embodiment, provided herein is a method for treating an adult patient with metastatic ROS1+ NSCLC, comprising administering to the patient a therapeutically effective amount of a solid form or a pharmaceutical composition provided herein, e.g., Form 1 of a compound of Formula (I), or a stereoisomer, or a mixture of stereoisomers thereof, or a pharmaceutically acceptable salt thereof, wherein the patient has progressed on or is intolerant of at least 1 prior TKI therapy.

In one embodiment, provided herein is a method for treating an adult patient with metastatic NSCLC that is ROS1+ with solvent front mutation G2032R, comprising administering to the patient a therapeutically effective amount of a solid form or a pharmaceutical composition provided herein, e.g., Form 1 of a compound of Formula (I), or a stereoisomer, or a mixture of stereoisomers thereof, or a pharmaceutically acceptable salt thereof, wherein the patient has progressed on or is intolerant of at least 1 prior TKI therapy.

In one embodiment, provided herein is a method for treating a ROS1-associated (or ROS1+) cancer in a subject in need thereof, wherein the cancer has developed resistance to a tyrosine kinase inhibitor (TKI), the method comprising administering to the subject a therapeutically effective amount of a solid form or a pharmaceutical composition provided herein, e.g., Form 1 of a compound of Formula (I), or a stereoisomer, or a mixture of stereoisomers thereof, or a pharmaceutically acceptable salt thereof.

In one embodiment, provided herein is a method for treating a ROS1-associated (or ROS1+) cancer in a subject in need thereof, wherein the cancer has developed resistance to a tyrosine kinase inhibitor (TKI), and wherein the cancer has been identified as having one or more ROS1 inhibitor resistance mutations, the method comprising administering to the subject a therapeutically effective amount of a solid form or a pharmaceutical composition provided herein, e.g., Form 1 of a compound of Formula (I), or a stereoisomer, or a mixture of stereoisomers thereof, or a pharmaceutically acceptable salt thereof. In one embodiment, the one or more ROS1 inhibitor resistance mutations comprise one or more amino acid substitutions at an amino acid position selected from 1986, 2004, 2026, 2032, and 2033. In one embodiment, the one or more ROS1 inhibitor resistance mutations comprise one or more amino acid substitutions selected from S1986F, S1986Y, F2004C, F2004V, L2026M, G2032R, D2033N, L2086F, and G2101A. In one embodiment, the one or more ROS1 inhibitor resistance mutations is G2032R. In one embodiment, the one or more ROS1 inhibitor resistance mutations comprise G2032R and one or more of S1986F, S1986Y, F2004C, F2004V, L2026M, D2033N, or G2101A. In one embodiment, the ROS1 inhibitor resistance mutation is L2086F.

In one embodiment, the TKI is a ROS1 inhibitor. In one embodiment, the TKI is an ALK inhibitor. In one embodiment, the TKI is crizotinib, ceritinib, alectinib, brigatinib, lorlatinib, entrectinib, repotrectinib, cabozantinib, foretinib, merestinib, taletrectinib, masitinib, or ensartinib. In one embodiment, the TKI is crizotinib. In one embodiment, the TKI is entrectinib.

In certain embodiments, the subject has relapsed after first-line treatment of the cancer. In other embodiments, the subject has relapsed after second-line treatment of the cancer.

In certain embodiments, the methods for treating or preventing cancer can be demonstrated by one or more responses such as increased apoptosis, inhibition of tumor growth, reduction of tumor metastasis, inhibition of tumor metastasis, reduction of microvessel density, decreased neovascularization, inhibition of tumor migration, tumor regression, and increased survival of the subject.

5.6. Combination Therapy

In some embodiments, the method of treating or preventing cancer may comprise administering a solid form or pharmaceutical composition provided herein, such as Form 1 of a compound of Formula (I), conjointly with one or more other chemotherapeutic agent(s).

As used herein and unless otherwise specified, by "conjointly" or "in combination with", it is not intended to imply that the other agent and the solid form or pharmaceutical composition provided herein must be administered at the same time and/or formulated for delivery together, although these methods of delivery are within the scope of this disclosure. The compound provided herein can be administered concurrently with, prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before), or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after), one or more other agents (e.g., one or more other additional agents). In general, each therapeutic agent is administered at a dose and/or on a time schedule determined for that particular agent. The other therapeutic agent can be administered with the compound provided herein in a single composition or separately in a different composition. Triple therapy is also contemplated herein.

Chemotherapeutic agents that may be conjointly administered with the solid form or pharmaceutical composition provided herein include: 1-amino-4-phenylamino-9,10-dioxo-9,10-dihydroanthracene-2-sulfonate (acid blue 25), 1-amino-4-[4-hydroxyphenyl-amino]-9,10-dioxo-9,10-dihydroanthracene-2-sulfonate, 1-amino-4-[4-aminophenylamino]-9,10-dioxo-9,10-dihydroanthracene-2-sulfonate, 1-amino-4-[1-naphthylamino]-9,10-dioxo-9,10-dihydroanthracene-2-sulfonate, 1-amino-4-[4-fluoro-2-carboxyphenylamino]-9,10-dioxo-9,10-dihydroanthracene-2-sulfonate, 1-amino-4-[2-anthracenylamino]-9,10-dioxo-9,10-dihydroanthracene-2-sulfonate, ABT-263, afatinib dimaleate, axitinib, aminoglutethimide, amsacrine, anastrozole, APCP, asparaginase, AZD5363, *Bacillus* Calmette-Guerin vaccine (bcg), bicalutamide, bleomycin, bortezomib, 3-methylene-ADP (AOPCP), buserelin, busulfan, cabazitaxel, cabozantinib, campothecin, capecitabine, carboplatin, carfilzomib, carmustine, ceritinib, chlorambucil, chloroquine, cisplatin, cladribine, clodronate, cobimetinib, colchicine, crizotinib, cyclophosphamide, cyproterone, cytarabine, dacarbazine, dactinomycin, daunorubicin, demethoxyviridin, dexamethasone, dichloroacetate, dienestrol, diethylstilbestrol, docetaxel, doxorubicin, epirubicin, eribulin, erlotinib, estradiol, estramustine, etoposide, everolimus, exemestane, filgrastim, fludarabine, fludrocortisone, fluorouracil, fluoxymesterone, flutamide, gefitinib, gemcitabine, genistein, goserelin, GSK1120212, hydroxyurea, idarubicin, ifosfamide, imatinib, interferon, irinotecan, ixabepilone, lenalidomide, letrozole, leucovorin, leuprolide, levamisole, lomustine, lonidamine, mechlorethamine, medroxyprogesterone, megestrol, melphalan, mercaptopurine, mesna, metformin, methotrexate, miltefosine, mitomycin, mitotane, mitoxantrone, MK-2206, mutamycin, N-(4-sulfamoylphenylcarbamothioyl) pivalamide, NF279, NF449, nilutamide, nocodazole, octreotide, olaparib, oxaliplatin, paclitaxel, pamidronate, pazopanib, pemexetred, pentostatin, perifosine, PF-04691502, plicamycin, pomalidomide, porfimer, PPADS, procarbazine, quercetin, raltitrexed, ramucirumab, reactive blue 2, rituximab, rolofylline, romidepsin, rucaparib, selumetinib, sirolimus, sodium 2,4-dinitrobenzenesulfonate, sorafenib, streptozocin, sunitinib, suramin, talazoparib, tamoxifen, temozolomide, temsirolimus, teniposide, testosterone, thalidomide, thioguanine, thiotepa, titanocene dichloride, tonapofylline, topotecan, trametinib, trastuzumab, tretinoin, veliparib, vinblastine, vincristine, vindesine, vinorelbine, and vorinostat (SAHA). In other embodiments, chemotherapeutic agents that may be conjointly administered with compounds provided herein include: ABT-263, dexamethasone, 5-fluorouracil, PF-04691502, romidepsin, and vorinostat (SAHA). In other embodiments, chemotherapeutic agents that may be conjointly administered with compounds provided herein include: 1-amino-4-phenylamino-9,10-dioxo-9,10-dihydroanthracene-2-sulfonate (acid blue 25), 1-amino-4-[4-hydroxyphenyl-amino]-9,10-dioxo-9,10-dihydroanthracene-2-sulfonate, 1-amino-4-[4-aminophenylamino]-9,10-dioxo-9,10-dihydroanthracene-2-sulfonate, 1-amino-4-[1-naphthylamino]-9,10-dioxo-9,10-dihydroanthracene-2-sulfonate, 1-amino-4-[4-fluoro-2-carboxyphenylamino]-9,10-dioxo-9,10-dihydroanthracene-2-sulfonate, 1-amino-4-[2-anthracenylamino]-9,10-dioxo-9,10-dihydroanthracene-2-sulfonate, APCP, β-methylene-ADP (AOPCP), capecitabine, cladribine, cytarabine, fludarabine, doxorubicin, gemcitabine, N-(4-sulfamoylphenylcarbamothioyl) pivalamide, NF279, NF449, PPADS, quercetin, reactive blue 2, rolofylline sodium 2,4-dinitrobenzenesulfonate, sumarin, and tonapofylline. In some embodiments, the chemotherapy agents are biologics such as ADCs or MET antibodies. In some embodiments, the chemotherapy agent is a MET inhibitor, a MEK inhibitor, a RET inhibitor, another ALK inhibitor, or ROS1 inhibitor. In some embodiments, the compound as described herein is used with one or more platinum based chemotherapy and/or immunotherapy (e.g. checkpoint inhibitors).

Many combination therapies have been developed for the treatment of cancer. In certain embodiments, a solid form or pharmaceutical composition provided herein (e.g., Form 1 of a compound of Formula (I)) may be conjointly administered with one or more combination therapies. Examples of combination therapies with which compounds provided herein may be conjointly administered are included in Table 1.

TABLE 1

Exemplary combinatorial therapies for the treatment of cancer

| Name | Therapeutic agents |
|---|---|
| ABV | Doxorubicin, Bleomycin, Vinblastine |
| ABVD | Doxorubicin, Bleomycin, Vinblastine, Dacarbazine |
| AC (Breast) | Doxorubicin, Cyclophosphamide |
| AC (Sarcoma) | Doxorubicin, Cisplatin |
| AC (Neuroblastoma) | Cyclophosphamide, Doxorubicin |
| ACE | Cyclophosphamide, Doxorubicin, Etoposide |
| ACe | Cyclophosphamide, Doxorubicin |
| AD | Doxorubicin, Dacarbazine |
| AP | Doxorubicin, Cisplatin |
| ARAC-DNR | Cytarabine, Daunorubicin |
| B-CAVe | Bleomycin, Lomustine, Doxorubicin, Vinblastine |
| BCVPP | Carmustine, Cyclophosphamide, Vinblastine, Procarbazine, Prednisone |

TABLE 1-continued

Exemplary combinatorial therapies for the treatment of cancer

| Name | Therapeutic agents |
|---|---|
| BEACOPP | Bleomycin, Etoposide, Doxorubicin, Cyclophosphamide, Vincristine, Procarbazine, Prednisone, Filgrastim |
| BEP | Bleomycin, Etoposide, Cisplatin |
| BIP | Bleomycin, Cisplatin, Ifosfamide, Mesna |
| BOMP | Bleomycin, Vincristine, Cisplatin, Mitomycin |
| CA | Cytarabine, Asparaginase |
| CABO | Cisplatin, Methotrexate, Bleomycin, Vincristine |
| CAF | Cyclophosphamide, Doxorubicin, Fluorouracil |
| CAL-G | Cyclophosphamide, Daunorubicin, Vincristine, Prednisone, Asparaginase |
| CAMP | Cyclophosphamide, Doxorubicin, Methotrexate, Procarbazine |
| CAP | Cyclophosphamide, Doxorubicin, Cisplatin |
| CAV | Cyclophosphamide, Doxorubicin, Vincristine |
| CAVE ADD | CAV and Etoposide |
| CA-VP16 | Cyclophosphamide, Doxorubicin, Etoposide |
| CC | Cyclophosphamide, Carboplatin |
| CDDP/VP-16 | Cisplatin, Etoposide |
| CEF | Cyclophosphamide, Epirubicin, Fluorouracil |
| CEPP(B) | Cyclophosphamide, Etoposide, Prednisone, with or without/Bleomycin |
| CEV | Cyclophosphamide, Etoposide, Vincristine |
| CF | Cisplatin, Fluorouracil or Carboplatin Fluorouracil |
| CHAP | Cyclophosphamide or Cyclophosphamide, Altretamine, Doxorubicin, Cisplatin |
| ChlVPP | Chlorambucil, Vinblastine, Procarbazine, Prednisone |
| CHOP | Cyclophosphamide, Doxorubicin, Vincristine, Prednisone |
| CHOP-BLEO | Add Bleomycin to CHOP |
| CISCA | Cyclophosphamide, Doxorubicin, Cisplatin |
| CLD-BOMP | Bleomycin, Cisplatin, Vincristine, Mitomycin |
| CMF | Methotrexate, Fluorouracil, Cyclophosphamide |
| CMFP | Cyclophosphamide, Methotrexate, Fluorouracil, Prednisone |
| CMFVP | Cyclophosphamide, Methotrexate, Fluorouracil, Vincristine, Prednisone |
| CMV | Cisplatin, Methotrexate, Vinblastine |
| CNF | Cyclophosphamide, Mitoxantrone, Fluorouracil |
| CNOP | Cyclophosphamide, Mitoxantrone, Vincristine, Prednisone |
| COB | Cisplatin, Vincristine, Bleomycin |
| CODE | Cisplatin, Vincristine, Doxorubicin, Etoposide |
| COMLA | Cyclophosphamide, Vincristine, Methotrexate, Leucovorin, Cytarabine |
| COMP | Cyclophosphamide, Vincristine, Methotrexate, Prednisone |
| Cooper Regimen | Cyclophosphamide, Methotrexate, Fluorouracil, Vincristine, Prednisone |
| COP | Cyclophosphamide, Vincristine, Prednisone |
| COPE | Cyclophosphamide, Vincristine, Cisplatin, Etoposide |
| COPP | Cyclophosphamide, Vincristine, Procarbazine, Prednisone |
| CP(Chronic lymphocytic leukemia) | Chlorambucil, Prednisone |
| CP (Ovarian Cancer) | Cyclophosphamide, Cisplatin |
| CVD | Cisplatin, Vinblastine, Dacarbazine |
| CVI | Carboplatin, Etoposide, Ifosfamide, Mesna |
| CVP | Cyclophosphamide, Vincristine, Prednisome |
| CVPP | Lomustine, Procarbazine, Prednisone |
| CYVADIC | Cyclophosphamide, Vincristine, Doxorubicin, Dacarbazine |
| DA | Daunorubicin, Cytarabine |
| DAT | Daunorubicin, Cytarabine, Thioguanine |
| DAV | Daunorubicin, Cytarabine, Etoposide |
| DCT | Daunorubicin, Cytarabine, Thioguanine |
| DHAP | Cisplatin, Cytarabine, Dexamethasone |
| DI | Doxorubicin, Ifosfamide |
| DTIC/Tamoxifen | Dacarbazine, Tamoxifen |
| DVP | Daunorubicin, Vincristine, Prednisone |

TABLE 1-continued

Exemplary combinatorial therapies for the treatment of cancer

| Name | Therapeutic agents |
|---|---|
| EAP | Etoposide, Doxorubicin, Cisplatin |
| EC | Etoposide, Carboplatin |
| EFP | Etoposie, Fluorouracil, Cisplatin |
| ELF | Etoposide, Leucovorin, Fluorouracil |
| EMA 86 | Mitoxantrone, Etoposide, Cytarabine |
| EP | Etoposide, Cisplatin |
| EVA | Etoposide, Vinblastine |
| FAC | Fluorouracil, Doxorubicin, Cyclophosphamide |
| FAM | Fluorouracil, Doxorubicin, Mitomycin |
| FAMTX | Methotrexate, Leucovorin, Doxorubicin |
| FAP | Fluorouracil, Doxorubicin, Cisplatin |
| F-CL | Fluorouracil, Leucovorin |
| FEC | Fluorouracil, Cyclophosphamide, Epirubicin |
| FED | Fluorouracil, Etoposide, Cisplatin |
| FL | Flutamide, Leuprolide |
| FZ | Flutamide, Goserelin acetate implant |
| HDMTX | Methotrexate, Leucovorin |
| Hexa-CAF | Altretamine, Cyclophosphamide, Methotrexate, Fluorouracil |
| IDMTX/6-MP | Methotrexate, Mercaptopurine, Leucovorin |
| IE | Ifosfamide, Etoposie, Mesna |
| IfoVP | Ifosfamide, Etoposide, Mesna |
| IPA | Ifosfamide, Cisplatin, Doxorubicin |
| M-2 | Vincristine, Carmustine, Cyclophosphamide, Prednisone, Melphalan |
| MAC-III | Methotrexate, Leucovorin, Dactinomycin, Cyclophosphamide |
| MACC | Methotrexate, Doxorubicin, Cyclophosphamide, Lomustine |
| MACOP-B | Methotrexate, Leucovorin, Doxorubicin, Cyclophosphamide, Vincristine, Bleomycin, Prednisone |
| MAID | Mesna, Doxorubicin, Ifosfamide, Dacarbazine |
| m-BACOD | Bleomycin, Doxorubicin, Cyclophosphamide, Vincristine, Dexamethasone, Methotrexate, Leucovorin |
| MBC | Methotrexate, Bleomycin, Cisplatin |
| MC | Mitoxantrone, Cytarabine |
| MF | Methotrexate, Fluorouracil, Leucovorin |
| MICE | Ifosfamide, Carboplatin, Etoposide, Mesna |
| MINE | Mesna, Ifosfamide, Mitoxantrone, Etoposide |
| mini-BEAM | Carmustine, Etoposide, Cytarabine, Melphalan |
| MOBP | Bleomycin, Vincristine, Cisplatin, Mitomycin |
| MOP | Mechlorethamine, Vincristine, Procarbazine |
| MOPP | Mechlorethamine, Vincristine, Procarbazine, Prednisone |
| MOPP/ABV | Mechlorethamine, Vincristine, Procarbazine, Prednisone, Doxorubicin, Bleomycin, Vinblastine |
| MP (multiple myeloma) | Melphalan, Prednisone |
| MP (prostate cancer) | Mitoxantrone, Prednisone |
| MTX/6-MO | Methotrexate, Mercaptopurine |
| MTX/6-MP/VP | Methotrexate, Mercaptopurine, Vincristine, Prednisone |
| MTX-CDDPAdr | Methotrexate, Leucovorin, Cisplatin, Doxorubicin |
| MV (breast cancer) | Mitomycin, Vinblastine |
| MV (acute myelocytic leukemia) | Mitoxantrone, Etoposide |
| M-VAC Methotrexate | Vinblastine, Doxorubicin, Cisplatin |
| MVP Mitomycin | Vinblastine, Cisplatin |
| MVPP | Mechlorethamine, Vinblastine, Procarbazine, Prednisone |
| NFL | Mitoxantrone, Fluorouracil, Leucovorin |
| NOVP | Mitoxantrone, Vinblastine, Vincristine |
| OPA | Vincristine, Prednisone, Doxorubicin |
| OPPA | Add Procarbazine to OPA. |
| PAC | Cisplatin, Doxorubicin |
| PAC-I | Cisplatin, Doxorubicin, Cyclophosphamide |
| PA-CI | Cisplatin, Doxorubicin |
| PCV | Lomustine, Procarbazine, Vincristine |
| PFL | Cisplatin, Fluorouracil, Leucovorin |
| POC | Prednisone, Vincristine, Lomustine |

TABLE 1-continued

| Exemplary combinatorial therapies for the treatment of cancer | |
|---|---|
| Name | Therapeutic agents |
| ProMACE | Prednisone, Methotrexate, Leucovorin, Doxorubicin, Cyclophosphamide, Etoposide |
| ProMACE/cytaBOM | Prednisone, Doxorubicin, Cyclophosphamide, Etoposide, Cytarabine, Bleomycin, Vincristine, Methotrexate, Leucovorin, Cotrimoxazole |
| PRoMACE/MOPP | Prednisone, Doxorubicin, Cyclophosphamide, Etoposide, Mechlorethamine, Vincristine, Procarbazine, Methotrexate, Leucovorin |
| Pt/VM | Cisplatin, Teniposide |
| PVA | Prednisone, Vincristine, Asparaginase |
| PVB | Cisplatin, Vinblastine, Bleomycin |
| PVDA | Prednisone, Vincristine, Daunorubicin, Asparaginase |
| SMF | Streptozocin, Mitomycin, Fluorouracil |
| TAD | Mechlorethamine, Doxorubicin, Vinblastine, Vincristine, Bleomycin, Etoposide, Prednisone |
| TTT | Methotrexate, Cytarabine, Hydrocortisone |
| Topo/CTX | Cyclophosphamide, Topotecan, Mesna |
| VAB-6 | Cyclophosphamide, Dactinomycin, Vinblastine, Cisplatin, Bleomycin |
| VAC | Vincristine, Dactinomycin, Cyclophosphamide |
| VACAdr | Vincristine, Cyclophosphamide, Doxorubicin, Dactinomycin, Vincristine |
| VAD | Vincristine, Doxorubicin, Dexamethasone |
| VATH | Vinblastine, Doxorubicin, Thiotepa, Flouxymesterone |
| VBAP | Vincristine, Carmustine, Doxorubicin, Prednisone |
| VBCMP | Vincristine, Carmustine, Melphalan, Cyclophosphamide, Prednisone |
| VC | Vinorelbine, Cisplatin |
| VCAP | Vincristine, Cyclophosphamide, Doxorubicin, Prednisone |
| VD | Vinorelbine, Doxorubicin |
| VelP | Vinblastine, Cisplatin, Ifosfamide, Mesna |
| VIP | Etoposide, Cisplatin, Ifosfamide, Mesna |
| VM | Mitomycin, Vinblastine |
| VMCP | Vincristine, Melphalan, Cyclophosphamide, Prednisone |
| VP | Etoposide, Cisplatin |
| V-TAD | Etoposide, Thioguanine, Daunorubicin, Cytarabine |
| 5 + 2 | Cytarabine, Daunorubicin, Mitoxantrone |
| 7 + 3 | Cytarabine with/, Daunorubicin or Idarubicin or Mitoxantrone |
| "8 in 1" | Methylprednisolone, Vincristine, Lomustine, Procarbazine, Hydroxyurea, Cisplatin, Cytarabine, Dacarbazine |

In certain embodiments, the conjoint therapies provided herein comprise conjoint administration with other types of chemotherapeutic agents, such as immuno-oncology agents. Cancer cells often have specific cell surface antigens that can be recognized by the immune system. Thus, immuno-oncology agents, such as monoclonal antibodies, can selectively bind to cancer cell antigens and effect cell death. Other immuno-oncology agents can suppress tumor-mediated inhibition of the native immune response or otherwise activate the immune response and thus facilitate recognition of the tumor by the immune system. Exemplary antibody immuno-oncology agents, include, but are not limited to, abagovomab, adecatumumab, afutuzumab, alemtuzumab, anatumomab mafenatox, apolizumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, and tremelimumab. In some embodiments, the antibody immuno-oncology agents are selected from anti-CD73 monoclonal antibody (mAb), anti-CD39 mAb, anti-PD-1 mAb, and anti-CTLA4 mAb. Thus, in some embodiments, the methods provided herein comprise conjoint administration of one or more immuno-oncology agents, such as the agents mentioned above.

In some embodiments, the combination therapy comprises conjoint administration of a solid form or pharmaceutical composition provided herein, such as Form 1 of a compound of Formula (I), with SH2 inhibitors, such as CGP78850, CPG85793, C90, C126, G7-18NATE, G7-B1, and NSC642056.

In some embodiments, the combination therapy comprises conjoint administration of a solid form or pharmaceutical composition provided herein, such as Form 1 of a compound of Formula (I), with ERK1/2 inhibitors such as ASN007, GDC-0994, KO-947, LTT462, LY3214996, MK-8353, ulixertinib. In some embodiments, the combination therapy comprises conjoint administration of a solid form or pharmaceutical composition provided herein, such as Form 1 of a compound of Formula (I), with MEK inhibitors, such as trametinib, cobimetinib, binimetinib, selumetinib, PD-325901, CI-1040, and TAK-733.

In some embodiments, the combination therapy comprises conjoint administration of a solid form or pharmaceutical composition provided herein, such as Form 1 of a compound of Formula (I), with a MET inhibitor selected from JNJ-38877605, PF-04217903, foretinib, AMG 458, tivantinib, cabozantinib, crizotinib, capmatinib hydrochloride, tepotinib hydrochloride, and savolitinib.

In some embodiments, the combination therapy comprises conjoint administration of solid form or pharmaceutical composition provided herein, such as Form 1 of a compound of Formula (I), with a SHP2 inhibitor selected from TNO-155, RMC-4630, JAB-3068, or RLY-1971.

In some embodiments, the combination therapy comprises conjoint administration of a solid form or pharmaceutical composition provided herein, such as Form 1 of a compound of Formula (I), with a RAS inhibitor selected from aliskiren, captopril, losartan, irbesartan, olmesartan, candesartan, valsartan, fimasartan, azilsartan, telmisartan, eprosartan, benazepril, enalapril, lisinopril, perindopril, quinapril, ramipril, and trandolapril.

In some embodiment, the combination therapy comprises administration of a solid form or pharmaceutical composition provided herein, such as Form 1 of a compound of Formula (I), in combination with a TKI. In one embodiment, the TKI is a ROS1 inhibitor. In one embodiment, the TKI is an ALK inhibitor. In one embodiment, the TKI is crizotinib, ceritinib, alectinib, brigatinib, lorlatinib, entrectinib, repotrectinib, cabozantinib, foretinib, merestinib, taletrectinib, masitinib, or ensartinib. In one embodiment, the TKI is crizotinib. In one embodiment, the TKI is entrectinib. In one embodiment, the TKI is alectinib. In one embodiment, the TKI is brigatinib.

In some embodiments, the combination therapy comprises conjoint administration of a solid form or pharmaceutical composition provided herein, such as Form 1 of a compound of Formula (I), with anti-PD-1 therapy. In certain embodiments, the combination therapy comprises conjoint administration of a compound provided herein, such as a compound of Formula (I), with oxaliplatin. In other embodiments, the combination therapy comprises conjoint administration of a compound provided herein, such as a compound of Formula (I), with doxorubicin.

In certain embodiments, a solid form or pharmaceutical composition provided herein, such as Form 1 of a compound of Formula (I), may be conjointly administered with non-chemical methods of cancer treatment. In certain embodiments, a solid form or pharmaceutical composition provided herein, such as Form 1 of a compound of Formula (I), may be conjointly administered with radiation therapy. In certain embodiments, a solid form or pharmaceutical composition provided herein, such as Form 1 of a compound of Formula (I), may be conjointly administered with surgery, with thermoablation, with focused ultrasound therapy, with cryotherapy, or with any combination of these.

In certain embodiments, a solid form or pharmaceutical composition provided herein, such as Form 1 of a compound of Formula (I), may be conjointly administered with one or more other compounds provided herein. Moreover, such combinations may be conjointly administered with other therapeutic agents, such as other agents suitable for the treatment of cancer, immunological or neurological diseases, such as the agents identified above. In certain embodiments, conjointly administering one or more additional chemotherapeutic agents with a compound provided herein provides a synergistic effect. In certain embodiments, conjointly administering one or more additional chemotherapeutic agents provides an additive effect.

| Abbreviations/Acronyms | Full Name/Description |
|---|---|
| ACN or MeCN | acetonitrile |
| DCM | dichloromethane |
| DMF | dimethylformamide |
| EtOAc | ethyl acetate |
| IPA | isopropyl alcohol |
| IPAc | isopropyl acetate |
| MEK | methyl ethyl ketone |
| 2-MeTHF | 2-methyltetrahydrofuran |
| MIBK | methyl iso-butyl ketone |
| MTBE or TBME | tert-butyl methyl ether |
| THF | tetrahydrofuran |
| DIPEA | diisopropylethylamine |
| DIPA | diisopropanolamine |
| DMA | dimethylacetamide |
| MeOH | methanol |
| EtOH | ethanol |
| XRPD | x-ray powder diffraction |

Example 1 of Compound 1

Scheme 1. Synthesis of Compound 6.

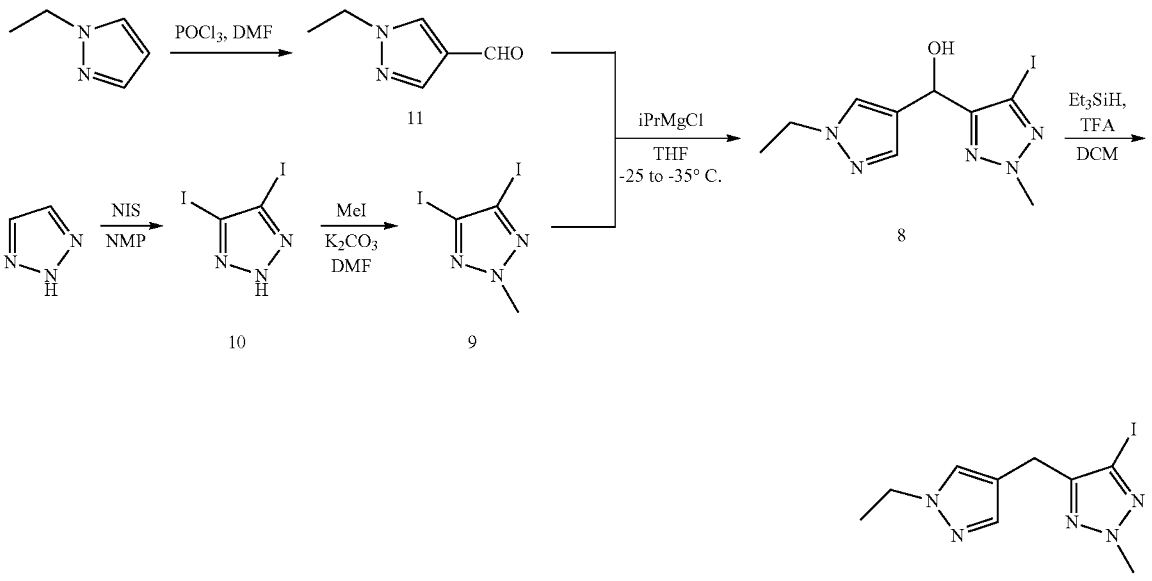

11

10

9

8

6

6. EXAMPLES

The examples and preparations provided below further illustrate and exemplify the compounds as provided herein and methods of preparing such compounds. It is to be understood that the scope of the present disclosure is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers can be obtained by methods known to those skilled in the art.

Synthesis of Compound 11. A reactor was charged 1-ethyl-1H-pyrazole (1.50 kg, 15.6 mol) and DMF (4.5 L, 3 vol.) at 20-30° C. under nitrogen. The reactor was heated to 50~60° C. and then $POCl_3$ (4.78 kg, 31.2 mol, 2 equiv.) was added drop-wise at 50~60° C. over 1-1.5 h. After addition was complete, the mixture was stirred for 16 h at 70~80° C. The mixture was then cooled to 15~20° C. and slowly charged into water (7.5 L, 5V) drop-wise at 15-35° C. After addition was complete, the mixture was stirred for 1 h at 25~35° C. Aqueous NaOH (9 L, 50 w %) was then added drop-wise to adjust the pH to 6-8 below 35° C. The mixture was extracted with EtOAc (5V×3), dried over $Na_2SO_4$ (1.0 kg) and concentrated at 40~50° C. to provide crude Compound 11. The crude compound was purified by silica gel chromatography (3× silica gel, 100-200 meshes, EtOAc/n-heptane=1:10~1:2) to afford Compound 10 as a light-yellow oil (1.52 kg, 98.3%/220 nm, 78.6% yield) with $^1$H NMR features matching an authentic sample.

Synthesis of Compound 10. A 50 L reactor was charged with NMP (12 L, 8 V) and NIS (12.2 kg, 2.5 eq.) at 20~30° C. The mixture was heated to 80~85° C., at which point a solution of 2H-1,2,3-triazole (1.5 kg, 1.0 eq.) in NMP (3 L, 2V) was added over 1-1.5 h at 80~85° C. After addition was complete, the mixture was stirred for 1-2 h at 80~85° C. The mixture was then cooled to 20~25° C. and poured into to water (90 L) with stirring at 0~10° C. The mixture was then stirred for 1 h at 0~10° C. and filtered. The wet filter cake was triturated in water (15 L) for 1-2 h at 20~25° C. and filtered again. The filter cake was washed with water (5 L) and dried at 60° C. to afford Compound 9 as a yellow solid (4.66 kg, 98%/210 nm, 0.2% KF, 67% yield) with $^1$H NMR features matching an authentic sample.

Synthesis of Compound 9. A 100 L reactor was charged with 4,5-diiodo-2H-1,2,3-triazole (4.6 kg, 1.0 eq.) and DMF (23 L, 5 V) at 20~25° C. The reaction mixture was cooled to −10~0° C. under $N_2$. Methyl iodide (2.45 kg, 1.2 eq.) was added to the reactor over 1.0 h at −10~0° C. After addition was complete, the reaction mixture was stirred for 2-3 h at −10~0° C. Water (23 L) and EtOAc (23 L) were then added to the reactor and the mixture stirred for 1.0 h at 515° C. After that time, the mixture was filtered, followed by separation of the aqueous phase and extracting with EtOAc (23 L). The combined organic phases were washed with brine (15 L×2) and concentrated to remove the solvents until ~12 L volume remained. The mixture was heated to 55~60° C., and n-heptane (4 L) was added slowly, followed by stirring for 1.0 h at 55~60° C. At this point, the mixture was cooled to 15~20° C. and filtered. The filter cake was washed with n-heptane (2 L). The solids were further purified by silica gel chromatography column (n-heptane/EtOAc=10/1) to give Compound 8 as an off-white solid (2.15 kg, 99.9%/240 nm, 45% yield) with $^1$H NMR features matching an authentic sample.

Synthesis of Compound 8. A 100 L reactor was charged with Compound 9 (2.1 kg, 6.27 mol, 1.05 equiv.) and THE (17 L) and stirred for 10~20 min at 10~20° C. under $N_2$. The mixture was cooled to −35~−25° C. with stirring and then charged slowly with i-PrMgCl (2.99 L, 2 M in THF, 5.98 mol) at −35~−25° C. over 1 h. The mixture was stirred for another 1 h at −10~0° C. A solution of Compound 11 (742 g, 5.98 mol) in THE (4 L) was then slowly charged into the reactor over 1-2 h at −15~0° C., and the mixture allowed then to stir for another 16 h at 0~20° C. At this point, the mixture was cooled to 0~5° C. and charged with aqueous $NH_4Cl$ solution (15 kg/15 L water) at 5~20° C. Ethyl acetate (20 L) was added and the mixture stirred for 0.5 h and separated. The aqueous layer was extracted additional EtOAc (10 L). The combined organic phases were washed with brine (5 w %, 20 L). The organic phase was concentrated under reduced pressure at 40~45° C. until no solvent distilled out. Heptane (4.2 L×2) was added and the solvent again concentrated under reduced pressure at 40~45° C. until around 2V. Ethyl acetate (2.1 L) was added at 40~45° C., followed by heptane (6.3 L) over 1 h at 40~45° C. The mixture was cooled to 20~25° C. over 1-2 h with stirring and filtered. The solids were dried in an oven at 55~60° C. until constant weight over 20 h to afford Compound 8 as an off-white solid (1.57 kg, 99.4%/220 nm, 98.8 w %, 79% yield). $^1$H NMR (400 MHz, DMSO-d6) δ 7.58 (s, 1H), 7.33 (s, 1H), 5.74 (d, J=4.9 Hz, 1H), 5.68 (d, J=4.9 Hz, 1H), 4.13 (s, 3H), 4.07 (q, J=7.3 Hz, 2H), 1.33 (t, J=7.3 Hz, 3H). MS (ESI, m/z): 334 $(M+H)^+$.

Synthesis of Compound 6. Compound 8 (1.50 kg, 4.5 mol) and DCM (15 L, 10 vol.) were charged into a 50 L reactor and stirred for 10-20 min at 15~20° C. The solution was then cooled to −5~0° C. with stirring under N2 and charged slowly with $Et_3SiH$ (1.57 kg, 13.5 mol, 3.0 equiv.) at −5~5° C. over 15 min. After addition was complete, the mixture was charge slowly with TFA (2.0 kg, 17.54 mol, 3.9 equiv.) over 1-1.5 h at 5~5° C. Once addition was complete, the mixture was stirred for another 2 h at −5~0° C. and then 16 h at 0~25° C. After this time, the reaction mixture was washed with aqueous $NaHCO_3$ solution (2.4 kg, 20 kg water) at 10~20° C. The aqueous phase was extracted with DCM (7.5 L). The combined organic phase was washed with water (12 L). The organics were then concentrated under reduced pressure at 40~45° C. until no solvent distilled out. MeCN (7.5 L) was added to get a solution of Compound 6, to which n-heptane (7.5 L) was added with stirring over 0.5 h at 15~25° C. The upper n-heptane layer was removed, and the acetonitrile layer again extracted with n-heptane (7.5 L) with stirring for 0.5 h at 15~25° C. The upper heptane layer was removed and the remaining acetonitrile solution of Compound 6 was concentrated at 40~45° C. until no solvent distilled out. The crude product was further purified by silica gel column (3 kg silica gel, 100-200 meshes, EtOAc/Heptane) to afford Compound 6 as a light brown oil. Upon cooling to −10° C. for 20 h, Compound 6 assumed the form of a pale-yellow solid (1.16 kg, 98.6%/220 nm, 98.6 w %, 81% yield). $^1$H NMR (400 MHz, $CDCl_3$) δ 7.41 (s, 1H), 7.27 (s, 1H), 4.16 (s, 3H), 4.12 (q, J=7.3 Hz, 2H), 3.80 (s, 2H), 1.46 (t, J=7.3 Hz, 3H). MS (ESI, m/z): 318 $(M+H)^+$.

Scheme 2. Synthesis of Compound 7.

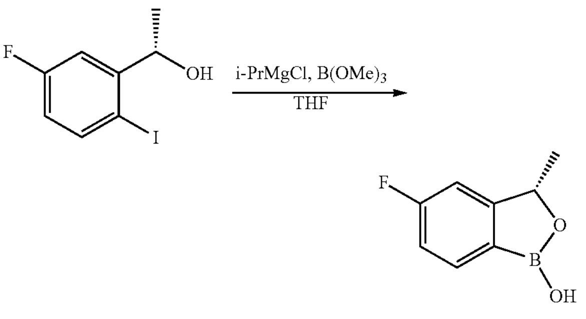

7

Synthesis of Compound 7. A 100 L reactor was charged with THE (33.6 L, 8 vol.) and (S)-1-(5-fluoro-2-iodophenyl)ethan-1-ol (4.2 kg, 1.0 eq.) and refilled with N2. The reactor was cooled to between −30 and −20° C., and i-PrMgCl (17.4 L, 2.2 eq., 2 M in THF) was added drop-wise over 1.5 h at −30 to −20° C. under N2. The mixture was stirred for 2 h at −30 to −20° C. $B(OMe)_3$ (4.10 kg, 2.5 eq.) was added to the reactor drop-wise over 1 h at −30 to −20° C. under N2. The mixture was warmed to −10 to 0° C. and stirred for another 2 h at −10 to 0° C. under $N_2$. The mixture was quenched with 20 w % aq. $NH_4C1$ solution (10 vol.) below 10° C. under $N_2$. EtOAc (10 vol.) was added and separated, the aqueous phase extracted again with EtOAc (10 vol.) and separated. The organic layers were combined, washed with water (5 vol.) and brine (5 vol.) separately. The organics were concentrated at 40-45° C. until around 2-3 vol., switched to n-heptane (3 vol.×2) twice and concentrated at 40-45° C. to get the crude product as oil. n-heptane (2 vol. relative to the crude product) was added, then heated to 40° C. and stirred for 1-2 h at 35~40° C. to get a clear solution. The solution was slowly cooled to 15-20° C. over 1 h and stirred for 1-2 h at 15-20° C. Then the mixture was slowly cooled to 0° C. over 2 h and stirred at 0~5° C. for 16 h. The mixture was filtered, and the filter cake rinsed with cooled n-heptane (0.5 vol., relative to crude product), and the collected solids dried in the oven at 40~45° C. to obtain Compound 7 as an off-white solid (1.45 kg, 99.8%/220 nm, 55.3% yield). $^1$H NMR (400 MHz, DMSO-d6) δ 9.18 (s, 1H), 7.73 (dd, J=8.1, 5.9 Hz, 1H), 7.27 (dd, J=9.5, 2.1 Hz, 1H), 7.17 (td, J=8.1, 4.1 Hz, 1H), 5.19 (q, J=6.6 Hz, 1H), 1.40 (d, J=6.6 Hz, 3H). MS (ESI, m/z): 167 $(M+H)^+$.

Scheme 3. Synthesis of Compound 1.

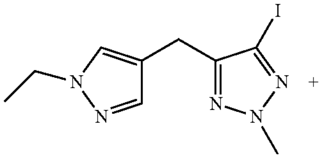

6

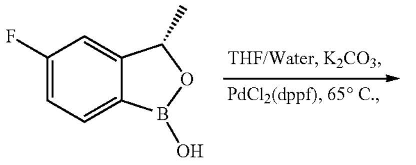

7

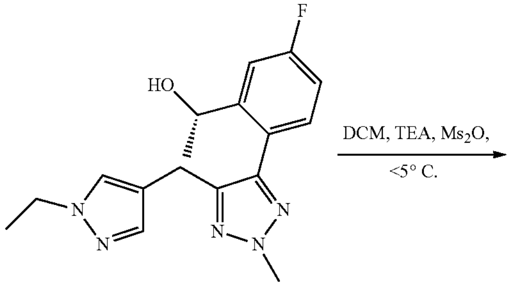

5

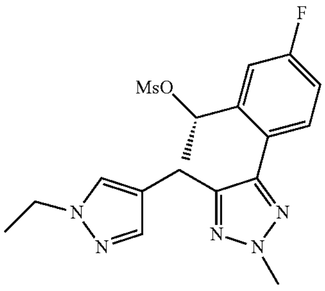

3

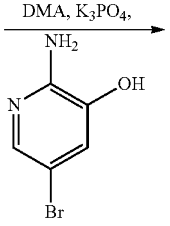

4

-continued

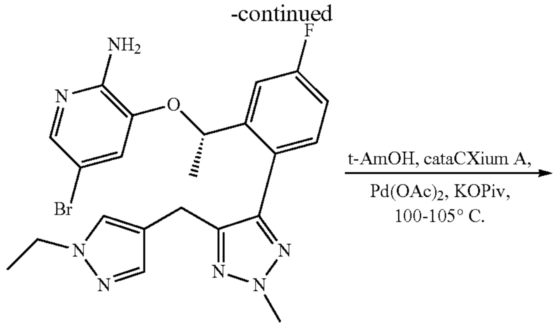

2

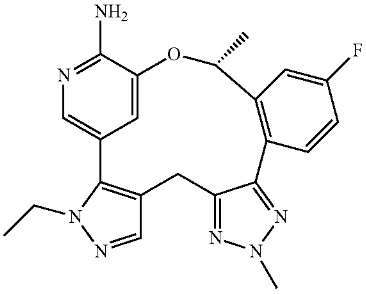

1

Synthesis of Compound 5. To a reactor was charged THE (10 vol.), water (1 vol.), followed by Compound 6 (850.0 g, 2.68 mol, 1 equiv.) and Compound 7 (534.0 g, 3.22 mol, 1.2 equiv.) at 20-30° C. The solids were completely dissolved at 20-30° C. while stirring for 15 min and $K_2CO_3$ (1.11 kg, 3 equiv.) was added in portions over 10-15 min at 20-30° C. The reaction mixture was fully refilled with nitrogen, and was added $Pd(dppf)Cl_2$ (78.5 g, 0.04 equiv.) in one portion under nitrogen. The reaction mixture was fully refilled with nitrogen again, then heated to 60-65° C. and stirred at 60-65° C. for 16 h under nitrogen. The reaction mixture was cooled to 20-30° C., filtered through a 10 cm celite pad (2×, 2.4 kg celite). The combined filtrates were washed with EtOAc (10 vol., 21 L) and separated. The organic phase was washed with water (5 vol., 10.5 L) and separated. The organic phase was stirred for 1 h at 40~45° C. in 5 w % aqueous L-cysteine (2.0 eq., 1.61 kg in 30.6 kg water) and separated. The organic phase was washed with water (5 vol., 10.5 L) and separated. The resulting organic phase was concentrated at 45~50° C. in vacuum to afford crude product as a light brown oil (2.28 kg). To the crude product was charged MTBE (228 mL, 0.1 vol. relative to crude product), heated to 50° C. over 15 min, followed by isopropyl ether (2.28 L, 1 vol.) dropwise over 1 h at 45~50° C., then cooled to 10° C. over 2 h. A large amount of solids came out and the resulting slurry was stirred for 2 h at 10~15° C. The solids were collected by filtration, dried in oven at 45° C. for 16 h to get crude Compound 5 as a pale-yellow solid (1.67 kg, 96.3%/220 nm, >99.9%/220 nm chiral purity). 1.67 kg of crude Compound 5 was purified by silica gel chromatography (EtOAc/n-heptane=1:1, 2.5× silica gel, 100-200 meshes) to get Compound 5 as an off-white solid (1.58 kg, 99.6%/220 nm, >99.9%/220 nm chiral purity, 97.9 w %, 72% yield). H NMR (400 MHz, DMSO) δ 7.44 (dd, J=10.5, 2.5 Hz, 1H), 7.36 (s, 1H), 7.22 (dd, J=8.3, 6.0 Hz, 1H), 7.16-7.08 (m, 2H), 5.25 (d, J=4.2 Hz, 1H), 4.86-4.68 (m, 1H), 4.14 (s, 3H), 4.00 (q, J=7.2 Hz, 2H), 3.72 (s, 2H), 1.27 (t, J=7.3 Hz, 3H), 1.11 (d, J=6.3 Hz, 3H). MS (ESI, m/z): 330.20 $(M+H)^+$.

In another example, a similar procedure was run in a 0.5:2 biphasic mixture of toluene and water (2.5 vol.) with a catalystic amount (e.g. 0.002 mol equiv.) Pd(Amphos)$Cl_2$ (instead of 0.04 mol equiv. of Pd(dppf)$_2$C12) used as the catalyst. Potassium phosphate ($K_3PO_4$ $3H_2O$) substituted potassium carbonate ($K_2CO_3$) 3.0 mol equiv. as the base, and the amount of Compound 7 employed was 1.02 mol equiv. The improved process was conducted at 50° C. At the end of the reaction, the organic layer was filtered and treated with activated carbon and concentrated, and the final material was crystallized from toluene/heptane/water to give Compound 5 in 92% yield and 99.9% purity.

Synthesis of Compound 3. To a 50 L reactor was charged dichloromethane (11.25 L), Compound 5 (750 g, >99.9%/220 nm chiral purity) and triethylamine (920.0 g) at r.t. (20-30° C.). The resulting mixture was refilled with nitrogen and cooled to 0° C. To it was added a solution of $Ms_2O$ (793.0 g) in dichloromethane (3.75 L) drop-wise over 45 min while keeping the temperature at 0~5° C. The reaction mixture was stirred at 0~5° C. for 1 h under nitrogen. The reaction mixture was quenched with cooled water (7.5 L) at 5~15° C. and separated. The organic phase was washed with cooled water (3.75 L) and separated. The organic phase was dried over anhydrous $Na_2SO_4$, filtered and concentrated at 25~30° C. in vacuum to around 2 vol., then switched to n-heptane (2.25 L) and concentrated at 25~30° C. in vacuum to around 2 vol. of Compound 3 in n-heptane. n-heptane/EtOAc (3.0 L, 10 v/1 v) was added to the above mixture and the mixture was slurried for 1 h at 0~10° C. under nitrogen and filtered. The filter cake was washed with n-heptane (1.5 L), dried in vacuum at 25~30° C. for 5 h to afford Compound 3 as an off-white solid (845 g, 98.9 w %, 99.98%/220 nm chiral purity, 91% yield). $^1$H NMR (400 MHz, CDCl3) δ 7.35 (dd, J=9.6, 2.5 Hz, 1H), 7.24-7.18 (m, 2H), 7.12 (s, 1H), 7.08 (td, J=8.3, 2.6 Hz, 1H), 5.78 (d, J=6.4 Hz, 1H), 4.21 (s, 3H), 4.05 (q, J=7.3 Hz, 2H), 3.90-3.76 (m, 2H), 2.78 (s, 3H), 1.58 (d, J=6.5 Hz, 3H), 1.40 (t, J=7.3 Hz, 3H). MS (ESI, m/z): 408.20 $(M+H)^+$.

In another example, triethylamine base (1.3 mol equiv.), $Ms_2O$ (1.2 mol equiv.), and dichloromethane solvent (10 vol) were used. The reaction mixture was quenched with aqueous sodium bicarbonate to remove excess $Ms_2O$, and crystallization from dichloromenthane/hexane results in 98% yield with 100% purity of Compound 3.

Synthesis of Compound 2. A 20 L reactor was refilled with nitrogen, then charged with DMA (12.6 L) at r.t. (20~25° C.). To the reactor was charged Compound 4 (390.0 g) and Compound 3 (840.0 g, 99.98%/220 nm chiral purity) in one portion at 20~25° C. through a dry nitrogen flow. The reaction mixture was heated to 35° C. over 15 min and stirred for 5-10 min at 35~40° C. to get a clear solution. To the reaction mixture was charged powder $K_3PO_4$ (875.0 g) in one portion at 35~45° C. After complete addition, the resulting mixture was heated to 60° C. over 20 min and stirred at 58~63° C. for 1.5 h through a dry nitrogen flow. The reaction mixture was cooled to 25~30° C., filtered through a celite pad (5 cm, 1.5 kg) and rinsed the filter cake with EtOAc (2 L, 2-3 vol.). The filtrate was poured into water (16.8 L, 20 vol.) at 0-10° C., extracted with EtOAc (10 L, 12 vol.) and separated. The aqueous phase was extracted with EtOAc (5 L, 6 vol.). The combined organic phases were washed with water (5 L×3, 6 vol.×3), concentrated at 50° C. in vacuum to afford crude product as a gray solid (956 g). The crude product was dissolved in EtOAc (950 mL, 1 vol. relative to crude product) at 35~40° C., then was added dropwise n-heptane (950 mL, 1 vol. relative to crude product) at 30~40° C. over 20 min. The resulting mixture was cooled to 20-25° C. over 30 min and stirred for 1 h at 30~40° C. Some solids came out slowly and n-heptane (1.9 L, 2 vol. relative to crude product) was added dropwise to the slurry mixture at 20-25° C. over 30 min. The precipitates were stirred at 15~20° C. for 3 h and filtered. The filter cake was washed with n-heptane (1.5 L) and dried in oven at 45~50° C. for 16 h to afford Compound 2 as a pale-yellow solid (743 g, 98.6%/220 nm, 96.9 w %, 99.98%/220 nm chiral purity, 0.48% KF, 72% yield). $^1$H NMR (400 MHz, DMSO) δ 7.54 (dd, J=10.2, 2.7 Hz, 1H), 7.51 (d, J=1.9 Hz, 1H), 7.42 (s, 1H), 7.31 (dd, J=8.5, 5.8 Hz, 1H), 7.22 (td, J=8.4, 2.7 Hz, 1H), 7.17 (s, 1H), 6.92 (d, J=1.8 Hz, 1H), 6.14 (s, 2H), 5.47 (q, J=6.0 Hz, 1H), 4.22 (s, 3H), 4.02 (q, J=7.3 Hz, 2H), 3.78 (q, J=16.1 Hz, 2H), 1.40 (d, J=6.3 Hz, 3H), 1.29 (t, J=7.3 Hz, 3H). MS (ESI, m/z): 500.30 $(M+H)^+$.

In another example, a process was developed where Compound 4 (1.1 mol equiv. to Compound 3) was used. Potassium phosphate base ($K_2PO_4$, 4.1 mol equiv.) and DMA (16 vol.) were substituted with cesium carbonate ($Cs_2CO_3$, 2.2 mol equiv.) and NMP (5.6 vol.). The reaction was carried out at 20-30° C. Following completion of the reaction, the crude product was precipitated with water. The material was then dissolved in ethyl acetate, washed with water, and treated with activated carbon. The product is subsequently crystallized from toluene/ethyl acetate/heptane to give Compound 2 in 80% yield and 99.9% purity.

Synthesis of Compound 1. To a reactor was charged t-AmOH (20 vol.), Compound 2 (700.0 g, 99.99% chiral purity) and potassium pivalate (588.0 g). The reaction mixture was fully refilled with nitrogen. To the reaction mixture was added cataCXium A (120.4 g) and Pd$(OAc)_2$ (37.8 g) at r.t. under nitrogen. The resulting mixture was heated to 100° C. and stirred for 18 h under nitrogen. The reaction mixture was cooled to 30° C., filtered through a celite pad and washed the filter cake with EtOAc (3 vol.). The filtrate was washed with water (5 vol.×2) and separated. The upper organic phase was concentrated in vacuum to afford a brown oil. The oil was dissolved in EtOAc (27 L) then added 5 w % aqueous L-cysteine (0.98 kg in 18.6 kg water), stirred for 1 h at 40~45° C. and separated. The organic phase was washed with water (6.75 L) and separated. 5 w % aqueous L-cysteine (0.98 kg in 18.6 kg water) was charged to the above organic phase, stirred for 1 h at 40~45° C. and separated. The organic phase was washed with water (6.75 L.) and separated. The organic phase was concentrated in vacuum at 45~50° C. to afford a brown solid (1.12 kg). The crude solid (1.12 kg) was further purified by silica gel chromatography eluted with EtOAc/DCM (dry loading, 3×, 100-200 meshes, EtOAc:DCM=1:1) to afford a pale-yellow solid (1.02 kg). The solid was dissolved in EtOAc (600 mL, 2 vol.) at 50~60° C., then was added n-heptane (1.8 L, 6 vol.) dropwise over 50 min at 50~60° C. A large of solids came out during addition. The resulting slurry was cooled to 15~20° C. over 50 min and stirred for 30 min at 15~20° C. The slurry was concentrated in vacuum at 45~50° C. to 2-3 vol. mixture. n-heptane (1.2 L, 4 vol.) was added to the above mixture (2-3 vol.), concentrated in vacuum at 45~50° C. to 2-3 vol. mixture. The mixture was cooled to 10~15° C. over 2 h, stirred at 10~15° C. for 1 h and filtered. The filtered cake was rinsed with n-heptane (600 mL) and dried in vacuum at 50° C. for 20 h to afford Form 1 of Compound 1 as an off-white solid (280 g, 99.0%). $^1$H NMR (400 MHz, DMSO) δ 7.79 (dd, J=10.3, 2.2 Hz, 1H), 7.58 (s, 1H), 7.43 (d, J=1.8 Hz, 1H), 7.24-7.16 (m, 2H), 6.13 (s, 2H), 6.08 (d, J=1.7 Hz, 1H), 5.31-5.23 (m, 1H), 4.16 (s, 3H), 4.05-3.94 (m, 2H), 3.78 (d, J=15.6 Hz, 1H), 2.98 (d, J=15.5 Hz, 1H), 1.71 (d, J=6.2 Hz, 3H), 1.26 (t, J=7.2 Hz, 3H). MS (ESI, m/z): 420.30 $(M+H)^+$. XRPD (FIG. 1), TG/DTA (FIG. 2), DSC (FIG. 3), DVS (FIG. 4), and FT-IR (FIG. 5) results for a sample of Form 1 were obtained.

In another example, a process was conducted in a manner analogous to that described above in the presence of about 0.02 equiv. of palladium acetate, 0.04 equiv. of CatacXiumA, 3.0 equiv. of potassium pivalate, and 8 vol. of t-amyl alcohol. The crystallization was carried out from ethyl acetate/heptane and a slurrying process in toluene/heptane.

Several impurities could be identified and/or separated in this cyclization step, including a regiosiomer (SP-7). $^1H$ NMR. (400 MHz, DMSO-d6) δ 7.86 (s, 1H), 7.71 (dd, J=2.5, 10.3 Hz, 1H), 7.62 (d, J=1.8 Hz, 1H), 7.41-7.16 (m, 2H), 6.20 (s, 1H), 5.86 (s, 2H), 5.14-5.07 (m, 1H), 4.20 (s, 3H), 4.11 (q, J=7.3 Hz, 2H), 3.89 (d, J=15.8 Hz, 1H), 3.61 (t, J=6.5 Hz, 2H), 3.11 (d, J=15.6 Hz, 1H), 1.77 (d, J=3.3 Hz, 1H), 1.76-1.69 (m, 4H), 1.40 (t. J=7.3 Hz, 3H).

Example 2. Solid Form Preparation

A. Preparation of amorphous material
1. Weight approx. 700 mg of Form 1 of Compound 1.
2. Add 10 ml of 1,4-dioxane to dissolve the solid.
3. Freeze at ca. −50° C. for 2 hours prior to freeze-drying for ca. 12 hours.
4. Analyze by XRPD to check for amorphous content.

B. Form 2 preparation
1. Use 700 mg of the amorphous material prepared.
2. Add 10 ml of MTBE to forma slurry.
3. Temperature cycled the slurry in an incubator shaker between ambient and 40° C. in 4-hours cycles for 24 hours.
4. After 24 hours, take a small sample for XRPD analysis.
5. XRPD (FIG. 7) and TG/DTA (FIG. 8) results were obtained for a sample of Form 2.

C. Form 3 preparation
1. Use 700 mg of the amorphous material prepared
2. Add 16 ml of water to form a slurry.
3. Left the sample to stand capped for at least 24 hours.
4. Temperature cycled the slurry in an incubator shaker between ambient and 40° C. in 4-hours cycles for 24 hours.
5. After 24 hours, take a small sample for XRPD analysis.
6. XRPD (FIG. 12) and TG/DTA (FIG. 13) for a sample of Form 3.

D. Form 4 preparation
1. Use 700 mg of the amorphous material prepared
2. Add 10 ml of acetonitrile to form a slurry.
3. Temperature cycled the slurry in an incubator shaker between ambient and 40° C. in 4-hours cycles for 72 hours.
4. After 72 hours, take a small sample for XRPD analysis.
5. XRPD (FIG. 14) and TG/DTA (FIG. 15) for a sample of Form 4

E. Form 5 preparation
1. Use 700 mg of the amorphous material prepared
2. Add 3.5 ml of acetonitrile to the solid.
3. Bead mill at 5500 rpm in cycles of 10 periods of 90 seconds milling. This cycle was repeated eight times for a total milling time of 2 hr.
4. Analyze the returned solid by XRPD.
5. XRPD (FIG. 16) result was obtained for a sample of Form 5.

F. Form 6 preparation
1. Use 700 mg of the amorphous material prepared.
2. Add 10 ml of 1,4-dioxane to the solid.
3. Temperature cycled the slurry in an incubator shaker between ambient and 40° C. in 4-hours cycles for 72 hours.
4. After 72 hours, take a small sample for XRPD analysis.
5. XRPD (FIG. 17) and TG/DTA (FIG. 18) results were obtained for a sample of Form 6.

G. Pattern 7 preparation
1. Use 700 mg of Form 2 prepared material, use a glass vial and spread the solid over one of the vial walls, to have a large surface area to promote the quick desolvation homogeneously over the solid.
2. Place the vial inside a glass oven (Buchi).
3. Heat the sample to 250° C. with a heating rate of ~20° C./min under vacuum (~10 mbar).
4. Once the oven reaches 250° C., keep the sample at that temperature and under vacuum for 6 min.
5. Cool quick as possible using wet paper towels to aid with the cooling (for approx. 15-20 min)
6. Take a small sample for XRPD analysis.
7. XRPD (FIG. 19), DSC (FIG. 20), DVS (FIG. 21), and FT-IR (FIG. 22) results were obtained for a sample of Form 7.

During the solid form screening, oil formation, due to high solubility, was observed in most of the samples of the evaporation experiments. Where solids were present, Form 2 and Form 1 were identified. Form 2 was observed first from MTBE in the solvent solubility screen, and from the temperature cycled experiments. In this set of experiments, however, Form 2 was observed from a different solvent, 1-butanol, which indicates that Form 2 could be an isostructural solvate.

For crash cooling experiments, all the samples formed oils and no solids were observed after 7 days at 2-8° C., except for the sample from MTBE (volume added: 200 μL) which solid returned as Form 2.

For anti-solvent addition experiments, Form 4 was obtained from acetonitrile with heptane anti-solvent. Form 1 was also identified in the antisolvent addition experiments.

Four solid forms were identified in solvent drop grinding experiments: Form 1, Form 2, Form 3, and a new form, defined as Form 5. 13 samples were found to be oils after the solvent drop grinding process. These samples were dried under vacuum as prior to XRPD analysis. 11 samples containing solids after the solvent drop grinding process were analyzed by XRPD.

Example 3: Single Crystal X-ray Diffraction Characterization of Form 1

Figure 6:
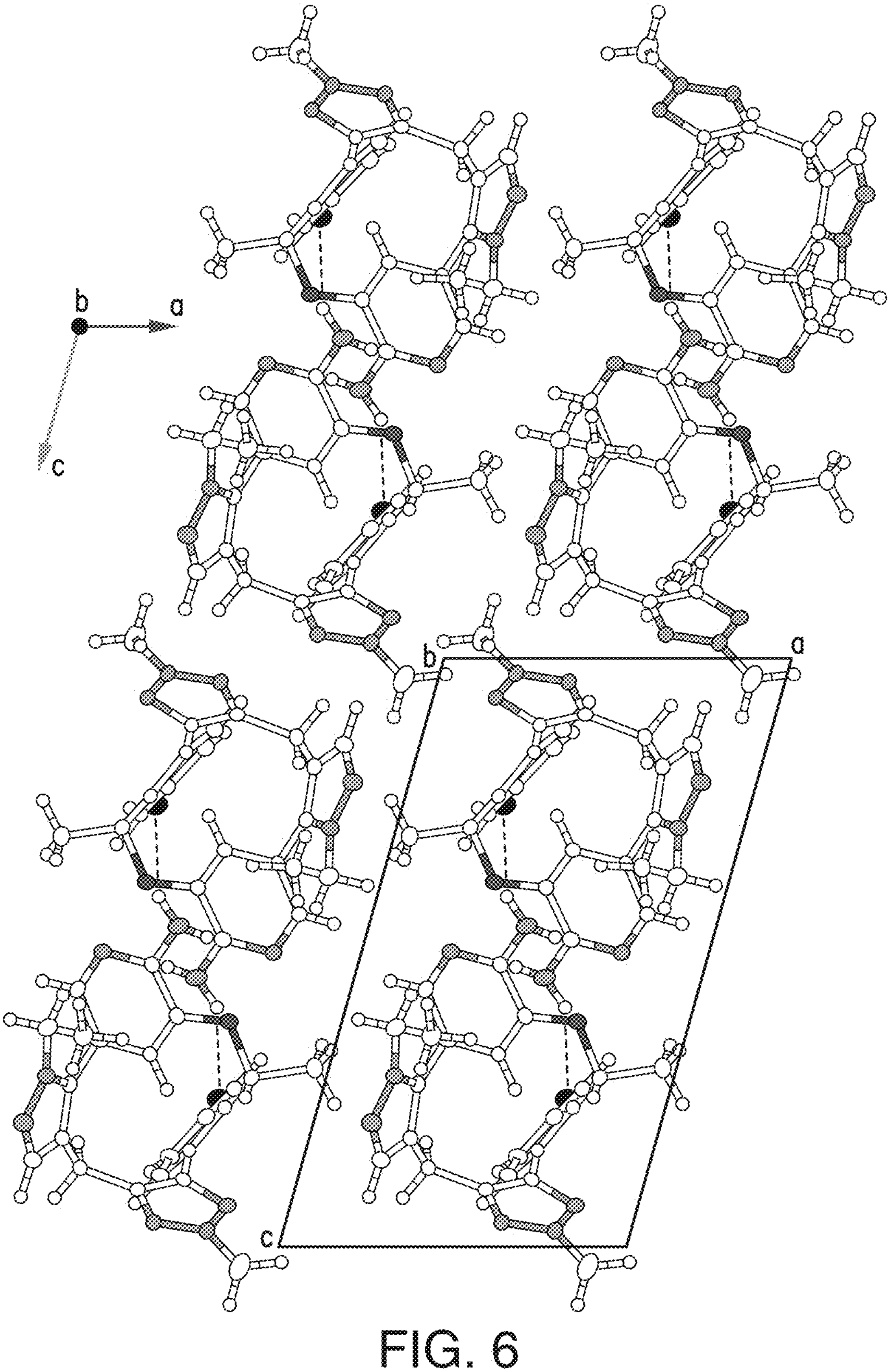
FIG. 6 is a representative depiction of the unit cell b axis of single-crystal X-ray diffraction studies of Form 1 of free base of Compound 1.

A full crystal structure of Form 1 was collected and solved. See FIG. 6 for a representative depiction of the structure determined from single-crystal X-ray diffraction studies of Form 1. A summary of structural data for Compound 1 Form 1 is provided in the table below. Form 1 crystallizes in the monoclinic system, space group $P2_1$ with the final R1 $[I>2\sigma(I)]$=2.85%.

TABLE 2

Crystallographic parameters and refinement indicators for Compound 1 Form 1

| Parameter | Value |
|---|---|
| Empirical formula | C22H22FN7O |
| Formula weight | 419.46 |
| Temperature/K | 100.00 |
| Crystal system | Monoclinic |
| Space group | $P2_1$ |
| Unit cell dimensions | a = 8.4315(10) Å α = 90°<br>b = 8.4413(10) Å β = 105.5522(7)°<br>c = 14.9146(2) Å γ = 90° |
| Volume | 1022.65(2) $Å^3$ |
| Z | 2 |
| Density (calculated) | 1.362 $g/cm^3$ |
| Absorption coefficient | 0.783 $mm^{-1}$ |
| F(000) | 440 |
| Crystal size/$mm^3$ | 0.1 × 0.02 × 0.01 |
| Radiation | CuKα (λ = 1.54178) |
| 2 Θ range for data collection/° | 6.15 to 149.008 |
| Index ranges | −10 ≤ h ≤ 10, −10 ≤ k ≤ 10, −18 ≤ l ≤ 18 |
| Reflections collected | 38630 |
| Independent reflections | 4160 [$R_{int}$ = 0.0446, $R_{sigma}$ = 0.0221] |
| Data/restraints/ parameters | 4160/1/289 |
| Goodness-of-fit on $F^2$ | 1.074 |
| Final R indexes [I >= 2 σ (I)] | $R_1$ = 0.0285, $wR_2$ = 0.0672 |
| Final R indexes [all data] | $R_1$ = 0.0314, $wR_2$ = 0.0687 |
| Largest diff. peak/ hole/e $Å^{-3}$ | 0.13/−0.19 |
| Flack parameter | 0.04(6) |

R1 = (Σ $|F_o|$ − $|F_c|$)/Σ $|F_o|$); wR2 = {Σ [$w(F_o^2 - F_c^2)^2$]/Σ [$w(F_o^2)^2$]}½; S = {Σ [$w(F_o^2 - F_c^2)^2$]/(n − p)}½.

The asymmetric unit of Form 1 contains one fully ordered molecule of Compound 1. Anisotropic atomic displacement ellipsoids for the non-hydrogen atoms are shown at the 50% probability level. Hydrogen atoms are displayed with an arbitrarily small radius.

The absolute configuration of Compound 1 has been determined as depicted below with the Flack parameter=−0.04(6). See Parsons, S and Flack, H., *Acta Cryst.* 2004, A60, s61. The chiral center has an R configuration.

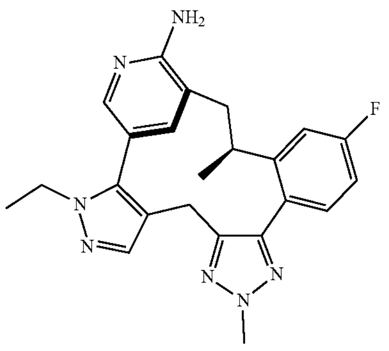

Example 4. Single Crystal X-ray Diffraction Characterization of Form 7 of Compound 1

Single crystals of Form 7 were obtained by first slurrying 500 mg of amphorus Compound 1 in MTBE. The sample was temperature cycled in an incubator shaker between ambient and 40° C. over 4 hour cycles for ca. 20 hours, at which point XRPD confirmed that the material had converted to Form 2. Ca. 100 mg of Form 2 material was placed in a 5 ml scintillation vial in a Buchi glass oven. The sample was heated up to 250° C. at a heating rate of 20° C./min. The sample was held at 250° C. for 6 min and then cooled down to room temperature as quickly as possible using wet paper towels and acetone to aid with the cooling. An aliquot was analyzed by XRPD and confirmed formation of Form 7.

Figure 23:
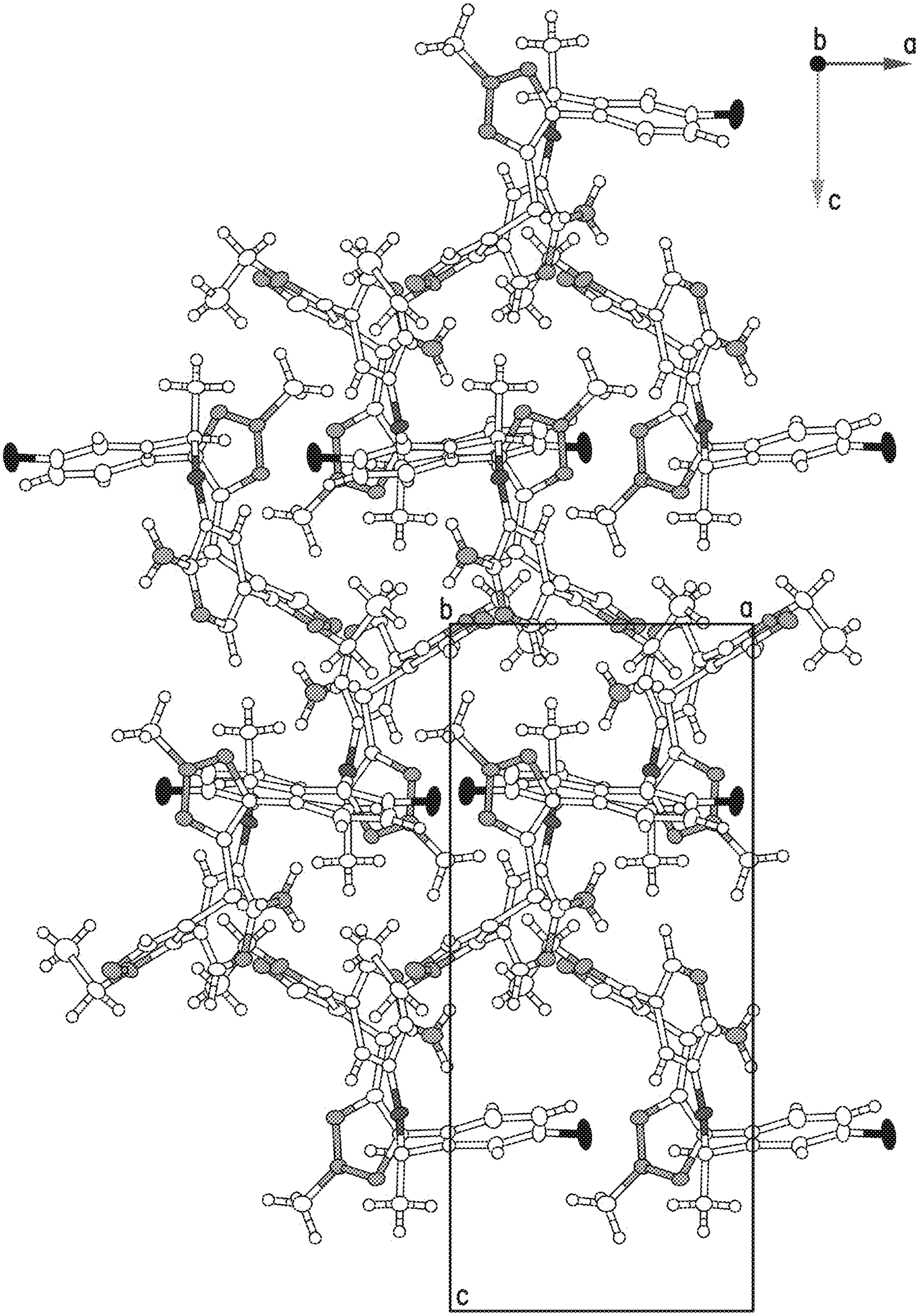
FIG. 23 is a representative depiction of the unit cell from single-crystal X-ray diffraction studies of Form 7 of free base of Compound 1.

A full crystal structure of Form 7 was collected and solved. See FIG. 23 for a representative depiction of the structure determined from single-crystal X-ray diffraction studies of Form 1. A summary of structural data for Compound 1 Form 7 is provided in the table below. Form 7 crystallizes in the orthorhombic system, space group $P2_12_12_1$ with the final R1 [I>2σ(I)]=2.61%.

TABLE 3

Crystallographic parameters and refinement indicators for Compound 1 Form 7

| Parameter | Value |
|---|---|
| Empirical formula | C22H22FN7O |
| Formula weight | 419.47 |
| Temperature/K | 100.00 |
| Crystal system | Orthorhombic |
| Space group | $P2_12_12_1$ |
| Unit cell dimensions | a = 7.9541(10) Å α = 90°<br>b = 14.8228(2) Å β = 90°<br>c = 18.0158(3) Å γ = 90° |
| Volume | 2124.10(5) $Å^3$ |
| Z | 4 |
| Density (calculated) | 1.312 $g/m^3$ |
| Absorption coefficient | 0.754 $mm^{-1}$ |
| F(000) | 880 |
| Crystal size/$mm^3$ | 0.16 × 0.12 × 0.08 |
| Radiation | CuKα (λ = 1.54178) |
| 2 Θ range for data collection/° | 7.724 to 144.218 |
| Index ranges | −9 ≤ h ≤ 9, −18 ≤ k ≤ 17, −22 ≤ l ≤ 22 |
| Reflections collected | 64015 |
| Independent reflections | 4177 [$R_{int}$ = 0.0325, $R_{sigma}$ = 0.0118] |
| Data/restraints/ parameters | 4177/0/291 |
| Goodness-of-fit on $F^2$ | 1.053 |
| Final R indexes [I >= 2 σ (I)] | $R_1$ = 0.0261, $wR_2$ = 0.0677 |
| Final R indexes [all data] | $R_1$ = 0.0266, $wR_2$ = 0.0684 |
| Largest diff. peak/ hole/e $Å^{-3}$ | 0.27/−0.19 |
| Flack parameter | 0.01(3) |

R1 = (Σ $|F_o|$ − $|F_c|$)/Σ $|F_o|$); wR2 = {Σ [$w(F_o^2 - F_c^2)^2$]/Σ [$w(F_o^2)^2$]}½; S = {Σ [$w(F_o^2 - F_c^2)^2$]/(n − p)}½.

The asymmetric unit of Form 7 contains one fully ordered molecule of Compound 1. Anisotropic atomic displacement ellipsoids for the non-hydrogen atoms are shown at the 50% probability level. Hydrogen atoms are displayed with an arbitrarily small radius.

The absolute configuration of Compound 1 has been determined as depicted below with the Flack parameter=−0.01(3). See Parsons, S and Flack, H., *Acta Cryst.* 2004, A60, s61. The chiral center has an R configuration.

Example 5. Stability Studies

Form 1 of Compound 1: Method. About 10 mg of Form 1 of Compound 1 was placed in a 2 ml vial and stored for 7 days under the following conditions: A) 40° C./75% RH (open vial); B) 25° C./60% RH (open vial); C) 80° C. (sealed vial). Solids were analyzed by XRPD and submitted for HPLC.

Form 1 of Compound 1: Results. About HPLC analysis of the three samples of Compound 1 pattern 1 after storage at 40° C./75% RH (open vial), 25° C./60% RH (open vial), and 80° C. (sealed vial), for one week, showed high purity (>99.5%) in all the samples. HPLC analysis results of the 7-days stability studies performed on Form 1 of Compound 1 can be found in the table below. Form 1 is stable under all tested conditions.

TABLE 4

HPLC analysis results of the 7-days stability studies performed on Form 1 of Compound 1

| Conditions (7 days) | % Purity by HPLC |
|---|---|
| 40° C./75% RH (open vial) | 99.66 |
| 25° C./60% RH (open vial) | 99.58 |
| 80° C. (sealed vial) | 99.58 |

Form 2 of Compound 1: Method. Portions of Form 1 of Compound 1 (10 mg) were placed in 1.5 ml vials. One vial was stored for 7 days under each of the following conditions: A) 40° C./75% RH (open vial); B) 25° C./60% RH (open vial); C) 80° C. (sealed vial). Solids were analyzed by XRPD and submitted for HPLC.

Form 2 of Compound 1: Results. Scaled up Form 2 was determined to be stable at 40° C./75% RH and 25° C./60% RH for 7 days as the XRPD pattern was observed to correspond to that of Form 2. However, for sample C stored at 80° C., the XRPD pattern was observed to correspond to that for Form 7.

Example 6. Compression Test at 100 and 250 MPa

Approximately 100 mg of Form 1 of Compound 1 was placed inside a FT-IR press, and a pressure of 100 MPa was applied and held for 60 seconds. The resulting material was analyzed by XRPD.

Approximately 100 mg of Form 1 of Compound 1 was placed inside the apparatus of the compression clamp. This apparatus was placed inside the compression clamp and a pressure of 250 MPa was applied and hold for 60 seconds. The resulting material was analyzed by XRPD.

XRPD diffractograms of both samples after the compression tests showed broader peaks due to a crystal lattice distortion. No change in the crystalline form was observed. Form 1 is stable under 100 MPa and 250 MPa for 60 seconds.

DSC thermograms of Form 1 post compression test at 100 and 250 MPa samples, respectively, showed a smooth exothermic event with an onset of ca. 255-260° C. prior to the melt, with an onset of ca. 275° C. related to exothermic degradation enhanced by the lattice disruption, followed by endothermic degradation. This is consistent with the presence of Form 1.

Modulated DSC thermograms of Form 1 after 100 MPa compression test sample showed an endothermic event in the non-reversing heat flow trace with an onset temperature of ca. 265° C., and an endothermic event in the reversing heat flow trace with an onset temperature of ca. 268° C. No exothermic events were observed in any of the traces for this sample. There was no evidence of amorphous content in the material.

Modulated DSC thermograms of Form 1 after 250 MPa compression test sample showed an endothermic event in the non-reversing heat flow trace with an onset temperature of ca. 266° C., and an endothermic event in the reversing heat flow trace with an onset temperature of ca. 266° C. No exothermic events were observed in any of the traces for this sample. There was no evidence of amorphous content in the material.

Example 7. Competitive Slurry with Forms 1 and 7

A. Competitive Slurring at Room Temperature and 80° C.

Competitive slurry experiments of Form 1 and Form 7 were performed in 4 solvents at room temperature and at elevated temperature (80° C.). An approximate 25 mg of each form in a 1:1 wt./wt. mix was slurried in the selected solvents and agitated for ca. five days in total. The resulting material was re-analyzed by XRPD to ascertain the form. See the table below for solvent conditions.

TABLE 5

Solvents used in the competitive slurry study at room temperature and 80° C.

| Temperature (° C.) | Antisolvent (500 μl) | Solvent 1 | Solvent 2 | Solvent 3 | Solvent 4 |
|---|---|---|---|---|---|
| 25 (r.t) | n-Heptane | Ethanol (40 μl) | Acetone (40 μl) | Ethyl Acetate (40 μl) | Tetrahydrofuran (40 μl) |
| 80 | n-Octane | 2-Butanol (40 μl) + (40 μl) | Methylisobutyl Ketone (40 μl) + (40 μl) | Isopropyl Acetate (40 μl) + (40 μl) | 1,2-Dimethoxy ethane (40 μl) + (40 μl) |

Competitive slurring at room temperature showed full conversion into Form 1 after 48 hours of stirring at room temperature for all the solvents screened according to XRPD.

Competitive slurring at 80° C. showed full conversion into Form 7 after five days of being heated at 80° C. for all the solvents screened according to XRPD.

B. Competitive Slurring at 40° C. and 60° C.

Competitive slurry experiments of Form 1 and Form 7 were performed in 4 solvents at 40 and 60° C., aiming to narrow down the transition temperature range. An approximate 25 mg of each form in a 1:1 wt./wt. mix was slurried in the selected solvents and agitated for ca. ten days. The resulting material was re-analyzed by Table 6. Solvents used in the competitive slurry study at 40 and 60° C.

TABLE 6

| Solvents used in the competitive slurry study at 40 and 60° C. | | | | | |
|---|---|---|---|---|---|
| Temperature (° C.) | Antisolvent (500 μl) | Solvent 1 (100 μl) | Solvent 2 (100 μl) | Solvent 3 (100 μl) | Solvent 4 (100 μl) |
| 40 | n-octane | 2-butanol | Methylisobutyl ketone | Isopropyl acetate | 1,2-dimethoxy ethane |
| 60 | n-octane | 2-butanol | Methylisobutyl ketone | Isopropyl acetate | 1,2-dimethoxy ethane |

Competitive slurring at 40° C. showed to be a mixture of Forms 1 and 7 after ten days at 40° C. for all the solvents screened according to XRPD.

Competitive slurring at 60° C. showed to be a mixture of Forms 1 and 7 after ten days at 60° C. for all the solvents screened according to XRPD.

C. Competitive Slurring at 40° C. and 60° C. with Pre-Grinding

Competitive slurry experiments of Form 1 and Form 7 were performed in 2 solvents at 40 and 60° C. with pre-grinding. An approximate 120 mg of each form 1:1 wt./wt. mix was ground using a mortar and a pestle for a minute to form a solid mixture. A small portion of this mixture was analyzed by XRPD to confirm the solid mixture. Ca. 30 mg of this mixture was weighed into a four separate 4 ml vials, pre-warmed to 40 or 60° C., respectively, and the appropriate solvent was added to the mixture to form a slurry. No antisolvent was used in these experiments. Slurries were heated up to 40 or 60° C., respectively for up to five days. The resulting material was re-analyzed by XRPD to ascertain the form. See the table below for solvent conditions.

TABLE 7

| Solvents used in the competitive slurry study at 40 and 60° C. | | |
|---|---|---|
| Temperature (° C.) | Solvent 1 (1200 μl) | Solvent 2 (800 μl) |
| 40 | 2-butanol | methylisobutyl ketone |
| 60 | 2-butanol | methylisobutyl ketone |

XRPD analysis confirmed the solid mixture formation of Form 1 and Form 7 after one full minute of grinding.

Competitive slurring at 40° C. showed full conversion into Form 1 after five days at 40° C. for all the solvents screened according to XRPD.

Competitive slurring at 60° C. showed full conversion into Form 1 after five days of being heated at 60° C. for the experiment performed in 2-butanol, however, in the methyl isobutyl ketone experiment the diffractogram of the resulting solid after five days indicated there was still a mixture of both Form 1 and Form 7 according to XRPD.

Example 8. Preparation and Characterization of Form A of a Besylate Salt of Compound 1

Approximately 60 mg of the Form 1 of the free base of Compound 1 was weighed into a 20 mL vial. A 600 μl portion of 2-methyl-THF was added to fully dissolve the material, followed by 1.1 equivalents of an aqueous 1M benzenesulfonic acid solution. The mixture then was manually agitated and left uncapped to let the solvent evaporate at ambient temperature. The solids obtained following evaporation were recovered and analyzed as described herein below.

XRPD analysis (FIG. 24) of the sample indicated that the besylate salt was successfully reproduced. The $^{1}H$ NMR and $^{19}F$ NMR spectra of Form A of a Besylate Salt of Compound 1 confirmed salt formation (e.g. $^{19}F$ signal observed at about −111 ppm) and retention of the bonding connectivity of Compound 1. By HPLC, the purity of Form A of a besylate salt of Compound 1 was observed to be 99.9%.

In the TG analysis (FIG. 25) two weight losses were observed. The first one of 2.8% upon heating from about 25° C. to about 125° C., most probably due to loss of 1 eq of water, and a second one of 1.2% upon heating from about 125° C. to about 275° C., attributed to degradation. This result suggests that the material is a monohydrate. In the DSC trace (FIG. 25), a melting endotherm event was observed with an onset of 119.2° C. In the first heating cycle of the DSC analysis (FIG. 26), a melting endotherm event was observed with an onset temperature of about 128° C. (18.6 J/g) and/or a peak temperature of about 136° C.

In the DVS analysis (FIG. 27), a 2% weight change between dryness and 90% RH was observed, indicating the material is hygroscopic. However, during this experiment, the monohydrate water was not fully lost. The XRPD diffractograms showed that Form A of a Besylate Salt of Compound 1 was retained during the DVS analysis the same crystalline form.

Stability studies indicated that Form A of a besylate salt of Compound 1 is physically stable at 40° C. and 75% RH for 7 days. No changes in form were observed by XRPD.

Example 9. Characterization of Form A of a Phosphate Salt of Compound 1

Form A of a phosphate salt of Compound 1 identified from the primary salt screen was analyzed by XRPD (FIG. 28). The $^{1}H$ NMR and $^{31}P$ NMR spectra of Form A of a phosphate salt of Compound 1 confirmed salt formation (e.g. $^{31}F$ signal observed at about 0.9 ppm) and retention of the bonding connectivity of Compound 1.

In the TG analysis (FIG. 29) of the phosphate salt, a 5.8% weight loss (equivalent to about 0.4 eq of 2-methyl-THF or about 1.8 eq of water) was observed upon heating from about 25° C. to about 175° C. In the DSC trace (FIG. 29), decomposition was observed above 200° C.

Example 10. Solid Form Characterization

X-Ray Powder Diffraction (XRPD)

Standard conditions: XRPD analysis was carried out on a PANalytical X'pert pro with PIXcel detector (128 channels), scanning the samples between 3 and 35° 2θ. The material was gently ground to release any agglomerates and loaded onto a multi-well plate with Mylar polymer film to support the sample. The multi-well plate was then placed into the diffractometer and analysed using Cu K radiation ($\alpha_1$ $\lambda$=1.54060 Å; $\alpha_2$=1.54443 Å; $\beta$=1.39225 Å; $\alpha_1$:$\alpha_2$ ratio=0.5) running in transmission mode (step size 0.0130° 2θ, step time 18.87 s) using 40 kV/40 mA generator settings. Data were visualized and images generated using the HighScore Plus 4.7 desktop application (PANalytical, 2017).

Variable-temperature experiments: VT-XRPD analysis was carried out on a Philips X'Pert Pro Multipurpose diffractometer equipped with a temperature chamber. The samples were scanned between 4 and 35.99°2θ using Cu K radiation ($\alpha_1$ λ=1.54060 Å; $\alpha_2$=1.54443 Å; β=1.39225 Å; $\alpha_1$:$\alpha_2$ ratio=0.5) running in Bragg-Brentano geometry (step size 0.008°2θ) using 40 kV/40 mA generator settings. Measurements were performed as follows: 1) Initial scan at 30° C.; 2) Heat to 30° C. at 10° C./min, 5-minute hold, scan; 3) Heat to 150° C. at 10° C./min, 5-minute hold, scan; 4) Heat to 225° C. at 5° C./min, 5-minute hold, scan; 5) Heat to 300° C. at 5° C./min, 5-minute hold, scan; 6) Cool to 30° C. at −10° C./min, scan.

Single Crystal X-Ray Diffraction (SCXRD)

Data were collected on an Oxford Diffraction Supernova Dual Source, Cu at Zero, Atlas CCD diffractometer equipped with an Oxford Cryosystems Cobra cooling device. The data was collected using CuKα radiation. Structures were typically solved using either the SHELXS or SHELXD programs and refined with the SHELXL program as part of the Bruker AXS SHELXTL suite (V6.10). Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

Nuclear Magnetic Resonance (NMR)

NMR experiments were performed on a Bruker AVIIIHD spectrometer equipped with a PRODIGY cryoprobe operating at 500.23 MHz for protons. Experiments were performed in deuterated dimethyl sulfoxide and each sample was prepared to ca. 10 mM concentration.

Infrared Spectroscopy (ATR-FTIR)

Infrared spectroscopy was carried out on a Bruker ALPHA P spectrometer. Sufficient material was placed onto the centre of the plate of the spectrometer and the spectra were obtained using the following parameters: Resolution: 4 $cm^{-1}$; Background Scan Time: 16 scans; Sample Scan Time: 16 scans; Data Collection: 4000 to 400 $cm^{-1}$; Result Spectrum: Transmittance; Software: OPUS version 6.

Differential Scanning Calorimetry (DSC)

Approximately, 1-5 mg of material was weighed into an aluminium DSC pan and sealed nonhermetically with an aluminium lid. The sample pan was then loaded into a TA Instruments Discovery DSC 2500 differential scanning calorimeter equipped with a RC90 cooler. The sample and reference were heated to 300° C. at a scan rate of 10° C./min and the resulting heat flow response monitored. The sample was re-cooled to 20° C. and then reheated again to 300° C. all at 10° C./min. Nitrogen was used as the purge gas, at a flow rate of 50 cm3/min.

Thermogravimetric/Differential Thermal Analysis (TG/DTA)

Approximately, 5-10 mg of material was weighed into an open aluminium pan and loaded into a simultaneous thermogravimetric/differential thermal analyser (TG/DTA) and held at room temperature. The sample was then heated at a rate of 10° C./min from 20° C. to 400° C. during which time the change in sample weight was recorded along with any differential thermal events (DTA). Nitrogen was used as the purge gas, at a flow rate of 300 cm3/min.

Thermogravimetric Analysis/Differential Scanning Calorimetry (TGA/DSC)

Approximately, 5-10 mg of material was added into a pre-tared open aluminum pan and loaded into a TA Instruments Discovery SDT 650 Auto-Simultaneous DSC and held at room temperature. The sample was then heated at a rate of 10° C./min from 30° C. to 400° C. during which time the change in sample weight was recorded along with the heat flow response (DSC). Nitrogen was used as the sample purge gas, at a flow rate of 200 cm3/min.

Dynamic Vapour Sorption (DVS)

Approximately, 10-20 mg of sample was placed into a mesh vapour sorption balance pan and loaded into a DVS Advantage dynamic vapour sorption balance by Surface Measurement Systems. The sample was subjected to a ramping profile from 40-90% relative humidity (RH) at 10% increments, maintaining the sample at each step until a stable weight had been achieved (dm/dt 0.004%, minimum step length 30 minutes, maximum step length 500 minutes) at 25° C. After completion of the sorption cycle, the sample was dried using the same procedure to 0% RH and then a second sorption cycle back to 40% RH. Two cycles were performed. The weight change during the sorption/desorption cycles were plotted, allowing for the hygroscopic nature of the sample to be determined. XRPD analysis was then carried out on any solid retained.

Example 11. Preparation of Tablets of Compound 1

A general description of the steps in the manufacturing process for Compound 1 tablets is provided below.

Compound 1 drug substance and each excipient are weighed and dispensed according to the batch formula. Intragranular excipients (mannitol, silicified microcrystalline cellulose, hydroxypropyl cellulose, and sodium starch glycolate) are screened with the Compound 1 drug substance to delump and subsequently blended to achieve an initial pre-granulation blend. Magnesium stearate is screened, combined with the pre-granulation blend, and blended. The resulting final pre-granulation blend is then fed through a roller compactor and comil to generate Compound 1 granules.

The Compound 1 granules are screened with the extragranular excipients (mannitol and sodium starch glycolate) and blended. Magnesium stearate is screened, combined with the extragranular blend, and blended to achieve the Compound 1 final blend.

The Compound 1 final blend is transferred to an automated tablet press set up to manufacture Compound 1 tablets in the appropriate shape, size, and weight. Throughout the compression run tablets are sampled and tested for weight, appearance, thickness, hardness, and friability. The resulting tablets are passed through a deduster and metal checker prior to film coating.

An aqueous suspension of Opadry® Pink II is prepared and sprayed onto the tablets in a pan-coater until the target weight gain is achieved. Mean tablet weights are monitored throughout the coating process to ensure proper weight control and achieve the coating endpoint.

A roller compacted batch of Compound 1 was manufactured with the formula and conditions in the following table.

TABLE 8

| Compound 1 Granule Formula | |
|---|---|
| Material | % w/w |
| Batch Size, g | 300.1 |
| Compound 1 | 30.03[1] |
| Mannitol (Pearlitol 200SD) | 43.22 |
| Silicified Microcrystalline Cellulose | 22.00 |
| Sodium Starch Glycolate | 2.50 |
| HPC (Klucel EXF) | 2.00 |
| Magnesium Stearate | 0.25 |
| TOTAL | 100.00 |

[1]Potency adjusted based on 99.9% assay

Two Compound 1 final blend batches were manufactured with the formula and conditions in the following table, to manufacture 5 mg and 25 mg Compound 1 tablets, respectively.

TABLE 9

| Compound 1 Tablet Formulas | | | | |
|---|---|---|---|---|
| | Dose | | | |
| | 5 mg | | 25 mg | |
| | Batch Size, g | | | |
| | 300.0 | | 144.0 | |
| Material | % w/w | mg/tab | % w/w | mg/tab |
| Compound 1 Granules, 30% | 16.67 | 16.67 | 55.55 | 83.33 |
| Mannitol (Pearlitol 200SD) | 79.83 | 79.83 | 40.95 | 61.43 |
| Sodium Starch Glycolate | 2.50 | 2.50 | 2.50 | 3.75 |
| Magnesium Stearate | 1.00 | 1.00 | 1.00 | 1.50 |
| TOTAL | 100.00 | 100.00 | 100.00 | 150.00 |

The quantitative compositions of the 5 mg and 25 mg Compound 1 tablets are provided in the following table.

TABLE 10

| Composition of Compound 1 Tablets, 5 mg and 25 mg | | |
|---|---|---|
| | Target Quantity (mg/tablet) | |
| Component | 5 mg | 25 mg |
| Compound 1 Drug Substance[a] | 5.00 | 25.00 |
| Mannitol[a] | 87.04 | 97.47 |
| Silicified Microcrystalline Cellulose | 3.67 | 18.33 |
| Hydroxypropyl Cellulose | 0.33 | 1.67 |
| Sodium Starch Glycolate | 2.92 | 5.83 |
| Magnesium Stearate | 1.04 | 1.71 |
| Opadry II Pink | 4.00 | 6.00 |
| Purified Water[b] | qs | qs |
| Total | 104.00 | 156.01 |

[a]The amount of drug substance and mannitol may be adjusted depending on the potency of the drug substance
[b]Removed during processing.
qs: quantity sufficient Example 12. Stability Studies of Compound 1

A stability study was conducted for Compound 1 (Form 1) at three storage conditions: (1) 5° C.±3° C., ambient relative humidity (RH), data collected at 0 and 1 month; (2) 25° C.±2° C., 60%±5% RH, data collected at 0, 1, 3, 6, 9, and 12 months; and (3) 40° C.±2° C., 75%±5% RH, data collected at 0, 1, 3, and 6 months.

Stability results demonstrated the chemical and physical stability of Compound 1 stored for 12 months at the proposed long-term condition of 25° C.±2° C./60%±5% RH and 6 months at the accelerated condition of 40° C.±2° C./75%±5% RH. No meaningful changes were observed in description, assay, related substances, water content, polymorphic form, and chiral purity. All results complied with the acceptance criteria (e.g. drug substance purity: at least 97%, individual impurities: each less than or equal to 0.2% by area, total amount of impurities: less than or equal to 2.0%, enantiomeric purity: at least 99.5%, solid form: Form 1) at all time points.

Example 13. Preparation of Tablets of Compound 1

A general description of the steps in another manufacturing process for Compound 1 tablets is provided below.

Compound 1 and each excipient are weighed and dispensed according to the batch formula. Mannitol, silicified microcrystalline cellulose, hydroxypropyl cellulose, and sodium starch glycolate are screened with the Compound 1 through a 20-mesh screen to delump and subsequently blended to form an initial blend. Magnesium stearate is screened and combined with the initial blend and blended to achieve a final blend.

The final blend is transferred to an automated tablet press set up to manufacture tablets in the appropriate shape, size, and weight. Throughout the compression run tablets are sampled and tested for weight, appearance, thickness, hardness, and friability. The resulting tablets are passed through a deduster and metal checker prior to film coating.

An aqueous suspension of Opadry® Pink II is prepared and sprayed onto the tablets in a pan-coater until the target weight gain (4%) is achieved. Mean tablet weights are monitored throughout the coating process to ensure proper weight control and achieve the coating endpoint.

The formulation is designed as dose proportional. Common blend is compressed into tablets with different strengths (e.g. 25 mg, 50 mg, 75 mg and 100 mg). Representative composition and formulation of tablets of Compound 1 is listed in the following table.

TABLE 11

| Formulation of Tablets of Compound 1 (Multiple strengths) | | | | | |
|---|---|---|---|---|---|
| | Quantity | Quantity per Tablet (mg) | | | |
| Component | (%) w/w % | 25 mg mg/tablet | 50 mg mg/tablet | 75 mg mg/tablet | 100 mg mg/tablet |
| Compound 1[a] | 16.67 | 25.0 | 50.0 | 75.0 | 100.0 |
| Spray Dried Mannitol (PEARLITOL SD200)[b] | 64.97 | 97.5 | 194.9 | 292.4 | 389.9 |
| Silicified Micro-crystalline Cellulose (PROSOLV SMCC 90) | 12.22 | 18.3 | 36.7 | 55.0 | 73.3 |
| Hydroxypropyl Cellulose (KLUCEL EXF PHARM) | 1.11 | 1.7 | 3.3 | 5.0 | 6.7 |
| Sodium Starch Glycolate (EXPLOTAB) | 3.89 | 5.8 | 11.7 | 17.5 | 23.3 |

TABLE 11-continued

| Formulation of Tablets of Compound 1 (Multiple strengths) | | | | | |
|---|---|---|---|---|---|
| | Quantity | Quantity per Tablet (mg) | | | |
| Component | (%) w/w % | 25 mg mg/tablet | 50 mg mg/tablet | 75 mg mg/tablet | 100 mg mg/tablet |
| Magnesium Stearate (HYQUAL 2257) | 1.14 | 1.7 | 3.4 | 5.1 | 6.8 |
| Core Tablet Weight | 100 | 150.0 | 300.0 | 450.0 | 600.0 |
| Opadry Complete Film Coating System 03K140041 Pink[c] | 4.0 | 6.0 | 12.0 | 18.0 | 24.0 |
| Purified Water[d] | qs | qs | qs | qs | qs |
| Total Tablet Weight | 104 | 156.0 | 312.0 | 468.0 | 624.0 |

[a]Does not include drug substance potency factor, which is applied during manufacturing
[b]Content of Compound 1 drug substance and Mannitol are adjusted for the potency of the active ingredient
[c]Non-functional, cosmetic film coating, 15% solid content for coating suspension, added to target theoretical weight gain of 4%
[d]Removed during manufacturing
qs: quantity sufficient

Example 14. Stability Studies of Tablets of Compound 1

A stability study was conducted for tablets of Compound 1 under various storage conditions.

Results for Tables Prepared as Described in Example 11: Results demonstrate the chemical and physical stability of tablets of Compound 1 upon storage for up to 12 months under the long-term ICH condition of 25° C.±2° C./60%±5% RH and under the ICH intermediate condition of 30° C.±2° C./65%±5% RH as well as 6 months under the ICH accelerated condition of 40° C.±2° C./75%±5% RH. No meaningful changes were observed in description, assay and degradation products, chiral purity, water content, and dissolution.

Results demonstrate the chemical and physical stability of tablets of Compound 1 upon storage for 12 months under long-term ICH condition of 30° C.±2° C./65%±5% RH as well as 6 months under the ICH accelerated condition of 40° C.±2° C./75%±5% RH. No meaningful changes were observed in description, assay and degradation products, water content, and dissolution.

All results complied with the acceptance criteria (e.g. drug product purity: at least 90%, individual degradation product: each less than or equal to 0.3% by area, total amount of degradation products: less than or equal to 3.0%, enantiomeric purity: at least 99.5%) at all time points.

Results for Tables Prepared as Described in Example 13: Results demonstrate the chemical and physical stability of tablets of Compound 1 upon storage for up to 6 months under long-term ICH conditions of 30° C.±2° C./65%±5% RH as well as ICH accelerated condition of 40° C.±2° C./75%±5% RH. No meaningful changes were observed in description, assay and degradation products, chiral purity, water content, and dissolution.

Results demonstrate the chemical and physical stability of tablets of Compound 1 upon storage for 3 months under long-term ICH condition of 30° C.±2° C./65%±5% RH as well as ICH accelerated condition of 40° C.±2° C./75%±5% RH. No meaningful changes were observed in description, assay and degradation products, water content, and dissolution.

All results complied with the acceptance criteria (e.g. drug product purity: at least 90%, individual degradation product: each less than or equal to 0.3% by area, total amount of degradation products: less than or equal to 3.0%, enantiomeric purity: at least 99.5%) at all time points.

Example 15. Particle Size of Compound 1

Wet Milling: A wet mill may be employed during crystallization of Compound 1 in order to control the particle size distribution of the formed material. In general, an IKA Works wet mill furnished with a 2P/4M rotor stator stack, is hooked up in line to the process tank. The wet mill is run at a speed such that the desired particle size (e.g., D50~50-100 microns, D10>10 microns, D90<150 microns) can be achieved after approximately 25 passes through the wet mill. The amount of milling time can be made shorter, or longer, by changing the rpms at which the mill operates at. It is important to note that the material is friable in nature, and can be over-milled if the wrong setting is chosen. Once milling is completed, the material is filtered, and dried with gentle agitation in a filter dryer.

Particle Size Determination: Particle size for milled samples is determined by filtering a sample from the reaction mixture, and suspending the sample in an appropriate dispersant. The appropriate dispersant for Compound 1 is water with a small amount of additional surfactant, such as Triton X. The material can then be measured for its particle size distribution using an instrument such as a Malvern Mastersizer 3000, or something analogous.

While exemplary embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments described herein can be employed in practicing the subject matter provided herein. All such equivalents are considered to be within the scope of the claimed subject matter and are encompassed by the appended claims.

What is claimed is:

1. A method of treating cancer, comprising administering a therapeutically effective amount of a solid form comprising a compound of Formula (I), or a pharmaceutically acceptable salt thereof:

(I)

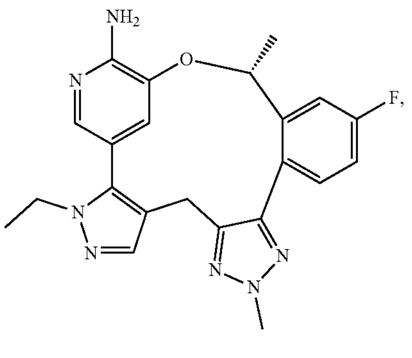

to a subject having the cancer, wherein:

(a) the solid form comprises a free base of a compound of formula (I), and is characterized by an XRPD pattern, when measured using Cu Kα radiation, comprising peaks at 10.7, 15.0, and 21.2° 2θ±0.2° 2θ;

(b) the solid form comprises a free base of a compound of formula (I), and is characterized by an XRPD pattern, when measured using Cu Kα radiation, comprising peaks at 8.6, 14.0, and 20.8° 2θ±0.2° 2θ;

(c) the solid form comprises a free base of a compound of formula (I), and is characterized by an XRPD pattern, when measured using Cu Kα radiation, comprising peaks at 13.4, 19.5, and 20.9° 2θ±0.2° 2θ;

(d) the solid form comprises a free base of a compound of formula (I), and is characterized by an XRPD pattern, when measured using Cu Kα radiation, comprising peaks at 12.1, 12.7, and 18.4° 2θ±0.2° 2θ;

(e) the solid form comprises a free base of a compound of formula (I), and is characterized by an XRPD pattern, when measured using Cu Kα radiation, comprising peaks at 10.5, 10.8, and 21.9° 2θ±0.2° 2θ;

(f) the solid form comprises a free base of a compound of formula (I), and is characterized by an XRPD pattern, when measured using Cu Kα radiation, comprising peaks at 8.6, 18.7, and 20.5° 2θ±0.2° 2θ;

(g) the solid form comprises a free base of a compound of formula (I), and is characterized by an XRPD pattern, when measured using Cu Kα radiation, comprising peaks at 12.5, 13.4, and 14.6° 2θ±0.2° 2θ;

(h) the solid form comprises a besylate salt of a compound of formula (I), and is characterized by an XRPD pattern, when measured using Cu Kα radiation, comprising peaks at 15.0, 17.9 and 23.0° 2θ±0.2° 2θ; or (i) the solid form comprises a phosphate salt of a compound of formula (I), and is characterized by an XRPD pattern, when measured using Cu Kα radiation, comprising peaks at 10.8, 18.5, and 24.8° 2θ±0.2° 2θ;

wherein the cancer is a ROS proto-oncogene 1, receptor tyrosine kinase (ROS1) positive cancer.

2. The method of claim 1, wherein the solid form comprises a free base of a compound of formula (I), and is characterized by an XRPD pattern, when measured using Cu Kα radiation, comprising peaks at 10.7, 15.0, and 21.2° 2θ±0.2° 2θ.

3. The method of claim 2, wherein the XRPD pattern further comprises peaks at 17.4 and 21.3° 2θ±0.2° 2θ.

4. The method of claim 3, wherein the XRPD pattern further comprises peaks at 12.0, 12.2, and 13.9° 2θ±0.2° 2θ.

5. The method of claim 2, wherein the solid form is characterized by an XRPD pattern that matches the XRPD pattern depicted in FIG. 1.

6. The method of claim 2, wherein the solid form exhibits an endothermic event, as characterized by DSC, with an onset temperature at 265° C.±2° C. and/or a peak temperature at 267° C.±2° C.

7. The method of claim 2, wherein the solid form is characterized by a DSC thermogram that matches the DSC thermogram depicted in FIG. 3.

8. The method of claim 2, wherein the solid form exhibits a weight increase of about 0.25% when subjected to an increase in relative humidity from about 0 to about 90% relative humidity.

9. The method of claim 2, wherein the solid form has approximately unit cell dimensions of: a=8.4 Å, b=8.4 Å, c=14.9 Å, α=90°, β=106°, and γ=90°.

10. The method of claim 1, wherein the solid form comprises a free base of a compound of formula (I), and is characterized by an XRPD pattern, when measured using Cu Kα radiation, comprising peaks at 8.6, 14.0, and 20.8° 2θ±0.2° 2θ.

11. The method of claim 1, wherein the solid form comprises a free base of a compound of formula (I), and is characterized by an XRPD pattern, when measured using Cu Kα radiation, comprising peaks at 13.4, 19.5, and 20.9° 2θ±0.2° 2θ.

12. The method of claim 1, wherein the solid form comprises a free base of a compound of formula (I), and is characterized by an XRPD pattern, when measured using Cu Kα radiation, comprising peaks at 12.1, 12.7, and 18.4° 2θ±0.2° 2θ.

13. The method of claim 1, wherein the solid form comprises a free base of a compound of formula (I), and is characterized by an XRPD pattern, when measured using Cu Kα radiation, comprising peaks at 10.5, 10.8, and 21.9° 2θ±0.2° 2θ.

14. The method of claim 1, wherein the solid form comprises a free base of a compound of formula (I), and is characterized by an XRPD pattern, when measured using Cu Kα radiation, comprising peaks at 8.6, 18.7, and 20.5° 2θ±0.2° 2θ.

15. The method of claim 1, wherein the solid form comprises a free base of a compound of formula (I), and is characterized by an XRPD pattern, when measured using Cu Kα radiation, comprising peaks at 12.5, 13.4, and 14.6° 2θ±0.2° 2θ.

16. The method of claim 15, wherein the XRPD pattern further comprises peaks at 20.9 and 22.8° 2θ±0.2° 2θ.

17. The method of claim 16, wherein the XRPD pattern further comprises peaks at 11.4 and 15.8° 2θ±0.2° 2θ.

18. The method of claim 15, wherein the solid form is characterized by an XRPD pattern that matches the XRPD pattern depicted in FIG. 19.

19. The method of claim 15, wherein the solid form has approximately unit cell dimensions of: a=8.0 Å, b=14.8 Å, c=18.0 Å, α=90°, β=90°, and γ=90°.

20. The method of claim 1, wherein the solid form comprises a besylate salt of a compound of formula (I), and is characterized by an XRPD pattern, when measured using Cu Kα radiation, comprising peaks at 15.0, 17.9 and 23.0° 2θ±0.2° 2θ.

21. The method of claim 1, wherein the solid form comprises a phosphate salt of a compound of formula (I), and is characterized by an XRPD pattern, when measured using Cu Kα radiation, comprising peaks at 10.8, 18.5, and 24.8° 2θ±0.2° 2θ.

22. The method of claim 1, comprising administering to the subject a pharmaceutical composition comprising the solid form and a pharmaceutically acceptable excipient.

23. The method of claim 2, comprising administering to the subject a pharmaceutical composition comprising the solid form and a pharmaceutically acceptable excipient.

24. The method of claim 15, comprising administering to the subject a pharmaceutical composition comprising the solid form and a pharmaceutically acceptable excipient.

25. The method of claim 1, wherein the cancer is a solid tumor.

26. The method of claim 1, wherein the cancer is a hematologic malignancy.

27. The method of claim 1, wherein the cancer is lung cancer, glioblastoma, inflammatory myofibroblastic tumor (IMT), bile duct cancer, ovarian cancer, gastric cancer, colorectal cancer, angiosarcoma, melanoma, epithelioid hemangioendothelioma, esophageal cancer, kidney cancer, breast cancer, colon cancer, thyroid cancer, spitzoid tumor, cholangiocarcinoma, neuroblastoma, anaplastic large cell lymphoma (ALCL), diffuse large B-cell lymphoma (DLBCL), or large B-cell lymphoma.

28. The method of claim 1, wherein the cancer is lung cancer.

29. The method of claim 1, wherein the cancer is non-small cell lung cancer.

30. The method of claim 1, wherein the cancer is spitzoid melanoma, esophageal squamous cell carcinoma, renal medullary carcinoma, renal cell carcinoma, papillary thyroid cancer, or serous ovarian carcinoma.

* * * * *